(12) United States Patent
Messerly et al.

(10) Patent No.: US 11,298,128 B2
(45) Date of Patent: Apr. 12, 2022

(54) SURGICAL SYSTEM COUPLABLE WITH STAPLE CARTRIDGE AND RADIO FREQUENCY CARTRIDGE, AND METHOD OF USING SAME

(71) Applicant: Cilag GmbH International, Zug (CH)

(72) Inventors: Jeffrey D. Messerly, Cincinnati, OH (US); David C. Yates, Morrow, OH (US); Jason L. Harris, Lebanon, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 617 days.

(21) Appl. No.: 15/636,096

(22) Filed: Jun. 28, 2017

(65) Prior Publication Data

US 2019/0000478 A1    Jan. 3, 2019

(51) Int. Cl.
*A61B 17/072* (2006.01)
*A61B 18/14* (2006.01)
(Continued)

(52) U.S. Cl.
CPC ........ *A61B 17/07207* (2013.01); *A61B 17/29* (2013.01); *A61B 18/00* (2013.01); *A61B 18/1206* (2013.01); *A61B 18/1445* (2013.01); *A61B 17/295* (2013.01); *A61B 2017/00026* (2013.01); *A61B 2017/0046* (2013.01); *A61B 2017/00075* (2013.01); *A61B 2017/00084* (2013.01); *A61B 2017/00115* (2013.01); *A61B 2017/00119* (2013.01); *A61B 2017/00128* (2013.01); *A61B 2017/00199* (2013.01); *A61B 2017/00353* (2013.01); *A61B 2017/00398* (2013.01); *A61B 2017/00464* (2013.01); *A61B 2017/00477* (2013.01); *A61B 2017/00734* (2013.01); *A61B 2017/07257* (2013.01); *A61B 2017/07271* (2013.01); *A61B 2017/07278* (2013.01); *A61B 2017/07285* (2013.01); *A61B 2017/2902* (2013.01);
(Continued)

(58) Field of Classification Search
CPC ...... A61B 2017/07214; A61B 18/1442; A61B 18/1445
See application file for complete search history.

(56) References Cited

U.S. PATENT DOCUMENTS

| 2,961,385 A | 11/1960 | McGall |
| 3,370,263 A | 2/1968 | Schreieck |

(Continued)

FOREIGN PATENT DOCUMENTS

| GB | 1526401 A | 9/1978 |
| JP | 2004130126 A | 4/2004 |
| WO | WO-9937225 A1 | 7/1999 |

OTHER PUBLICATIONS

Bay Area Circuits (https://bayareacircuits.com/multi-layer-stackups/) (Year: 2015).

*Primary Examiner* — Ronald Hupczey, Jr.

(57) ABSTRACT

A method is disclosed. The method includes delivering staples from a surgical staple cartridge of a surgical instrument to a first tissue during a first procedure; removing the surgical staple cartridge from the surgical instrument; and delivering radio-frequency energy from a radio-frequency cartridge of the surgical instrument to a second tissue during a second procedure.

21 Claims, 54 Drawing Sheets

(51) Int. Cl.

| | | |
|---|---|---|
| *A61B 18/00* | (2006.01) | |
| *A61B 17/29* | (2006.01) | |
| *A61B 18/12* | (2006.01) | |
| *A61B 17/00* | (2006.01) | |
| *A61B 90/00* | (2016.01) | |
| *A61B 17/295* | (2006.01) | |

(52) U.S. Cl.
CPC ............. *A61B 2017/2927* (2013.01); *A61B 2018/00005* (2013.01); *A61B 2018/0063* (2013.01); *A61B 2018/00172* (2013.01); *A61B 2018/00589* (2013.01); *A61B 2018/00642* (2013.01); *A61B 2018/00791* (2013.01); *A61B 2018/00875* (2013.01); *A61B 2018/00898* (2013.01); *A61B 2018/00988* (2013.01); *A61B 2018/1452* (2013.01); *A61B 2018/1455* (2013.01); *A61B 2018/1495* (2013.01); *A61B 2090/061* (2016.02); *A61B 2090/065* (2016.02)

(56) References Cited

U.S. PATENT DOCUMENTS

| | | |
|---|---|---|
| D278,081 S | 3/1985 | Green |
| D297,764 S | 9/1988 | Hunt et al. |
| 5,007,907 A | 4/1991 | Nishigaki et al. |
| 5,364,395 A | 11/1994 | West, Jr. |
| 5,403,312 A | 4/1995 | Yates et al. |
| D360,688 S | 7/1995 | Ferragamo et al. |
| 5,485,947 A | 1/1996 | Olson et al. |
| 5,658,281 A | 8/1997 | Heard |
| 5,673,842 A | 10/1997 | Bittner et al. |
| 5,735,848 A | 4/1998 | Yates et al. |
| 5,817,093 A | 10/1998 | Williamson, IV et al. |
| 5,827,279 A | 10/1998 | Hughett et al. |
| 5,833,690 A | 11/1998 | Yates et al. |
| 5,835,829 A | 11/1998 | Genovese et al. |
| 6,004,320 A | 12/1999 | Casscells et al. |
| D480,808 S | 10/2003 | Wells et al. |
| 6,730,081 B1 | 5/2004 | Desai |
| 6,905,497 B2 | 6/2005 | Truckai et al. |
| 6,918,906 B2 | 7/2005 | Long |
| D509,297 S | 9/2005 | Wells |
| 6,988,649 B2 | 1/2006 | Shelton, IV et al. |
| 7,044,352 B2 | 5/2006 | Shelton, IV et al. |
| 7,223,267 B2 | 5/2007 | Isola et al. |
| 7,383,611 B2 | 6/2008 | Foster |
| D576,278 S | 9/2008 | Nalagatla et al. |
| 7,476,222 B2 | 1/2009 | Sun et al. |
| 7,517,356 B2 * | 4/2009 | Heinrich ............ A61B 17/0686 227/176.1 |
| 7,559,452 B2 | 7/2009 | Wales et al. |
| 7,575,144 B2 | 8/2009 | Ortiz et al. |
| 7,617,961 B2 | 11/2009 | Viola |
| D605,762 S | 12/2009 | Nalagatla et al. |
| 7,673,781 B2 | 3/2010 | Swayze et al. |
| 7,722,607 B2 | 5/2010 | Dumbauld et al. |
| 7,780,663 B2 | 8/2010 | Yates et al. |
| 7,819,296 B2 | 10/2010 | Hueil et al. |
| 7,861,906 B2 | 1/2011 | Doll et al. |
| 7,896,877 B2 | 3/2011 | Hall et al. |
| 7,901,400 B2 | 3/2011 | Wham et al. |
| 7,953,823 B2 | 5/2011 | Rider et al. |
| D650,074 S | 12/2011 | Hunt et al. |
| 8,277,446 B2 | 10/2012 | Heard |
| 8,453,906 B2 * | 6/2013 | Huang ............. A61B 17/07207 227/175.2 |
| 8,465,534 B2 | 6/2013 | Schechter |
| 8,485,413 B2 | 7/2013 | Scheib et al. |
| 8,517,239 B2 | 8/2013 | Scheib et al. |
| 8,523,043 B2 | 9/2013 | Ullrich et al. |
| 8,573,461 B2 | 11/2013 | Shelton, IV et al. |
| 8,579,176 B2 | 11/2013 | Smith et al. |
| 8,608,045 B2 | 12/2013 | Smith et al. |
| 8,622,274 B2 | 1/2014 | Yates et al. |
| 8,636,736 B2 | 1/2014 | Yates et al. |
| 8,663,222 B2 | 3/2014 | Anderson et al. |
| 8,746,533 B2 | 6/2014 | Whitman et al. |
| 8,764,747 B2 | 7/2014 | Cummings et al. |
| 8,784,415 B2 | 7/2014 | Malackowski et al. |
| 8,820,603 B2 | 9/2014 | Shelton, IV et al. |
| 8,840,603 B2 | 9/2014 | Shelton, IV et al. |
| 8,858,547 B2 | 10/2014 | Brogna |
| 8,876,858 B2 | 11/2014 | Braun |
| 8,888,771 B2 | 11/2014 | Twomey |
| 8,888,776 B2 | 11/2014 | Dietz et al. |
| 8,926,607 B2 | 1/2015 | Norvell et al. |
| 8,968,317 B2 | 3/2015 | Evans et al. |
| 8,979,890 B2 | 3/2015 | Boudreaux |
| 8,998,060 B2 | 4/2015 | Bruewer et al. |
| 9,005,199 B2 | 4/2015 | Beckman et al. |
| 9,060,775 B2 | 6/2015 | Wiener et al. |
| 9,060,776 B2 | 6/2015 | Yates et al. |
| 9,072,535 B2 | 7/2015 | Shelton, IV et al. |
| 9,149,325 B2 | 10/2015 | Worrell et al. |
| 9,161,802 B2 | 10/2015 | Przybyszewski |
| 9,161,803 B2 | 10/2015 | Yates et al. |
| 9,326,788 B2 | 5/2016 | Batross et al. |
| 9,345,481 B2 | 5/2016 | Hall et al. |
| 9,358,003 B2 | 6/2016 | Hall et al. |
| 9,402,627 B2 | 8/2016 | Stevenson et al. |
| 9,510,906 B2 | 12/2016 | Boudreaux et al. |
| 9,526,564 B2 | 12/2016 | Rusin |
| 9,549,733 B2 | 1/2017 | Knodel |
| 9,561,031 B2 | 2/2017 | Heinrich et al. |
| 9,566,062 B2 | 2/2017 | Boudreaux |
| 9,572,622 B2 | 2/2017 | Shelton, IV et al. |
| 9,579,143 B2 | 2/2017 | Ullrich et al. |
| 9,585,657 B2 | 3/2017 | Shelton, IV et al. |
| 9,629,627 B2 | 4/2017 | Kostrzewski et al. |
| 9,629,628 B2 | 4/2017 | Aranyi |
| 9,700,309 B2 | 7/2017 | Jaworek et al. |
| 9,706,993 B2 | 7/2017 | Hessler et al. |
| 9,707,028 B2 | 7/2017 | Batchelor et al. |
| 9,724,095 B2 | 8/2017 | Gupta et al. |
| 9,743,929 B2 | 8/2017 | Leimbach et al. |
| 9,757,142 B2 | 9/2017 | Shimizu |
| D800,904 S | 10/2017 | Leimbach et al. |
| 9,788,835 B2 | 10/2017 | Morgan et al. |
| 9,788,836 B2 | 10/2017 | Overmyer et al. |
| 9,795,379 B2 | 10/2017 | Leimbach et al. |
| 9,808,246 B2 | 11/2017 | Shelton, IV et al. |
| 9,814,514 B2 | 11/2017 | Shelton, IV et al. |
| 9,839,421 B2 | 12/2017 | Zerkle et al. |
| 9,844,375 B2 | 12/2017 | Overmyer et al. |
| 9,877,722 B2 | 1/2018 | Schellin et al. |
| D809,659 S | 2/2018 | Menn |
| 9,888,958 B2 | 2/2018 | Evans et al. |
| 9,913,642 B2 | 3/2018 | Leimbach et al. |
| 9,924,942 B2 | 3/2018 | Swayze et al. |
| 9,924,944 B2 | 3/2018 | Shelton, IV et al. |
| 9,924,998 B2 | 3/2018 | Martin et al. |
| 9,968,355 B2 | 5/2018 | Shelton, IV et al. |
| 9,980,769 B2 | 5/2018 | Trees et al. |
| 10,010,366 B2 | 7/2018 | Strobl |
| 10,016,186 B2 | 7/2018 | Benn |
| 10,052,100 B2 | 8/2018 | Morgan et al. |
| D831,209 S | 10/2018 | Huitema et al. |
| D836,198 S | 12/2018 | Harris et al. |
| 10,178,992 B2 | 1/2019 | Wise et al. |
| 10,194,912 B2 | 2/2019 | Scheib et al. |
| 10,201,348 B2 | 2/2019 | Scheib et al. |
| 10,211,586 B2 | 2/2019 | Adams et al. |
| 10,213,198 B2 | 2/2019 | Aronhalt et al. |
| 10,231,776 B2 | 3/2019 | Artale et al. |
| 10,238,385 B2 | 3/2019 | Yates et al. |
| 10,245,027 B2 | 4/2019 | Shelton, IV et al. |
| 10,265,120 B2 | 4/2019 | Yates et al. |
| D847,989 S | 5/2019 | Shelton, IV et al. |
| D850,617 S | 6/2019 | Shelton, IV et al. |
| 10,327,776 B2 | 6/2019 | Harris et al. |
| 10,335,147 B2 | 7/2019 | Rector et al. |
| 10,357,305 B2 | 7/2019 | Esch et al. |
| 10,413,291 B2 | 9/2019 | Worthington et al. |

(56) References Cited

U.S. PATENT DOCUMENTS

| | | | |
|---|---|---|---|
| D865,175 S | 10/2019 | Widenhouse et al. | |
| 10,456,137 B2 | 10/2019 | Vendely et al. | |
| 10,470,768 B2 | 11/2019 | Harris et al. | |
| 10,485,567 B2 | 11/2019 | Piskun | |
| 10,548,504 B2 | 2/2020 | Shelton, IV et al. | |
| 10,548,655 B2 | 2/2020 | Scheib et al. | |
| 10,595,930 B2 | 3/2020 | Scheib et al. | |
| 10,603,117 B2 | 3/2020 | Schings et al. | |
| 10,610,289 B2 | 4/2020 | Jensen | |
| 10,617,412 B2 | 4/2020 | Shelton, IV et al. | |
| 10,639,037 B2 | 5/2020 | Shelton, IV et al. | |
| D893,717 S | 8/2020 | Messerly et al. | |
| D908,216 S | 1/2021 | Messerly et al. | |
| 2004/0122423 A1 | 6/2004 | Dycus et al. | |
| 2005/0113821 A1* | 5/2005 | Pendekanti | A61B 17/072 606/41 |
| 2006/0064086 A1 | 3/2006 | Odom | |
| 2007/0102472 A1 | 5/2007 | Shelton | |
| 2007/0175949 A1* | 8/2007 | Shelton, IV | A61B 34/76 227/176.1 |
| 2008/0147062 A1 | 6/2008 | Truckai et al. | |
| 2009/0206133 A1 | 8/2009 | Morgan et al. | |
| 2010/0193566 A1 | 8/2010 | Scheib et al. | |
| 2010/0228250 A1 | 9/2010 | Brogna | |
| 2011/0028964 A1 | 2/2011 | Edwards | |
| 2011/0106076 A1 | 5/2011 | Hernandez Zendejas | |
| 2011/0125176 A1 | 5/2011 | Yates et al. | |
| 2012/0016413 A1 | 1/2012 | Timm et al. | |
| 2012/0132450 A1* | 5/2012 | Timm | A61B 17/07207 173/47 |
| 2012/0245576 A1 | 9/2012 | Epstein et al. | |
| 2014/0263541 A1 | 9/2014 | Leimbach et al. | |
| 2014/0263552 A1 | 9/2014 | Hall et al. | |
| 2015/0060519 A1 | 3/2015 | Shelton, IV et al. | |
| 2015/0080876 A1 | 3/2015 | Worrell et al. | |
| 2015/0080887 A1 | 3/2015 | Sobajima et al. | |
| 2016/0066913 A1 | 3/2016 | Swayze et al. | |
| 2016/0120545 A1 | 5/2016 | Shelton, IV et al. | |
| 2016/0270842 A1 | 9/2016 | Strobl et al. | |
| 2017/0119388 A1 | 5/2017 | Kostrzewski | |
| 2017/0143336 A1 | 5/2017 | Shah et al. | |
| 2017/0296213 A1 | 10/2017 | Swensgard et al. | |
| 2017/0312019 A1 | 11/2017 | Trees et al. | |
| 2018/0168621 A1 | 6/2018 | Shelton, IV et al. | |
| 2018/0168650 A1 | 6/2018 | Shelton, IV et al. | |
| 2018/0360452 A1 | 12/2018 | Shelton, IV et al. | |
| 2019/0000463 A1 | 1/2019 | Shelton, IV et al. | |
| 2019/0000468 A1 | 1/2019 | Adams et al. | |
| 2019/0000470 A1 | 1/2019 | Yates et al. | |
| 2019/0000472 A1 | 1/2019 | Shelton, IV et al. | |
| 2019/0000479 A1 | 1/2019 | Harris et al. | |
| 2019/0000525 A1 | 1/2019 | Messerly et al. | |
| 2019/0000528 A1 | 1/2019 | Yates et al. | |
| 2019/0000530 A1 | 1/2019 | Yates et al. | |
| 2019/0000531 A1 | 1/2019 | Messerly et al. | |
| 2019/0000532 A1 | 1/2019 | Shelton, IV et al. | |
| 2019/0000533 A1 | 1/2019 | Messerly et al. | |
| 2019/0000534 A1 | 1/2019 | Messerly et al. | |
| 2019/0000535 A1 | 1/2019 | Messerly et al. | |
| 2019/0000537 A1 | 1/2019 | Widenhouse et al. | |
| 2019/0000538 A1 | 1/2019 | Widenhouse et al. | |
| 2019/0000539 A1 | 1/2019 | Messerly et al. | |
| 2020/0397432 A1 | 12/2020 | Messerly et al. | |
| 2021/0068891 A1 | 3/2021 | Messerly et al. | |
| 2021/0093322 A1 | 4/2021 | Adams et al. | |

\* cited by examiner

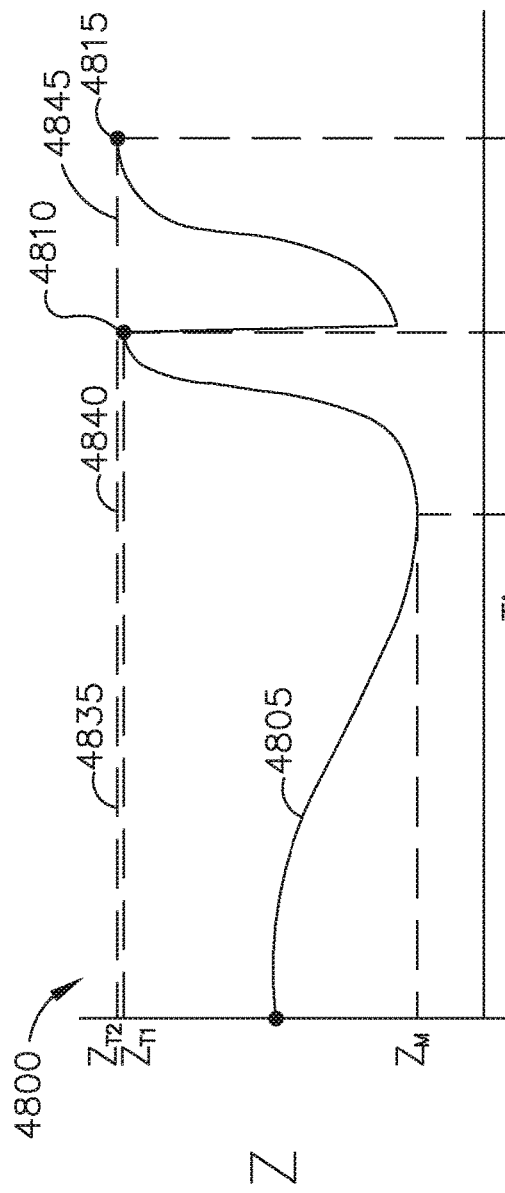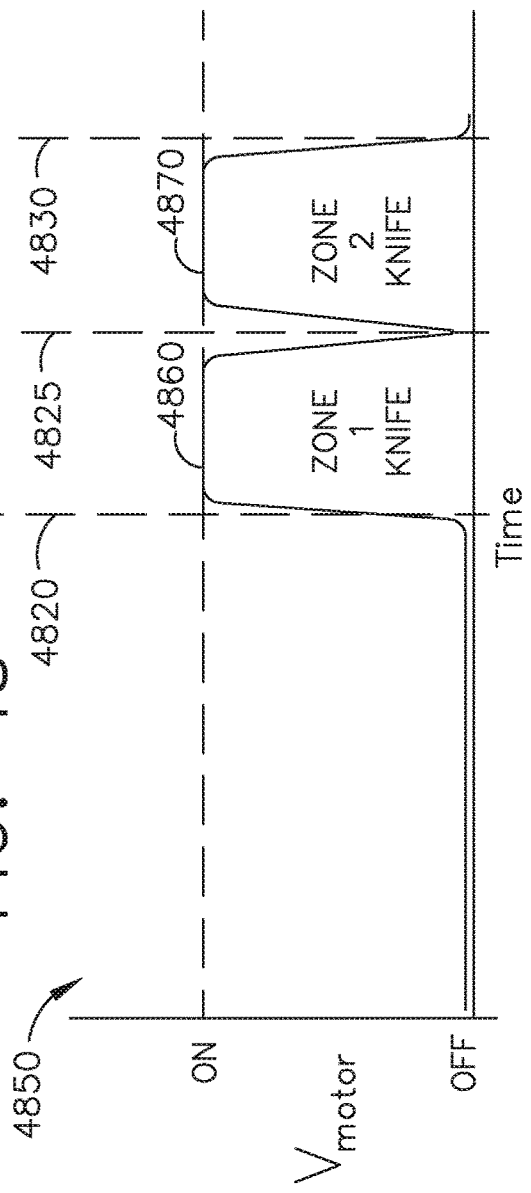
FIG. 48
FIG. 49

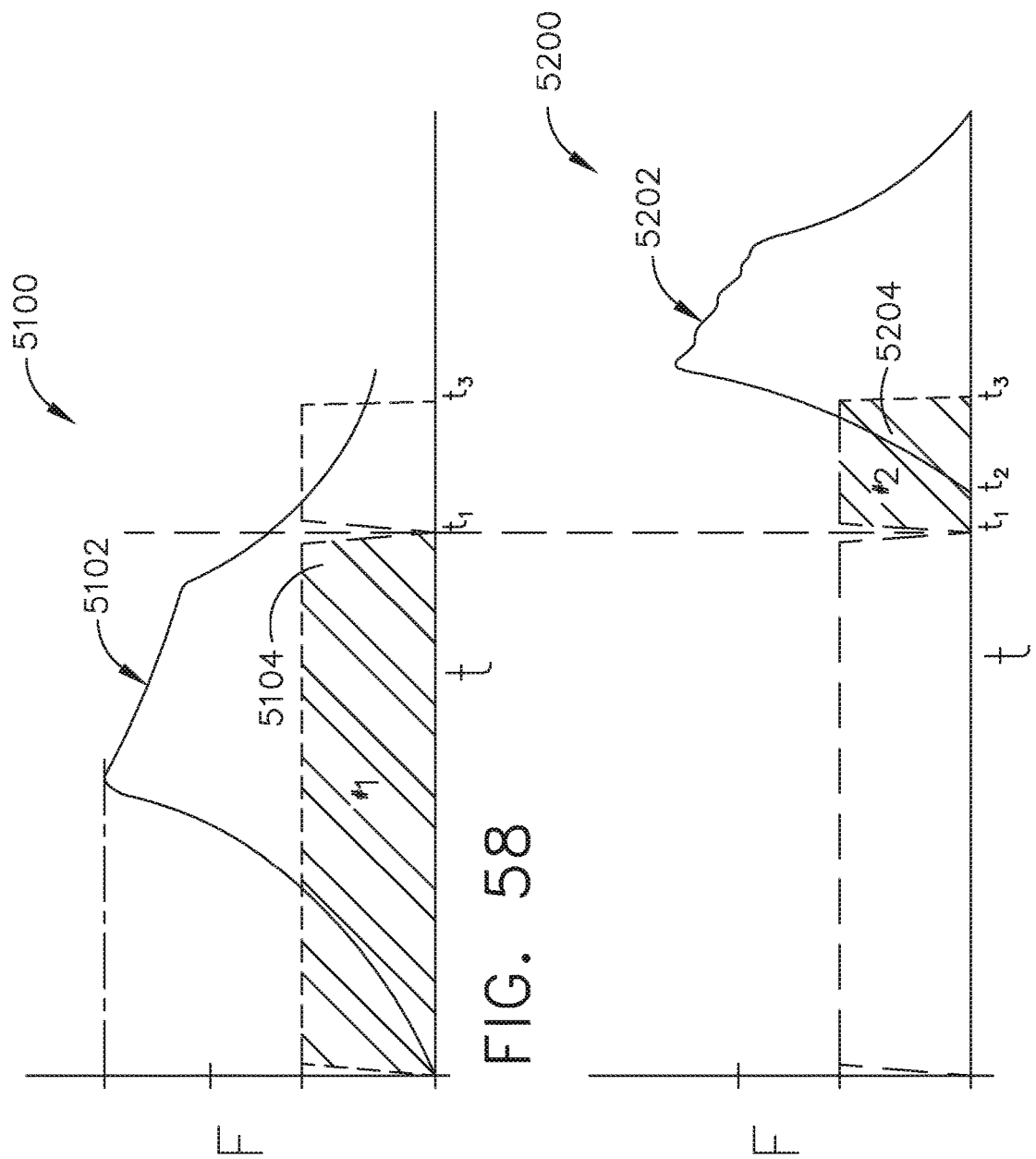

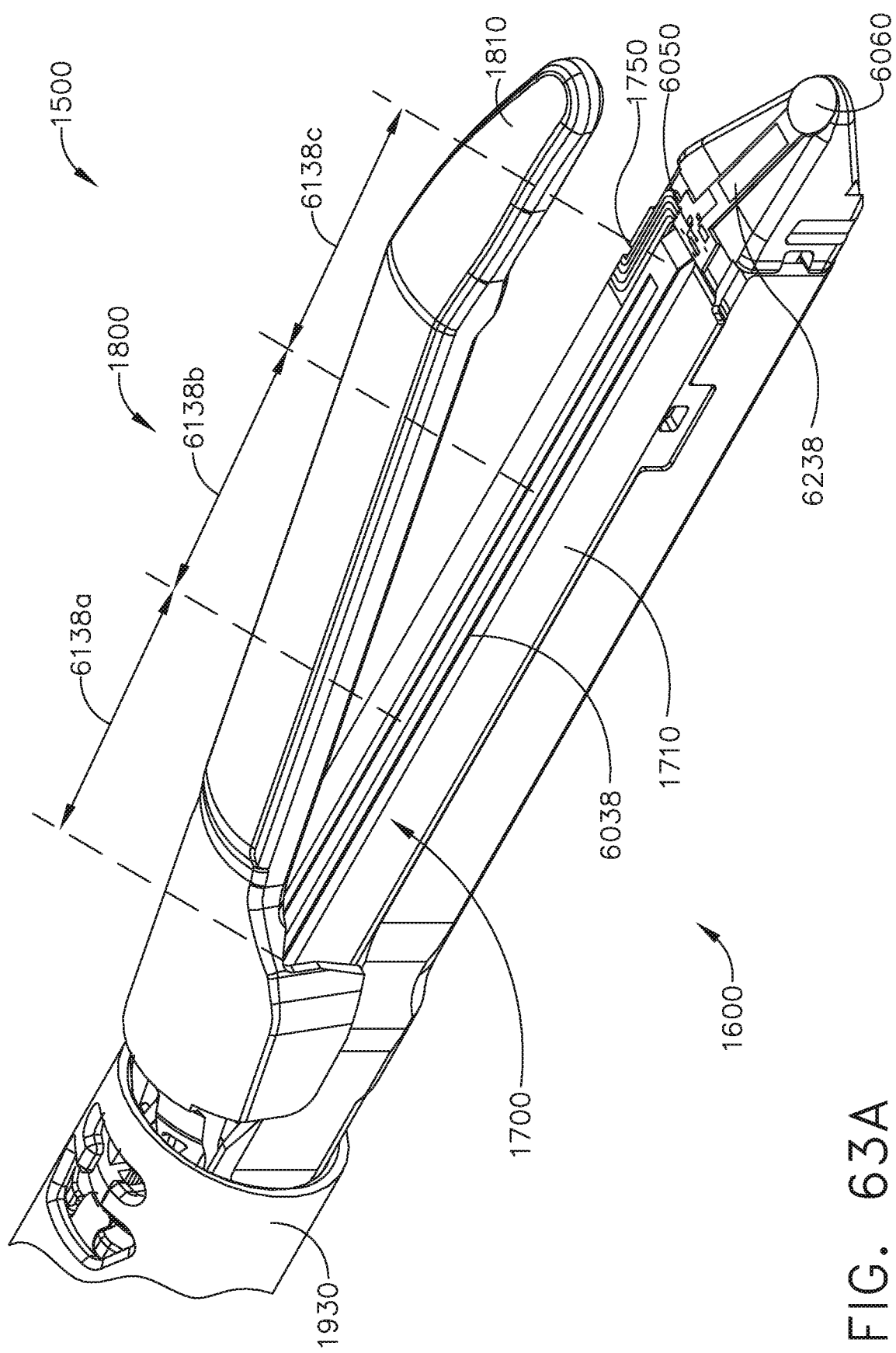

SURGICAL SYSTEM COUPLABLE WITH STAPLE CARTRIDGE AND RADIO FREQUENCY CARTRIDGE, AND METHOD OF USING SAME

TECHNICAL FIELD

The present disclosure relates to surgical instruments and, in various circumstances, surgical sealing and cutting instruments and RF cartridges and staple cartridges therefore that are designed to seal and cut tissue.

BACKGROUND

When using a surgical sealing and stapling instrument, it may be useful to have an interchangeable portion of the surgical instrument so that the operator may utilize the most effective technology during various aspects of a surgical procedure. Having an interchangeable tool assembly allows the operator, for example, to utilize one type of end effector, performing a first function, during a first portion of a procedure then switch to a second type of end effector, performing a second function, during a second portion of the procedure.

SUMMARY

In one aspect, a method includes delivering staples from a surgical staple cartridge of a surgical instrument to a first tissue during a first procedure; removing the surgical staple cartridge from the surgical instrument; and delivering radio-frequency energy from a radio-frequency cartridge of the surgical instrument to a second tissue during a second procedure.

In another aspect, a method of utilizing an interchangeable tool assembly includes utilizing a staple cartridge coupled to the interchangeable tool assembly to deliver staples to seal a first tissue during the first period of time; replacing the staple cartridge; and utilizing a radio-frequency cartridge coupled to the interchangeable tool assembly to deliver radio-frequency energy to seal a second tissue during a second period of time.

In another aspect, a method includes sealing a first tissue with staples from a removable staple cartridge of a surgical instrument; sterilizing the surgical instrument; and sealing a second tissue with radio-frequency energy delivered by a removable radio-frequency cartridge of the surgical instrument.

FIGURES

The novel features of the aspects described herein are set forth with particularity in the appended claims. These aspects, however, both as to organization and methods of operation may be better understood by reference to the following description, taken in conjunction with the accompanying drawings.

Figure 39:
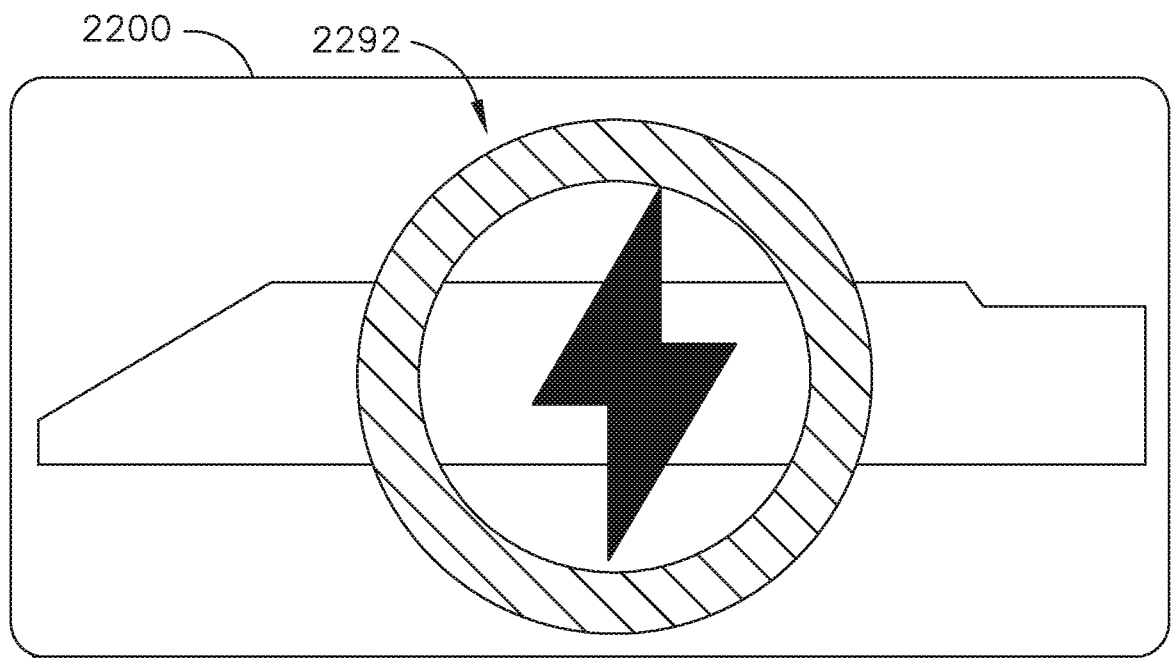
Figure 40:
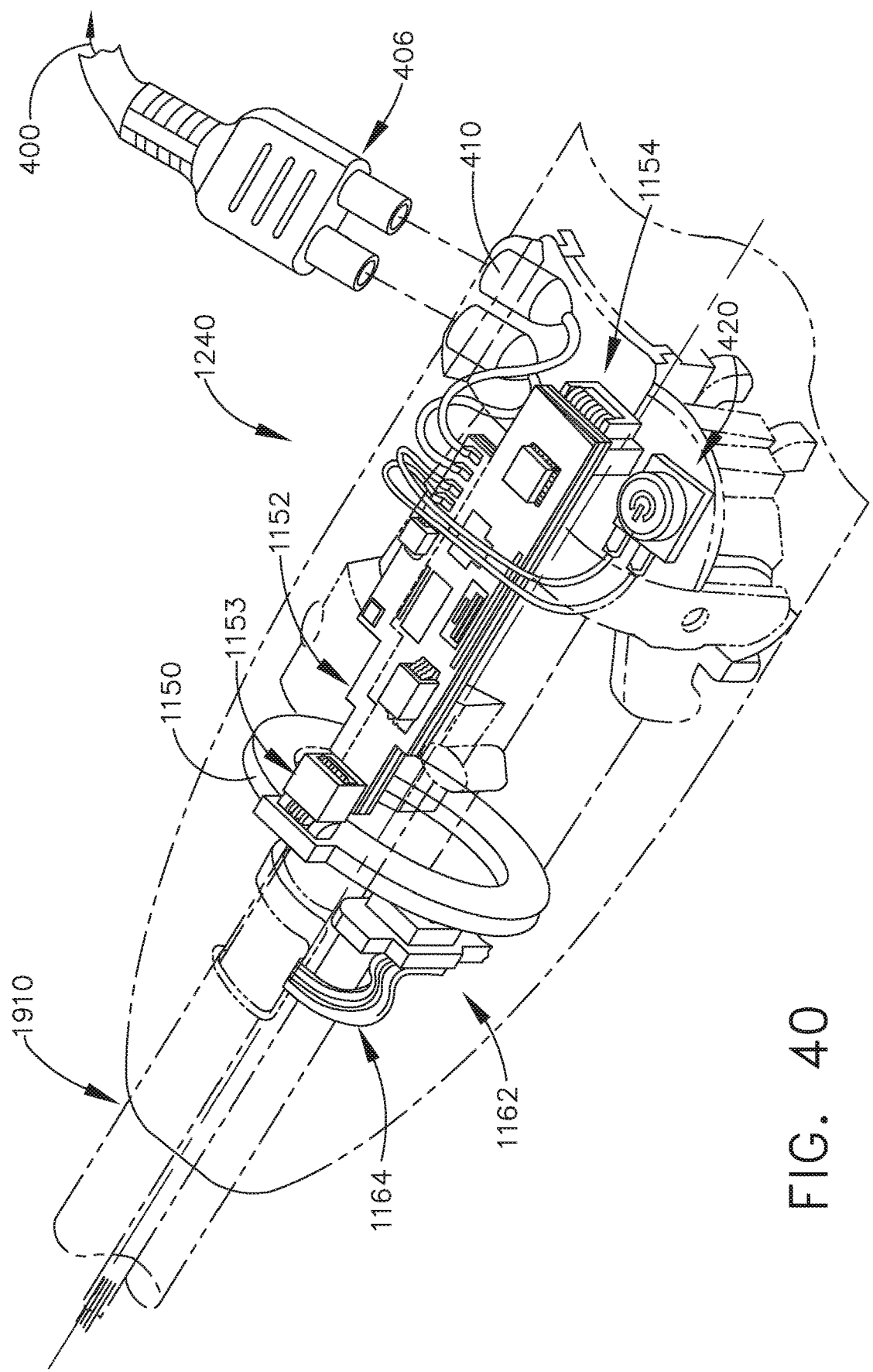

FIG. 39 is a display depicting RF cartridge status information of the surgical instrument according to one aspect of this disclosure FIG. 40 shows a nozzle assembly that constitutes a modular portion of the surgical tool assembly may include shaft module circuitry uniquely configured to control various functions in the shaft assembly while also communicating with the handle assembly and allowing for an electrosurgical generator to be controlled from the powered stapling handle, according to some aspects.

Figure 41:
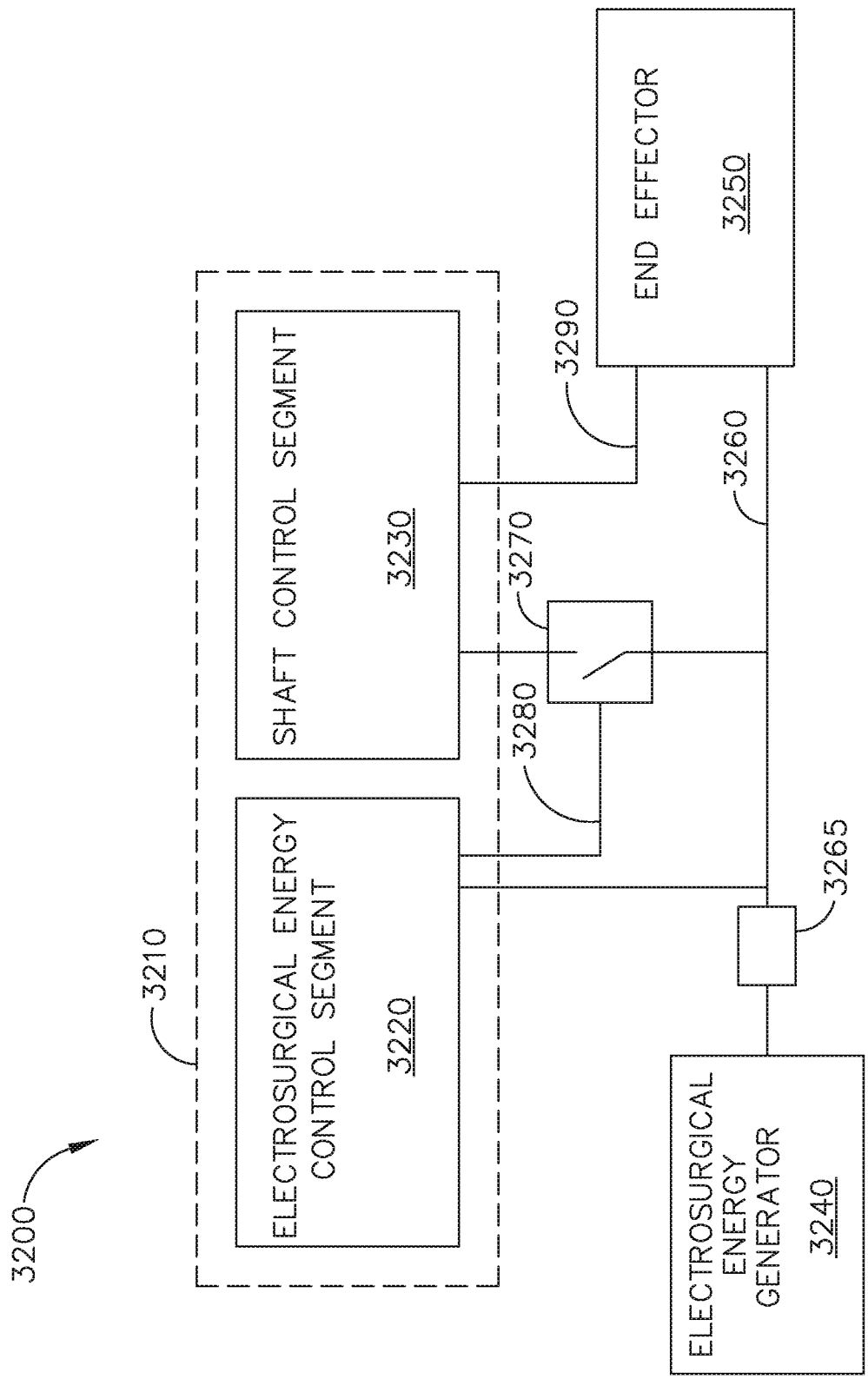

FIG. 41 illustrates a block diagram of a surgical system programmed to communicate power and control signals with an end effector, according to one aspect of this disclosure.

Figure 42:
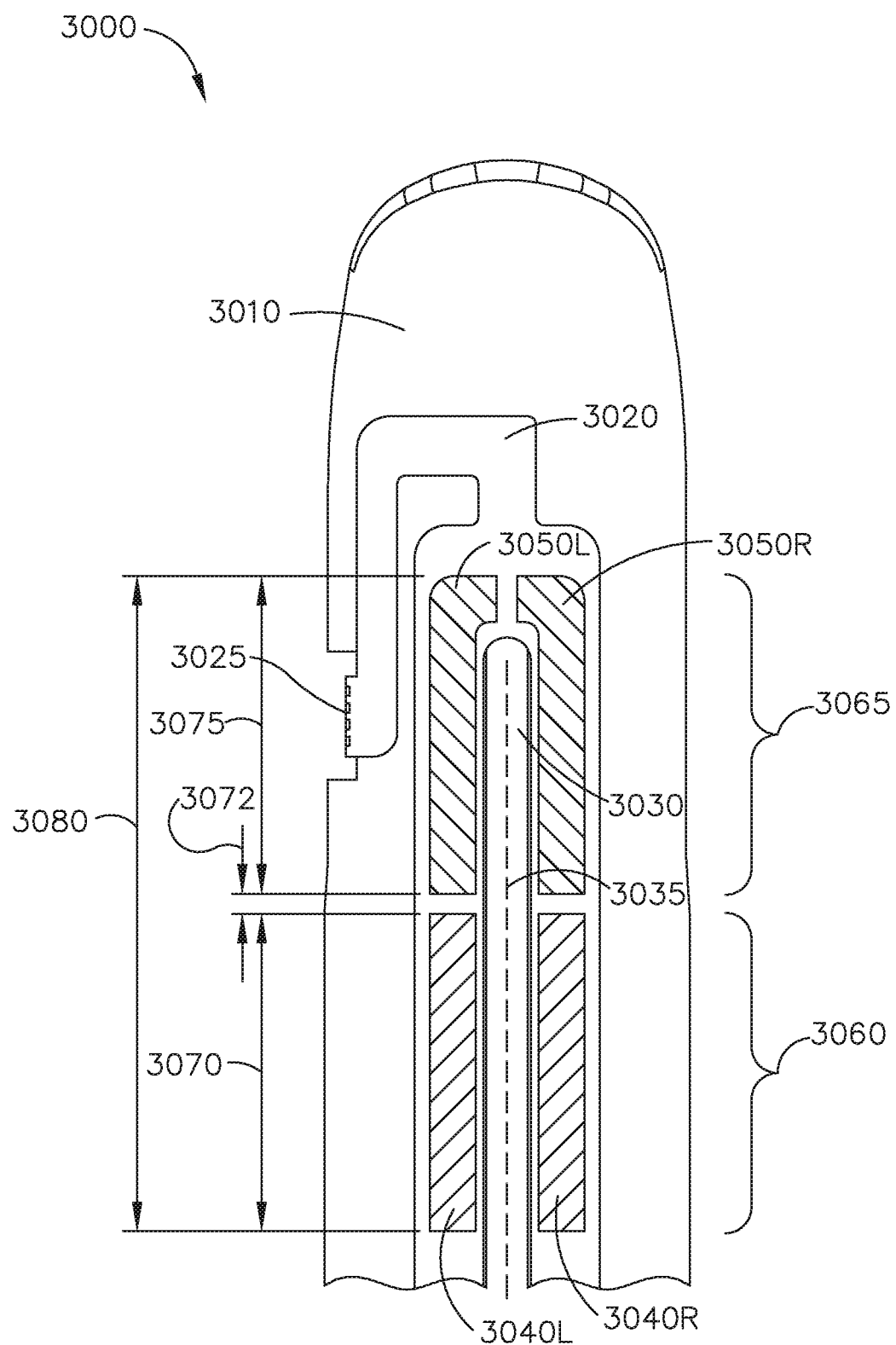

FIG. 42 is a schematic top view of a jaw in an end effector according to one aspect of this disclosure.

Figure 43:
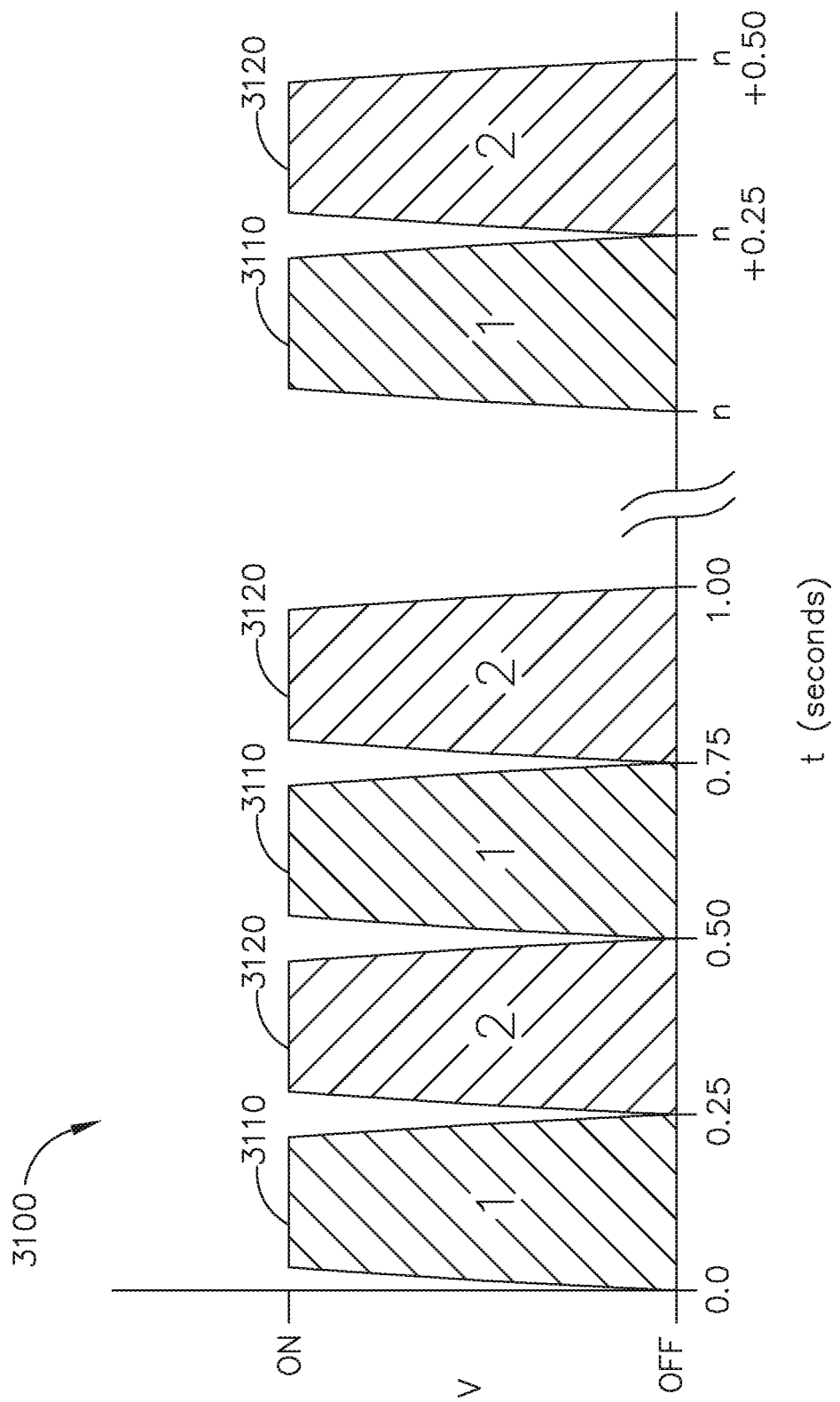

FIG. 43 is a graph depicting voltage applied to electrodes as a function of time according to one aspect of this disclosure.

Figure 44:
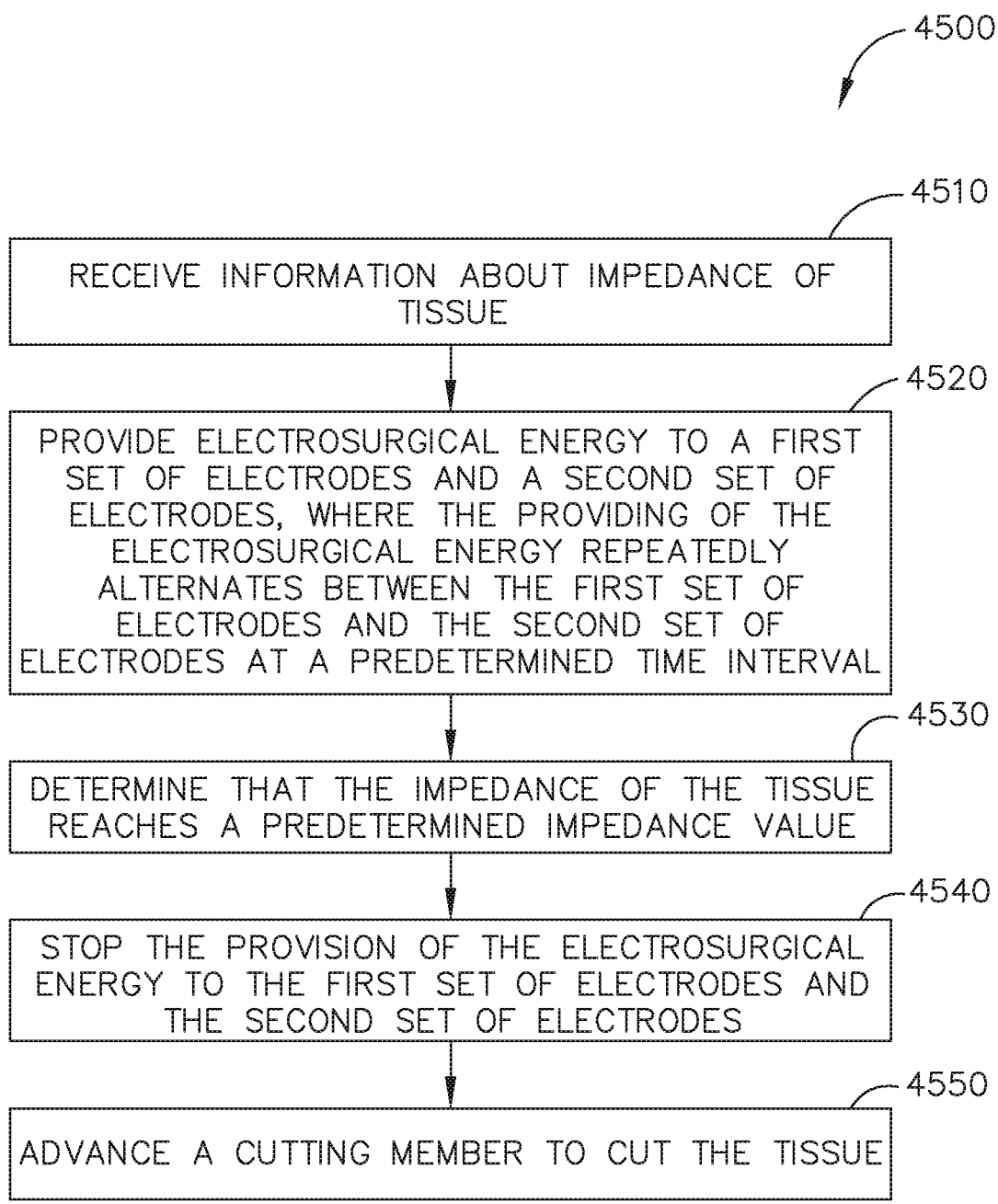

FIG. 44 is a logic flow diagram depicting a process of a control program or a logic configuration for operating the surgical instrument according to one aspect of this disclosure.

Figure 45:
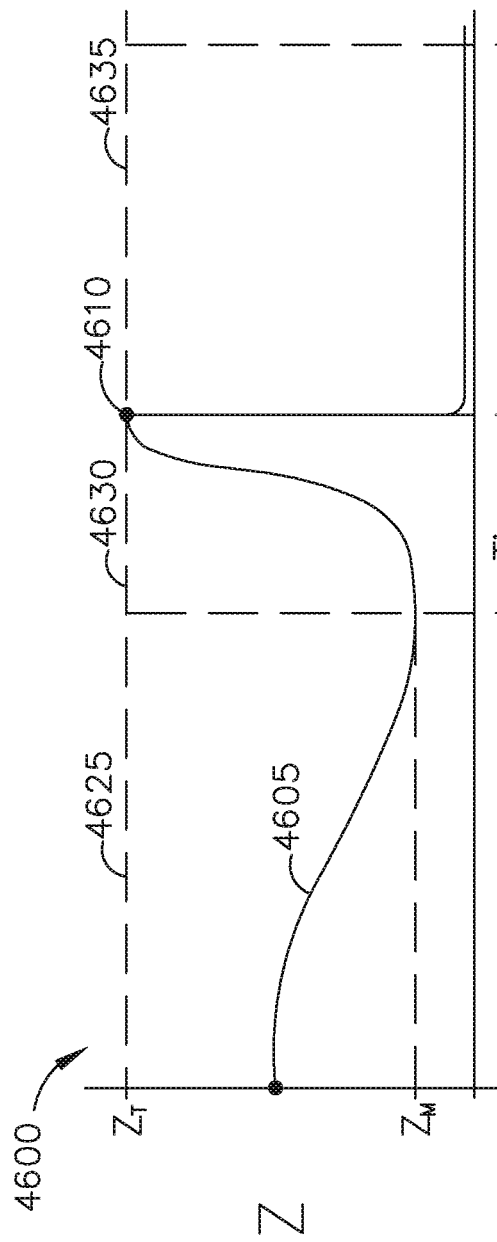

FIG. 45 is a graph of a tissue impedance curve as a function of time according to one aspect of this disclosure.

Figure 46:
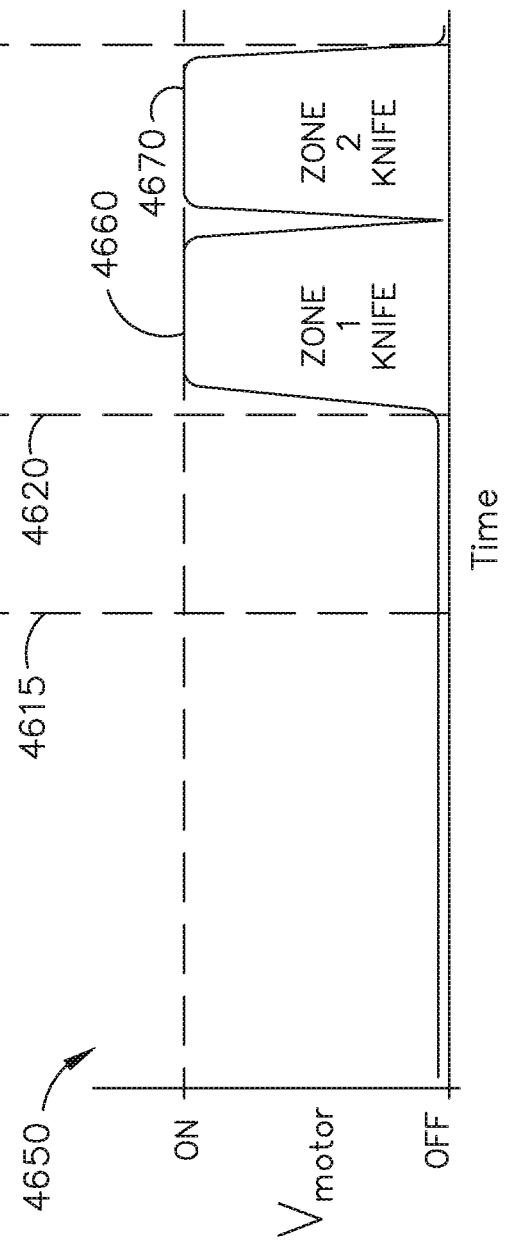

FIG. 46 is a graph depicting an example motor voltage curve according to one aspect of this disclosure.

Figure 47:
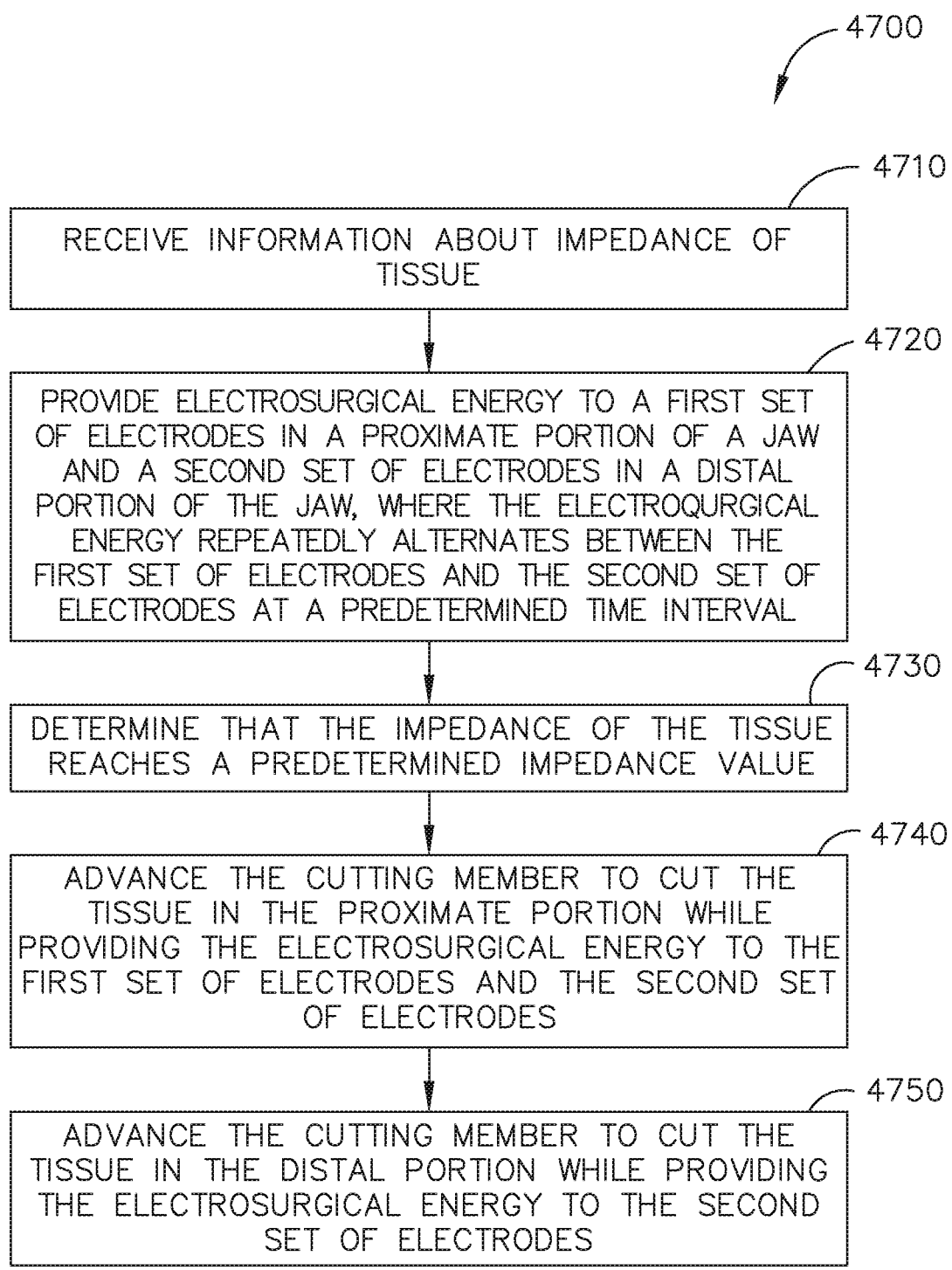

FIG. 47 is a logic flow diagram depicting a process of a control program or a logic configuration for operating the surgical instrument according to one aspect of this disclosure.

FIG. 48 is a graph of a tissue impedance curve as a function of time according to one aspect of this disclosure.

FIG. 49 is a graph depicting an example motor voltage curve according to one aspect of this disclosure.

Figure 14:
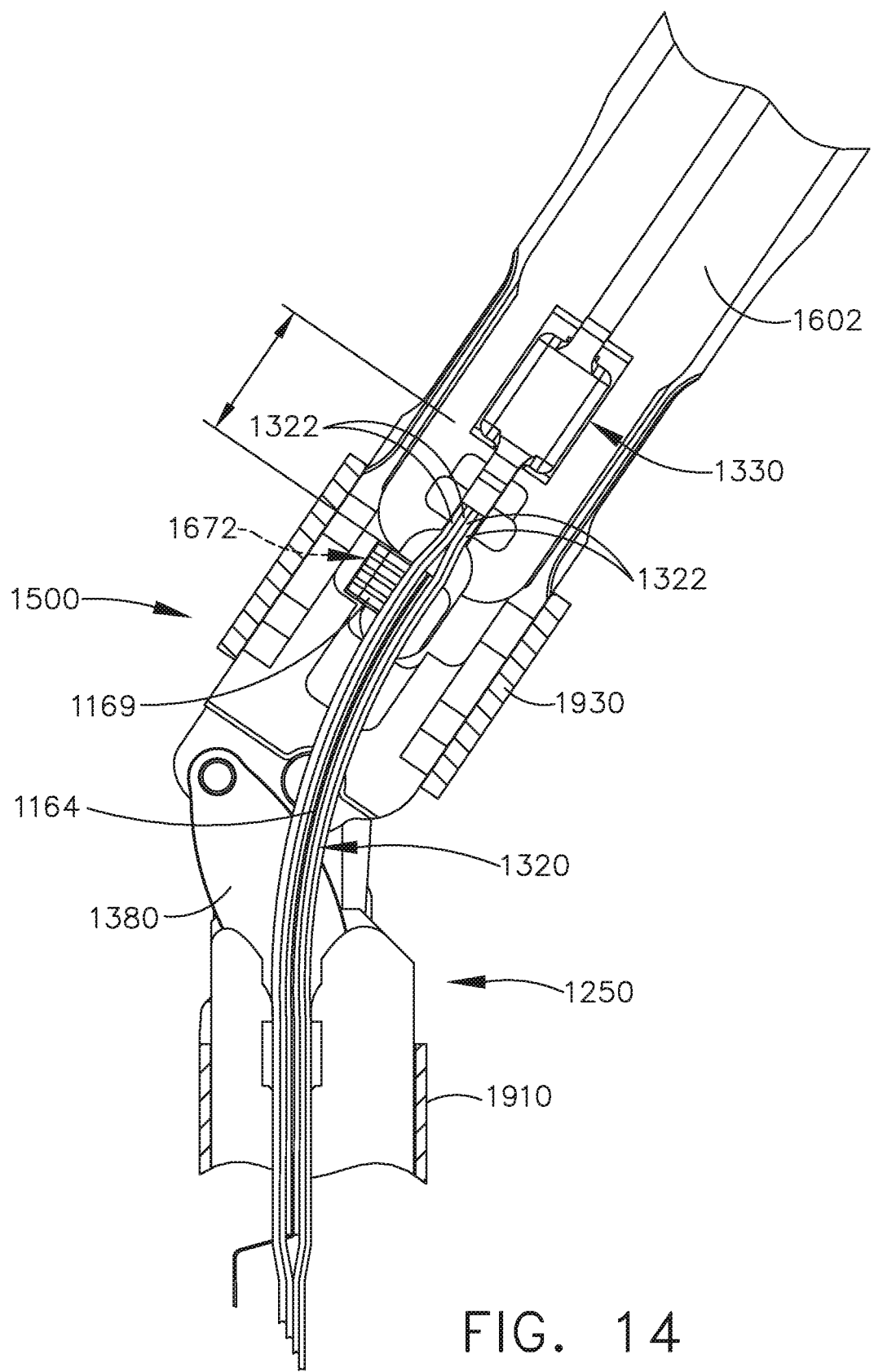
FIG. 14 is a top cross-sectional view of a portion of the interchangeable surgical tool assembly of FIGS. 1 and 5 with the end effector thereof in an articulated position according to one aspect of this disclosure.
Figure 50:
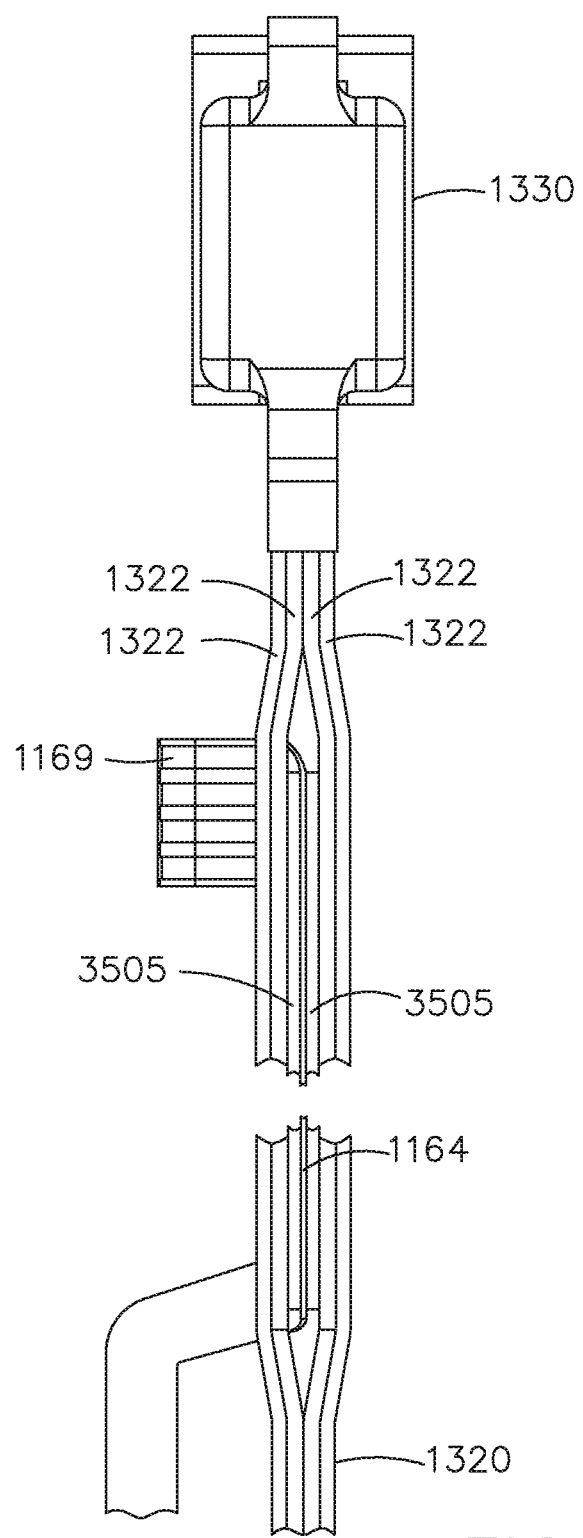

FIG. 50 is a top cross-section view of an aspect of a flexible assembly depicted in FIG. 14 according to one aspect of this disclosure.

Figure 51A:
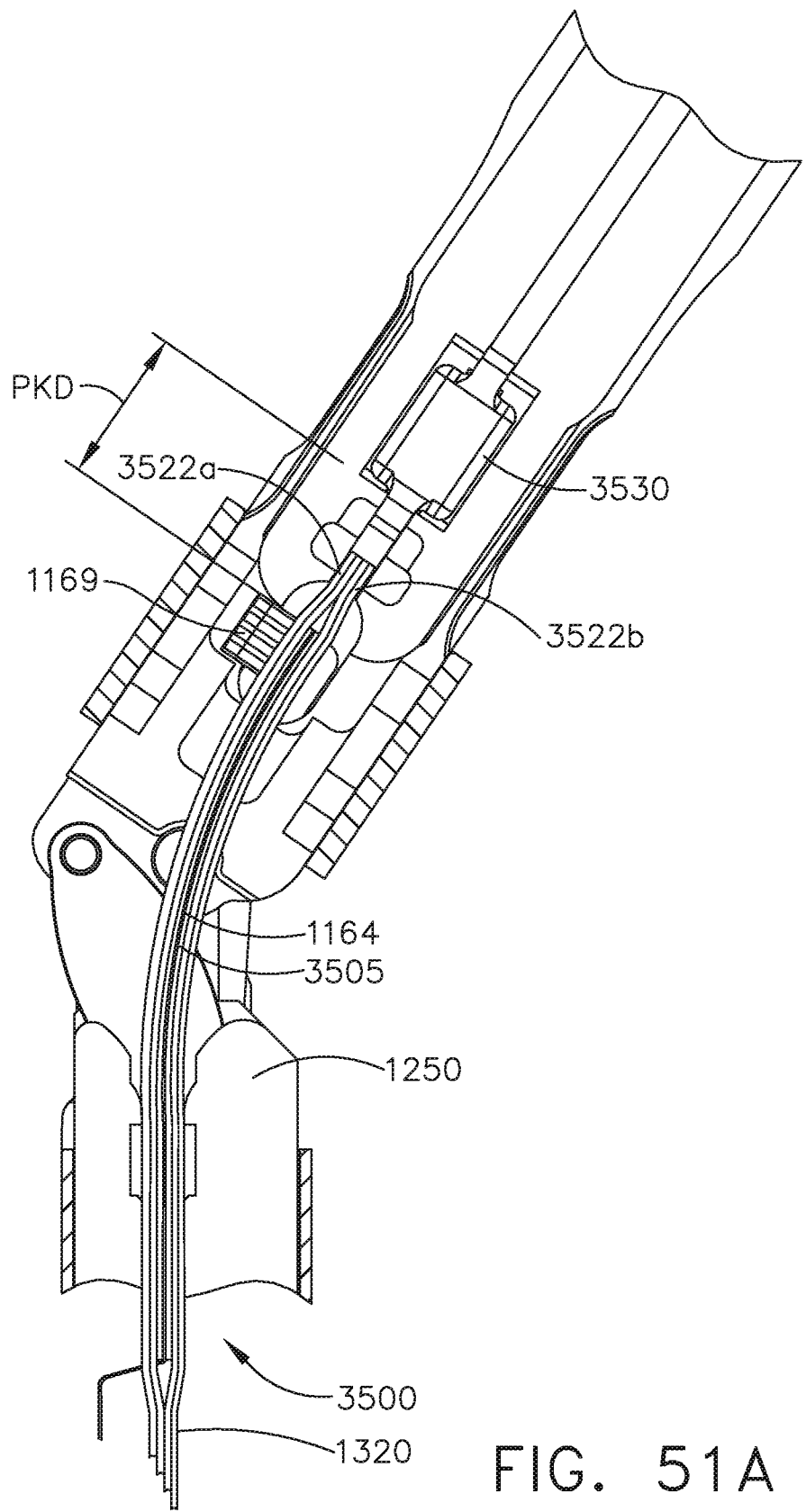

FIG. 51A is a top cross-section view of an aspect of the flexible assembly depicted in FIG. 14 for a knife member disposed at a proximal position as disposed within an aspect of an electrosurgical device according to one aspect of this disclosure.

Figure 51B:
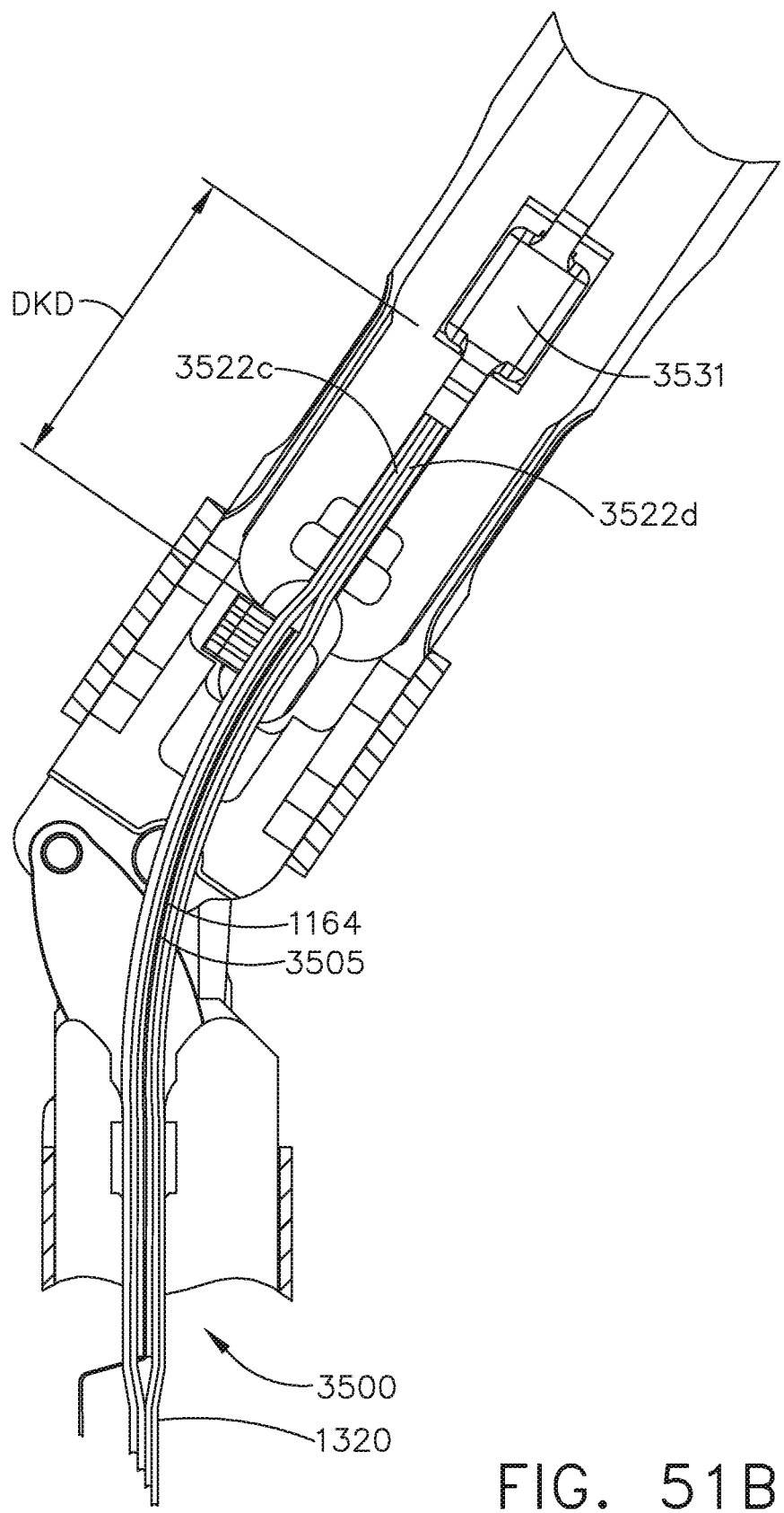

FIG. 51B is a top cross-section view of an aspect of the flexible assembly depicted in FIG. 14 for a knife member disposed at a distal position disposed within an aspect of an electrosurgical device according to one aspect of this disclosure.

Figures 52A, 52B:
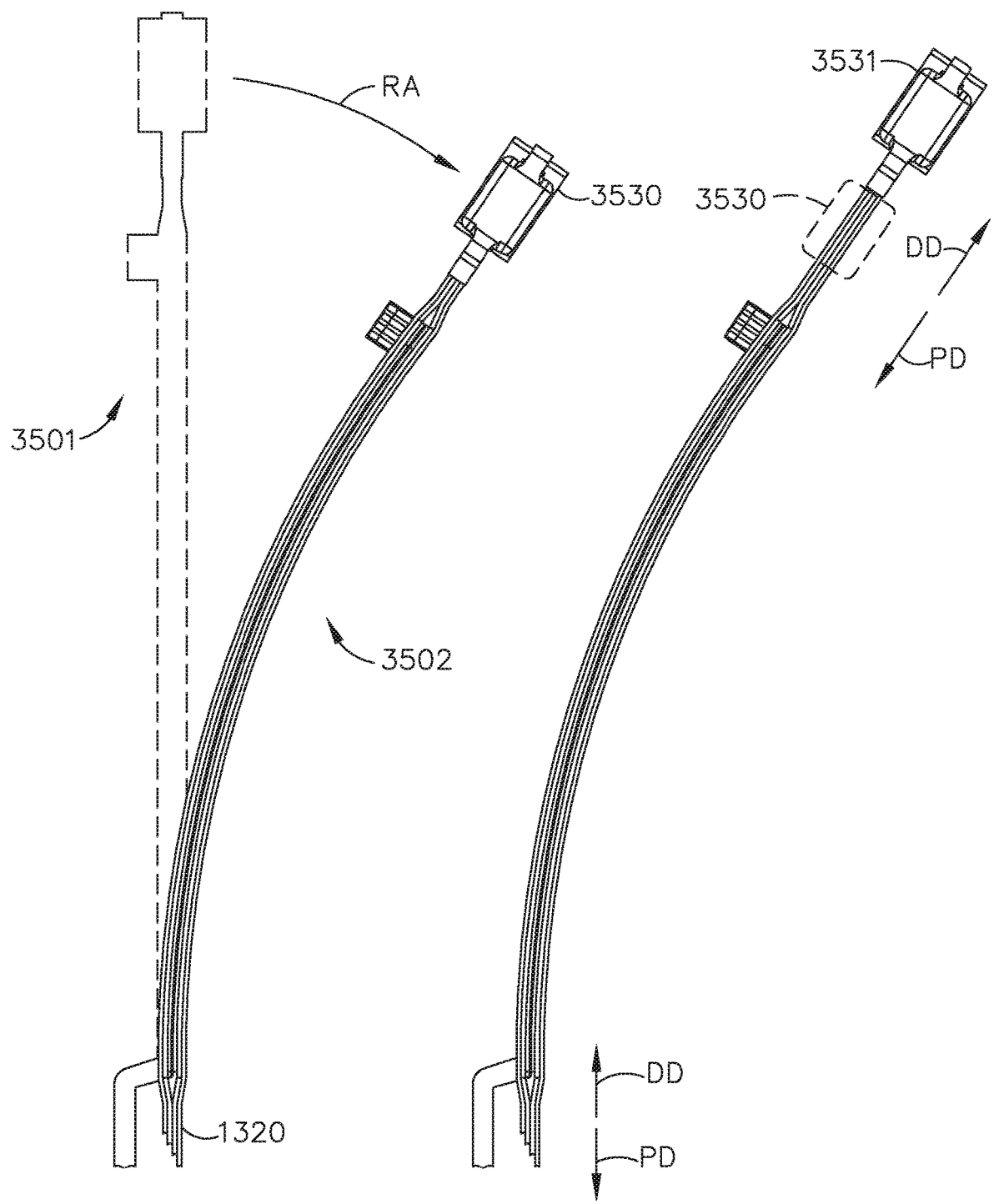

FIG. 52A is a top cross-section view of an aspect of the flexible assembly depicted in FIG. 14 for a knife member disposed at a proximal position according to one aspect of this disclosure.

FIG. 52B is a top cross-section view of an aspect of the flexible assembly depicted in FIG. 14 for a knife member disposed at a distal position according to one aspect of this disclosure.

Figure 53:
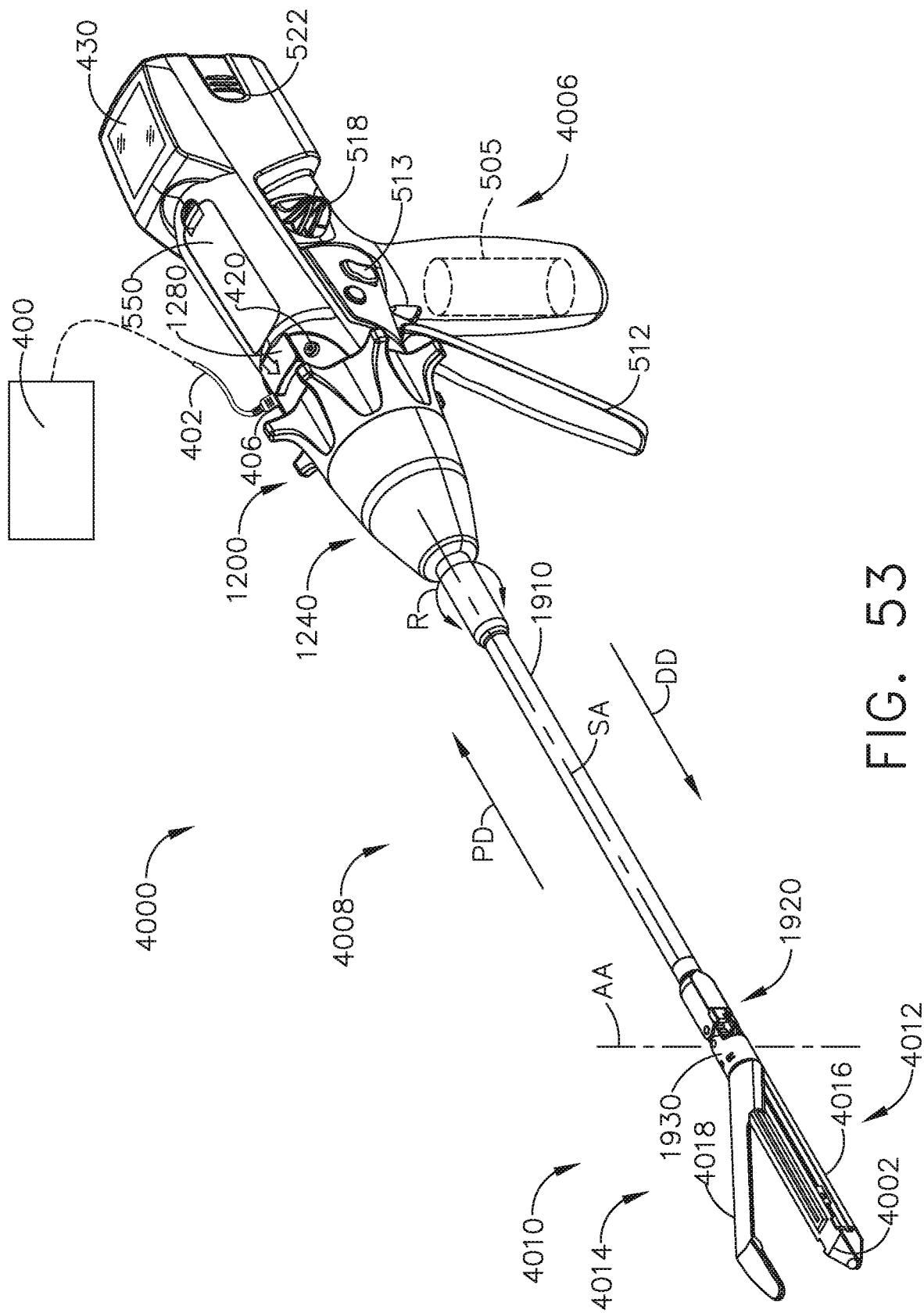

FIG. 53 is a perspective view of various aspects of a surgical system according to one aspect of this disclosure.

Figure 54:
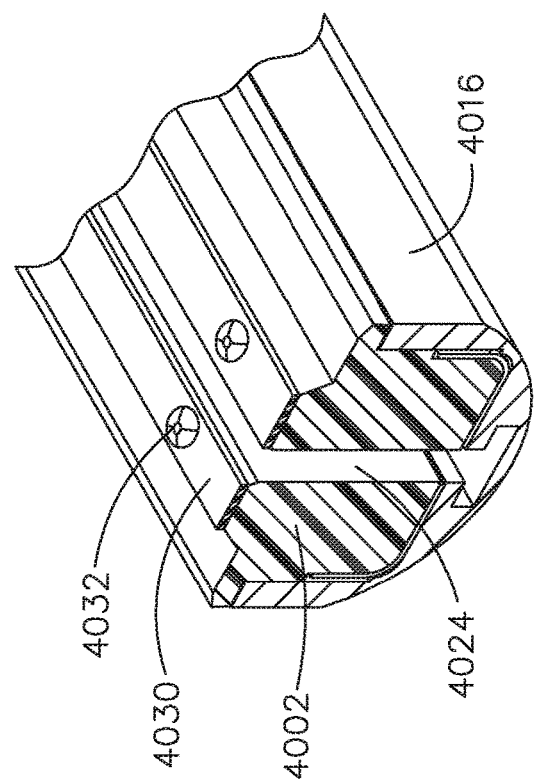

FIG. 54 is a partial cross-section of an end effector of the surgical system of FIG. 53 according to one aspect of this disclosure.

Figure 55:
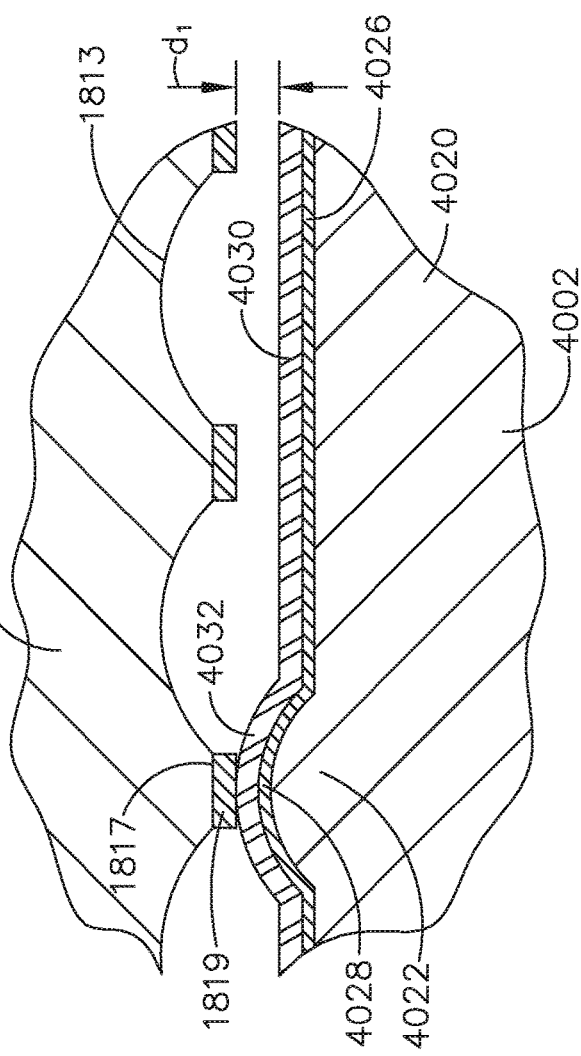

FIG. 55 is a partial perspective view of a radio-frequency cartridge supported by an elongate channel of the end effector of FIG. 54 according to one aspect of this disclosure.

Figure 56:
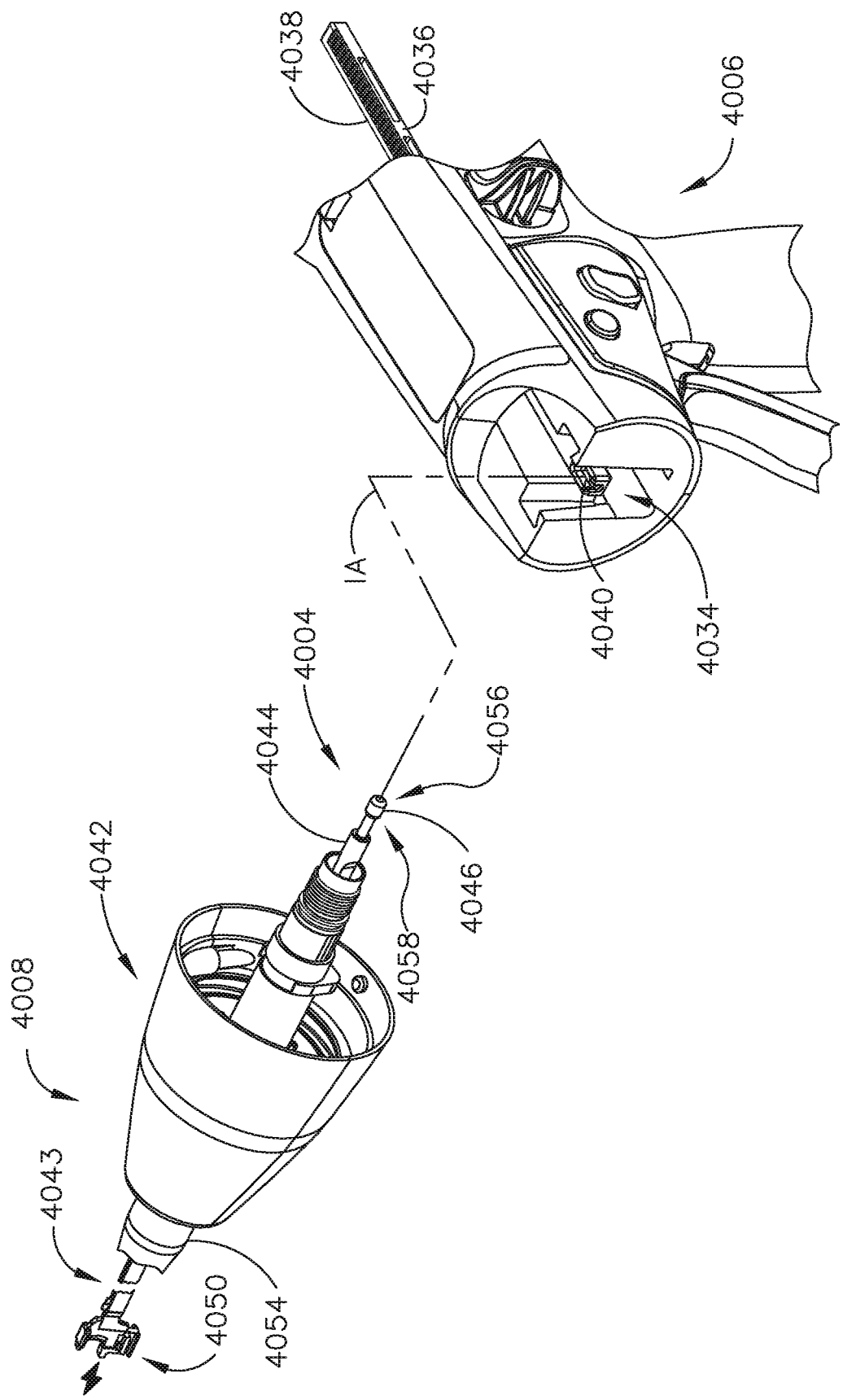

FIG. 56 is an exploded perspective assembly view of portions of a handle assembly and an interchangeable tool assembly of the surgical system of FIG. 53 according to one aspect of this disclosure.

Figure 57:
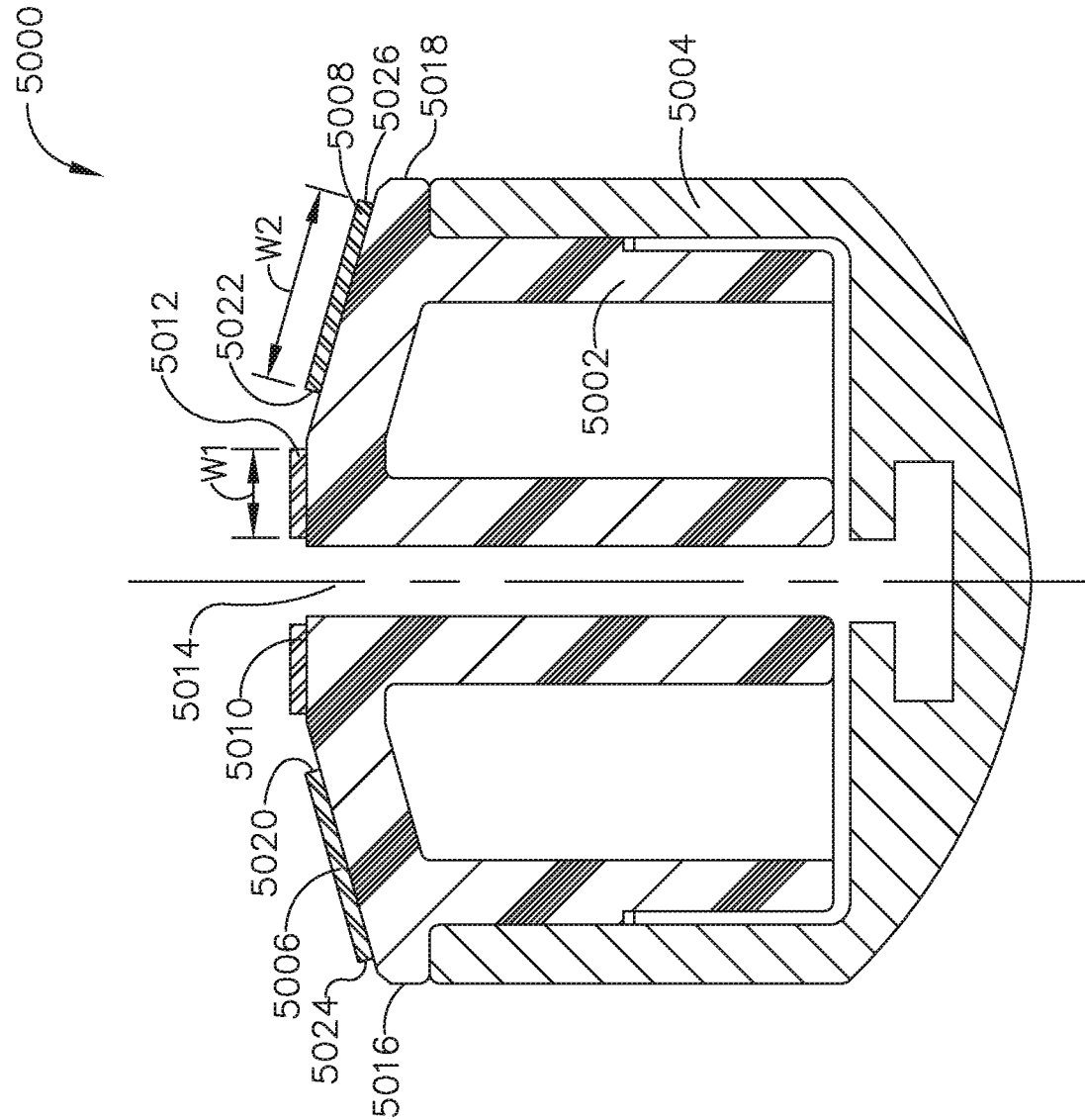

FIG. 57 is a cross-sectional view of a jaw member comprising an electrosurgical cartridge supported by an elongated channel, according to some aspects of the present disclosure.

FIG. 58 is a diagram illustrating an operation of a first electrode, according to some aspects of the present disclosure.

FIG. 59 is a diagram illustrating an operation of a second electrode, according to some aspects of the present disclosure.

Figure 60:
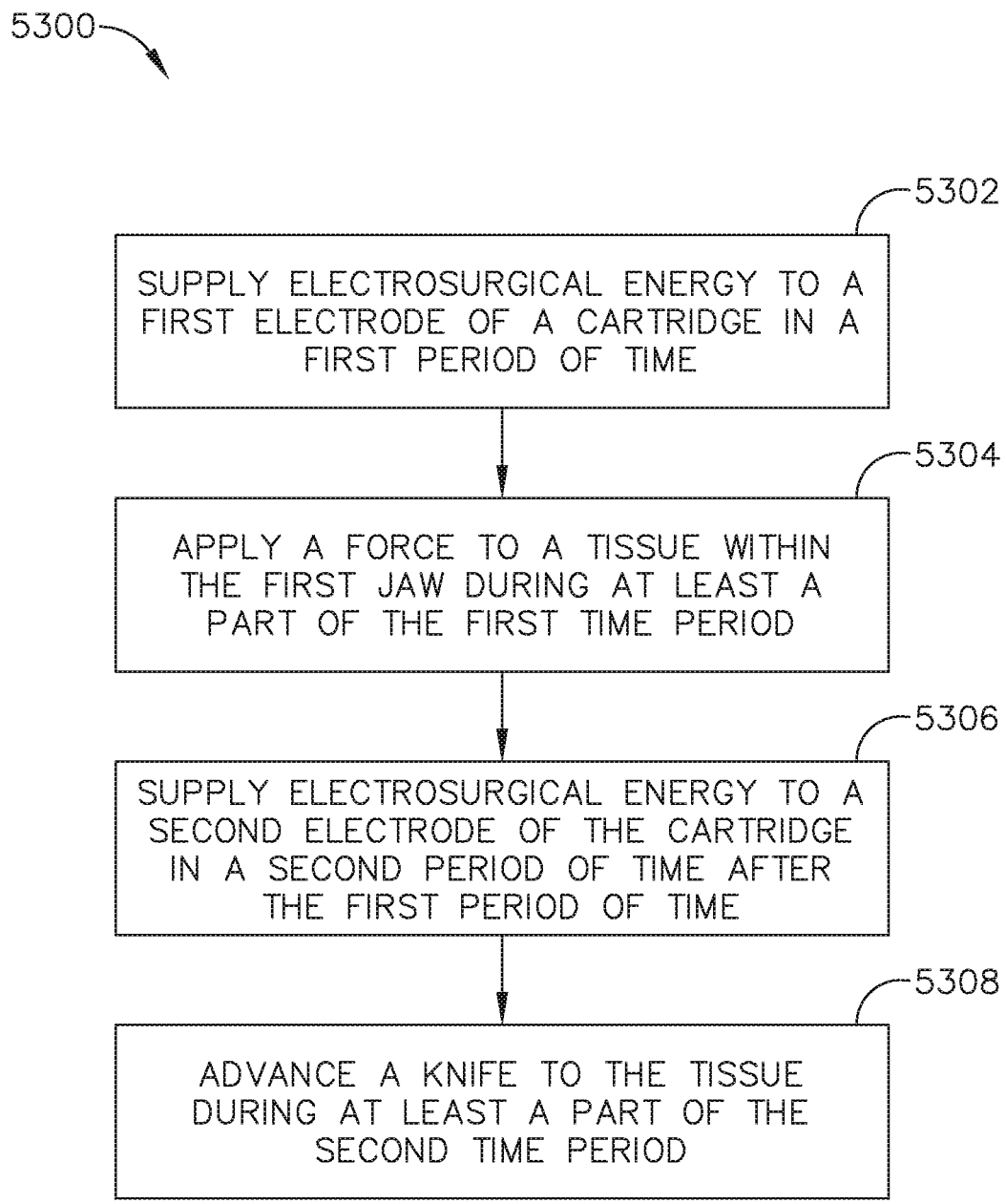

FIG. 60 is a logic flow diagram of a process depicting a control program or a logic configuration for applying therapeutic electrosurgical energy according to one aspect of this disclosure.

Figure 61:
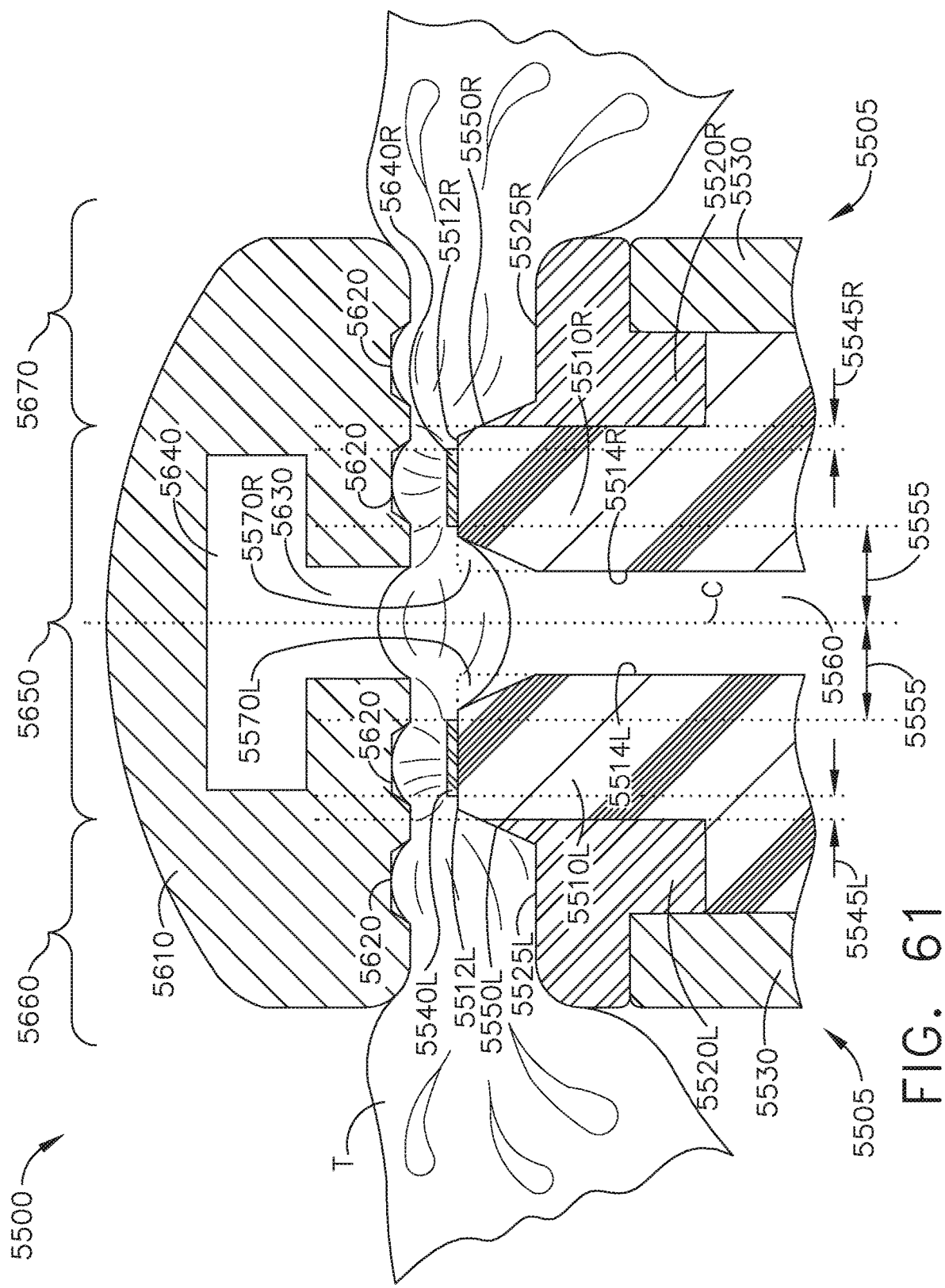

FIG. 61 is a schematic cross-sectional view of an electrosurgical end effector according to one aspect of this disclosure.

Figure 62:
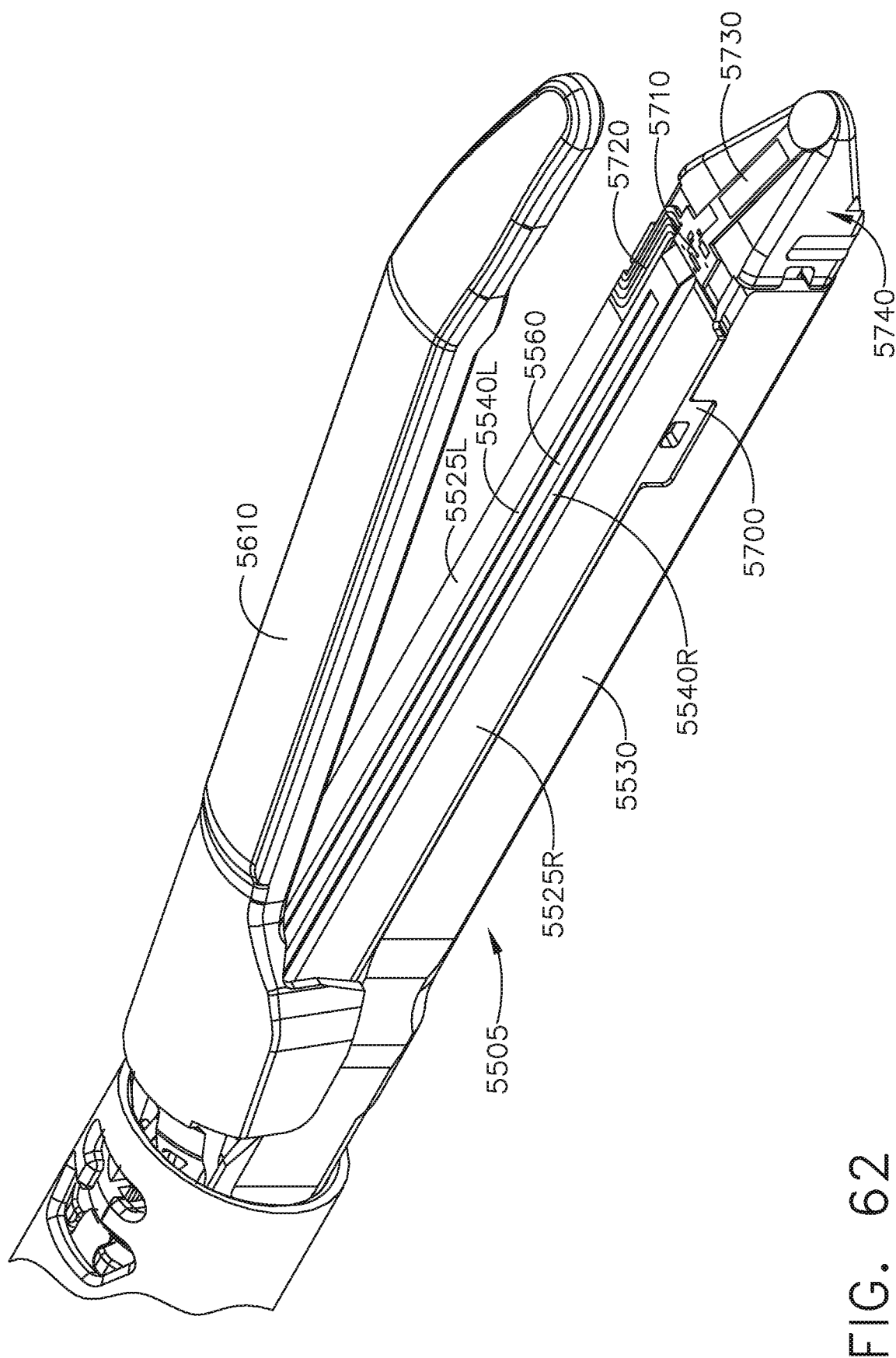

FIG. 62 is a perspective view of an end effector according to one aspect of this disclosure.

FIG. 63A is a perspective view of an aspect of an end effector in an open configuration.

Figure 63B:
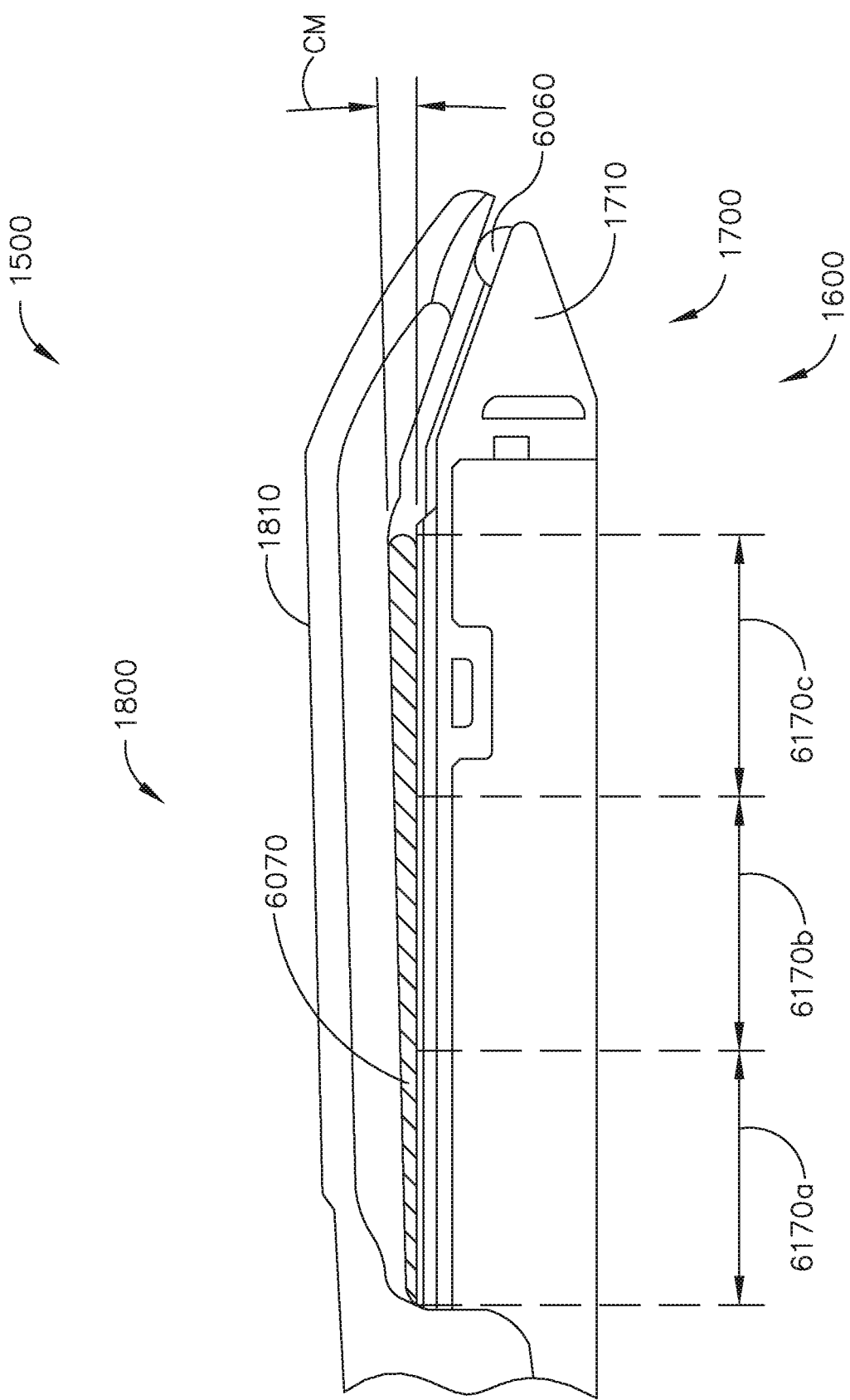

FIG. 63B is a side cross-section view of the aspect of the end effector depicted in FIG. 63A.

Figure 64:
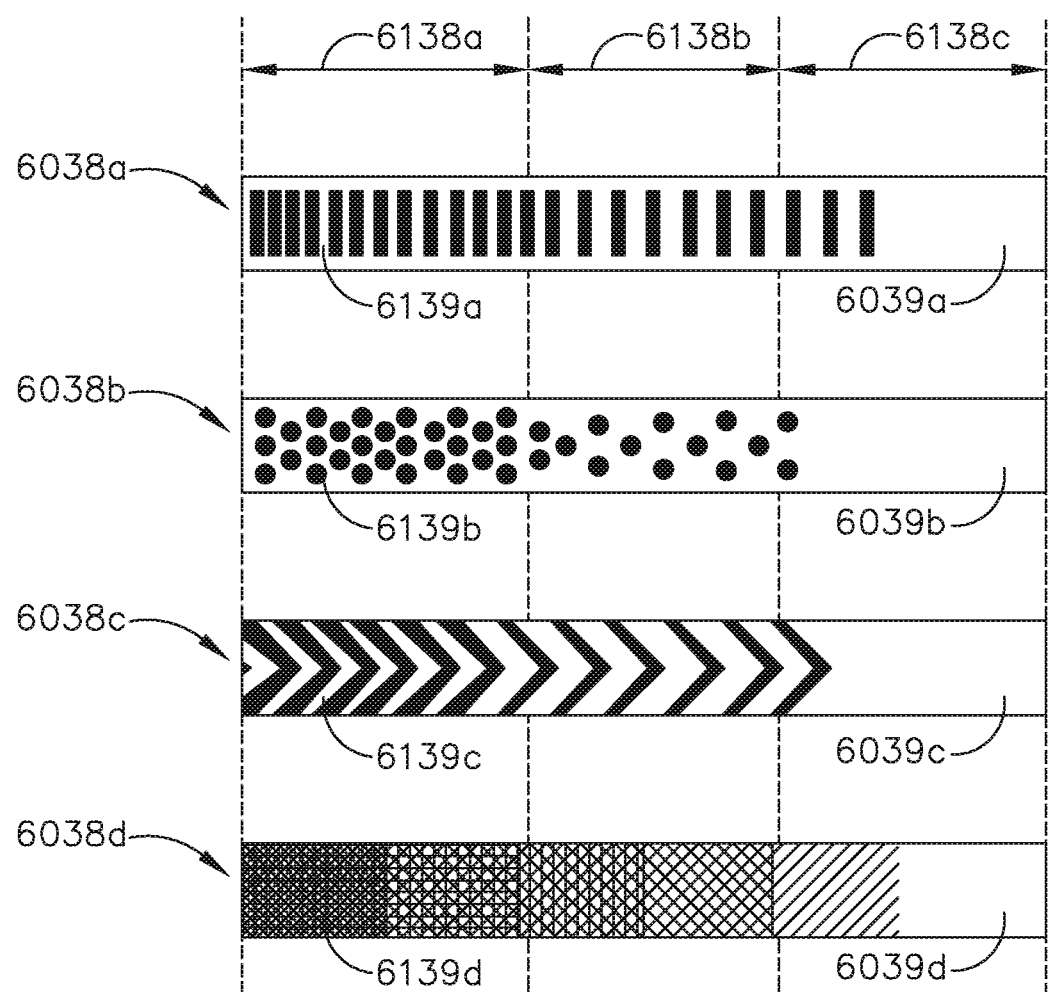

FIG. 64 is a diagram of aspects of surface features that may be disposed along a shear electrode as depicted in FIG. 63A.

Figure 65:
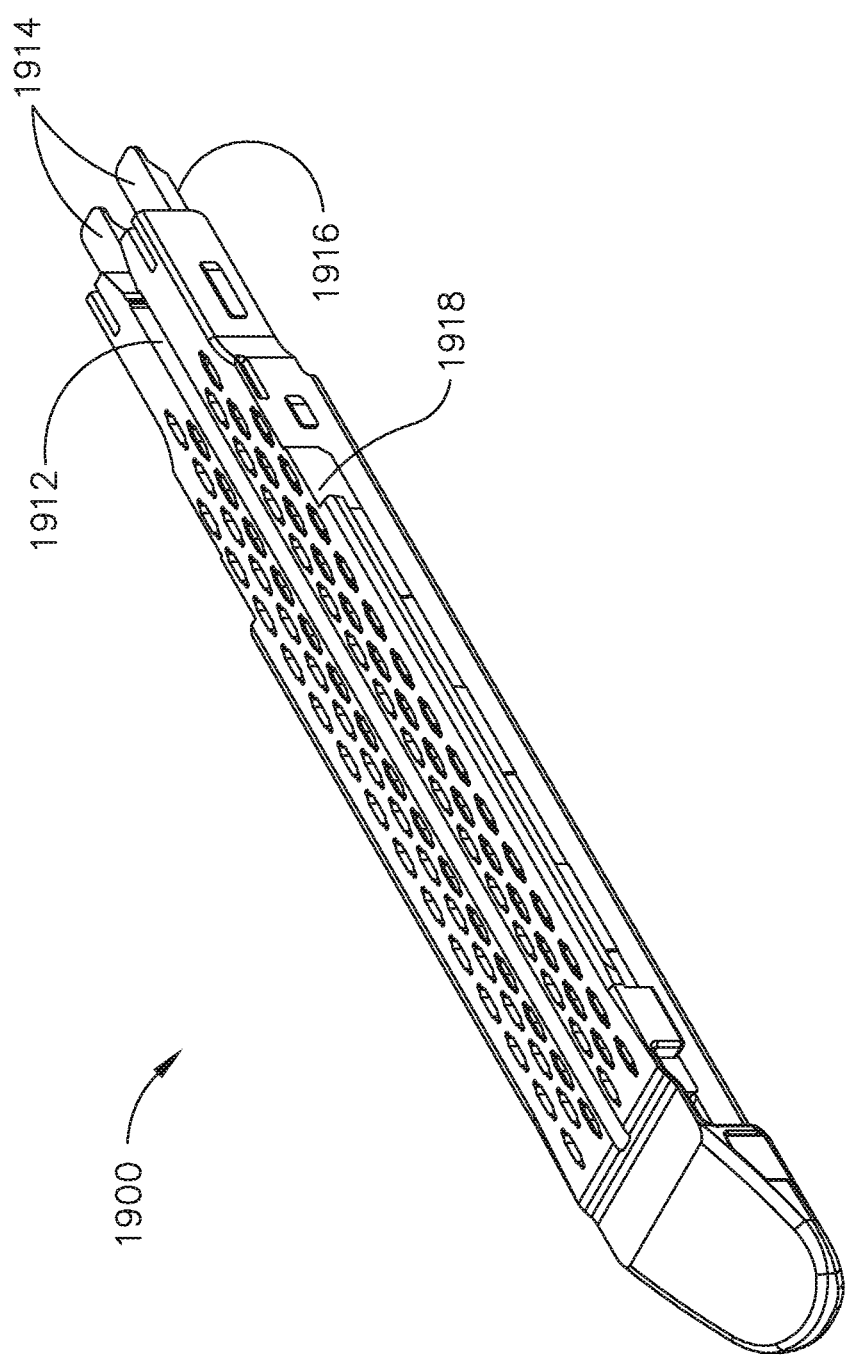

FIG. 65 is a perspective view of a staple cartridge of the interchangeable surgical tool assembly of FIGS. 1-5 according to one aspect of this disclosure.

Figure 1:
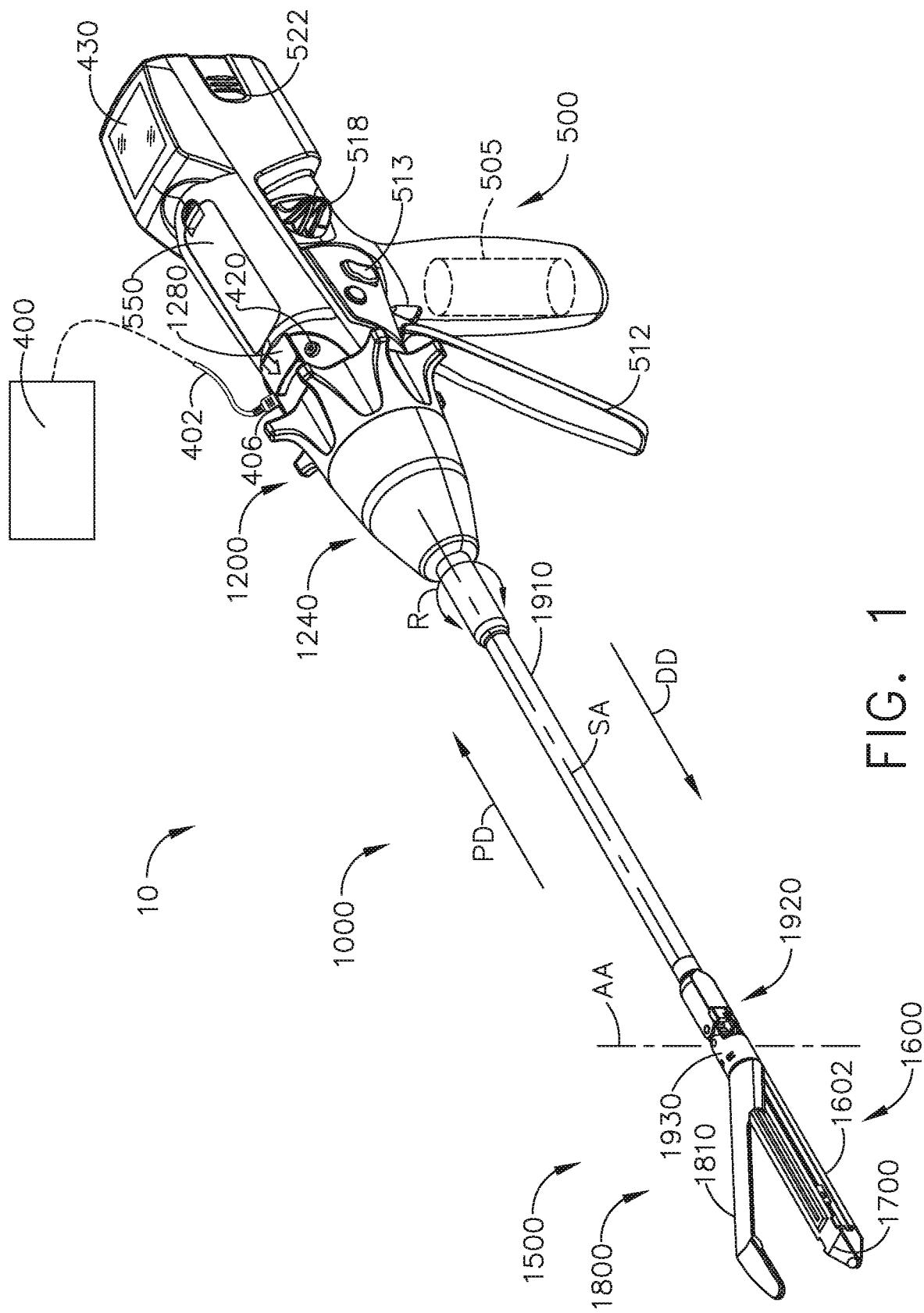
FIG. 1 is a perspective view of a surgical system including a handle assembly coupled to an interchangeable surgical tool assembly that is configured to be used in connection with conventional surgical staple/fastener cartridges and radio frequency (RF) cartridges according to one aspect of this disclosure.
Figure 66:
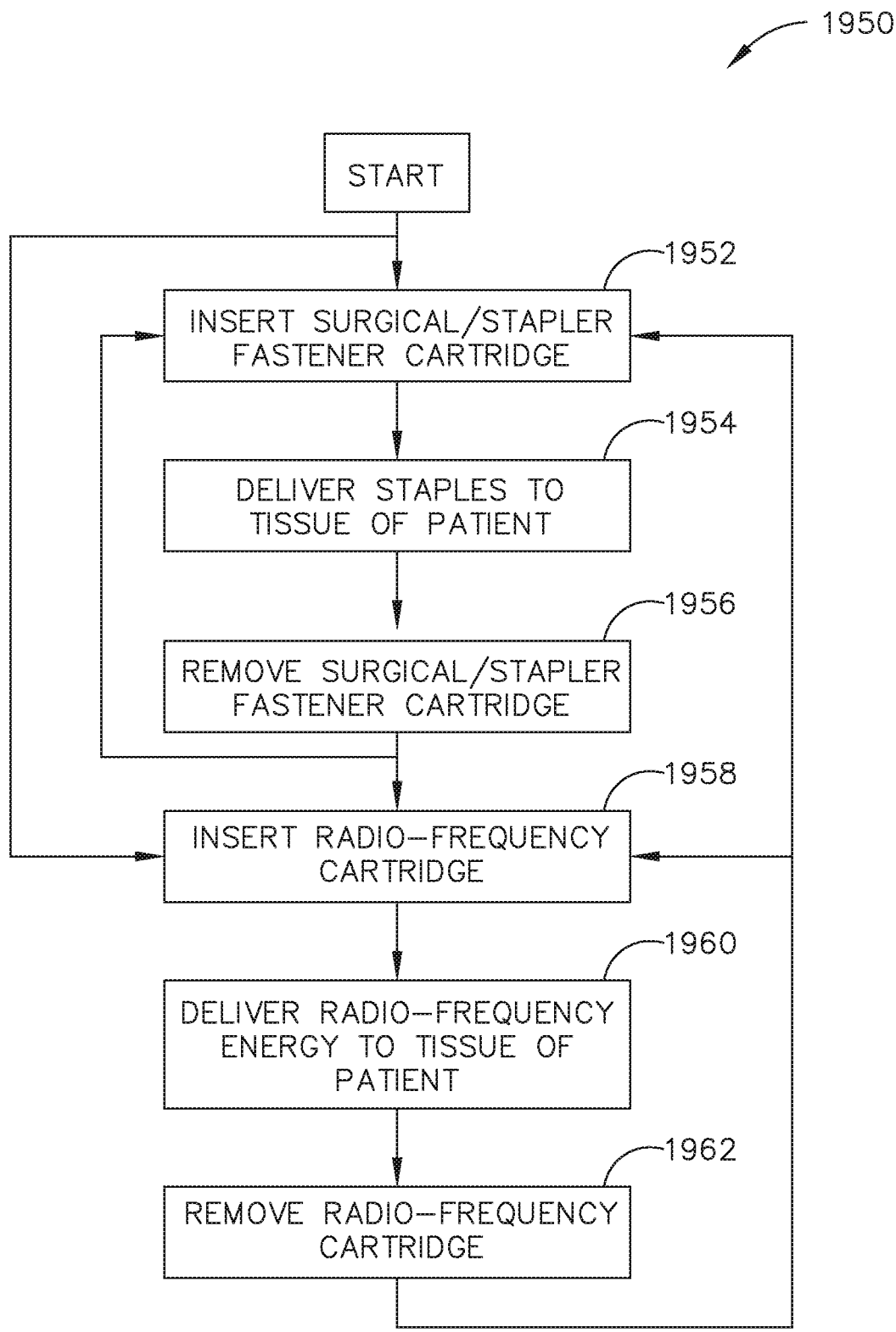

FIG. 66 illustrates a method of utilizing the interchangeable tool assembly of FIG. 1 according to various aspects.

DESCRIPTION

Applicant of the present application owns the following patent applications filed on Jun. 28, 2017 and which are each herein incorporated by reference in their respective entireties:

U.S. patent application Ser. No. 15/636,103, titled SYSTEMS AND METHODS OF DISPLAYING SURGICAL INSTRUMENT STATUS, by inventors Jeffrey D. Messerly et al., filed Jun. 28, 2017.

U.S. patent application Ser. No. 15/636,110, titled SHAFT MODULE CIRCUITRY ARRANGEMENTS, by inventors Jeffrey D. Messerly et al., filed Jun. 28, 2017.

U.S. patent application Ser. No. 15/636,116, titled SYSTEMS AND METHODS FOR CONTROLLING CONTROL CIRCUITS FOR INDEPENDENT ENERGY DELIVERY OVER SEGMENTED SECTIONS, by inventors Jeffrey D. Messerly et al., filed Jun. 28, 2017.

U.S. patent application Ser. No. 15/636,123, titled FLEXIBLE CIRCUIT ARRANGEMENT FOR SURGICAL FASTENING INSTRUMENTS, by inventors Jeffrey D. Messerly et al., filed Jun. 28, 2017.

U.S. patent application Ser. No. 15/636,134, titled SURGICAL SYSTEM COUPLEABLE WITH STAPLE CARTRIDGE AND RADIO FREQUENCY CARTRIDGE, AND HAVING A PLURALITY OF RADIO-FREQUENCY ENERGY RETURN PATHS, by inventors Jeffrey D. Messerly et al., filed Jun. 28, 2017.

U.S. patent application Ser. No. 15/636,144, titled SYSTEMS AND METHODS FOR CONTROLLING CONTROL CIRCUITS FOR AN INDEPENDENT ENERGY DELIVERY OVER SEGMENTED SECTIONS, by inventors David C. Yates et al., filed Jun. 28, 2017.

U.S. patent application Ser. No. 15/636,150, titled SURGICAL END EFFECTOR FOR APPLYING ELECTROSURGICAL ENERGY TO DIFFERENT ELECTRODES ON DIFFERENT TIME PERIODS, by inventors Tamara Widenhouse et al., filed Jun. 28, 2017.

U.S. patent application Ser. No. 15/636,162, titled ELECTROSURGICAL CARTRIDGE FOR USE IN THIN PROFILE SURGICAL CUTTING AND STAPLING INSTRUMENT, by inventors Tamara Widenhouse et al., filed Jun. 28, 2017.

U.S. patent application Ser. No. 15/636,169, titled SURGICAL END EFFECTOR TO ADJUST JAW COMPRESSION, by inventors Frederick E. Shelton, IV et al., filed Jun. 28, 2017.

U.S. patent application Ser. No. 15/636,177, titled CARTRIDGE ARRANGEMENTS FOR SURGICAL CUTTING AND FASTENING INSTRUMENTS WITH LOCKOUT DISABLEMENT FEATURES, by inventors Jason L. Harris et al., filed Jun. 28, 2017.

U.S. patent application Ser. No. 15/636,180, titled SURGICAL CUTTING AND FASTENING INSTRUMENTS WITH DUAL POWER SOURCES, by inventors Jeffrey D. Messerly et al., filed Jun. 28, 2017.

Electrosurgical devices may be used in many surgical operations. Electrosurgical devices may apply electrical energy to tissue in order to treat tissue. An electrosurgical device may comprise an instrument having a distally mounted end effector comprising one or more electrodes. The end effector can be positioned against tissue such that electrical current may be introduced into the tissue. Electrosurgical devices can be configured for monopolar or bipolar operation. During monopolar operation, current may be introduced into the tissue by an active (or source) electrode on the end effector and returned through a return electrode. The return electrode may be a grounding pad and separately located on a patient's body. During bipolar operation, current may be introduced into and returned from the tissue by the active and return electrodes, respectively, of the end effector.

The end effector may include two or more jaw members. At least one of the jaw members may have at least one electrode. At least one jaw may be moveable from a position spaced apart from the opposing jaw for receiving tissues to a position in which the space between the jaw members is less than that of the first position. This movement of the moveable jaw may compress the tissue held between. Heat generated by the current flow through the tissue in combination with the compression achieved by the jaw's movement may form hemostatic seals within the tissue and/or between tissues and, thus, may be particularly useful for sealing blood vessels, for example. The end effector may comprise a cutting member. The cutting member may be movable relative to the tissue and the electrodes to transect the tissue.

Electrosurgical devices also may include mechanisms to clamp tissue together, such as a stapling device, and/or mechanisms to sever tissue, such as a tissue knife. An electrosurgical device may include a shaft for placing the end effector proximate to tissue undergoing treatment. The shaft may be straight or curved, bendable or non-bendable. In an electrosurgical device including a straight and bendable shaft, the shaft may have one or more articulation joints to permit controlled bending of the shaft. Such joints may permit a user of the electrosurgical device to place the end effector in contact with tissue at an angle to the shaft when the tissue being treated is not readily accessible using an electrosurgical device having a straight, non-bending shaft.

Electrical energy applied by electrosurgical devices can be transmitted to the instrument by a generator in communication with the hand piece. The electrical energy may be in the form of radio frequency ("RF") energy. RF energy is a form of electrical energy that may be in the frequency range of 200 kilohertz (kHz) to 1 megahertz (MHz). In application, an electrosurgical instrument can transmit low frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy is useful for removing, shrinking, or sculpting soft tissue while simultaneously sealing blood vessels. RF energy works particularly well on connective tissue, which is primarily comprised of collagen and shrinks when contacted by heat.

The RF energy may be in a frequency range described in EN 60601-2-2:2009+A11:2011, Definition 201.3.218—HIGH FREQUENCY. For example, the frequency in monopolar RF applications may be typically restricted to less than 5 MHz. However, in bipolar RF applications, the frequency can be almost anything. Frequencies above 200 kHz can be typically used for monopolar applications in order to avoid the unwanted stimulation of nerves and muscles that would result from the use of low frequency current. Lower frequencies may be used for bipolar applications if the risk analysis shows the possibility of neuromuscular stimulation has been mitigated to an acceptable level. Normally, frequencies above 5 MHz are not used in order to minimize the problems associated with high frequency leakage currents. Higher frequencies may, however, be used in the case of bipolar applications. It is generally recognized that 10 mA is the lower threshold of thermal effects on tissue.

Figure 2:
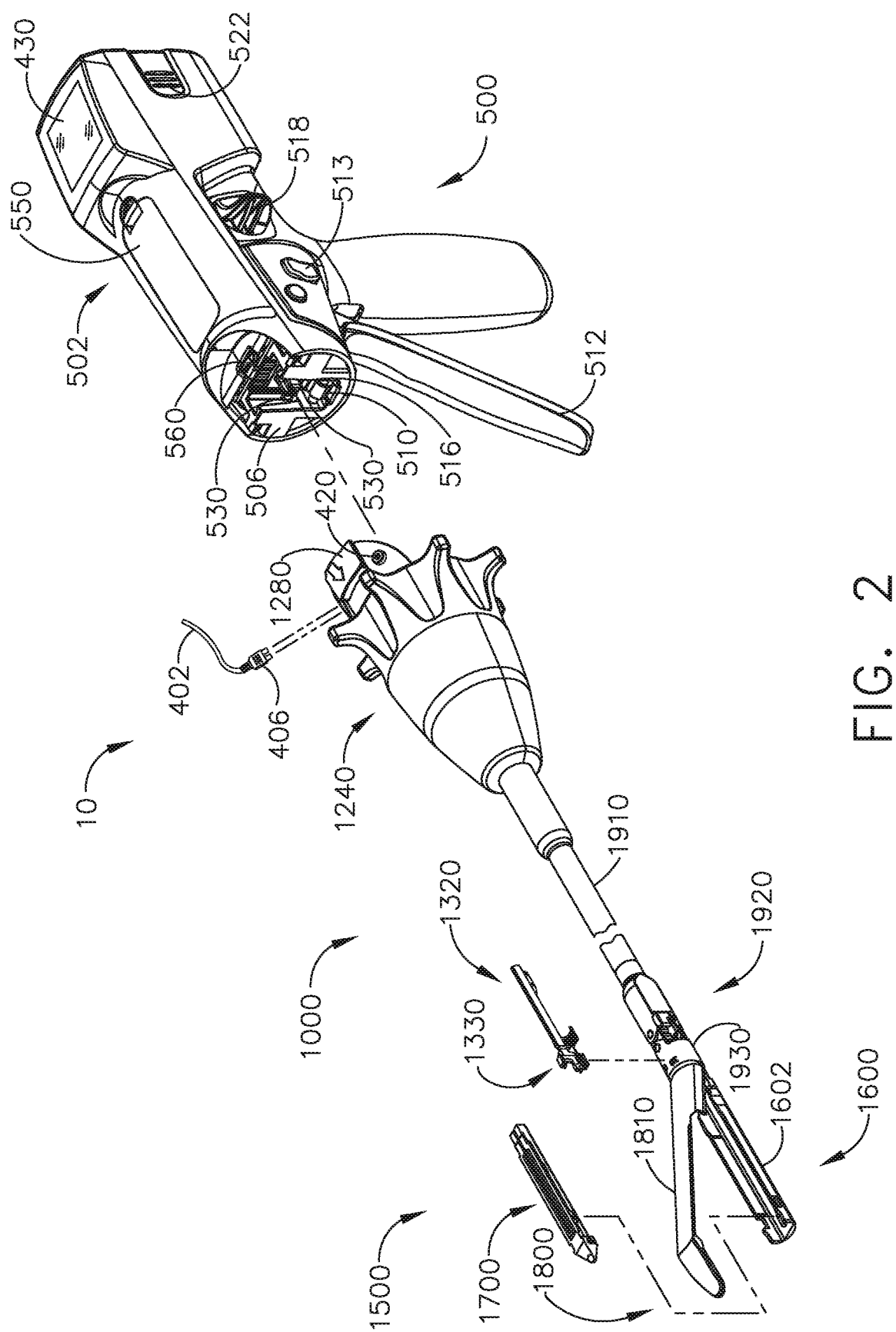
FIG. 2 is an exploded perspective assembly view of the surgical system of FIG. 1 according to one aspect of this disclosure.

FIGS. 1 and 2 depict a motor-driven surgical system 10 that may be used to perform a variety of different surgical procedures. In the illustrated arrangement, the surgical system 10 comprises an interchangeable surgical tool assembly 1000 that is operably coupled to a handle assembly 500. In another surgical system aspect, the interchangeable surgical tool assembly 1000 may also be effectively employed with a tool drive assembly of a robotically controlled or automated surgical system. For example, the surgical tool assembly 1000 disclosed herein may be employed with various robotic systems, instruments, components and methods such as, but not limited to, those disclosed in U.S. Pat. No. 9,072,535, entitled SURGICAL STAPLING INSTRUMENTS WITH ROTATABLE STAPLE DEPLOYMENT ARRANGEMENTS, which is hereby incorporated by reference herein in its entirety.

In the illustrated aspect, the handle assembly 500 may comprise a handle housing 502 that includes a pistol grip portion 504 that can be gripped and manipulated by the clinician. As will be briefly discussed below, the handle assembly 500 operably supports a plurality of drive systems that are configured to generate and apply various control motions to corresponding portions of the interchangeable surgical tool assembly 1000. As shown in FIG. 2, the handle assembly 500 may further include a handle frame 506 that operably supports the plurality of drive systems. For example, the handle frame 506 can operably support a "first" or closure drive system, generally designated as 510, which may be employed to apply closing and opening motions to the interchangeable surgical tool assembly 1000. In at least one form, the closure drive system 510 may include an actuator in the form of a closure trigger 512 that is pivotally supported by the handle frame 506. Such arrangement enables the closure trigger 512 to be manipulated by a clinician such that when the clinician grips the pistol grip portion 504 of the handle assembly 500, the closure trigger 512 may be easily pivoted from a starting or "unactuated" position to an "actuated" position and more particularly to a fully compressed or fully actuated position. In use, to actuate the closure drive system 510, the clinician depresses the closure trigger 512 towards the pistol grip portion 504. As described in further detail in U.S. patent application Ser. No. 14/226,142, entitled SURGICAL INSTRUMENT COMPRISING A SENSOR SYSTEM, now U.S. Patent Application Publication No. 2015/0272575, which is hereby incorporated by reference in its entirety herein, when the clinician fully depresses the closure trigger 512 to attain the full closure stroke, the closure drive system 510 is configured to lock the closure trigger 512 into the fully depressed or fully actuated position. When the clinician desires to unlock the closure trigger 512 to permit it to be biased to the unactuated position, the clinician simply activates a closure release button assembly 518 which enables the closure trigger to return to unactuated position. The closure release button assembly 518 may also be configured to interact with various sensors that communicate with a microcontroller in the handle assembly 500 for tracking the position of the closure trigger 512. Further details concerning the configuration and operation of the closure release button assembly 518 may be found in U.S. Patent Application Publication No. 2015/0272575.

In at least one form, the handle assembly 500 and the handle frame 506 may operably support another drive system referred to herein as a firing drive system 530 that is configured to apply firing motions to corresponding portions of the interchangeable surgical tool assembly that is attached thereto. As was described in detail in U.S. Patent Application Publication No. 2015/0272575, the firing drive system 530 may employ an electric motor 505 that is located in the pistol grip portion 504 of the handle assembly 500. In various forms, the motor 505 may be a DC brushed driving motor having a maximum rotation of, approximately, 25,000 RPM, for example. In other arrangements, the motor 505 may include a brushless motor, a cordless motor, a synchronous motor, a stepper motor, or any other suitable electric motor. The motor 505 may be powered by a power source 522 that in one form may comprise a removable power pack. The power pack may support a plurality of Lithium Ion ("LI") or other suitable batteries therein. A number of batteries may be connected in series may be used as the power source 522 for the surgical system 10. In addition, the power source 522 may be replaceable and/or rechargeable.

The electric motor 505 is configured to axially drive a longitudinally movable drive member 540 (FIG. 3) in a distal and proximal directions depending upon the polarity of the motor. For example, when the motor 505 is driven in one rotary direction, the longitudinally movable drive member will be axially driven in a distal direction "DD". When the motor 505 is driven in the opposite rotary direction, the longitudinally movable drive member 540 will be axially driven in a proximal direction "PD". The handle assembly 500 can include a switch 513 which can be configured to reverse the polarity applied to the electric motor 505 by the power source 522 or otherwise control the motor 505. The handle assembly 500 can also include a sensor or sensors (not shown) that is configured to detect the position of the drive member and/or the direction in which the drive member is being moved. Actuation of the motor 505 can be controlled by a firing trigger (not shown) that is adjacent to the closure trigger 512 and pivotally supported on the handle assembly 500. The firing trigger may be pivoted between an unactuated position and an actuated position. The firing trigger may be biased into the unactuated position by a spring or other biasing arrangement such that when the clinician releases the firing trigger, it may be pivoted or otherwise returned to the unactuated position by the spring or biasing arrangement. In at least one form, the firing trigger can be positioned "outboard" of the closure trigger 512. As discussed in U.S. Patent Application Publication No. 2015/0272575, the handle assembly 500 may be equipped with a firing trigger safety button (not shown) to prevent inadvertent actuation of the firing trigger. When the closure trigger 512 is in the unactuated position, the safety button is contained in the handle assembly 500 where the clinician cannot readily access it and move it between a safety position preventing actuation of the firing trigger and a firing position wherein the firing trigger may be fired. As the clinician depresses the closure trigger, the safety button and the firing trigger pivot down wherein they can then be manipulated by the clinician.

In at least one form, the longitudinally movable drive member 540 may have a rack of teeth 542 formed thereon for meshing engagement with a corresponding drive gear arrangement (not shown) that interfaces with the motor. See FIG. 3. Further details regarding those features may be found in U.S. Patent Application Publication No. 2015/0272575. In at least one arrangement, however, the longitudinally movable drive member is insulated to protect it from inadvertent RF energy. At least one form also includes a manually-actuatable "bailout" assembly that is configured to enable the clinician to manually retract the longitudinally movable drive member should the motor 505 become disabled. The bailout assembly may include a lever or bailout handle assembly that is stored within the handle assembly 500 under a releasable door 550. See FIG. 2. The lever may be configured to be manually pivoted into ratcheting engagement with the teeth in the drive member. Thus, the clinician can manually retract the drive member 540 by using the bailout handle assembly to ratchet the drive member in the proximal direction "PD". U.S. Pat. No. 8,608,045, entitled POWERED SURGICAL CUTTING AND STAPLING APPARATUS WITH MANUALLY RETRACTABLE FIRING SYSTEM, the entire disclosure of which is hereby incorporated by reference herein, discloses bailout arrangements and other components, arrangements and systems that may also be employed with any one of the various interchangeable surgical tool assemblies disclosed herein.

In the illustrated aspect, the interchangeable surgical tool assembly 1000 includes a surgical end effector 1500 that comprises a first jaw 1600 and a second jaw 1800. In one arrangement, the first jaw comprises an elongate channel 1602 that is configured to operably support a conventional (mechanical) surgical staple/fastener cartridge 1400 (FIG. 4) or a radio frequency (RF) cartridge 1700 (FIGS. 1 and 2) therein. The second jaw 1800 comprises an anvil 1810 that is pivotally supported relative to the elongate channel 1602. The anvil 1810 may be is selectively moved toward and away from a surgical cartridge supported in the elongate channel 1602 between open and closed positions by actuating the closure drive system 510. In the illustrated arrangement, the anvil 1810 is pivotally supported on a proximal end portion of the elongate channel 1602 for selective pivotal travel about a pivot axis that is transverse to the shaft axis SA. Actuation of the closure drive system 510 may result in the distal axial movement of a proximal closure member or proximal closure tube 1910 that is attached to an articulation connector 1920.

Figure 3:
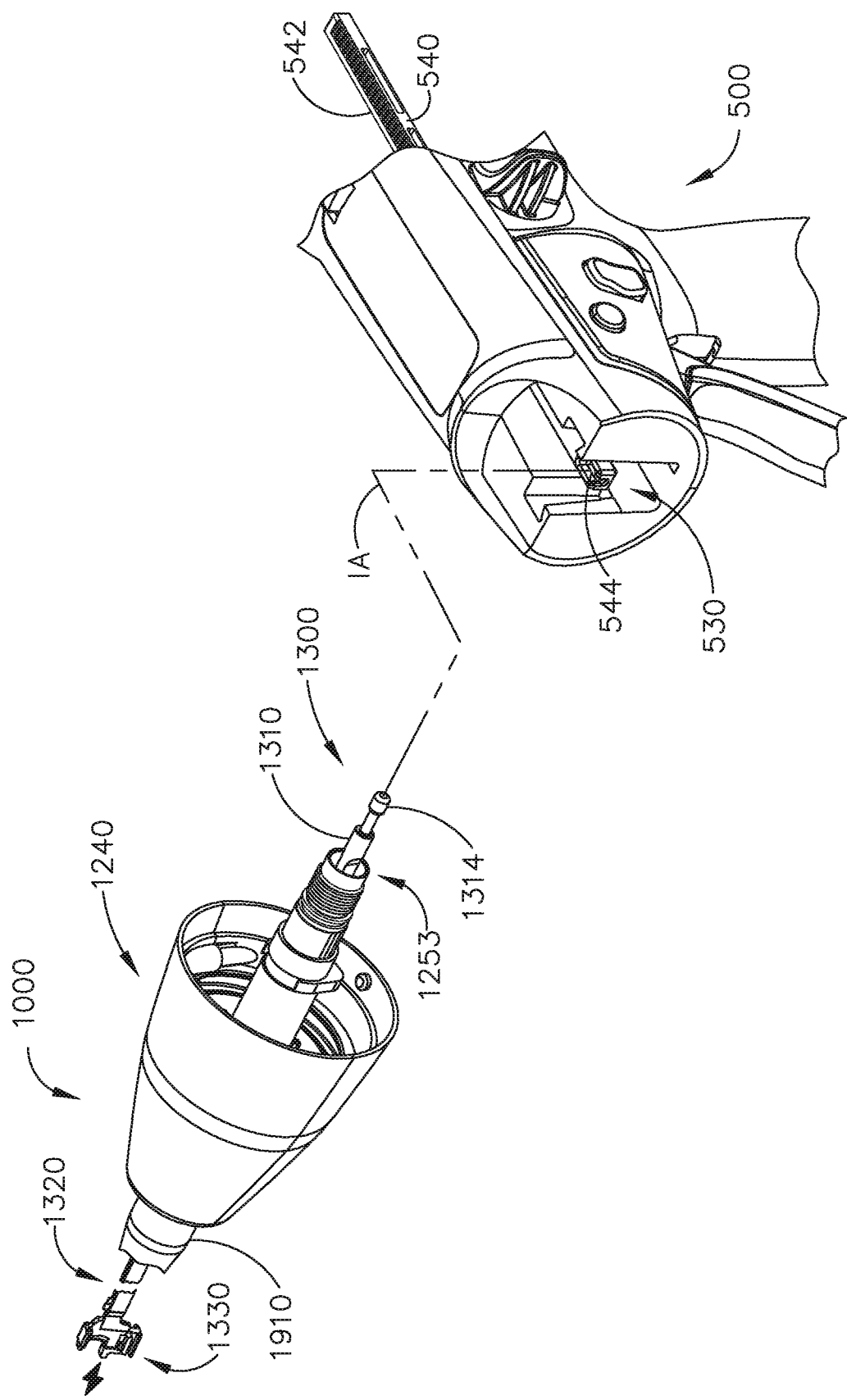
FIG. 3 is another exploded perspective assembly view of portions of the handle assembly and interchangeable surgical tool assembly of FIGS. 1 and 2 according to one aspect of this disclosure.
Figure 4:
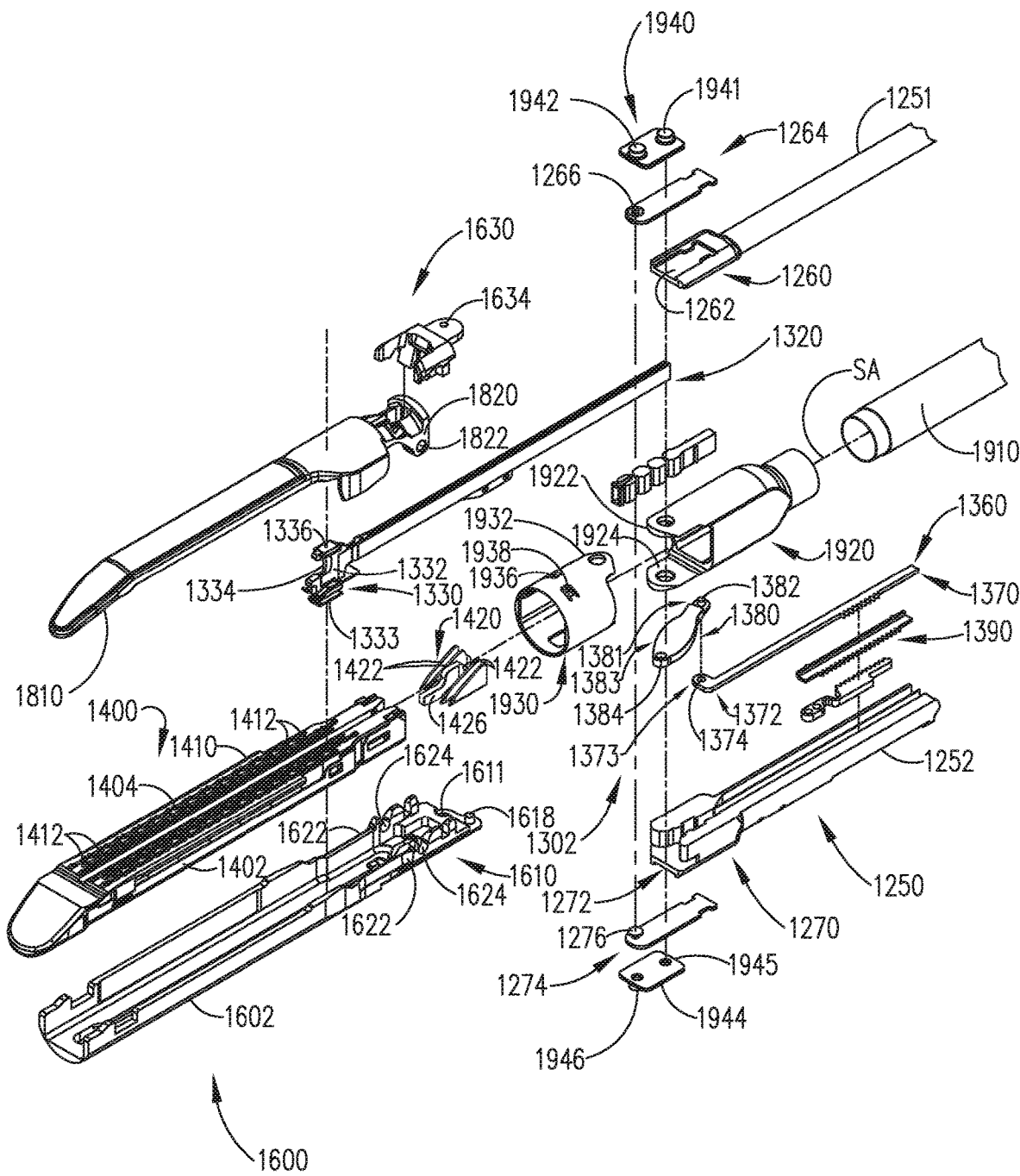
FIG. 4 is an exploded assembly view of a proximal portion of the interchangeable surgical tool assembly of FIGS. 1-3 according to one aspect of this disclosure.

Turning to FIG. 4, the articulation connector 1920 includes upper and lower tangs 1922, 1924 protrude distally from a distal end of the articulation connector 1920 to be movably coupled to an end effector closure sleeve or distal closure tube segment 1930. See FIG. 3. The distal closure tube segment 1930 includes an upper tang 1932 and a lower tang (not shown) that protrude proximally from a proximal end thereof. An upper double pivot link 1940 includes proximal and distal pins 1941, 1942 that engage corresponding holes in the upper tangs 1922, 1932 of the articulation connector 1920 and distal closure tube segment 1930, respectively. Similarly, a lower double pivot link 1944 includes proximal and distal pins 1945, 1946 that engage corresponding holes in the lower tangs 1924 of the articulation connector 1920 and distal closure tube segment 1930, respectively.

Still referring to FIG. 4, in the illustrated example, the distal closure tube segment 1930 includes positive jaw opening features or tabs 1936, 1938 that correspond with corresponding portions of the anvil 1810 to apply opening motions to the anvil 1810 as the distal closure tube segment 1930 is retracted in the proximal direction PD to a starting position. Further details regarding the opening and closing of the anvil 1810 may be found in U.S. patent application Ser. No. 15/635,621 entitled SURGICAL INSTRUMENT WITH POSITIVE JAW OPENING FEATURES, filed on Jun. 28, 2017, the entire disclosure of which is hereby incorporated by reference herein.

Figure 5:
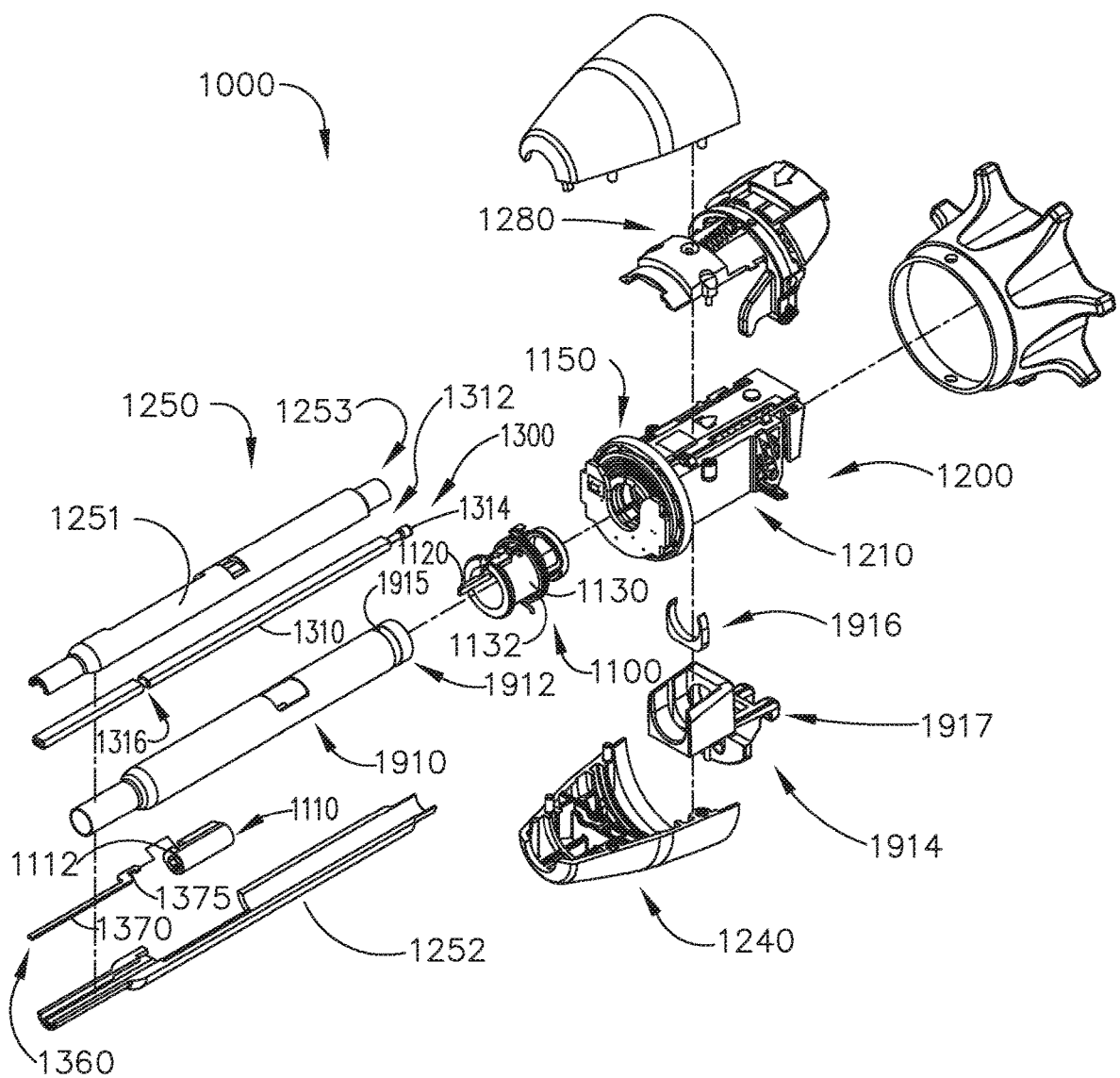
FIG. 5 is another exploded assembly view of a distal portion of the interchangeable surgical tool assembly of FIGS. 1-5 according to one aspect of this disclosure.

As shown in FIG. 5, in at least one arrangement, the interchangeable surgical tool assembly 1000 includes a tool frame assembly 1200 that comprises a tool chassis 1210 that operably supports a nozzle assembly 1240 thereon. As further discussed in detail in U.S. patent application Ser. No. 15/635,631 entitled SURGICAL INSTRUMENT WITH AXIALLY MOVABLE CLOSURE MEMBER, filed on Jun. 28, 2017, and which is hereby incorporated by reference in its entirety herein, the tool chassis 1210 and nozzle arrangement 1240 facilitate rotation of the surgical end effector 1500 about a shaft axis SA relative to the tool chassis 1210. Such rotational travel is represented by arrow R in FIG. 1. As also shown in FIGS. 4 and 5, the interchangeable surgical tool assembly 1000 includes a spine assembly 1250 that operably supports the proximal closure tube 1910 and is coupled to the surgical end effector 1500. In various circumstances, for ease of assembly, the spine assembly 1250 may be fabricated from an upper spine segment 1251 and a lower spine segment 1252 that are interconnected together by snap features, adhesive, welding, etc. In assembled form, the spine assembly 1250 includes a proximal end 1253 that is rotatably supported in the tool chassis 1210. In one arrangement, for example, the proximal end 1253 of the spine assembly 1250 is attached to a spine bearing (not shown) that is configured to be supported within the tool chassis 1210. Such arrangement facilitates rotatable attachment of the spine assembly 1250 to the tool chassis such that the spine assembly 1250 may be selectively rotated about a shaft axis SA relative to the tool chassis 1210.

As shown in FIG. 4, the upper spine segment 1251 terminates in an upper lug mount feature 1260 and the lower spine segment 1252 terminates in a lower lug mount feature 1270. The upper lug mount feature 1260 is formed with a lug slot 1262 therein that is adapted to mountingly support an upper mounting link 1264 therein. Similarly, the lower lug mount feature 1270 is formed with a lug slot 1272 therein that is adapted to mountingly support a lower mounting link 1274 therein. The upper mounting link 1264 includes a pivot socket 1266 therein that is offset from the shaft axis SA. The pivot socket 1266 is adapted to rotatably receive therein a pivot pin 1634 that is formed on a channel cap or anvil retainer 1630 that is attached to a proximal end portion 1610 of the elongate channel 1602. The lower mounting link 1274 includes lower pivot pin 1276 that adapted to be received within a pivot hole 1611 formed in the proximal end portion 1610 of the elongate channel 1602. The lower pivot pin 1276 as well as the pivot hole 1611 is offset from the shaft axis SA. The lower pivot pin 1276 is vertically aligned with the pivot socket 1266 to define the articulation axis AA about which the surgical end effector 1500 may articulate relative to the shaft axis SA. See FIG. 1. Although the articulation axis AA is transverse to the shaft axis SA, in at least one arrangement, the articulation axis AA is laterally offset therefrom and does not intersect the shaft axis SA.

Turning to FIG. 5, a proximal end 1912 of the proximal closure tube 1910 is rotatably coupled to a closure shuttle 1914 by a connector 1916 that is seated in an annular groove 1915 in the proximal closure tube segment 1910. The closure shuttle 1914 is supported for axial travel within the tool chassis 1210 and has a pair of hooks 1917 thereon configured to engage the closure drive system 510 when the tool chassis 1210 is coupled to the handle frame 506. The tool chassis 1210 further supports a latch assembly 1280 for releasably latching the tool chassis 1210 to the handle frame 506. Further details regarding the tool chassis 1210 and latch assembly 1280 may be found in U.S. patent application Ser. No. 15/635,631 entitled SURGICAL INSTRUMENT WITH AXIALLY MOVABLE CLOSURE MEMBER, filed on Jun. 28, 2017 and which is the entire disclosure of which is hereby incorporated by reference herein.

The firing drive system 530 in the handle assembly 500 is configured to be operably coupled to a firing system 1300 that is operably supported in the interchangeable surgical tool assembly 1000. The firing system 1300 may include an intermediate firing shaft portion 1310 that is configured to be axially moved in the distal and proximal directions in response to corresponding firing motions applied thereto by the firing drive system 530. See FIG. 4. As shown in FIG. 5, a proximal end 1312 of the intermediate firing shaft portion 1310 has a firing shaft attachment lug 1314 formed thereon that is configured to be seated into an attachment cradle 544 (FIG. 3) that is on the distal end of the longitudinally movable drive member 540 of the firing drive system 530 within the handle assembly 500. Such arrangement facilitates the axial movement of the intermediate firing shaft portion 1310 upon actuation of the firing drive system 530. In the illustrated example, the intermediate firing shaft portion 1310 is configured for attachment to a distal cutting portion or knife bar 1320. As shown in FIG. 4, the knife bar 1320 is connected to a firing member or knife member 1330. The knife member 1330 comprises a knife body 1332 that operably supports a tissue cutting blade 1334 thereon. The knife body 1332 may further include anvil engagement tabs or features 1336 and channel engagement features or a foot 1338. The anvil engagement features 1336 may serve to apply additional closure motions to the anvil 1810 as the knife member 1330 is advanced distally through the end effector 1500.

In the illustrated example, the surgical end effector 1500 is selectively articulatable about the articulation axis AA by an articulation system 1360. In one form, the articulation system 1360 includes proximal articulation driver 1370 that is pivotally coupled to an articulation link 1380. As can be most particularly seen in FIG. 4, an offset attachment lug 1373 is formed on a distal end 1372 of the proximal articulation driver 1370. A pivot hole 1374 is formed in the offset attachment lug 1373 and is configured to pivotally receive therein a proximal link pin 1382 formed on the proximal end 1381 of the articulation link 1380. A distal end 1383 of the articulation link 1380 includes a pivot hole 1384 that is configured to pivotally receive therein a channel pin 1618 formed on the proximal end portion 1610 of the elongate channel 1602. Thus, axial movement of proximal articulation driver 1370 will thereby apply articulation motions to the elongate channel 1602 to thereby cause the surgical end effector 1500 to articulate about the articulation axis AA relative to the spine assembly 1250. In various circumstances, the proximal articulation driver 1370 can be held in position by an articulation lock 1390 when the proximal articulation driver 1370 is not being moved in the proximal or distal directions. Further details regarding an example form of articulation lock 1390 may be found in U.S. patent application Ser. No. 15/635,837, entitled SURGICAL INSTRUMENT COMPRISING AN ARTICULATION SYSTEM LOCKABLE TO A FRAME, filed on Jun. 28, 2017, the entire disclosure of which is hereby incorporated by reference herein.

Further to the above, the interchangeable surgical tool assembly 1000 can include a shifter assembly 1100 which can be configured to selectively and releasably couple the proximal articulation driver 1310 to the firing system 1300. As illustrated in FIG. 5, for example, in one form, the shifter assembly 1100 includes a lock collar, or lock sleeve 1110, positioned around the intermediate firing shaft portion 1310 of the firing system 1300 wherein the lock sleeve 1110 can be rotated between an engaged position in which the lock sleeve 1110 operably couples the proximal articulation driver 1370 to the firing member assembly 1300 and a disengaged position in which the proximal articulation driver 1370 is not operably coupled to the firing member assembly 1300. When lock sleeve 1110 is in its engaged position, distal movement of the firing member assembly 1300 can move the proximal articulation driver 1370 distally and, correspondingly, proximal movement of the firing member assembly 1300 can move the proximal articulation driver 1370 proximally. When lock sleeve 1110 is in its disengaged position, movement of the firing member assembly 1300 is not transmitted to the proximal articulation driver 1370 and, as a result, the firing member assembly 1300 can move independently of the proximal articulation driver 1370. In various circumstances, the proximal articulation driver 1370 can be held in position by the articulation lock 1390 when the proximal articulation driver 1370 is not being moved in the proximal or distal directions by the firing member assembly 1300.

In the illustrated arrangement, the intermediate firing shaft portion 1310 of the firing member assembly 1300 is formed with two opposed flat sides with a drive notch 1316 formed therein. See FIG. 5. As can also be seen in FIG. 5, the lock sleeve 1110 comprises a cylindrical, or an at least substantially cylindrical, body that includes a longitudinal aperture that is configured to receive the intermediate firing shaft portion 1310 therethrough. The lock sleeve 1110 can comprise diametrically-opposed, inwardly-facing lock protrusions that, when the lock sleeve 1110 is in one position, are engagingly received within corresponding portions of the drive notch 1316 in the intermediate firing shaft portion 1310 and, when in another position, are not received within the drive notch 1316 to thereby permit relative axial motion between the lock sleeve 1110 and the intermediate firing shaft 1310. As can be further seen in FIG. 5, the lock sleeve 1110 further includes a lock member 1112 that is sized to be movably received within a notch 1375 in a proximal end of the proximal articulation driver 1370. Such arrangement permits the lock sleeve 1110 to slightly rotate into and out of engagement with the intermediate firing shaft portion 1310 while remaining in position for engagement or in engagement with the notch 1375 in the proximal articulation driver 1370. For example, when the lock sleeve 1110 is in its engaged position, the lock protrusions are positioned within the drive notch 1316 in the intermediate firing shaft portion 1310 such that a distal pushing force and/or a proximal pulling force can be transmitted from the firing member assembly 1300 to the lock sleeve 1110. Such axial pushing or pulling motion is then transmitted from the lock sleeve 1110 to the proximal articulation driver 1370 to thereby articulate the surgical end effector 1500. In effect, the firing member assembly 1300, the lock sleeve 1110, and the proximal articulation driver 1370 will move together when the lock sleeve 1110 is in its engaged (articulation) position. On the other hand, when the lock sleeve 1110 is in its disengaged position, the lock protrusions are not received within the drive notch 1316 in the intermediate firing shaft portion 1310 and, as a result, a distal pushing force and/or a proximal pulling force may not be transmitted from the firing member assembly 1300 to the lock sleeve 1110 (and the proximal articulation driver 1370).

In the illustrated example, relative movement of the lock sleeve 1110 between its engaged and disengaged positions may be controlled by the shifter assembly 1100 that interfaces with the proximal closure tube 1910. Still referring to FIG. 5, the shifter assembly 1100 further includes a shifter key 1120 that is configured to be slidably received within a key groove formed in the outer perimeter of the lock sleeve 1110. Such arrangement enables the shifter key 1120 to move axially with respect to the lock sleeve 1110. As discussed in further detail in U.S. patent application Ser. No. 15/635,631 entitled SURGICAL INSTRUMENT WITH AXIALLY MOVABLE CLOSURE MEMBER, filed on Jun. 28, 2017, the entire disclosure of which is hereby incorporated by reference herein, a portion of the shifter key 1120 is configured to cammingly interact with a cam opening (not shown) in the proximal closure tube portion 1910. Also in the illustrated example, the shifter assembly 1100 further includes a switch drum 1130 that is rotatably received on a proximal end portion of the proximal closure tube portion 1910. A portion of the shifter key 1120 extends through an axial slot segment in the switch drum 1130 and is movably received within an arcuate slot segment in the switch drum 1130. A switch drum torsion spring 1132 is mounted on the switch drum 1130 and engages a portion of the nozzle assembly 1240 to apply a torsional bias or rotation which serves to rotate the switch drum 1130 until the portion of the shifter key 1120 reaches an end portion of the cam opening in the proximal closure tube portion 1910. When in this position, the switch drum 1130 may provide a torsional bias to the shifter key 1120 which thereby causes the lock sleeve 1110 to rotate into its engaged position with the intermediate firing shaft portion 1310. This position also corresponds to the unactuated configuration of the proximal closure tube 1910 (and distal closure tube segment 1930).

In one arrangement, for example, when the proximal closure tube 1910 is in an unactuated configuration (anvil 1810 is in an open position spaced away from the cartridge mounted in the elongate channel 1602) actuation of the intermediate firing shaft portion 1310 will result in the axial movement of the proximal articulation driver 1370 to facilitate articulation of the end effector 1500. Once the user has articulated the surgical end effector 1500 to a desired orientation, the user may then actuate the proximal closure tube portion 1910. Actuation of the proximal closure tube portion 1910 will result in the distal travel of the distal closure tube segment 1930 to ultimately apply a closing motion to the anvil 1810. This distal travel of the proximal closure tube portion 1910 will result in the cam opening therein cammingly interacting with a cam portion of the shifter key 1120 to thereby cause the shifter key 1120 to rotate the lock sleeve 1110 in an actuation direction. Such rotation of the lock sleeve 1110 will result in the disengagement of the lock protrusions from the drive notch 1316 in the intermediate firing shaft portion 1310. When in such configuration, the firing drive system 530 may be actuated to actuate the intermediate firing shaft portion 1310 without actuating the proximal articulation driver 1370. Further details concerning the operation of the switch drum 1130 and lock sleeve 1110, as well as alternative articulation and firing drive arrangements that may be employed with the various interchangeable surgical tool assemblies described herein, may be found in U.S. patent application Ser. No. 13/803,086, now U.S. Patent Application Publication No. 2014/0263541, and U.S. patent application Ser. No. 15/019,196, the entire disclosures of which are hereby incorporated by reference herein.

Figure 15:
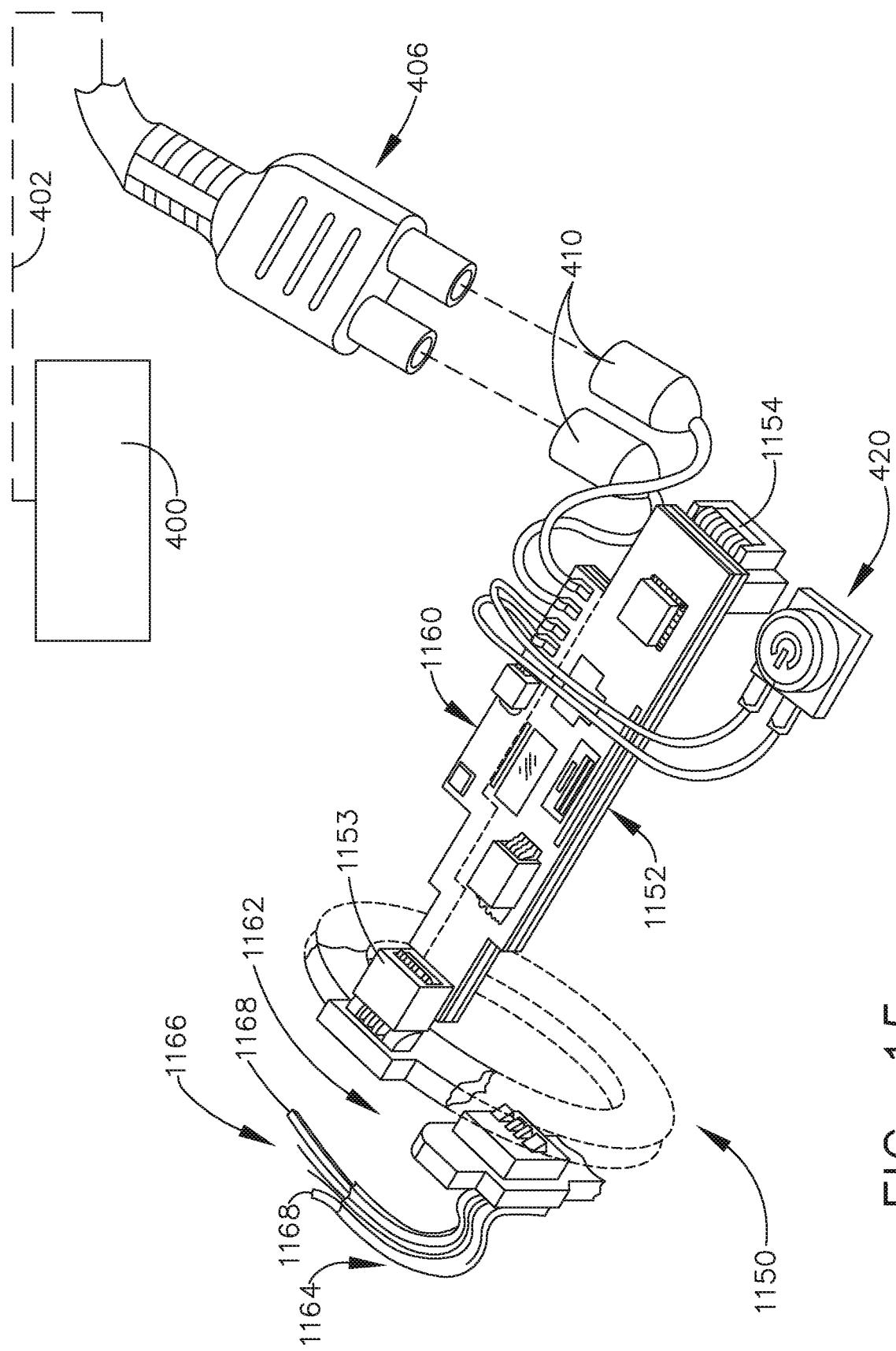
FIG. 15 is a perspective view of an onboard circuit board arrangement and RF generator plus configuration according to one aspect of this disclosure.

As also illustrated in FIGS. 5 and 15, the interchangeable surgical tool assembly 1000 can comprise a slip ring assembly 1150 which can be configured to conduct electrical power to and/or from the surgical end effector 1500 and/or communicate signals to and/or from the surgical end effector 1500, back to an onboard circuit board 1152, while facilitating rotational travel of the shaft and end effector 1500 about the shaft axis SA relative to the tool chassis 1210 by rotating the nozzle assembly 1240. As shown in FIG. 15, in at least one arrangement, the onboard circuit board 1152 includes an onboard connector 1154 that is configured to interface with a housing connector 562 (FIG. 9) communicating with a microprocessor 560 that is supported in the handle assembly 500 or robotic system controller, for example. The slip ring assembly 1150 is configured to interface with a proximal connector 1153 that interfaces with the onboard circuit board 1152. Further details concerning the slip ring assembly 1150 and associated connectors may be found in U.S. patent application Ser. No. 13/803,086, now U.S. Patent Application Publication No. 2014/0263541, and U.S. patent application Ser. No. 15/019,196 which have each been herein incorporated by reference in their respective entirety as well as in U.S. patent application Ser. No. 13/800,067, entitled STAPLE CARTRIDGE TISSUE THICKNESS SENSOR SYSTEM, now U.S. Patent Application Publication No. 2014/0263552, which is hereby incorporated by reference herein in its entirety.

An example version of the interchangeable surgical tool assembly 1000 disclosed herein may be employed in connection with a standard (mechanical) surgical fastener cartridge 1400 or a cartridge 1700 that is configured to facilitate cutting of tissue with the knife member and seal the cut tissue using radio frequency (RF) energy. Turning again to FIG. 4, a conventional or standard mechanical-type cartridge 1400 is depicted. Such cartridge arrangements are known and may comprise a cartridge body 1402 that is sized and shaped to be removably received and supported in the elongate channel 1602. For example, the cartridge body 1402 may be configured to be removably retained in snap engagement with the elongate channel 1602. The cartridge body 1402 includes an elongate slot 1404 to accommodate axial travel of the knife member 1330 therethrough. The cartridge body 1402 operably supports therein a plurality of staple drivers (not shown) that are aligned in rows on each side of the centrally disposed elongate slot 1404. The drivers are associated with corresponding staple/fastener pockets 1412 that open through the upper deck surface 1410 of the cartridge body 1402. Each of the staple drivers supports one or more surgical staple or fastener (not shown) thereon. A sled assembly 1420 is supported within a proximal end of the cartridge body 1402 and is located proximal to the drivers and fasteners in a starting position when the cartridge 1400 is new and unfired. The sled assembly 1420 includes a plurality of sloped or wedge-shaped cams 1422 wherein each cam 1422 corresponds to a particular line of fasteners or drivers located on a side of the slot 1404. The sled assembly 1420 is configured to be contacted and driven by the knife member 1330 as the knife member is driven distally through the tissue that is clamped between the anvil and the cartridge deck surface 1410. As the drivers are driven upward toward the cartridge deck surface 1410, the fastener(s) supported thereon are driven out of their staple pockets 1412 and through the tissue that is clamped between anvil and the cartridge.

Figure 7:
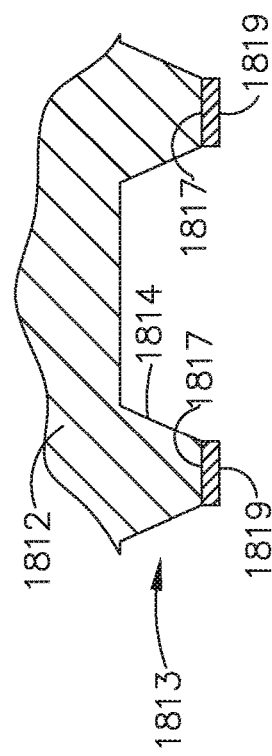
FIG. 7 is a partial cross-sectional view of the anvil of FIG. 6 according to one aspect of this disclosure.
Figure 6:
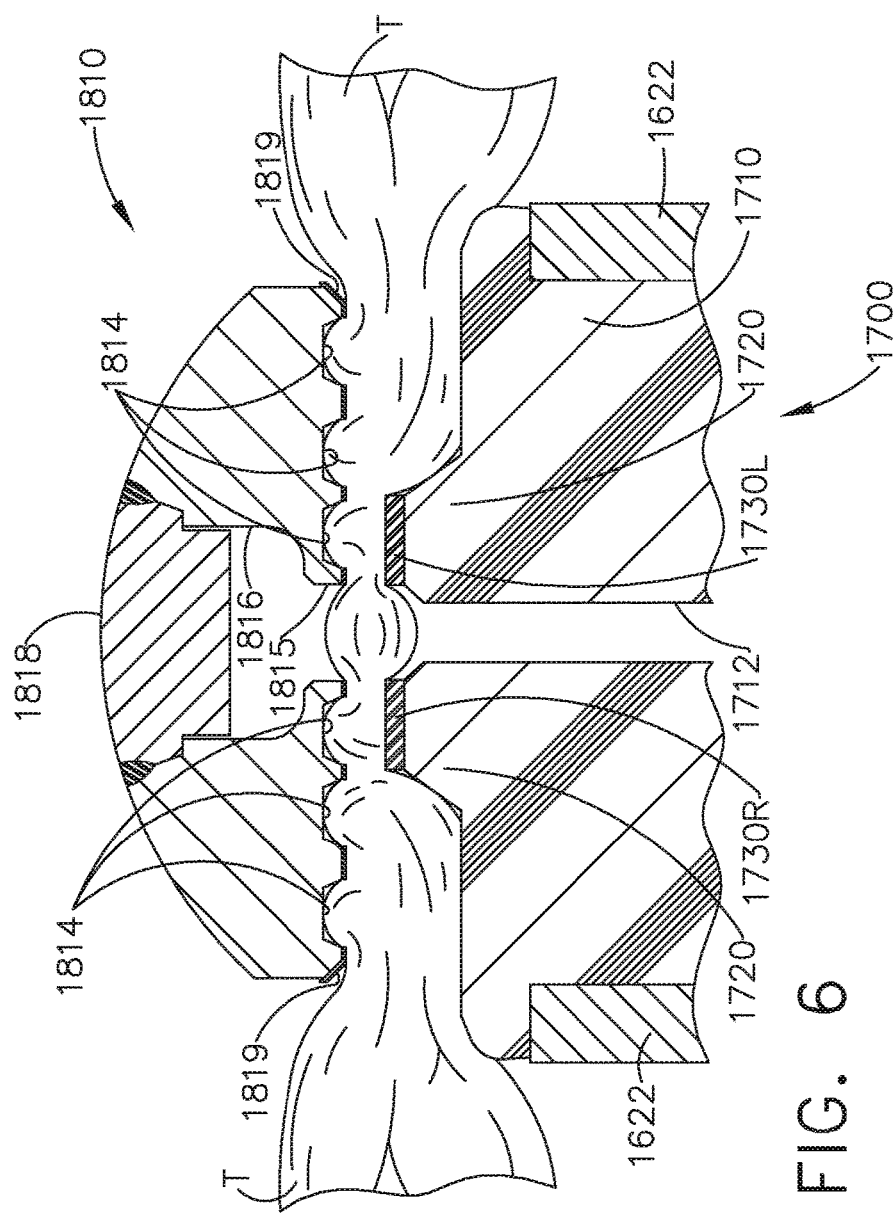
FIG. 6 is a partial cross-sectional view of the end effector depicted in FIGS. 1-5 supporting an RF cartridge therein and with tissue clamped between the cartridge and the anvil according to one aspect of this disclosure.

Still referring to FIG. 4, the anvil 1810 in at least one form includes an anvil mounting portion 1820 that has a pair of anvil trunnions 1822 protruding laterally therefrom to be pivotally received in corresponding trunnion cradles 1614 formed in the upstanding walls 1622 of the proximal end portion 1610 of the elongate channel 1602. The anvil trunnions 1822 are pivotally retained in their corresponding trunnion cradle 1614 by the channel cap or anvil retainer 1630. The anvil mounting portion 1820 is movably or pivotably supported on the elongate channel 1602 for selective pivotal travel relative thereto about a fixed anvil pivot axis that is transverse to the shaft axis SA. As shown in FIGS. 6 and 7, in at least one form, the anvil 1810 includes an anvil body portion 1812 that is fabricated from an electrically conductive metal material for example and has a staple forming undersurface 1813 that has a series of fastener forming pockets 1814 formed therein on each side of a centrally disposed anvil slot 1815 that is configured to slidably accommodate the knife member 1330 therein. The anvil slot 1815 opens into an upper opening 1816 that extends longitudinally through the anvil body 1812 to accommodate the anvil engagement features 1336 on the knife member 1330 during firing. When a conventional mechanical surgical staple/fastener cartridge 1400 is installed in the elongate channel 1602, the staples/fasteners are driven through the tissue T and into forming contact with the corresponding fastener forming pockets 1814. The anvil body 1812 may have an opening in the upper portion thereof to facilitate ease of installation for example. An anvil cap 1818 may be inserted therein and welded to the anvil body 1812 to enclose the opening and improve the overall stiffness of the anvil body 1812. As shown in FIG. 7, to facilitate use of the end effector 1500 in connection with RF cartridges 1700, the tissue facing segments 1817 of the fastener forming undersurface 1813 may have electrically insulative material 1819 thereon.

Figure 8:
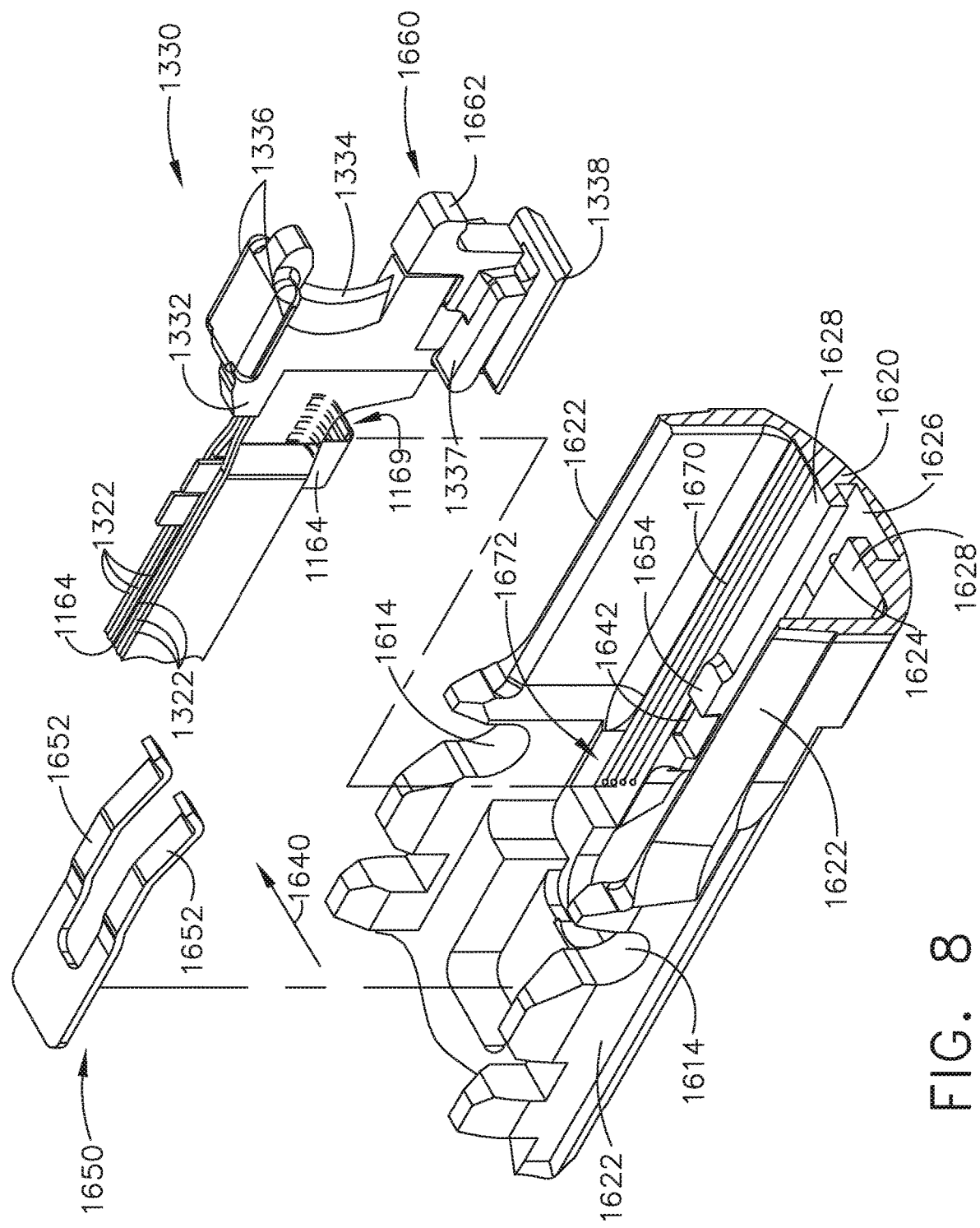
FIG. 8 is another exploded assembly view of a portion of the interchangeable surgical tool assembly of FIGS. 1-5 according to one aspect of this disclosure.

In the illustrated arrangement, the interchangeable surgical tool assembly 1000 is configured with a firing member lockout system, generally designated as 1640. See FIG. 8. As shown in FIG. 8, the elongate channel 1602 includes a bottom surface or bottom portion 1620 that has two upstanding side walls 1622 protruding therefrom. A centrally disposed longitudinal channel slot 1624 is formed through the bottom portion 1620 to facilitate the axial travel of the knife member 1330 therethrough. The channel slot 1624 opens into a longitudinal passage 1626 that accommodates the channel engagement feature or foot 1338 on the knife member 1330. The passage 1626 serves to define two inwardly extending ledge portions 1628 that serve to engage corresponding portions of the channel engagement feature or foot 1338. The firing member lockout system 1640 includes proximal openings 1642 located on each side of the channel slot 1624 that are each configured to receive corresponding portions of the channel engagement feature or foot 1338 when the knife member 1330 is in a starting position. A knife lockout spring 1650 is supported in the proximal end 1610 of the elongate channel 1602 and serves to bias the knife member 1330 downward. As shown in FIG. 8, the knife lockout spring 1650 includes two distally ending spring arms 1652 that are configured to engage corresponding central channel engagement features 1337 on the knife body 1332. The spring arms 1652 are configured to bias the central channel engagement features 1337 downward. Thus, when in the starting (unfired position), the knife member 1330 is biased downward such that the channel engagement features or foot 1338 is received within the corresponding proximal openings 1642 in the elongate 1602 channel. When in that locked position, if one were to attempt to distally advance the knife 1330, the central channel engagement features 1137 and/or foot 1338 would engage upstanding ledges 1654 on the elongate channel 1602 (FIGS. 8 and 11) and the knife 1330 could not be fired.

Still referring to FIG. 8, the firing member lockout system 1640 also includes an unlocking assembly 1660 formed or supported on a distal end of the firing member body 1332. The unlocking assembly 1660 includes a distally extending ledge 1662 that is configured to engage an unlocking feature 1426 formed on the sled assembly 1420 when the sled assembly 1420 is in its starting position in an unfired surgical staple cartridge 1400. Thus, when an unfired surgical staple cartridge 1400 is properly installed in the elongate channel 1602, the ledge 1662 on the unlocking assembly 1660 contacts the unlocking feature 1426 on the sled assembly 1420 which serves to bias the knife member 1330 upward such that the central channel engagement features 1137 and/or foot 1338 clear the upstanding ledges 1654 in the channel bottom 1620 to facilitate axial passage of the knife member 1330 through the elongate channel 1602. If a partially fired cartridge 1400 is unwittingly installed in the elongate channel, the sled assembly 1420 will not be in the starting position and the knife member 1330 will remain in the locked position.

Figure 9:
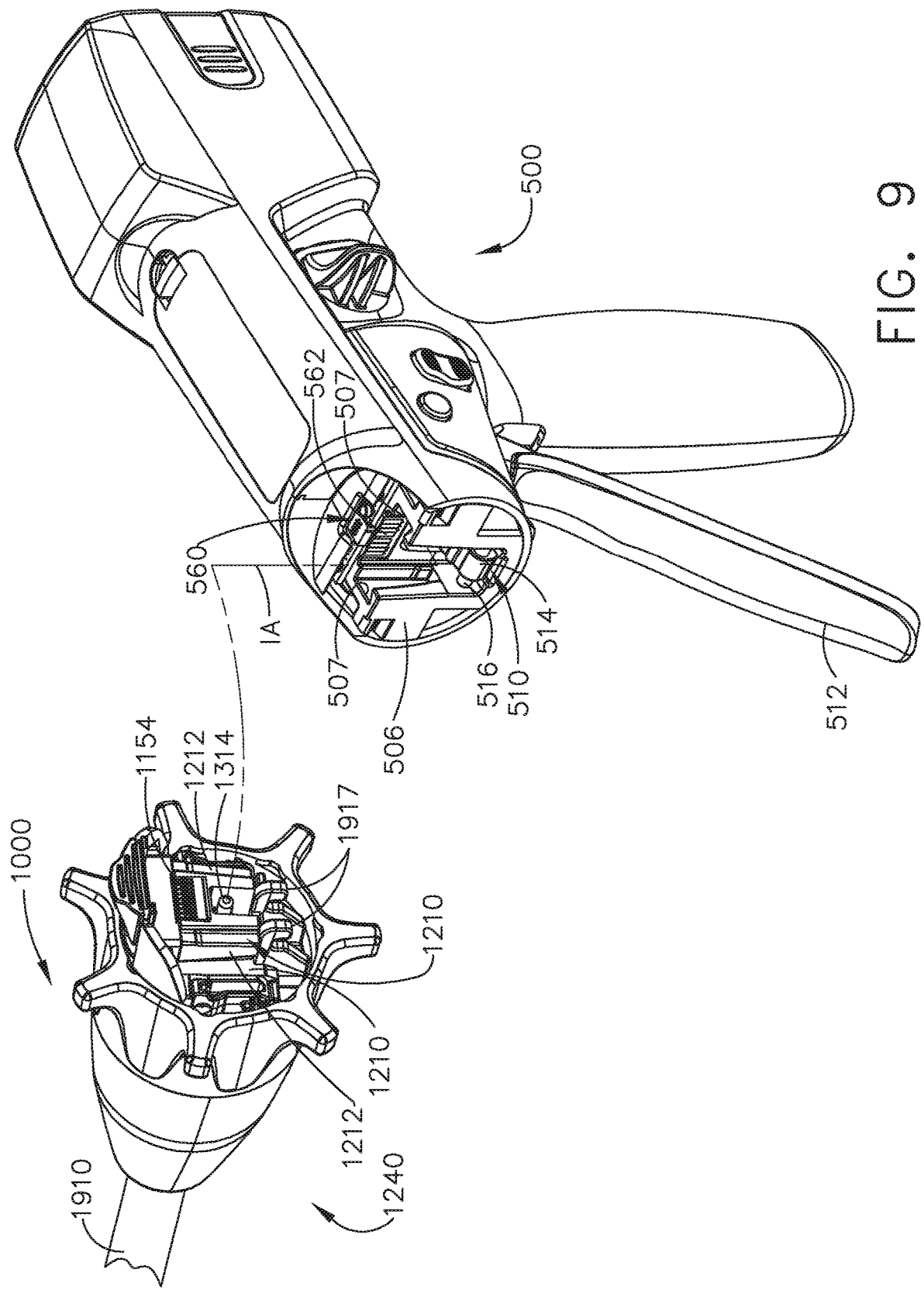
FIG. 9 is another exploded assembly view of the interchangeable surgical tool assembly and handle assembly of FIGS. 1 and 2 according to one aspect of this disclosure.

Attachment of the interchangeable surgical tool assembly 1000 to the handle assembly 500 will now be described with reference to FIGS. 3 and 9. To commence the coupling process, the clinician may position the tool chassis 1210 of the interchangeable surgical tool assembly 1000 above or adjacent to the distal end of the handle frame 506 such that tapered attachment portions 1212 formed on the tool chassis 1210 are aligned with dovetail slots 507 in the handle frame 506. The clinician may then move the surgical tool assembly 1000 along an installation axis IA that is perpendicular to the shaft axis SA to seat the tapered attachment portions 1212 in "operable engagement" with the corresponding dovetail receiving slots 507 in the distal end of the handle frame 506. In doing so, the firing shaft attachment lug 1314 on the intermediate firing shaft portion 1310 will also be seated in the cradle 544 in the longitudinally movable drive member 540 within the handle assembly 500 and the portions of a pin 516 on a closure link 514 will be seated in the corresponding hooks 1917 in the closure shuttle 1914. As used herein, the term "operable engagement" in the context of two components means that the two components are sufficiently engaged with each other so that upon application of an actuation motion thereto, the components may carry out their intended action, function and/or procedure. Also during this process, the onboard connector 1154 on the surgical tool assembly 1000 is coupled to the housing connector 562 that communicates with the microprocessor 560 that is supported in the handle assembly 500 or robotic system controller, for example.

During a typical surgical procedure, the clinician may introduce the surgical end effector 1500 into the surgical site through a trocar or other opening in the patient to access the target tissue. When doing so, the clinician typically axially aligns the surgical end effector 1500 along the shaft axis SA (unarticulated state). Once the surgical end effector 1500 has passed through the trocar port, for example, the clinician may need to articulate the end effector 1500 to advantageously position it adjacent the target tissue. This is prior to closing the anvil 1810 onto the target tissue, so the closure drive system 510 would remain unactuated. When in this position, actuation of the firing drive system 530 will result in the application of articulation motions to the proximal articulation driver 1370. Once the end effector 1500 has attained the desired articulated position, the firing drive system 530 is deactivated and the articulation lock 1390 may retain the surgical end effector 1500 in the articulated position. The clinician may then actuate the closure drive system 510 to close the anvil 1810 onto the target tissue. Such actuation of the closure drive system 510 may also result in the shifter assembly 1100 delinking the proximal articulation driver 1370 from the intermediate firing shaft portion 1310. Thus, once the target tissue has been captured in the surgical end effector 1500, the clinician may once again actuate the firing drive system 530 to axially advance the firing member 1330 through the surgical staple/fastener cartridge 1400 or RF cartridge 1700 to cut the clamped tissue and fire the staples/fasteners into the cut tissue T. Other closure and firing drive arrangements, actuator arrangements (both handheld, manual and automated or robotic) may also be employed to control the axial movement of the closure system components, the articulation system components and/or the firing system components of the surgical tool assembly 1000 without departing from the scope of the present disclosure.

As indicated above, the surgical tool assembly 1000 is configured to be used in connection with conventional mechanical surgical staple/fastener cartridges 1400 as well as with RF cartridges 1700. In at least one form, the RF cartridge 1700 may facilitate mechanical cutting of tissue that is clamped between the anvil 1810 and the RF cartridge 1700 with the knife member 1330 while coagulating electrical current is delivered to the tissue in the current path. Alternative arrangements for mechanically cutting and coagulating tissue using electrical current are disclosed in, for example, U.S. Pat. Nos. 5,403,312; 7,780,663 and U.S. patent application Ser. No. 15/142,609, entitled ELECTROSURGICAL INSTRUMENT WITH ELECTRICALLY CONDUCTIVE GAP SETTING AND TISSUE ENGAGING MEMBERS, the entire disclosures of each said references being incorporated by reference herein. Such instruments, may, for example, improve hemostasis, reduce surgical complexity as well as operating room time.

Figure 10:
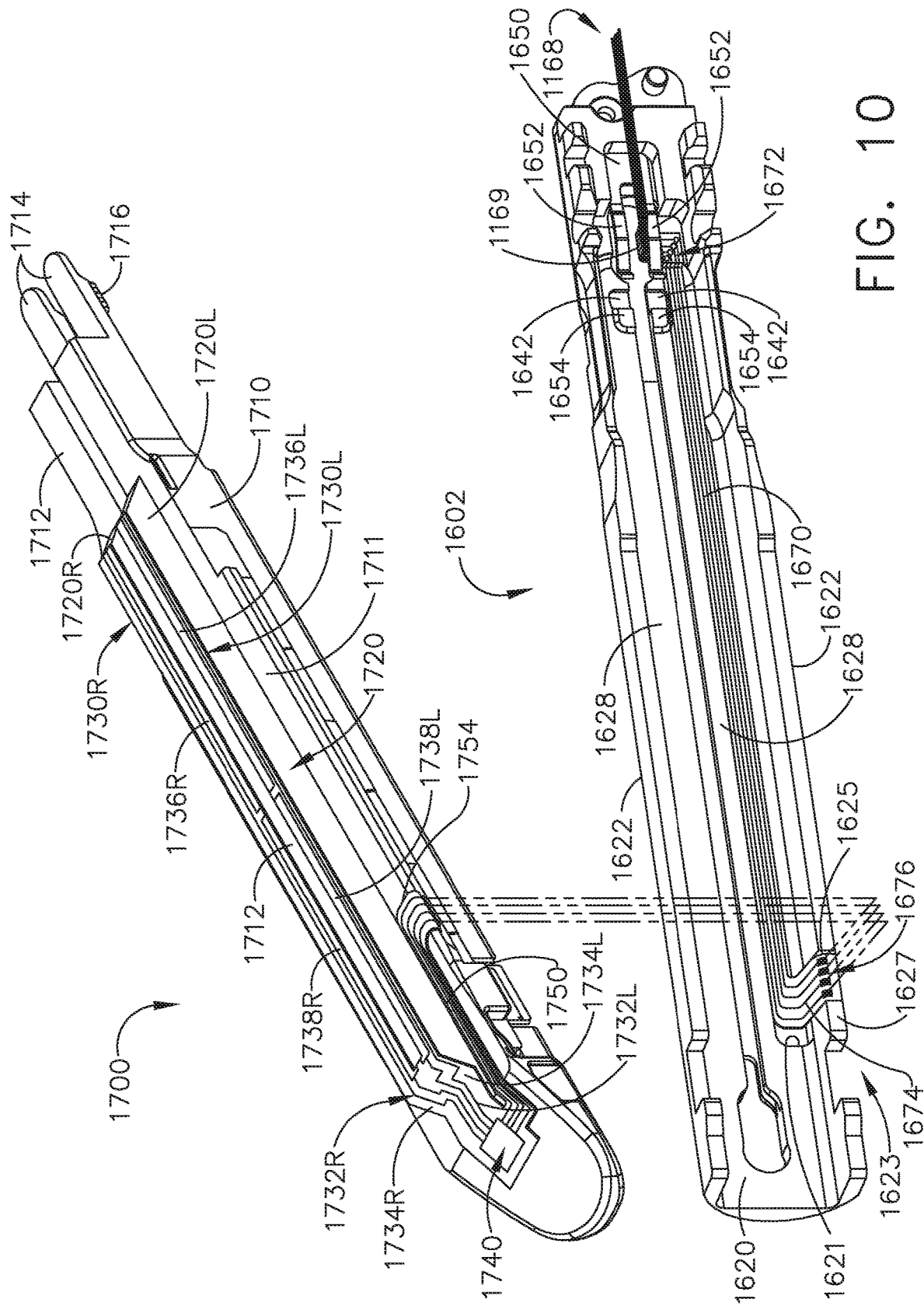
FIG. 10 is a perspective view of an RF cartridge and an elongate channel of the interchangeable surgical tool assembly of FIGS. 1-5 according to one aspect of this disclosure.
Figure 11:
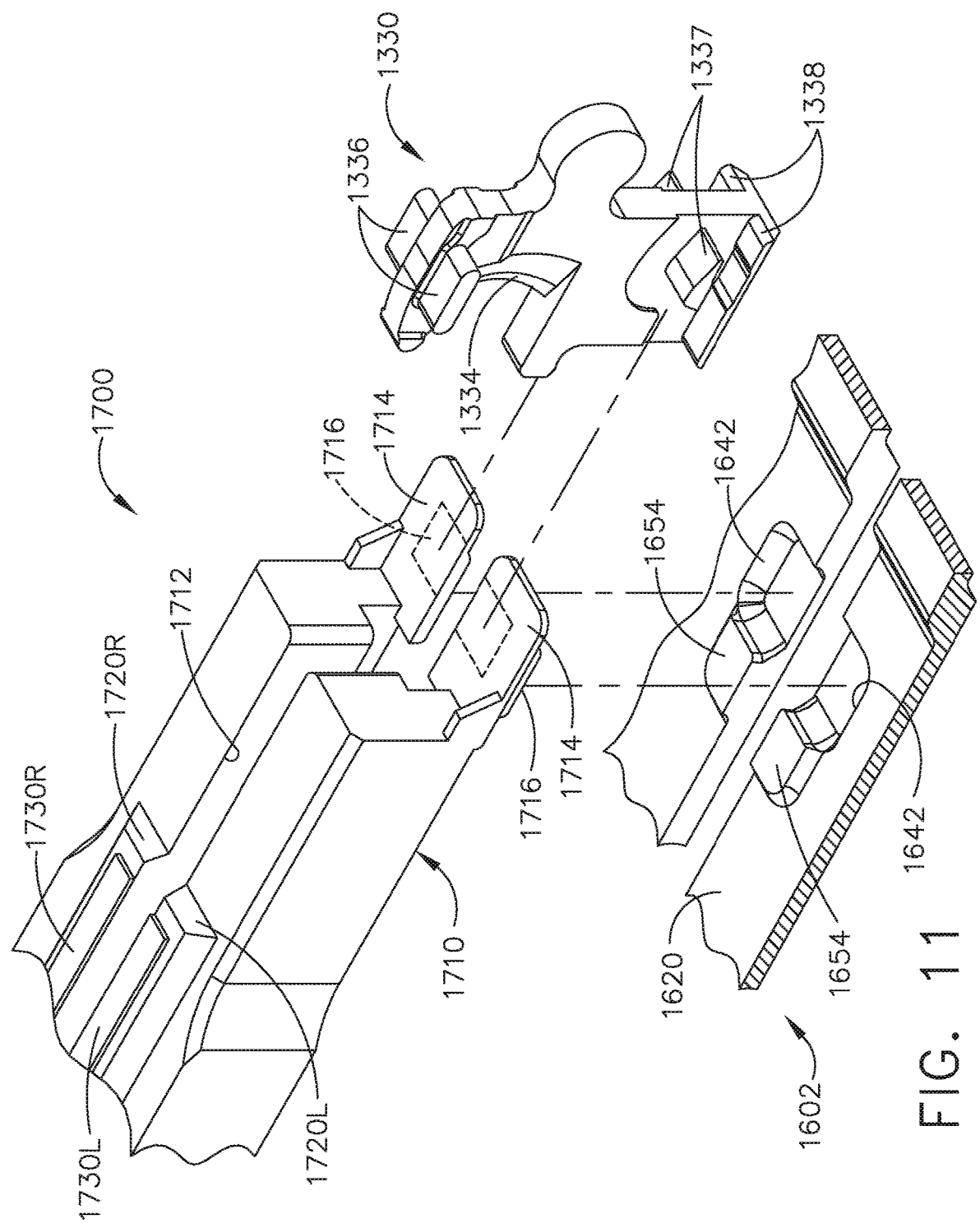
FIG. 11 is a partial perspective view of portions of the RF cartridge and elongate channel of FIG. 10 with a knife member aspect according to one aspect of this disclosure.
Figure 12:
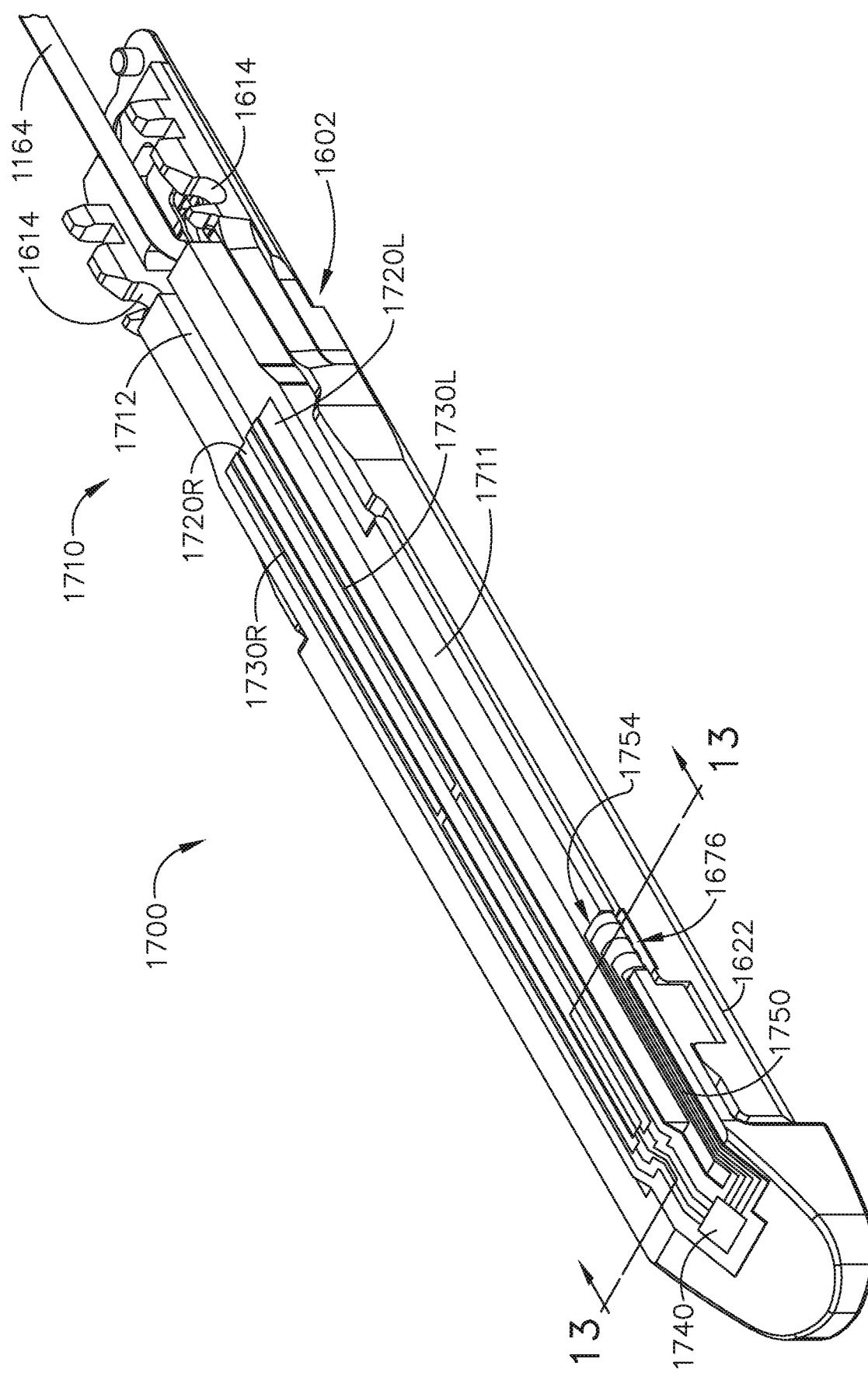
FIG. 12 is another perspective view of the RF cartridge installed in the elongate channel of FIG. 10 and illustrating a portion of a flexible shaft circuit arrangement according to one aspect of this disclosure.
Figure 13:
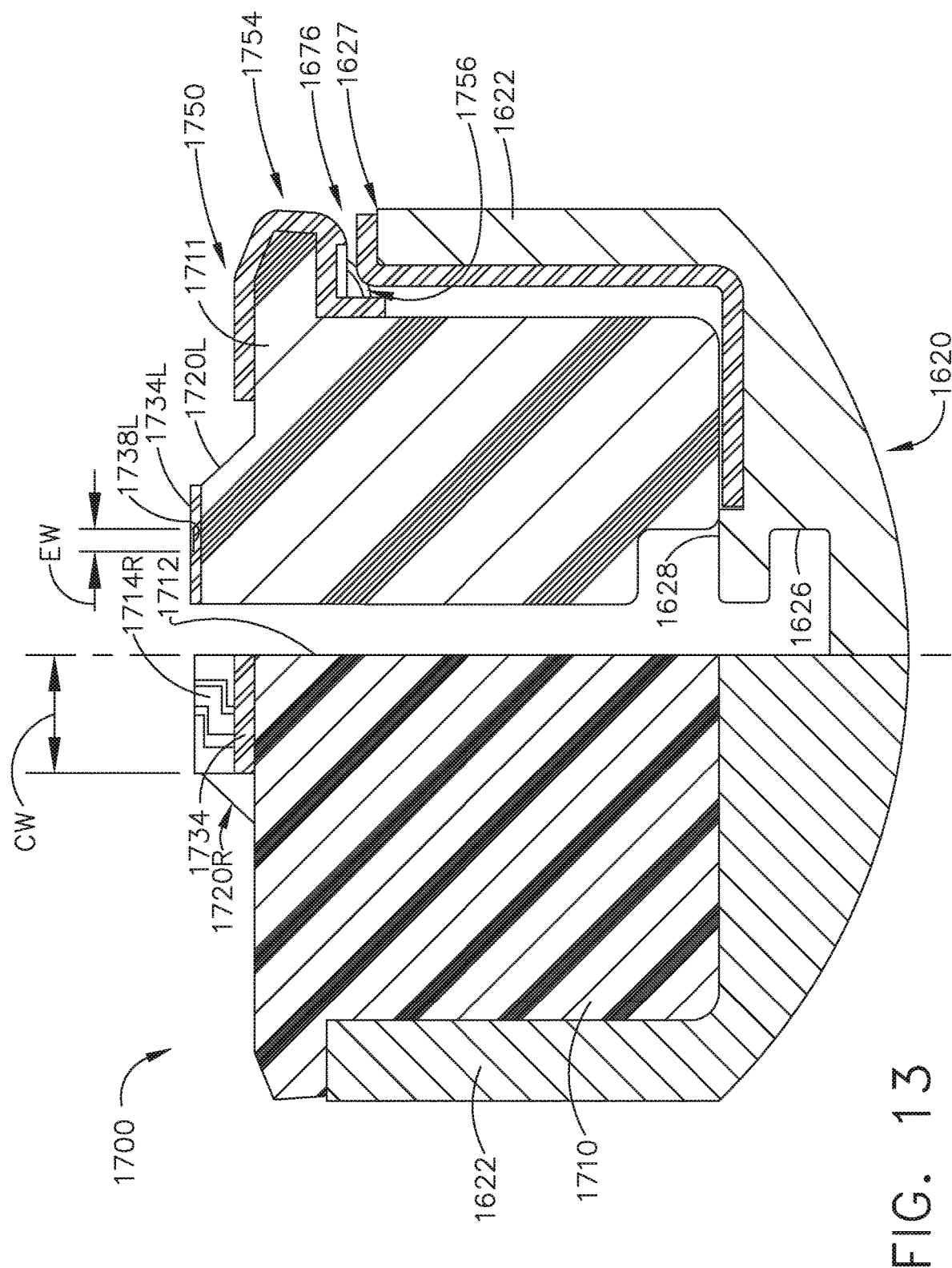
FIG. 13 is a cross-sectional end view of the RF cartridge and elongate channel of FIG. 12 taken along lines 13-13 in FIG. 12 according to one aspect of this disclosure.

As shown in FIGS. 10-12, in at least one arrangement, the RF surgical cartridge 1700 includes a cartridge body 1710 that is sized and shaped to be removably received and supported in the elongate channel 1602. For example, the cartridge body 1710 may be configured to be removably retained in snap engagement with the elongate channel 1602. In various arrangements, the cartridge body 1710 may be fabricated from a polymer material, such as, for example, an engineering thermoplastic such as the liquid crystal polymer (LCP) VECTRA™ and the elongate channel 1602 may be fabricated from metal. In at least one aspect, the cartridge body 1710 includes a centrally disposed elongate slot 1712 that extends longitudinally through the cartridge body to accommodate longitudinal travel of the knife 1330 therethrough. As shown in FIGS. 10 and 11, a pair of lockout engagement tails 1714 extend proximally from the cartridge body 1710. Each lockout engagement tail 1714 has a lockout pad 1716 formed on the underside thereof that are sized to be received within a corresponding proximal opening portion 1642 in the channel bottom 1620. Thus, when the cartridge 1700 is properly installed in the elongate channel 1602, the lockout engagement tails 1714 cover the openings 1642 and ledges 1654 to retain the knife 1330 in an unlocked position ready for firing.

Turning now to FIGS. 10-13, in the illustrated example, the cartridge body 1710 is formed with a centrally disposed raised electrode pad 1720. As can be most particularly seen in FIG. 6, the elongate slot 1712 extends through the center of the electrode pad 1720 and serves to divide the pad 1720 into a left pad segment 1720L and a right pad segment 1720R. A right flexible circuit assembly 1730R is attached to the right pad segment 1720R and a left flexible circuit assembly 1730L is attached to the left pad segment 1720L. In at least one arrangement for example, the right flexible circuit 1730R comprises a plurality of electrical conductors 1732R that may include, for example, wider electrical conductors/conductors for RF purposes and thinner electrical conductors for conventional stapling purposes that are supported or attached or embedded into a right insulator sheath/member 1734R that is attached to the right pad 1720R. In addition, the right flexible circuit assembly 1730R includes a "phase one", proximal right electrode 1736R and a "phase two" distal right electrode 1738R. Likewise, the left flexible circuit assembly 1730L comprises a plurality of electrical conductors 1732L that may include, for example, wider electrical conductors/conductors for RF purposes and thinner electrical conductors for conventional stapling purposes that are supported or attached or embedded into a left insulator sheath/member 1734L that is attached to the left pad 1720L. In addition, the left flexible circuit assembly 1730L includes a "phase one", proximal left electrode 1736L and a "phase two" distal left electrode 1738L. The left and right electrical conductors 1732L, 1732R are attached to a distal micro-chip 1740 mounted to the distal end portion of the cartridge body 1710. In one arrangement, for example, each of the right and left flexible circuits 1730R, 1730L may have an overall width "CW" of approximately 0.025 inches and each of the electrodes 1736R, 1736L, 1738R, 1738R has a width "EW" of approximately 0.010 inches for example. See FIG. 13. However, other widths/sizes are contemplated and may be employed in alternative aspects.

In at least one arrangement, RF energy is supplied to the surgical tool assembly 1000 by a conventional RF generator 400 through a supply lead 402. In at least one arrangement, the supply lead 402 includes a male plug assembly 406 that is configured to be plugged into corresponding female connectors 410 that are attached to a segmented RF circuit 1160 on the an onboard circuit board 1152. See FIG. 15. Such arrangement facilitates rotational travel of the shaft and end effector 1500 about the shaft axis SA relative to the tool chassis 1210 by rotating the nozzle assembly 1240 without winding up the supply lead 402 from the generator 400. An onboard on/off power switch 420 is supported on the latch assembly 1280 and tool chassis 1210 for turning the RF generator on and off. When the tool assembly 1000 is operably coupled to the handle assembly 500 or robotic system, the onboard segmented RF circuit 1160 communicates with the microprocessor 560 through the connectors 1154 and 562. As shown in FIG. 1, the handle assembly 500 may also include a display screen 430 for viewing information about the progress of sealing, stapling, knife location, status of the cartridge, tissue, temperature, etc. As can also be seen FIG. 15, the slip ring assembly 1150 interfaces with a distal connector 1162 that includes a flexible shaft circuit strip or assembly 1164 that may include a plurality of narrow electrical conductors 1166 for stapling related activities and wider electrical conductors 1168 used for RF purposes. As shown in FIGS. 14 and 15, the flexible shaft circuit strip 1164 is centrally supported between the laminated plates or bars 1322 that form the knife bar 1320. Such arrangement facilitates sufficient flexing of the knife bar 1320 and flexible shaft circuit strip 1164 during articulation of the end effector 1500 while remaining sufficiently stiff so as to enable the knife member 1330 to be distally advanced through the clamped tissue.

Turning again to FIG. 10, in at least one illustrated arrangement, the elongate channel 1602 includes a channel circuit 1670 supported in a recess 1621 that extends from the proximal end 1610 of the elongate channel 1602 to a distal location 1623 in the elongate channel bottom portion 1620. The channel circuit 1670 includes a proximal contact portion 1672 that contacts a distal contact portion 1169 of the flexible shaft circuit strip 1164 for electrical contact therewith. A distal end 1674 of the channel circuit 1670 is received within a corresponding wall recess 1625 formed in one of the channel walls 1622 and is folded over and attached to an upper edge 1627 of the channel wall 1622. A series of corresponding exposed contacts 1676 are provided in the distal end 1674 of the channel circuit 1670 As shown in FIG. 10. As can also be seen in FIG. 10, an end 1752 of a flexible cartridge circuit 1750 is attached to the distal micro-chip 1740 and is affixed to the distal end portion of the cartridge body 1710. Another end 1754 is folded over the edge of the cartridge deck surface 1711 and includes exposed contacts 1756 configured to make electrical contact with the exposed contacts 1676 of the channel circuit 1670. Thus, when the RF cartridge 1700 is installed in the elongate channel 1602, the electrodes as well as the distal micro-chip 1740 are powered and communicate with the onboard circuit board 1152 through contact between the flexible cartridge circuit 1750, the flexible channel circuit 1670, the flexible shaft circuit 1164 and the slip ring assembly 1150.

Figure 16A:
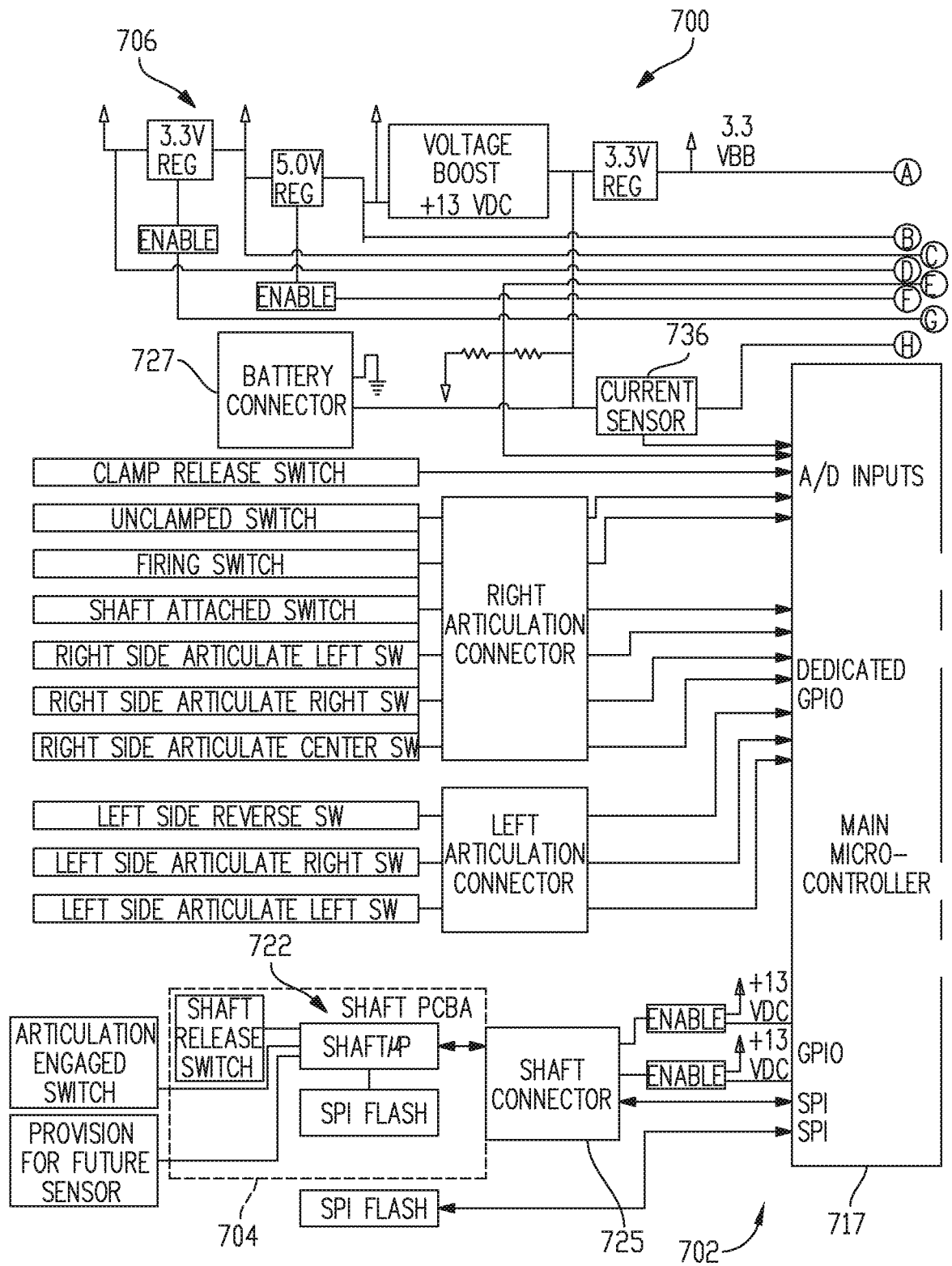
FIGS. 16A-16B is a block diagram of a control circuit of the surgical instrument of FIG. 1 spanning two drawing sheets according to one aspect of this disclosure.
Figure 16B:
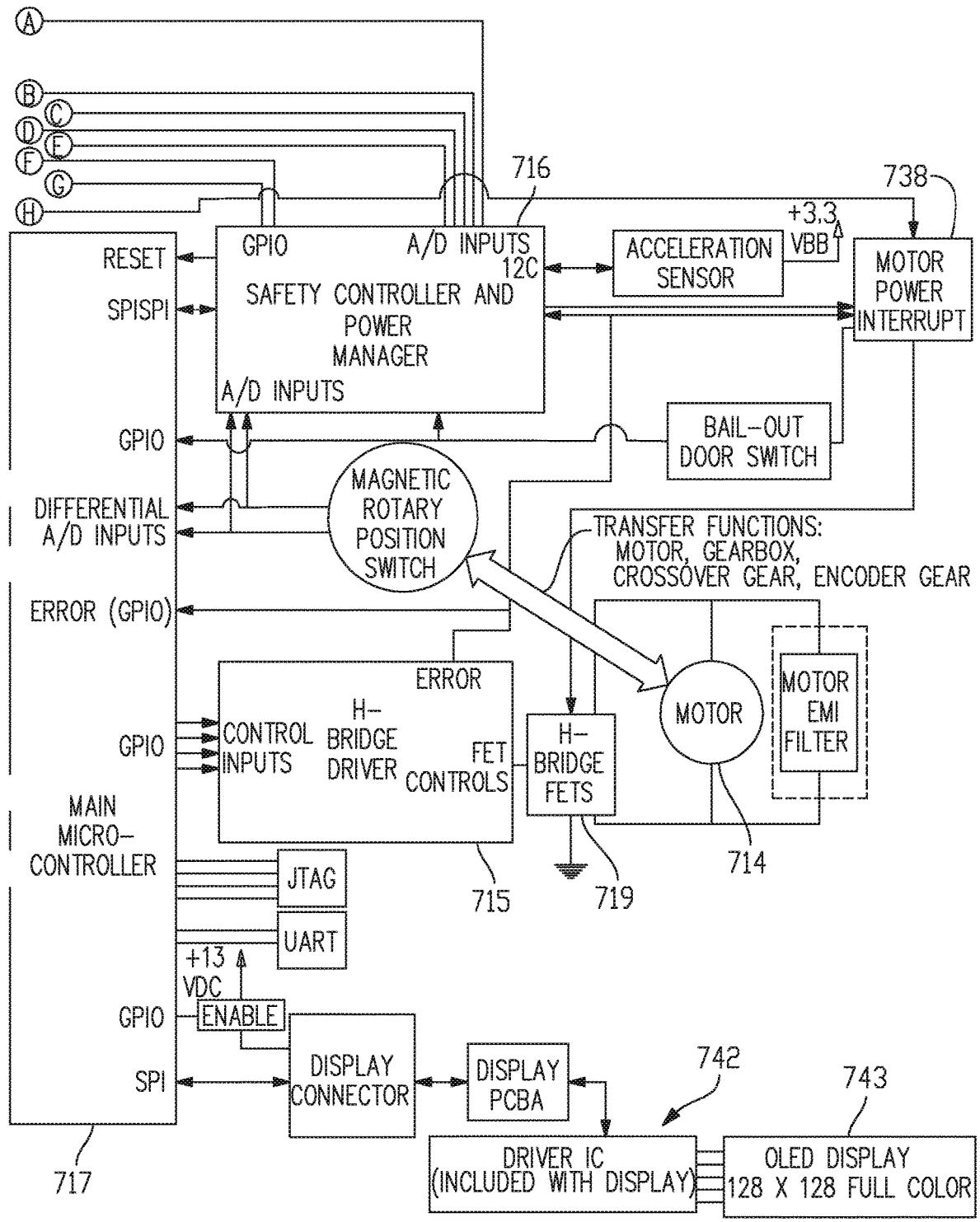

FIGS. 16A-16B is a block diagram of a control circuit 700 of the surgical instrument 10 of FIG. 1 spanning two drawing sheets according to one aspect of this disclosure. Referring primarily to FIGS. 16A-16B, a handle assembly 702 may include a motor 714 which can be controlled by a motor driver 715 and can be employed by the firing system of the surgical instrument 10. In various forms, the motor 714 may be a DC brushed driving motor having a maximum rotational speed of approximately 25,000 RPM. In other arrangements, the motor 714 may include a brushless motor, a cordless motor, a synchronous motor, a stepper motor, or any other suitable electric motor. The motor driver 715 may comprise an H-Bridge driver comprising field-effect transistors (FETs) 719, for example. The motor 714 can be powered by the power assembly 706 releasably mounted to the handle assembly 500 for supplying control power to the surgical instrument 10. The power assembly 706 may comprise a battery which may include a number of battery cells connected in series that can be used as the power source to power the surgical instrument 10. In certain circumstances, the battery cells of the power assembly 706 may be replaceable and/or rechargeable. In at least one example, the battery cells can be Lithium-Ion batteries which can be separably couplable to the power assembly 706.

The shaft assembly 704 may include a shaft assembly controller 722 which can communicate with a safety controller and power management controller 716 through an interface while the shaft assembly 704 and the power assembly 706 are coupled to the handle assembly 702. For example, the interface may comprise a first interface portion 725 which may include one or more electric connectors for coupling engagement with corresponding shaft assembly electric connectors and a second interface portion 727 which may include one or more electric connectors for coupling engagement with corresponding power assembly electric connectors to permit electrical communication between the shaft assembly controller 722 and the power management controller 716 while the shaft assembly 704 and the power assembly 706 are coupled to the handle assembly 702. One or more communication signals can be transmitted through the interface to communicate one or more of the power requirements of the attached interchangeable shaft assembly 704 to the power management controller 716. In response, the power management controller may modulate the power output of the battery of the power assembly 706, as described below in greater detail, in accordance with the power requirements of the attached shaft assembly 704. The connectors may comprise switches which can be activated after mechanical coupling engagement of the handle assembly 702 to the shaft assembly 704 and/or to the power assembly 706 to allow electrical communication between the shaft assembly controller 722 and the power management controller 716.

The interface can facilitate transmission of the one or more communication signals between the power management controller 716 and the shaft assembly controller 722 by routing such communication signals through a main controller 717 residing in the handle assembly 702, for example. In other circumstances, the interface can facilitate a direct line of communication between the power management controller 716 and the shaft assembly controller 722 through the handle assembly 702 while the shaft assembly 704 and the power assembly 706 are coupled to the handle assembly 702.

The main controller 717 may be any single core or multicore processor such as those known under the trade name ARM Cortex by Texas Instruments. In one aspect, the main controller 717 may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

The safety controller may be a safety controller platform comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The power assembly 706 may include a power management circuit which may comprise the power management controller 716, a power modulator 738, and a current sense circuit 736. The power management circuit can be configured to modulate power output of the battery based on the power requirements of the shaft assembly 704 while the shaft assembly 704 and the power assembly 706 are coupled to the handle assembly 702. The power management controller 716 can be programmed to control the power modulator 738 of the power output of the power assembly 706 and the current sense circuit 736 can be employed to monitor power output of the power assembly 706 to provide feedback to the power management controller 716 about the power output of the battery so that the power management controller 716 may adjust the power output of the power assembly 706 to maintain a desired output. The power management controller 716 and/or the shaft assembly controller 722 each may comprise one or more processors and/or memory units which may store a number of software modules.

The surgical instrument 10 (FIGS. 1-5) may comprise an output device 742 which may include devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 742 may comprise a display 743 which may be included in the handle assembly 702. The shaft assembly controller 722 and/or the power management controller 716 can provide feedback to a user of the surgical instrument 10 through the output device 742. The interface can be configured to connect the shaft assembly controller 722 and/or the power management controller 716 to the output device 742. The output device 742 can instead be integrated with the power assembly 706. In such circumstances, communication between the output device 742 and the shaft assembly controller 722 may be accomplished through the interface while the shaft assembly 704 is coupled to the handle assembly 702.

The control circuit 700 comprises circuit segments configured to control operations of the powered surgical instrument 10. A safety controller segment (Segment 1) comprises a safety controller and the main controller 717 segment (Segment 2). The safety controller and/or the main controller 717 are configured to interact with one or more additional circuit segments such as an acceleration segment, a display segment, a shaft segment, an encoder segment, a motor segment, and a power segment. Each of the circuit segments may be coupled to the safety controller and/or the main controller 717. The main controller 717 is also coupled to a flash memory. The main controller 717 also comprises a serial communication interface. The main controller 717 comprises a plurality of inputs coupled to, for example, one or more circuit segments, a battery, and/or a plurality of switches. The segmented circuit may be implemented by any suitable circuit, such as, for example, a printed circuit board assembly (PCBA) within the powered surgical instrument 10. It should be understood that the term processor as used herein includes any microprocessor, processors, controller, controllers, or other basic computing device that incorporates the functions of a computer's central processing unit (CPU) on an integrated circuit or at most a few integrated circuits. The main controller 717 is a multipurpose, programmable device that accepts digital data as input, processes it according to instructions stored in its memory, and provides results as output. It is an example of sequential digital logic, as it has internal memory. The control circuit 700 can be configured to implement one or more of the processes described herein.

The acceleration segment (Segment 3) comprises an accelerometer. The accelerometer is configured to detect movement or acceleration of the powered surgical instrument 10. Input from the accelerometer may be used to transition to and from a sleep mode, identify an orientation of the powered surgical instrument, and/or identify when the surgical instrument has been dropped. In some examples, the acceleration segment is coupled to the safety controller and/or the main controller 717.

The display segment (Segment 4) comprises a display connector coupled to the main controller 717. The display connector couples the main controller 717 to a display through one or more integrated circuit drivers of the display. The integrated circuit drivers of the display may be integrated with the display and/or may be located separately from the display. The display may comprise any suitable display, such as, for example, an organic light-emitting diode (OLED) display, a liquid-crystal display (LCD), and/or any other suitable display. In some examples, the display segment is coupled to the safety controller.

The shaft segment (Segment 5) comprises controls for an interchangeable shaft assembly 500 coupled to the surgical instrument 10 (FIGS. 1-5) and/or one or more controls for an end effector 1500 coupled to the interchangeable shaft assembly 500. The shaft segment comprises a shaft connector configured to couple the main controller 717 to a shaft PCBA. The shaft PCBA comprises a low-power microcontroller with a ferroelectric random access memory (FRAM), an articulation switch, a shaft release Hall effect switch, and a shaft PCBA EEPROM. The shaft PCBA EEPROM comprises one or more parameters, routines, and/or programs specific to the interchangeable shaft assembly 500 and/or the shaft PCBA. The shaft PCBA may be coupled to the interchangeable shaft assembly 500 and/or integral with the surgical instrument 10. In some examples, the shaft segment comprises a second shaft EEPROM. The second shaft EEPROM comprises a plurality of algorithms, routines, parameters, and/or other data corresponding to one or more shaft assemblies 500 and/or end effectors 1500 that may be interfaced with the powered surgical instrument 10.

The position encoder segment (Segment 6) comprises one or more magnetic angle rotary position encoders. The one or more magnetic angle rotary position encoders are configured to identify the rotational position of the motor 714, an interchangeable shaft assembly 500, and/or an end effector 1500 of the surgical instrument 10 (FIGS. 1-5). In some examples, the magnetic angle rotary position encoders may be coupled to the safety controller and/or the main controller 717.

The motor circuit segment (Segment 7) comprises a motor 714 configured to control movements of the powered surgical instrument 10 (FIGS. 1-5). The motor 714 is coupled to the main microcontroller processor 717 by an H-bridge driver comprising one or more H-bridge field-effect transistors (FETs) and a motor controller. The H-bridge driver is also coupled to the safety controller. A motor current sensor is coupled in series with the motor to measure the current draw of the motor. The motor current sensor is in signal communication with the main controller 717 and/or the safety controller. In some examples, the motor 714 is coupled to a motor electromagnetic interference (EMI) filter.

The motor controller controls a first motor flag and a second motor flag to indicate the status and position of the motor 714 to the main controller 717. The main controller 717 provides a pulse-width modulation (PWM) high signal, a PWM low signal, a direction signal, a synchronize signal, and a motor reset signal to the motor controller through a buffer. The power segment is configured to provide a segment voltage to each of the circuit segments.

The power segment (Segment 8) comprises a battery coupled to the safety controller, the main controller 717, and additional circuit segments. The battery is coupled to the segmented circuit by a battery connector and a current sensor. The current sensor is configured to measure the total current draw of the segmented circuit. In some examples, one or more voltage converters are configured to provide predetermined voltage values to one or more circuit segments. For example, in some examples, the segmented circuit may comprise 3.3V voltage converters and/or 5V voltage converters. A boost converter is configured to provide a boost voltage up to a predetermined amount, such as, for example, up to 13V. The boost converter is configured to provide additional voltage and/or current during power intensive operations and prevent brownout or low-power conditions.

A plurality of switches are coupled to the safety controller and/or the main controller 717. The switches may be configured to control operations of the surgical instrument 10 (FIGS. 1-5), of the segmented circuit, and/or indicate a status of the surgical instrument 10. A bail-out door switch and Hall effect switch for bailout are configured to indicate the status of a bail-out door. A plurality of articulation switches, such as, for example, a left side articulation left switch, a left side articulation right switch, a left side articulation center switch, a right side articulation left switch, a right side articulation right switch, and a right side articulation center switch are configured to control articulation of an interchangeable shaft assembly 500 (FIGS. 1 and 3) and/or the end effector 300 (FIGS. 1 and 4). A left side reverse switch and a right side reverse switch are coupled to the main controller 717. The left side switches comprising the left side articulation left switch, the left side articulation right switch, the left side articulation center switch, and the left side reverse switch are coupled to the main controller 717 by a left flex connector. The right side switches comprising the right side articulation left switch, the right side articulation right switch, the right side articulation center switch, and the right side reverse switch are coupled to the main controller 717 by a right flex connector. A firing switch, a clamp release switch, and a shaft engaged switch are coupled to the main controller 717.

Any suitable mechanical, electromechanical, or solid state switches may be employed to implement the plurality of switches, in any combination. For example, the switches may be limit switches operated by the motion of components associated with the surgical instrument 10 (FIGS. 1-5) or the presence of an object. Such switches may be employed to control various functions associated with the surgical instrument 10. A limit switch is an electromechanical device that consists of an actuator mechanically linked to a set of contacts. When an object comes into contact with the actuator, the device operates the contacts to make or break an electrical connection. Limit switches are used in a variety of applications and environments because of their ruggedness, ease of installation, and reliability of operation. They can determine the presence or absence, passing, positioning, and end of travel of an object. In other implementations, the switches may be solid state switches that operate under the influence of a magnetic field such as Hall-effect devices, magneto-resistive (MR) devices, giant magneto-resistive (GMR) devices, magnetometers, among others. In other implementations, the switches may be solid state switches that operate under the influence of light, such as optical sensors, infrared sensors, ultraviolet sensors, among others. Still, the switches may be solid state devices such as transistors (e.g., FET, Junction-FET, metal-oxide semiconductor-FET (MOSFET), bipolar, and the like). Other switches may include electrical conductorless switches, ultrasonic switches, accelerometers, inertial sensors, among others.

Figure 17:
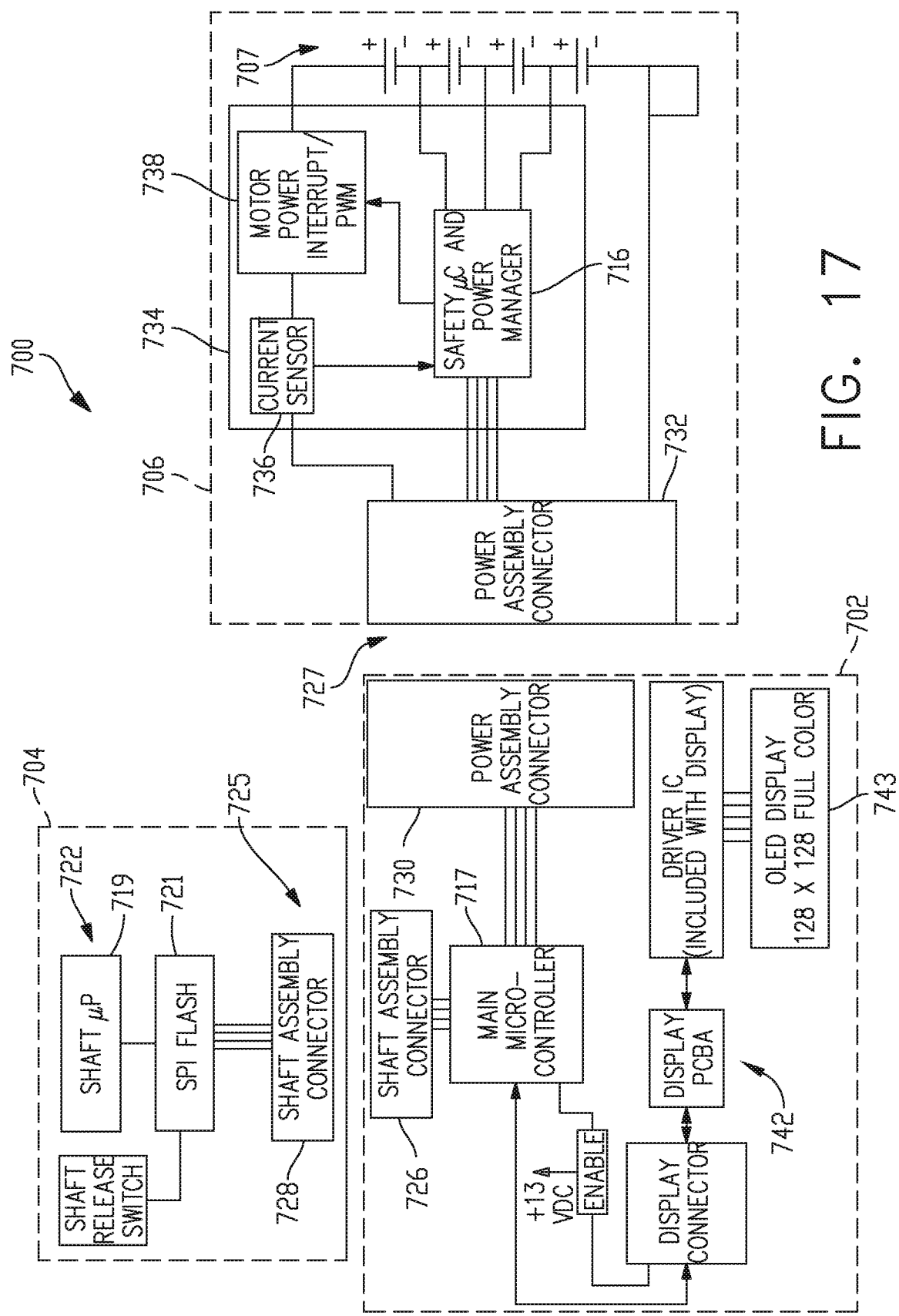
FIG. 17 is a block diagram of the control circuit of the surgical instrument of FIG. 1 illustrating interfaces between the handle assembly, the power assembly, and the handle assembly and the interchangeable shaft assembly according to one aspect of this disclosure.

FIG. 17 is another block diagram of the control circuit 700 of the surgical instrument of FIG. 1 illustrating interfaces between the handle assembly 702 and the power assembly 706 and between the handle assembly 702 and the interchangeable shaft assembly 704 according to one aspect of this disclosure. The handle assembly 702 may comprise a main controller 717, a shaft assembly connector 726 and a power assembly connector 730. The power assembly 706 may include a power assembly connector 732, a power management circuit 734 that may comprise the power management controller 716, a power modulator 738, and a current sense circuit 736. The shaft assembly connectors 730, 732 form an interface 727. The power management circuit 734 can be configured to modulate power output of the battery 707 based on the power requirements of the interchangeable shaft assembly 704 while the interchangeable shaft assembly 704 and the power assembly 706 are coupled to the handle assembly 702. The power management controller 716 can be programmed to control the power modulator 738 of the power output of the power assembly 706 and the current sense circuit 736 can be employed to monitor power output of the power assembly 706 to provide feedback to the power management controller 716 about the power output of the battery 707 so that the power management controller 716 may adjust the power output of the power assembly 706 to maintain a desired output. The shaft assembly 704 comprises a shaft processor 719 coupled to a non-volatile memory 721 and shaft assembly connector 728 to electrically couple the shaft assembly 704 to the handle assembly 702. The shaft assembly connectors 726, 728 form interface 725. The main controller 717, the shaft processor 719, and/or the power management controller 716 can be configured to implement one or more of the processes described herein.

The surgical instrument 10 (FIGS. 1-5) may comprise an output device 742 to a sensory feedback to a user. Such devices may comprise visual feedback devices (e.g., an LCD display screen, LED indicators), audio feedback devices (e.g., a speaker, a buzzer), or tactile feedback devices (e.g., haptic actuators). In certain circumstances, the output device 742 may comprise a display 743 that may be included in the handle assembly 702. The shaft assembly controller 722 and/or the power management controller 716 can provide feedback to a user of the surgical instrument 10 through the output device 742. The interface 727 can be configured to connect the shaft assembly controller 722 and/or the power management controller 716 to the output device 742. The output device 742 can be integrated with the power assembly 706. Communication between the output device 742 and the shaft assembly controller 722 may be accomplished through the interface 725 while the interchangeable shaft assembly 704 is coupled to the handle assembly 702. Having described a control circuit 700 (FIGS. 16A-16B and 6) for controlling the operation of the surgical instrument 10 (FIGS. 1-5), the disclosure now turns to various configurations of the surgical instrument 10 (FIGS. 1-5) and control circuit 700.

Figure 18:
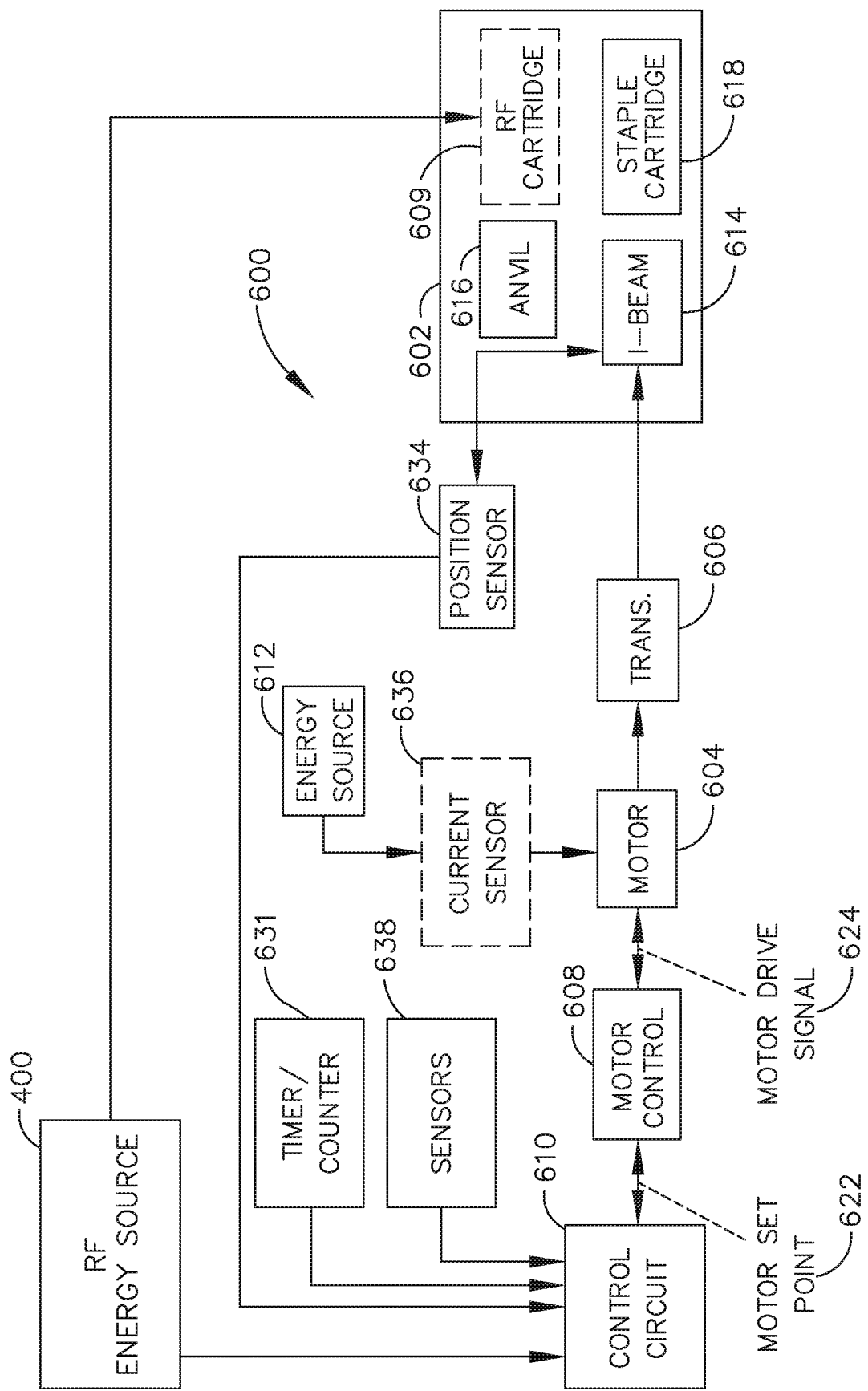
FIG. 18 is a schematic diagram of a surgical instrument configured to control various functions according to one aspect of this disclosure.

FIG. 18 is a schematic diagram of a surgical instrument 600 configured to control various functions according to one aspect of this disclosure. In one aspect, the surgical instrument 600 is programmed to control distal translation of a displacement member such as the I-beam 614. The surgical instrument 600 comprises an end effector 602 that may comprise an anvil 616, an I-beam 614, and a removable staple cartridge 618 which may be interchanged with an RF cartridge 609 (shown in dashed line). The end effector 602, anvil 616, I-beam 614, staple cartridge 618, and RF cartridge 609 may be configured as described herein, for example, with respect to FIGS. 1-15. For conciseness and clarity of disclosure, several aspects of the present disclosure may be described with reference to FIG. 18. It will be appreciated that the components shown schematically in FIG. 18 such as the control circuit 610, sensors 638, position sensor 634, end effector 602, I-beam 614, staple cartridge 618, RF cartridge 609, anvil 616, are described in connection with FIGS. 1-17 of this disclosure.

Accordingly, the components represented schematically in FIG. 18 may be readily substituted with the physical and functional equivalent components described in connection with FIGS. 1-17. For example, in one aspect, the control circuit 610 may be implemented as the control circuit 700 shown and described in connection with FIGS. 16-17. In one aspect, the sensors 638 may be implemented as a limit switch, electromechanical device, solid state switches, Hall-effect devices, magneto-resistive (MR) devices, giant magneto-resistive (GMR) devices, magnetometers, among others. In other implementations, the sensors 638 may be solid state switches that operate under the influence of light, such as optical sensors, infrared sensors, ultraviolet sensors, among others. Still, the switches may be solid state devices such as transistors (e.g., FET, Junction-FET, metal-oxide semiconductor-FET (MOSFET), bipolar, and the like). In other implementations, the sensors 638 may include electrical conductorless switches, ultrasonic switches, accelerometers, inertial sensors, among others. In one aspect, the position sensor 634 may be implemented as an absolute positioning system comprising a magnetic rotary absolute positioning system implemented as an AS5055EQFT single-chip magnetic rotary position sensor available from Austria Microsystems, AG. The position sensor 634 may interface with the control circuit 700 to provide an absolute positioning system. The position may include multiple Hall-effect elements located above a magnet and coupled to a CORDIC processor (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. In one aspect, the end effector 602 may be implemented as surgical end effector 1500 shown and described in connection with FIGS. 1, 2, and 4. In one aspect, the I-beam 614 may be implemented as the knife member 1330 comprising a knife body 1332 that operably supports a tissue cutting blade 1334 thereon and may further include anvil engagement tabs or features 1336 and channel engagement features or a foot 1338 as shown and described in connection with FIGS. 2-4, 8, 11 and 14. In one aspect, the staple cartridge 618 may be implemented as the standard (mechanical) surgical fastener cartridge 1400 shown and described in connection with FIG. 4. In one aspect, the RF cartridge 609 may be implemented as the radio frequency (RF) cartridge 1700 shown and described in connection with FIGS. 1, 2, 6, and 10-13. In one aspect, the anvil 616 may be implemented the anvil 1810 shown and described in connection with FIGS. 1, 2, 4, and 6. These and other sensors arrangements are described in commonly owned U.S. patent application Ser. No. 15/628,175, entitled TECHNIQUES FOR ADAPTIVE CONTROL OF MOTOR VELOCITY OF A SURGICAL STAPLING AND CUTTING INSTRUMENT, which is incorporated herein by reference in its entirety.

The position, movement, displacement, and/or translation of a liner displacement member, such as the I-beam 614, can be measured by an absolute positioning system, sensor arrangement, and position sensor represented as position sensor 634. Because the I-beam 614 is coupled to the longitudinally movable drive member 540, the position of the I-beam 614 can be determined by measuring the position of the longitudinally movable drive member 540 employing the position sensor 634. Accordingly, in the following description, the position, displacement, and/or translation of the I-beam 614 can be achieved by the position sensor 634 as described herein. A control circuit 610, such as the control circuit 700 described in FIGS. 16A and 16B, may be programmed to control the translation of the displacement member, such as the I-beam 614, as described herein. The control circuit 610, in some examples, may comprise one or more microcontrollers, microprocessors, or other suitable processors for executing instructions that cause the processor or processors to control the displacement member, e.g., the I-beam 614, in the manner described. In one aspect, a timer/counter circuit 631 provides an output signal, such as elapsed time or a digital count, to the control circuit 610 to correlate the position of the I-beam 614 as determined by the position sensor 634 with the output of the timer/counter circuit 631 such that the control circuit 610 can determine the position of the I-beam 614 at a specific time (t) relative to a starting position. The timer/counter circuit 631 may be configured to measure elapsed time, count external evens, or time external events.

The control circuit 610 may generate a motor set point signal 622. The motor set point signal 622 may be provided to a motor controller 608. The motor controller 608 may comprise one or more circuits configured to provide a motor drive signal 624 to the motor 604 to drive the motor 604 as described herein. In some examples, the motor 604 may be a brushed DC electric motor, such as the motor 505 shown in FIG. 1. For example, the velocity of the motor 604 may be proportional to the motor drive signal 624. In some examples, the motor 604 may be a brushless direct current (DC) electric motor and the motor drive signal 624 may comprise a pulse-width-modulated (PWM) signal provided to one or more stator windings of the motor 604. Also, in some examples, the motor controller 608 may be omitted and the control circuit 610 may generate the motor drive signal 624 directly.

The motor 604 may receive power from an energy source 612. The energy source 612 may be or include a battery, a super capacitor, or any other suitable energy source 612. The motor 604 may be mechanically coupled to the I-beam 614 via a transmission 606. The transmission 606 may include one or more gears or other linkage components to couple the motor 604 to the I-beam 614. A position sensor 634 may sense a position of the I-beam 614. The position sensor 634 may be or include any type of sensor that is capable of generating position data that indicates a position of the I-beam 614. In some examples, the position sensor 634 may include an encoder configured to provide a series of pulses to the control circuit 610 as the I-beam 614 translates distally and proximally. The control circuit 610 may track the pulses to determine the position of the I-beam 614. Other suitable position sensor may be used, including, for example, a proximity sensor. Other types of position sensors may provide other signals indicating motion of the I-beam 614. Also, in some examples, the position sensor 634 may be omitted. Where the motor 604 is a stepper motor, the control circuit 610 may track the position of the I-beam 614 by aggregating the number and direction of steps that the motor 604 has been instructed to execute. The position sensor 634 may be located in the end effector 602 or at any other portion of the instrument.

The control circuit 610 may be in communication with one or more sensors 638. The sensors 638 may be positioned on the end effector 602 and adapted to operate with the surgical instrument 600 to measure the various derived parameters such as gap distance versus time, tissue compression versus time, and anvil strain versus time. The sensors 638 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 602. The sensors 638 may include one or more sensors.

The one or more sensors 638 may comprise a strain gauge, such as a micro-strain gauge, configured to measure the magnitude of the strain in the anvil 616 during a clamped condition. The strain gauge provides an electrical signal whose amplitude varies with the magnitude of the strain. The sensors 638 may comprise a pressure sensor configured to detect a pressure generated by the presence of compressed tissue between the anvil 616 and the staple cartridge 618. The sensors 638 may be configured to detect impedance of a tissue section located between the anvil 616 and the staple cartridge 618 that is indicative of the thickness and/or fullness of tissue located therebetween.

The sensors 638 may be is configured to measure forces exerted on the anvil 616 by the closure drive system. For example, one or more sensors 638 can be at an interaction point between the closure tube 1910 (FIGS. 1-4) and the anvil 616 to detect the closure forces applied by the closure tube 1910 to the anvil 616. The forces exerted on the anvil 616 can be representative of the tissue compression experienced by the tissue section captured between the anvil 616 and the staple cartridge 618. The one or more sensors 638 can be positioned at various interaction points along the closure drive system to detect the closure forces applied to the anvil 616 by the closure drive system. The one or more sensors 638 may be sampled in real time during a clamping operation by a processor as described in FIGS. 16A-16B. The control circuit 610 receives real-time sample measurements to provide analyze time based information and assess, in real time, closure forces applied to the anvil 616.

A current sensor 636 can be employed to measure the current drawn by the motor 604. The force required to advance the I-beam 614 corresponds to the current drawn by the motor 604. The force is converted to a digital signal and provided to the control circuit 610.

The RF energy source 400 is coupled to the end effector 602 and is applied to the RF cartridge 609 when the RF cartridge 609 is loaded in the end effector 602 in place of the staple cartridge 618. The control circuit 610 controls the delivery of the RF energy to the RF cartridge 609.

Systems and Methods of Displaying Surgical Instrument Status

In a surgical sealing and stapling instrument, it may be useful to display a variety of information captured by the sensors of the surgical instrument to the operator so that the operator can ensure that the instrument is functioning properly or take corrective action if unexpected tissue conditions are being encountered or if the instrument is not functioning properly.

In various aspects, the surgical instrument can include one or more sensors that are configured to measure a variety of different parameters associated with the operation of the surgical instrument. Such parameters can include the status of the RF energy applied by the surgical instrument, the temperature of the tissue being sealed by the surgical instrument, the water content of the tissue, the operational status of the surgical instrument, and the thickness of the clamped tissue. The surgical instrument can be configured to monitor these various parameters and present information associated with them to the operator of the instrument via, for example, the display 430 (FIG. 1). In various aspects, the display 430 can present the monitored parameters to the operator via a graphical display.

Figure 19:
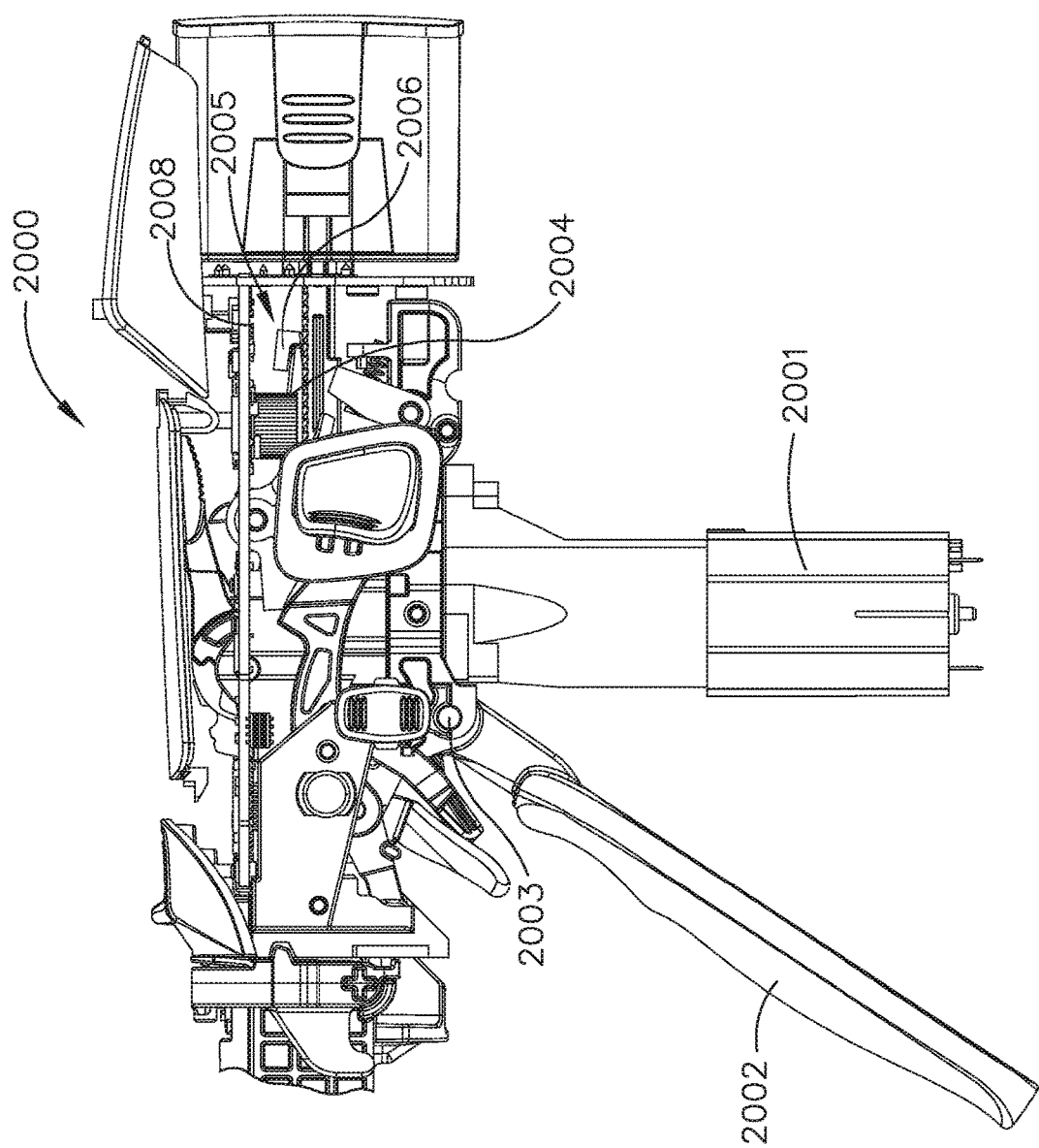
FIG. 19 is side elevational view of the surgical instrument with the casing removed displaying a trigger sensing assembly, wherein the closure trigger is in the unactuated position according to one aspect of this disclosure.
Figure 20:
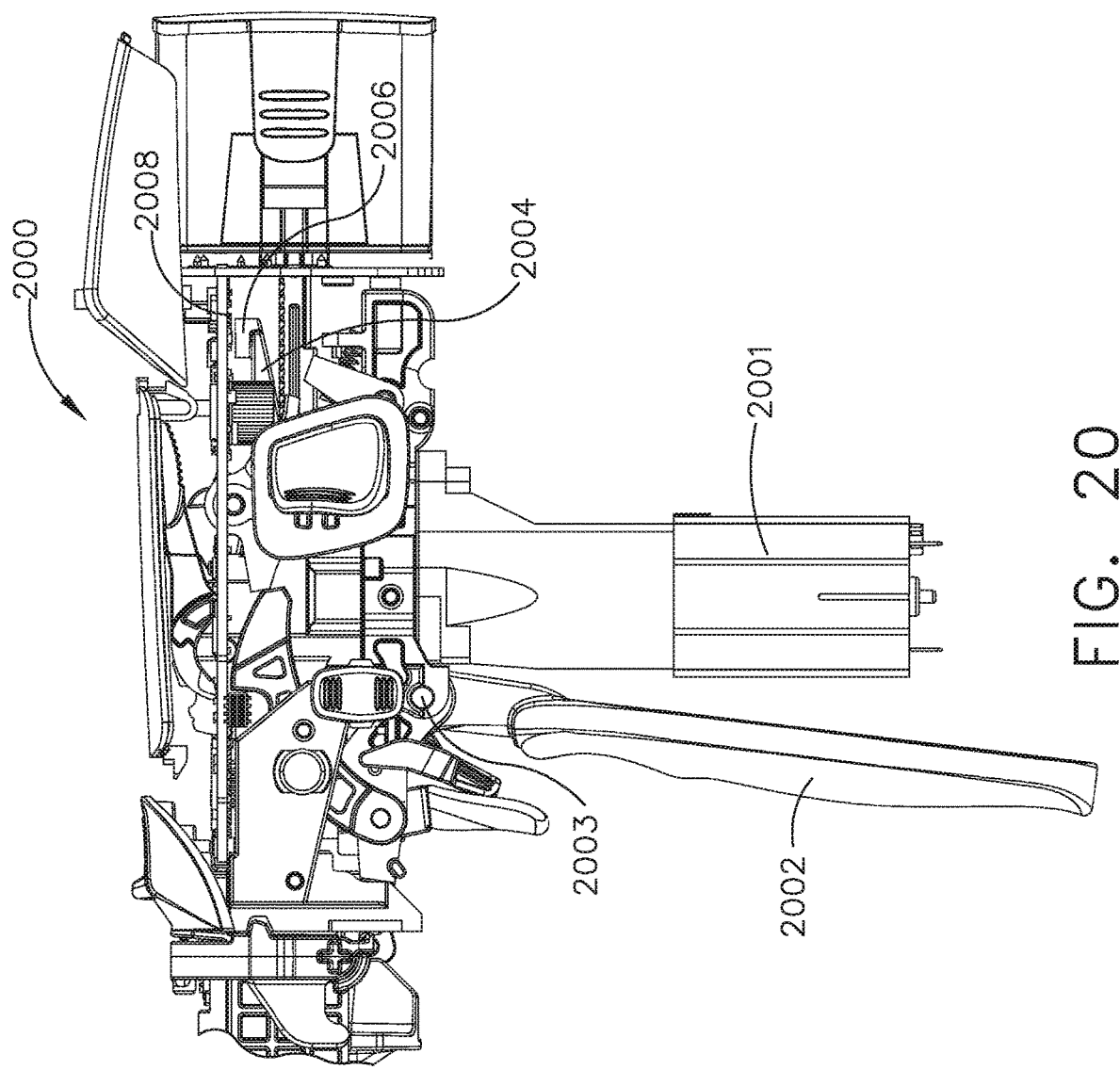
FIG. 20 is a side elevational view if the surgical instrument with the casing removed displaying a trigger sensing assembly, wherein the closure trigger is in the actuated position according to one aspect of this disclosure.

In some aspects, the surgical instrument can include a sensor or sensor assembly configured to detect the position of the closure trigger, i.e., whether the closure trigger is actuated. One such aspect is depicted in FIGS. 19-20, which are side elevational views of the surgical instrument 2000 with the casing removed, wherein the closure trigger 2002 is alternatively in the actuated and unactuated positions, in accordance with one or more aspects of the present disclosure. As described in more detail above, the unactuated position of the closure trigger 2002 is associated with an open or unclamped position for the end effector 1500 (FIG. 1) in which tissue can be positioned between the jaws 1600, 1800 and the actuated position of the closure trigger 2002 is associated with a closed or clamped position for the end effector 1500 in which tissue can be clamped between the jaws 1600, 1800. The closure trigger 2002 can comprise an arm 2004 that is connected either directly thereto or indirectly thereto via a mechanical linkage, such that the arm 2004 rotates upon actuation of the closure trigger 2002. In one aspect, a trigger sensing assembly 2005 comprises a magnetic element 2006, such as a permanent magnet, disposed at a distal end of the arm 2004 and a sensor 2008 that is configured to detect the movement of the magnetic element 2006. The sensor 2008 can comprise, for example, a Hall effect sensor configured to detect changes in a magnetic field surrounding the Hall effect sensor caused by the movement of the magnetic element 2006. As the sensor 2008 can detect the movement of the magnetic element 2006 and the movement of the magnetic element 2006 corresponds to the position of the closure trigger 2002 in a known manner, the trigger sensing assembly 2005 can therefore detect whether the closure trigger 2002 is in the actuated position, the unactuated position, or another position therebetween.

In another aspect, the trigger sensing assembly 2005 comprises a sensor or switch that is tripped when the closure drive system 510 (FIG. 1) locks the closure trigger 2002 into the fully depressed or fully actuated position. In such an aspect, the switch can generate a signal indicating that the lock is engaged and thus that the closure trigger 2002 is fully depressed.

In another aspect described in U.S. Patent Application Pub. No. 2014/0296874, entitled ROBOTICALLY-CONTROLLED END EFFECTOR, which is incorporated by reference in its entirety, the trigger sensing assembly 2005 comprises a force sensor positioned between the closure trigger 2002 and the pivot pin 2003 about which the closure trigger 2002 pivots. In this aspect, pulling the closure trigger 2002 towards the pistol grip portion 2001 causes the closure trigger 512 to exert a force on the pivot pin 2003. The force sensor is configured to detect this force and generate a signal in response thereto.

The trigger sensing assembly 2005 can be in signal communication with a controller 2102 (FIG. 25) via a wired or wireless connection such that any signal generated by the trigger sensing assembly 2005 is relayed to the controller 2102. The trigger sensing assembly 2005 can be configured to continuously monitor the position of the closure trigger 2002 throughout the operation of the instrument by sampling the sensed parameter(s) or transmitting a feedback signal indicative of the sensed parameter(s) with a minimal time delay. In various aspects, the trigger sensing assembly 2005 can comprise an analog sensor configured to generate a signal corresponding to the degree of force exerted on the closure trigger 2002 and/or a particular position of the closure trigger 2002. In such aspects, an analog-to-digital converter may be positioned between the trigger sensing assembly 2005 and the controller 2102. In various other aspects, the trigger sensing assembly 2005 can comprise a digital sensor configured to generate a signal indicative only of whether the closure trigger 2002 is actuated or unactuated.

Figure 21:
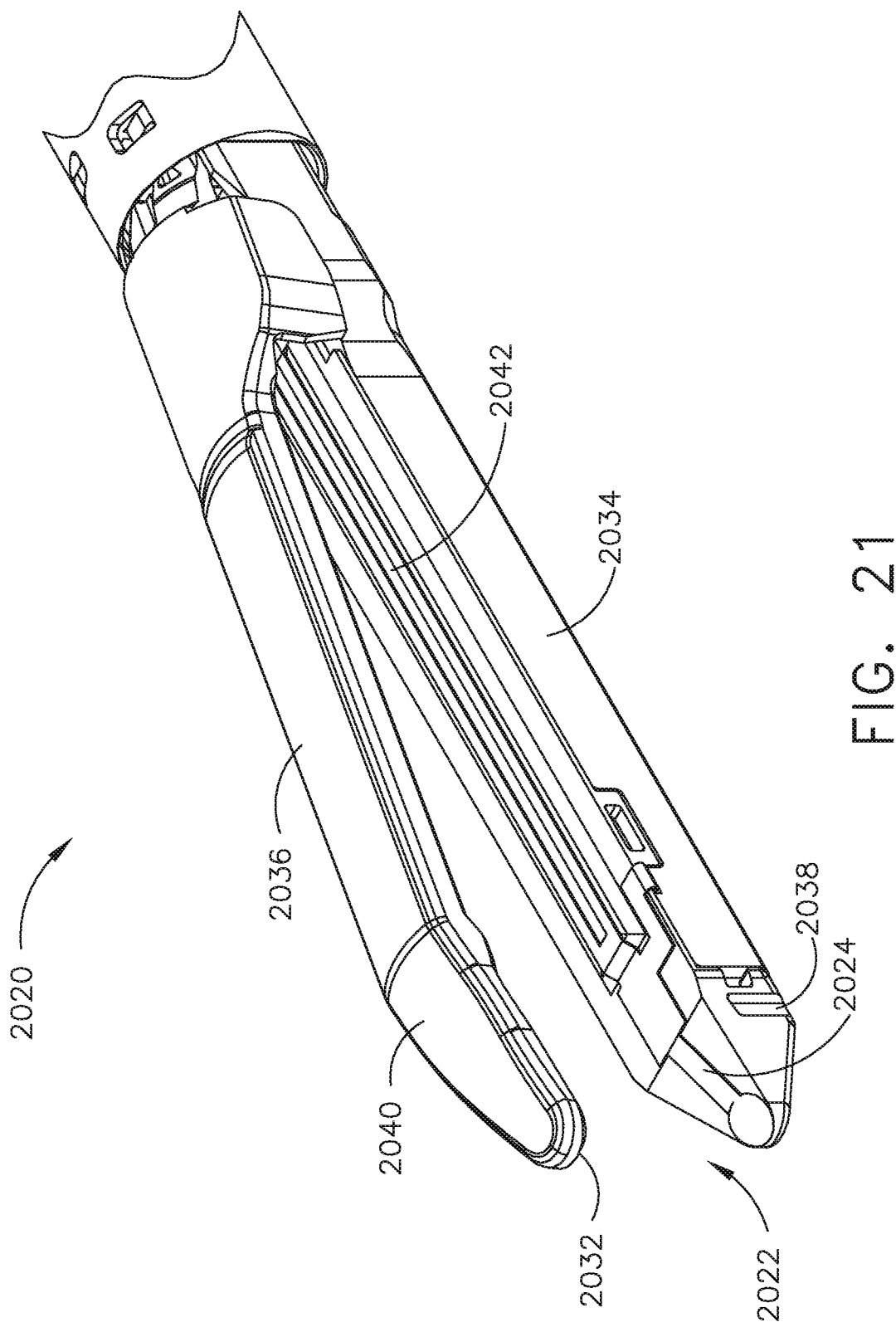
FIG. 21 is a perspective view of an end effector comprising a tissue thickness sensing assembly according to one aspect of this disclosure.
Figure 22:
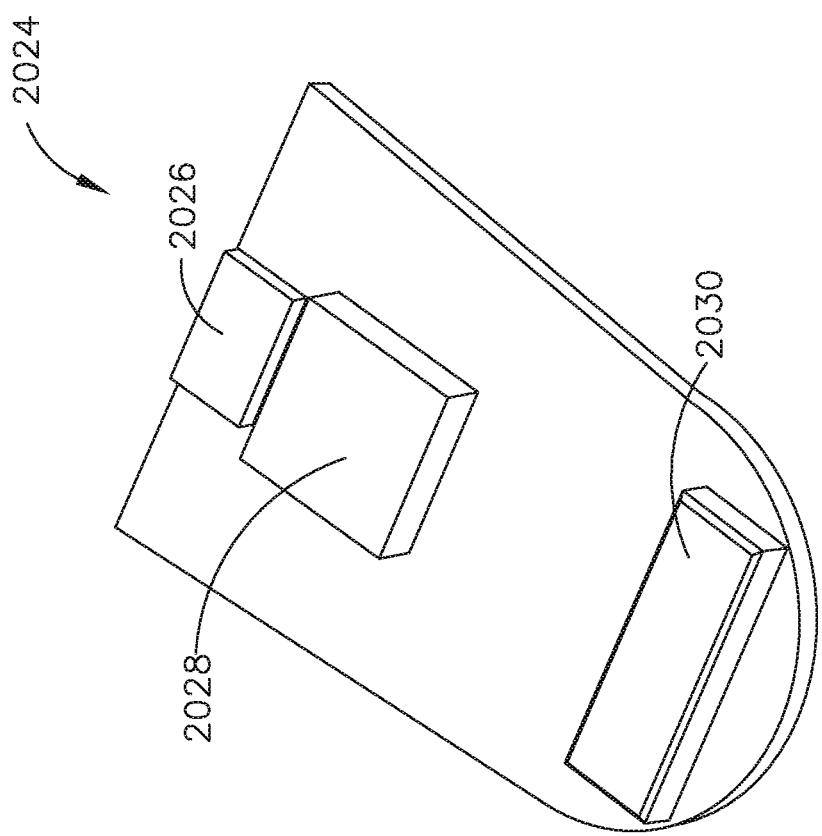
FIG. 22 is a schematic view of a sensor of the tissue thickness sensing assembly according to one aspect of this disclosure.

In some aspects, the surgical instrument can include a sensor or sensor assembly that is configured to detect the thickness of tissue clamped by the end effector. One such aspect is depicted in FIGS. 21-22, which are a perspective view of an end effector 2020 comprising a tissue thickness sensing assembly 2022 and a schematic view of a sensor 2024 of the tissue thickness sensing assembly 2022, in accordance with one or more aspects of the present disclosure. The tissue thickness sensing assembly 2022 can comprise a sensor 2024 disposed on a first jaw 2034 or RF cartridge 2042 and a magnetic element 2032, such as a permanent magnet, disposed on a second jaw 2036 of the end effector 2020. In one aspect, the sensor 2024 is disposed at or adjacent to the distal end 2038 of the first jaw 2034, such that it is positioned distally with respect to the electrodes of the RF cartridge, and the magnetic element 2032 is correspondingly disposed at or adjacent to the distal end 2040 of the second jaw 2036. The sensor 2024 can comprise a magnetic field sensing element 2026 that is configured to detect the movement of the magnetic element 2006, such as a Hall effect sensor configured to detect changes in a magnetic field surrounding the Hall effect sensor caused by the movement of the magnetic element 2032. When the operator closes the end effector 2020, the magnetic element 2032 rotates downwardly closer to the magnetic field sensing element 2026, thereby varying the magnetic field detected by the magnetic field sensing element 2026 as the jaw or jaws rotate into the closed (or clamped position). The strength of the magnetic field from the magnetic element 2032 sensed by the magnetic field sensing element 2026 is indicative of the distance between the first jaw 2034 and the second jaw 2036, which in turn is indicative of the thickness of the tissue clamped therebetween. For instance, a larger distance between the first jaw 2034 and the second jaw 2036, and therefore a weaker magnetic field detected by the magnetic field sensing element 2026, may indicate that thick tissue is present between the first jaw 2034 and the second jaw 2036. Conversely, a shorter distance between the first jaw 2034 and the second jaw 2036, and therefore a stronger magnetic field detected by the magnetic field sensing element 2026, may indicate that thin tissue is present between the first jaw 2034 and the second jaw 2036. The magnetic field sensing element 2026 can be configured to detect and generate a signal corresponding to the relative or absolute strength of the sensed magnetic field, thereby allowing the surgical instrument to detect the relative or absolute thickness of the clamped tissue according to the resolution of the magnetic field sending elements 2026.

In another aspect, the tissue thickness sensing assembly 2022 can comprise a displacement sensor that is disposed at the pivot joint between the first jaw 2034 and the second jaw 2036. In this aspect, the displacement sensor is configured to detect the position of the jaws 2034, 2036 relative to each other, which in turn is indicative of the thickness of the tissue grasped therebetween when the end effector 2020 is in the clamped position. For example, in one aspect described in U.S. Patent Application Pub. No. 2014/0296874 wherein the anvil 1810 comprises pivot pins that are received within corresponding openings disposed on the elongate channel (FIG. 4), the tissue thickness sensing assembly 2022 can comprise a sensor positioned adjacent to, or within, the openings of the elongate channel 1602. In this aspect, as the anvil 1810 is closed, the pivot pins slide through the openings and into contact with the sensor, causing the sensor to generate a signal indicating that the anvil 1810 is closed.

In other aspects, the tissue thickness sensing assembly 2022 can further comprise a reed switch sensor, a displacement sensor, an optical sensor, a magneto-inductive sensor, a force sensor, a pressure sensor, a piezo-resistive film sensor, an ultrasonic sensor, an eddy current sensor, an accelerometer, a pulse oximetry sensor, a temperature sensor, a sensor configured to detect an electrical characteristic of a tissue path (such as capacitance or resistance), or any combination thereof. In one such aspect, the tissue thickness sensing assembly 2022 can comprise a first electrical sensor disposed on the first jaw 2034 and a corresponding second electrical sensor disposed on the second jaw 2036, wherein the first sensor is configured to transmit an electrical current that is detected by the second sensor through tissue captured by the end effector 2020. The detected current can be utilized by the tissue thickness sensing assembly 2022 to determine the thickness of the clamped tissue as tissue resistivity is a function of its thickness (and tissue type, among a variety of other factors).

The tissue thickness sensing assembly 2022 can be in signal communication with a controller 2102 via a wired or wireless connection such that any signal generated by the tissue thickness sensing assembly 2022 is relayed to the controller 2102. For example, the tissue thickness sensing assembly 2022 can comprise a transmitter 2028 configured to transmit the signals generated by the magnetic field sensing element 2026 via a wired or wireless connection to a receiver, which in turn is communicably coupled to the controller 2102. The tissue thickness sensing assembly 2022 can be configured to continuously monitor the thickness of the clamped tissue throughout the operation of the instrument by sampling the sensed parameter(s) or transmitting a feedback signal indicative of the sensed parameter(s) with a minimal time delay. In various aspects, the tissue thickness sensing assembly 2022 can comprise an analog sensor configured to generate a signal corresponding to relative or absolute thickness of the clamped tissue and/or a particular position of either of the first jaw 2034 or the second jaw 2036. In such aspects, an analog-to-digital converter may be positioned between the tissue thickness sensing assembly 2022 and the controller 2102. In various other aspects, the tissue thickness sensing assembly 2022 can comprise a digital sensor configured to generate a signal indicative only of whether the jaws 2034, 2036 are opened or closed.

In some aspects, the tissue thickness sensing assembly 2022 can further comprise a power source 2030 operably connected to the magnetic field sensing element 2026. The power source 2030 can be separate from any other power source associated with the surgical instrument. Alternatively, the issue thickness sensing assembly 2022 can be interconnected with one or more power sources associated with the surgical instrument.

Figure 23:
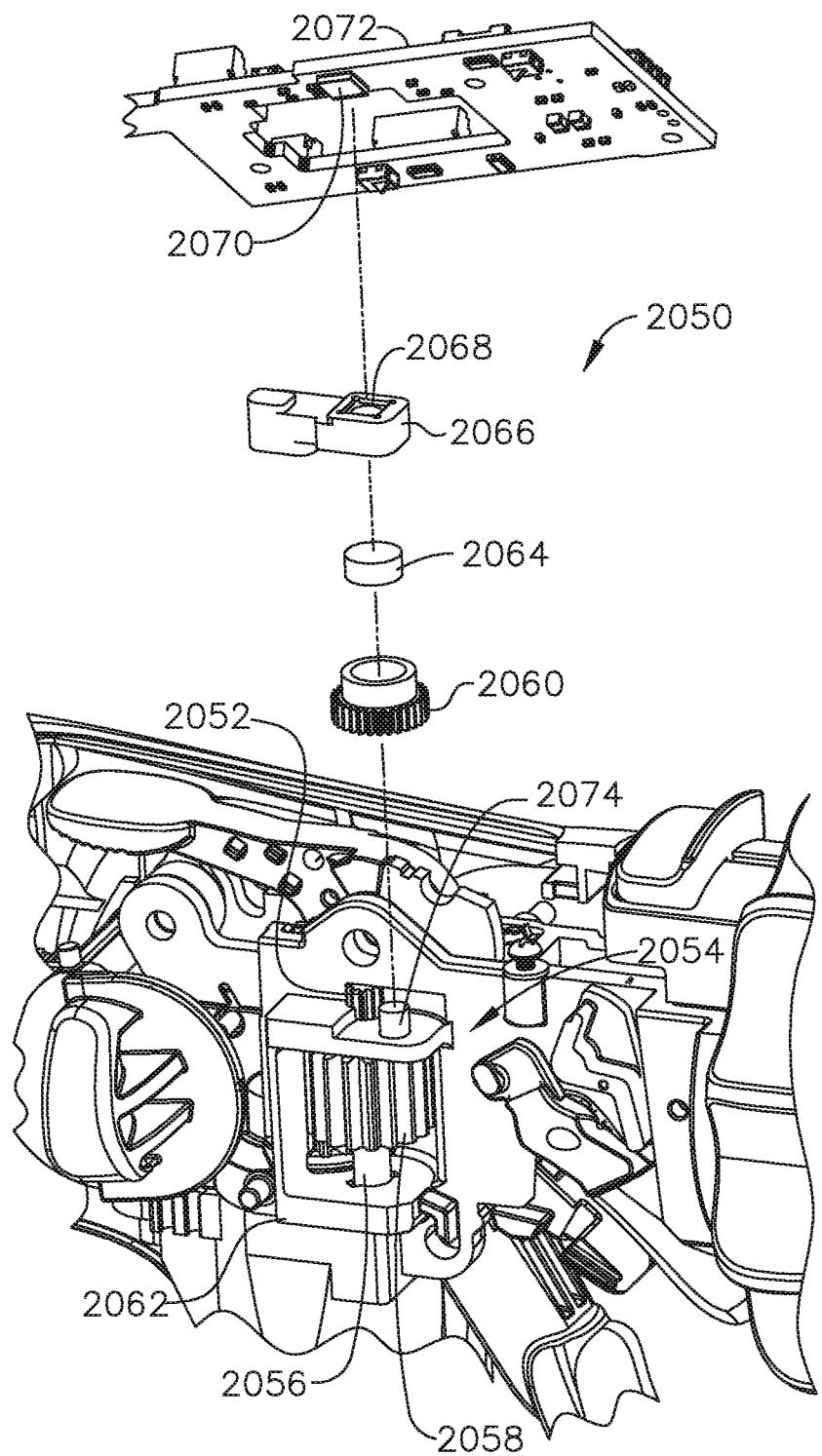
FIG. 23 is an exploded perspective view of a position sensing assembly according to one aspect of this disclosure.

In some aspects, the surgical instrument can include a sensor or sensor assembly configured to detect the position of the longitudinally movable drive member 540 (FIG. 3), knife bar 1320 (FIG. 4), knife member 1330 (FIG. 4), cutting blade 1334 (FIG. 4), and/or other components of the firing drive system 530 (FIG. 3). In various aspects, the position sensing assembly 2050 can be configured to track the linear displacement of the component of the firing drive system 530 utilizing sensors configured to track the rotation of a gear arrangement 2054 engaged with the firing drive system 530. For example, FIG. 23 is an exploded perspective view of a position sensing assembly 2050 configured to detect and track the linear position of the longitudinally movable drive member 540. In the aspect illustrated in FIG. 23, the surgical instrument comprises a drive gear 2058 that is operably driven through a drive shaft 2056 by the electric motor 505 (FIG. 1). The drive gear 2058 meshingly engages the rack of drive teeth 542 (FIG. 3) of the longitudinally movable drive member 540, thereby allowing the motor 505 to drive the linear displacement of the longitudinally movable drive member 540. Rotation of the drive gear 2058 in a first direction causes the longitudinally movable drive member 540 to advance in a distal direction and rotation of the drive gear 2058 in a second direction causes the longitudinally movable drive member 540 to retract in a proximal direction P. In various aspects, the gear arrangement 2054 of the position sensing assembly 2050 can be positioned at or adjacent to the drive gear 2058 engaged with the longitudinally movable drive member 540, as illustrated in FIG. 23. In other aspects, the gear arrangement 2054 of the position sensing assembly 2050 can be positioned downstream of the drive gear 2058 in the firing drive system 530 and/or engaged with other components of the firing drive system 530.

In the illustrated aspect, the gear arrangement 2054 of the position sensing assembly 2050 comprises a first gear 2052 that rotates about the shaft 2056 accordingly to the rotation of the drive gear 2058. Thus, rotation of the first gear 2052 about the shaft 2056 corresponds to the longitudinal translation of the longitudinally movable drive member 540 as driven by the drive gear 2058. The position sensing assembly 2050 further comprises a magnet 2064 that rotates in a manner corresponding to the rotation of the first gear 2052. In one aspect, the magnet 2064 is disposed on the first gear 2052. In this aspect, one revolution of the first gear 2052, and thus the magnet 2064, corresponds to one revolution of the drive gear 2058. In another aspect, the gear arrangement 2054 is configured to serve as a gear reducer assembly providing an alternative ratio between the number of revolutions of the drive gear 2058 and the magnet 2064. In one such aspect illustrated in FIG. 23, the gear arrangement 2054 comprises a second gear 2060, which is meshingly engaged with the first gear 2052. In this aspect, the magnet 2064 is disposed on the second gear 2060. The gear ratio connection between the first gear 2052 and the second gear 2060 can be configured such that a single revolution of the magnet 2064 corresponds to a set linear displacement of the longitudinally movable drive member 540. For example, the gear ratio connection between the first gear 2052 and the second gear 2060 can be configured such that a single revolution of the magnet 2064 can correspond to a full stroke of the longitudinally movable drive member 540. Thus, one full stroke of the longitudinally movable drive member 540 in either the distal or proximal directions corresponds to a single rotation of the second gear 2060. Since the magnet 2064 is coupled to the second gear 260, the magnet 2064 thus makes one full rotation with each full stroke of the longitudinally movable drive member 540.

The position sensing assembly 2050 further comprises a position sensor 2070 operably connected to a circuit 2072. The position sensor 2070 comprises one or more magnetic sensing elements, such as Hall effect elements, and is positioned in proximity to the magnet 2064. As the magnet 2064 rotates, the magnetic sensing elements of the position sensor 2070 determine the absolute angular position of the magnet 2064 over a revolution. In aspects of the surgical instrument wherein one revolution of the magnet 2064 corresponds to one full stroke of the longitudinally movable drive member 540, the particular angular position of the magnet 2064 thus corresponds to a particular linear position of the longitudinally movable drive member 540. In one aspect, the position sensing assembly 2050 is configured to provide a unique position signal corresponding to the location of the longitudinally movable drive member 540 according to the precise angular position of the magnet 2064 as detected by the position sensor 2070.

The position sensor 2070 can comprise any number of magnetic sensing elements, such as magnetic sensors classified according to whether they measure the total magnetic field or the vector components of the magnetic field. A series of n switches, where n is an integer greater than one, may be employed alone or in combination with gear reduction to provide a unique position signal for more than one revolution of the magnet 2064. The state of the switches can be fed back to a controller 2080 that applies logic to determine a unique position signal corresponding to the linear displacement of the longitudinally movable drive member 540.

In one aspect, the position sensor 2070 is supported by a position sensor holder 2066 defining an aperture 2068 configured to contain the position sensor 270 in precise alignment with the magnet 2064 rotating below. The magnet 2064 can be coupled to a structural element 2062, such as a bracket, that supports to gear arrangement 2054 and to the circuit 2072.

Figure 24:
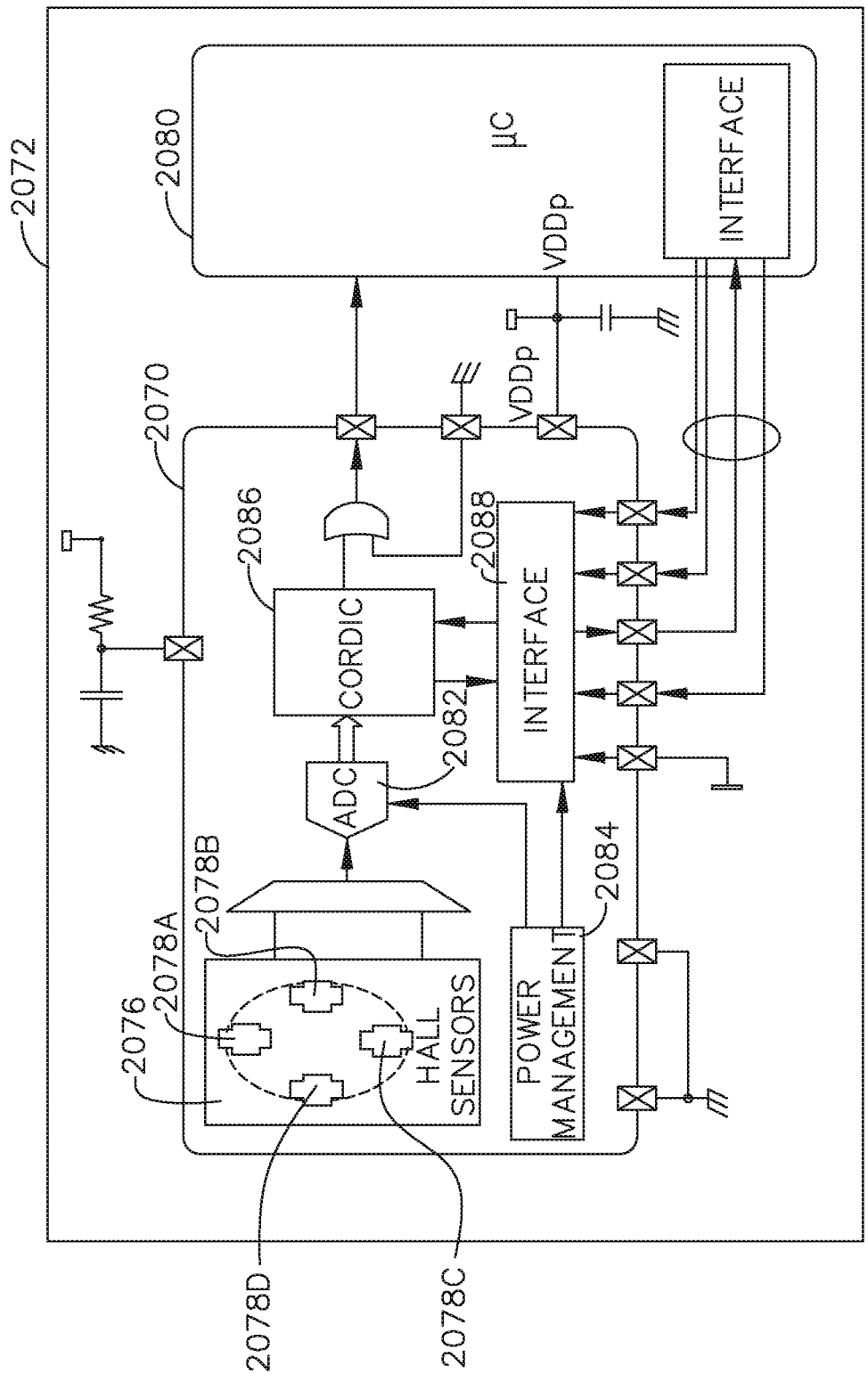
FIG. 24 is a diagram of a circuit and a position sensor of a position sensing assembly according to one aspect of this disclosure.

FIG. 24 is a diagram of a circuit 2072 and a position sensor 2070 of a position sensing assembly 2050, in accordance with one or more aspects of the present disclosure. The position sensor 2070 may be implemented as an AS5055EQFT single-chip magnetic rotary position sensor available from Austria Microsystems, AG. The position sensor 2070 is interfaced with a controller 2080, such as a microcontroller, to provide a system that is able to detect the absolute position of the longitudinally movable drive member 540 and/or other components of the firing drive system 530. In one aspect, the position sensor 2070 is a low-voltage and low-power component and includes four Hall effect elements 2078A, 2078B, 2078C, 2078D in an area 2076 of the position sensor 2070 that is located above the magnet 2064. A high-resolution ADC 2082 and a smart power management controller 2084 are also provided on the chip. A CORDIC (Coordinate Rotation Digital Computer) processor 2086, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as an SPI interface 2088, to the controller 2080. The position sensor 2070 provides 12 or 14 bits of resolution. The position sensor 2070 may be an AS5055 chip provided in a small QFN 16-pin 4×4×0.85 mm package. In the AS5055 position sensor 2070, the Hall effect elements 2078A, 2078B, 2078C, 2078D are capable producing a voltage signal that is indicative of the absolute position of the magnet 2064 in terms of the angle over a single revolution of the magnet 264. This value of the angle, which is unique position signal, is calculated by the CORDIC processor 286 is stored onboard the AS5055 position sensor 2070 in a register or memory. The value of the angle that is indicative of the position of the magnet 2064 over one revolution is provided to the controller 2080 in a variety of techniques, e.g., upon power up or upon request by the controller 2080.

Although the position sensor 2070 is depicted in FIG. 24 as including four Hall effect elements, in other aspects of the surgical instrument, the number of Hall effect elements included in the position sensor 2070 can vary. Generally, the number of Hall effect elements will correspond to the degree of resolution desired for the position sensor 2070 as a larger number of Hall effect elements would allow the position sensor 2070 to detect finer movements of the longitudinally movable drive member 540. In various aspects, the distance between the Hall effect elements can be uniform, i.e., the Hall effect elements can be evenly positioned, so that each Hall effect element corresponds to a set displacement distance of the longitudinally movable drive member 540. Additional aspects of the position sensing assembly 2050, the circuit 2072, and the position sensor 2070 are described in U.S. Patent Application Ser. No. 15/130,590, entitled SYSTEMS AND METHODS FOR CONTROLLING A SURGICAL STAPLING AND CUTTING INSTRUMENT, which is incorporated by reference in its entirety.

In other aspects, the knife bar 1320, knife member 1330, cutting blade 1334, and/or other components of the firing drive system 530 could alternatively be configured to include a rack of drive teeth that meshingly engage the gear arrangement 2054 of the position sensing assembly 2050. In such aspects of the surgical instrument, the position sensing assembly 2050 is configured to track the linear displacement of the particular component of the firing drive system 530, rather than being connected to the drive gear 2058 and/or shaft 2056 driving the displacement of the longitudinally movable drive member 540. Accordingly, it should be appreciated that the principles discussed with respect to the aspect wherein the displacement of the longitudinally movable drive member 540 is tracked are equally applicable to aspects of a position sensing assembly 2050 configured to detect the linear displacement of the knife bar 1320, knife member 1330, cutting blade 1334, and/or other components of the firing drive system 530.

In other aspects, the position sensing assembly 2050 comprises contact or non-contact linear displacement sensors configured to track the linear displacement of the firing drive system 530. The linear displacement sensors can comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable linearly arranged Hall effect sensors, an optical sensing system comprising a movable light source and a series of linearly arranged photo diodes or photo detectors, or an optical sensing system comprising a fixed light source and a series of movable linearly arranged photo diodes or photo detectors, or any combination thereof.

Figure 25:
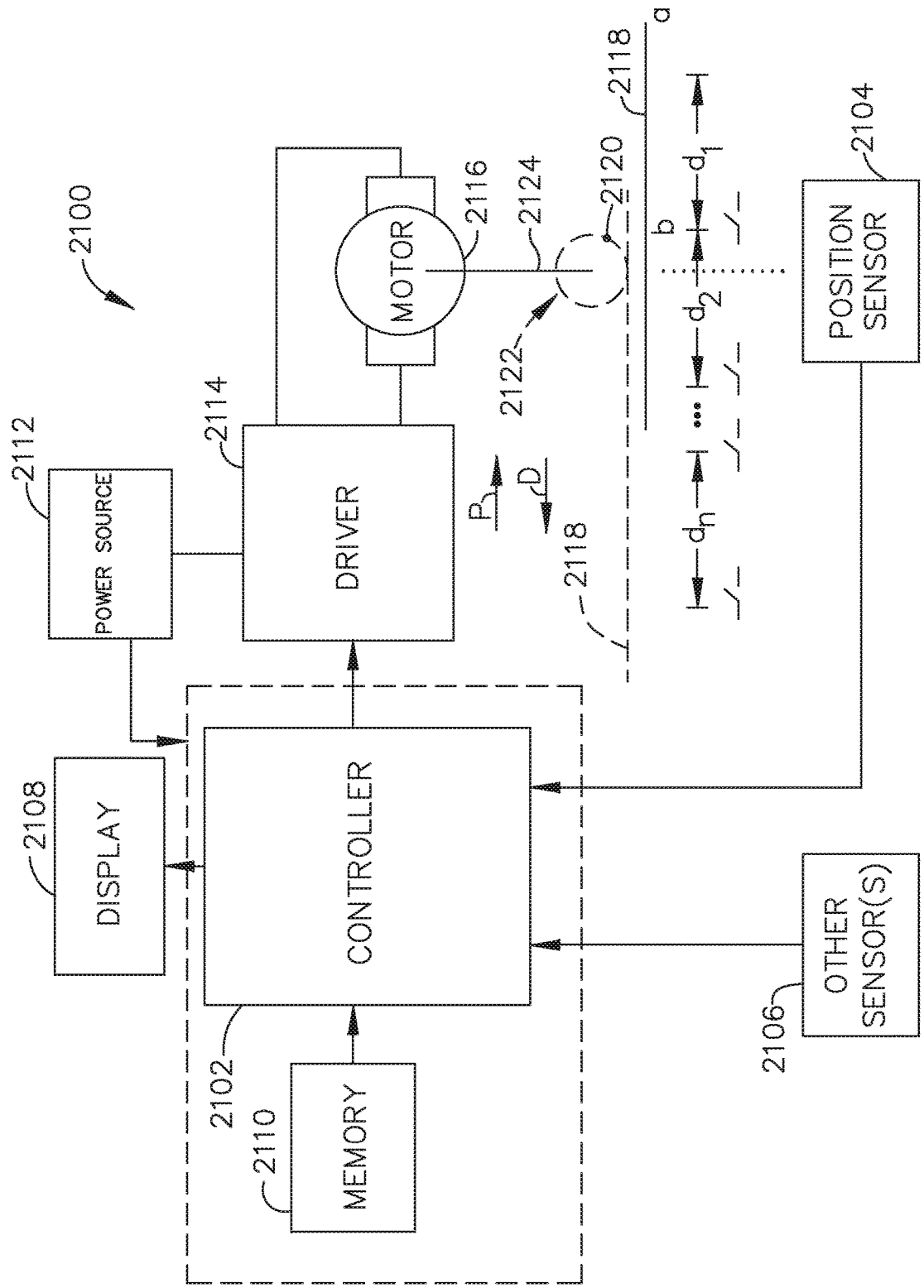
FIG. 25 is a block diagram of one example of a surgical instrument configured to display various statuses of the surgical instrument according to one aspect of this disclosure.
Figure 26:
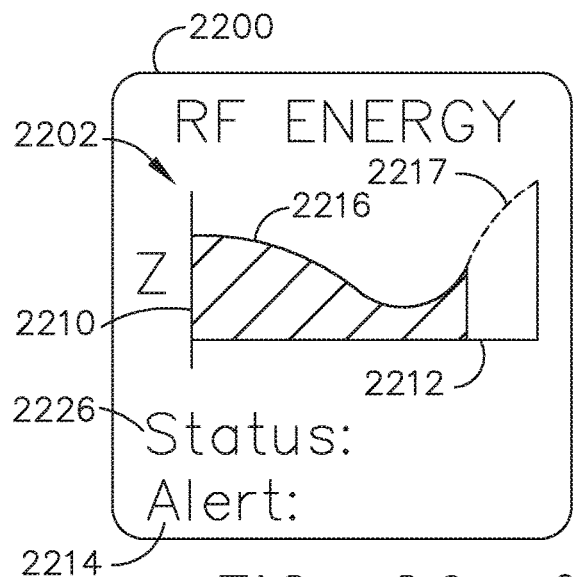
FIG. 26 is a display depicting RF energy status information of the surgical instrument according to one aspect of this disclosure.
Figure 27:
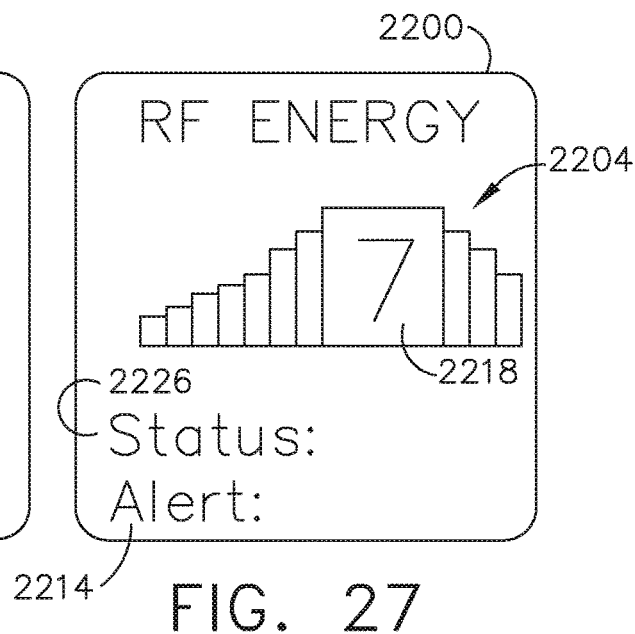
FIG. 27 is a display depicting RF energy status information of the surgical instrument according to one aspect of this disclosure.
Figure 28:
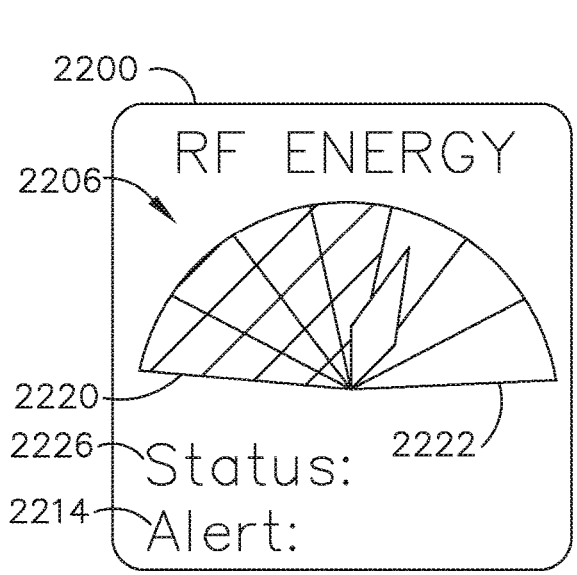
FIG. 28 is a display depicting RF energy status information of the surgical instrument according to one aspect of this disclosure.
Figure 29:
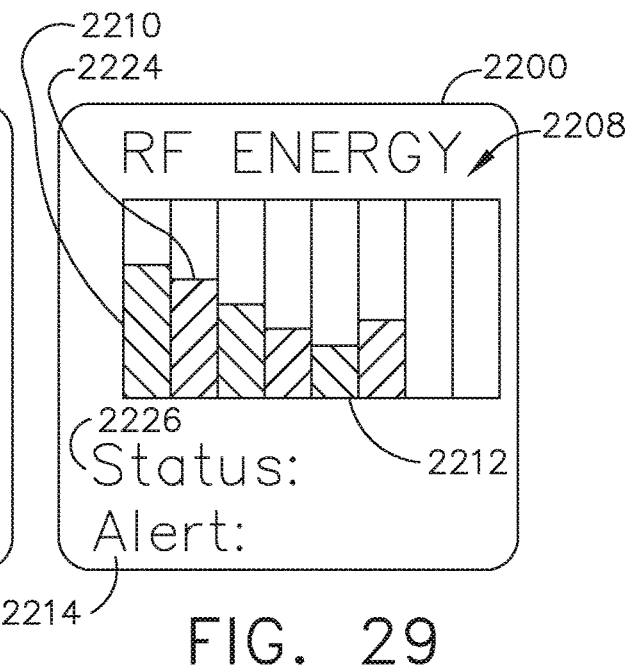
FIG. 29 is a display depicting RF energy status information of the surgical instrument according to one aspect of this disclosure.
Figure 30:
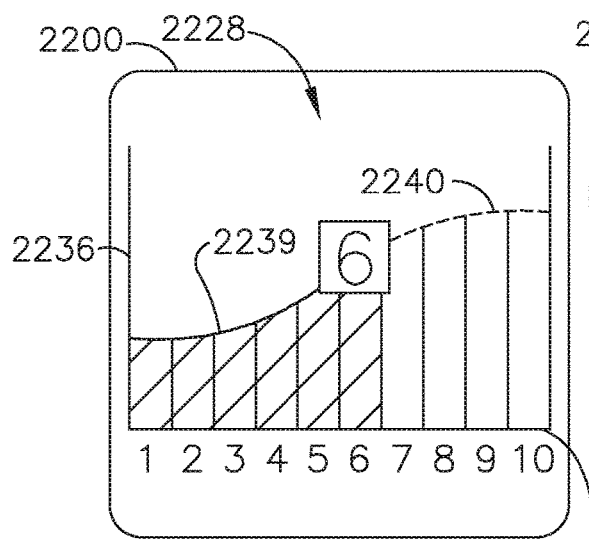
FIG. 30 is a display depicting temperature information of the surgical instrument according to one aspect of this disclosure.
Figure 31:
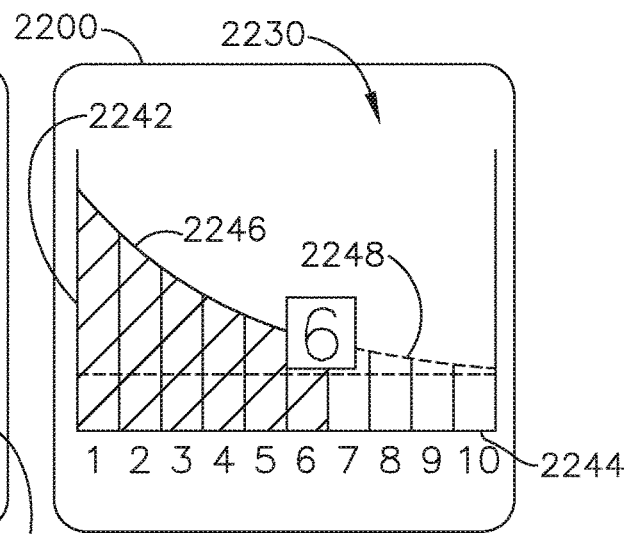
FIG. 31 is a display depicting tissue water content information of the surgical instrument according to one aspect of this disclosure.
Figure 32:
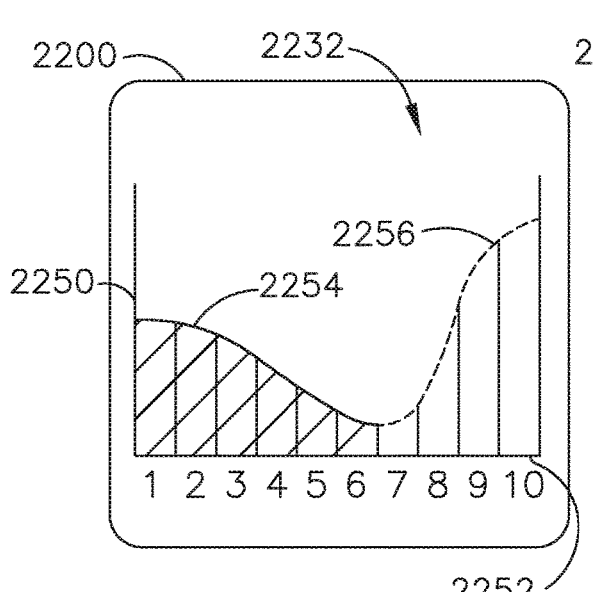
FIG. 32 is a display depicting operational progress information of the surgical instrument according to one aspect of this disclosure.
Figure 33:
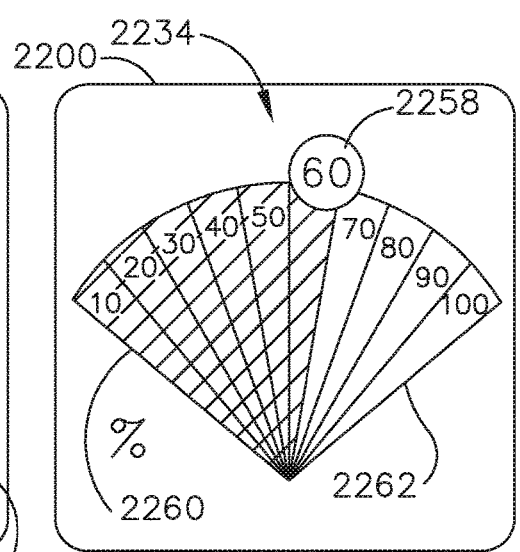
FIG. 33 is a display depicting operational progress information of the surgical instrument according to one aspect of this disclosure.
Figure 34:
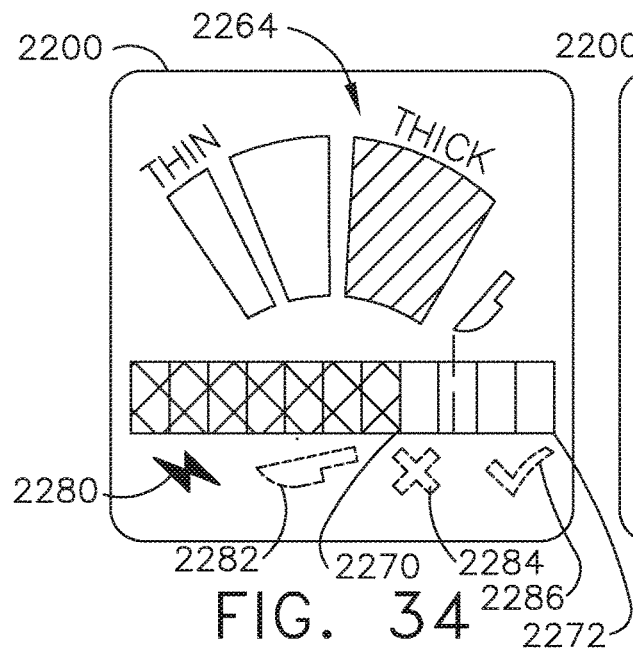
FIG. 34 is a display depicting tissue and operational progress information of the surgical instrument according to one aspect of this disclosure.

FIG. 25 is a block diagram of one example of a surgical instrument 2100 programmed to display various statuses of the surgical instrument 2100, in accordance with one or more aspects of the present disclosure. The surgical instrument 2100 comprises a controller 2102 that is operably connected to one or more sensors 2104, 2106 and a display 2108, which may be disposed on the exterior casing of the surgical instrument 2100. The controller 2102 embodies or executes a logic that controls the operation of the surgical instrument 2100 according to a variety of inputs, such as signals received from the one or more sensors 2104, 2106 with which the controller 2102 is in signal communication. In various aspects, the controller 2102 comprises a processor, such as a CPU, operably connected to a memory 2110 storing program instructions that, when executed by the processor, cause the controller 2102 and/or surgical instrument 2100 to execute a process dictated by the program instructions. In other aspects, the controller 2102 comprises a control circuit that is configured to execute a process according to digital or analog signal input. The control circuit can comprise an ASIC, a FPGA, or any other circuit that is manufacturable or programmable to execute a logic.

The controller 2102 is configured to display various statuses associated with the use of the surgical instrument 2100 on the display 2108 according to input received from a variety of sensors. One such sensor includes the position sensor 2104, which can include the position sensing assembly 2050 (FIG. 23), as described above. Other sensors 2106 from which the controller 2102 receives input can include the trigger sensing assembly 2005 (FIGS. 19-20) and the tissue thickness sensing assembly 2022 (FIGS. 21-22), as described above.

The surgical instrument 2100 further includes a motor 2116, such as an electric motor, that drives a rotatable shaft 224, which operably interfaces with a gear assembly 2122 that is mounted in meshing engagement with a set, or rack, of drive teeth, such as in a rack and pinion arrangement, on a displacement member 2118. In the position sensing assembly 2050, the displacement member 2118 can include, for example, the longitudinally movable drive member 540 of the firing drive system 530. A sensor element or magnet 2120 can be operably coupled to a gear assembly 2122 such that a single revolution of the magnet 2120 corresponds to some linear longitudinal translation of the displacement member 2118. The position sensor 2104 can then further include a plurality of magnetic sensing elements configured to detect the angular position of the magnet 2120, which corresponds to the linear position of the displacement member 2118 and thus allows the position sensor 2104 to detect the absolute or relative position of the displacement member 2118. The position sensor 2104 can further be configured to relay a feedback signal to the controller 2102 that is indicative of the position of the displacement member 2118. A driver 2114 is operably connected to the motor 2116 and configured to provide a drive signal thereto that sets the velocity at which the motor 2116 is driven, the current drawn by the motor 2116, the voltage at which the motor 2116 is set, or a variety of other motor 2116 characteristics. A power source 2112 supplies power to any or all of the driver 2114, motor 2116, controller 2102, display 2108, sensors 2104, 2106, or other components of the surgical instrument 2100.

In some aspects, the surgical instrument 2100 can include a sensing assembly that is configured to detect the progress or advancement of the closure mechanism. In various aspects, the closure mechanism sensing assembly can comprise the trigger sensing assembly 2005 described above. As the closure trigger 512 is utilized to actuate the closure drive system 510, which in turn causes the closure shuttle 1914 (FIG. 5) to advance, the actuation or position of the closure trigger 512 can thus be detected as a proxy for the progress or advancement of the closure mechanism.

In other aspects, the closure mechanism sensing assembly can be similar to the position sensing assembly 2050 described above with respect to the firing drive system 530 and illustrated in FIGS. 23-24. The closure mechanism sensing assembly of the surgical instrument 2100 can include the position sensor 2104, which can be provided in addition to or in lieu of the position sensor described with respect to the position sensing assembly 2050. In these aspects, the displacement member 2118 can include one or more components of the closure mechanism, such as the closure shuttle 1914, proximal closure tube 1910, and/or distal closure tube 1930, comprise rack of drive teeth that are meshingly engaged with a corresponding gear assembly 2122 supporting a magnet 2120 thereon. As the displacement member 2118 of the closure mechanism advances distally or proximally, the magnet 2120 is caused to rotate in a first direction or a second direction. The position sensor 2104 further includes a plurality of magnetic sensing elements, such as Hall effect elements, that are positioned in proximity to the magnet 2120. As the magnet 2120 rotates, the magnetic sensing elements of the position sensor 2104 determine the absolute angular position of the magnet 2120 over a revolution. As the angular position of the magnet 2120 corresponds to the position of the displacement member 2118 of the closure mechanism with which the gear assembly 2122 is engaged, the closure tube sensing assembly can thus detect the absolute position of the component of the closure mechanism. Additional details regarding these aspects of the closure mechanism sensing assembly are described above with respect to the position sensing assembly 2050.

The velocity at which the knife bar 1320 is being translated by the firing drive system 530 and/or the end effector 1500 is being closed by the closure mechanism can be determined in various aspects utilizing a position sensor 2104 to track the position of a displacement member 2118 in combination with a timer or timing circuit. As the displacement member 2118 is being translated, the position sensor 2104 can determine its position $d_1, d_2, \ldots d_n$ at a series of discrete time intervals or time stamps $t_1, t_2, \ldots t_n$ provided by the timer. The timer can include a continuously running timer, i.e., a clock, or a timer that is initiated upon activation of either of the firing or closure mechanisms. In one aspect, for each discrete position measurement taken by the position sensor 2104, the controller 2102 accesses the timer to retrieve a time stamp according to the receipt time of the position measurement. The controller 2102 can then calculate the velocity of the displacement member 2118 over a set time period according to the change in its displacement position over time. As the velocity of the displacement member 2118 corresponds in a known manner to either the velocity at which the knife bar 1320 is translated or the velocity at which the end effector 1500 is closed, the controller 2102 can thus determine the firing or closure velocity of the surgical instrument 2100.

The other sensors 2106 can additionally include a cartridge sensor. In one aspect, the cartridge sensor includes the channel circuit 1670 (FIG. 10), which can be configured to detect the presence and/or status of an RF cartridge 1700 via the exposed contacts 1676 positioned to make electrical contact with the corresponding exposed contacts 1756 of the RF cartridge 1700. In another aspect, the cartridge sensor includes a sensor, such as the cartridge present sensor and/or cartridge condition sensor disclosed in U.S. Patent Application Pub. No. 2014/0296874, that is positioned with the elongated channel 1602 comprising electrical contacts that output a logic zero when the circuit is open and a logic one when the circuit is closed, i.e., the RF cartridge 1700 is positioned correctly within the elongated channel 1602.

The other sensors 2106 can additionally include a temperature sensor that is configured to detect the temperature of the tissue being sealed by the RF energy. In one aspect, the temperature sensor includes a temperature sensing circuit disclosed as described in U.S. Pat. No. 8,888,776, entitled ELECTROSURGICAL INSTRUMENT EMPLOYING AN ELECTRODE, which is incorporated by reference in its entirety. In this aspect, the temperature sensing circuit can be configured to apply a voltage potential that is a function of the temperature sensed by the temperature sensing circuit. The temperature sensing circuit can be configured to apply a first voltage potential to the gate terminal when it detects a first temperature, a second voltage potential when it detects a second temperature, and a third voltage potential when it detects a third temperature, and so forth. In various aspects, the temperature sensing circuit can decrease the voltage potential applied to the gate terminal as the temperature of the electrode increases. For example, the temperature sensing circuit can be configured to apply a first voltage potential to the gate terminal when a first temperature is detected by the temperature sensing circuit and, in addition, a second voltage potential, which is lower than the first voltage potential, when the temperature sensing circuit detects a second temperature which is higher than the first temperature. Correspondingly, the temperature sensing circuit can increase the voltage potential applied to the gate terminal as the temperature of the electrode decreases. The change in the voltage potential generated by the temperature sensing circuit can be detected by, for example, a circuit in order to generate a feedback signal indicative of the temperature experienced or sensed by the circuit that is then transmitted to the controller 2102. The temperature sensing circuit can be included with the first jaw 1600 (FIG. 3), the second jaw 1800 (FIG. 3), and/or the cartridge 1700 (FIG. 2). In aspects wherein the cartridge 1700 includes the temperature sensing circuit, the feedback signal generated by the temperature sensing circuit can be transmitted to the channel circuit 1670 through the electrical connection between the corresponding exposed contacts 1676, 1756. The channel circuit 1670 can then transmit the feedback signal to the controller 2102.

The other sensors 2106 can additionally include tissue sensors that are configured to measure one or more characteristics of the tissue undergoing to clamping, sealing, stapling, and/or cutting operations of the surgical instrument 2100. In one aspect, the other sensors 2106 comprise a tissue impedance sensor that is configured to measure the impedance of the clamped tissue as RF energy is applied. The tissue impedance sensor comprises, for example, electrodes and an impedance monitoring circuit that are configured to measure the current between the electrodes and/or the impedance of the tissue between the electrodes, as described in U.S. Pat. No. 5,817,093, entitled IMPEDANCE FEEDBACK MONITOR WITH QUERY ELECTRODE FOR ELECTROSURGICAL INSTRUMENT, which is incorporated by reference in its entirety. The electrodes of the tissue impedance sensor can be the same electrodes 1736R, 1736L, 1738R, 1738R for delivery of the therapeutic RF energy or different electrodes. In aspects wherein the tissue impedance sensor electrodes are different than the therapeutic electrodes, the frequency of RF energy delivered through the tissue impedance sensor electrodes can be different from the frequency of energy delivered through the therapeutic electrodes to reduce electrical interference. The tissue impedance sensor electrodes comprise at least two electrically opposite electrodes that are arranged on the end effector 1500 such that they contact the tissue clamped thereby. The tissue impedance sensor electrodes can be located either on the same surface or opposing surfaces of the end effector 1500 between a portion of the engaged tissue. As the voltage supplied to the tissue impedance sensor electrodes by, for example, the RF generator 400 (FIG. 1) is known and the current between the electrodes is detectable by the impedance monitoring circuit, the impedance of the tissue is thus calculable. In one aspect, the impedance monitoring circuit can calculate the impedance of the clamped tissue itself and then transmit a feedback signal indicative of the impedance to the controller 2102. In another aspect, the impedance monitoring circuit can transmit a feedback signal indicative of the detected current between the electrodes to the controller 2102, which then calculates the impedance of the tissue.

In totality, the various sensors or sensor assemblies disclosed herein can be utilized by the surgical instrument 2100 to monitor the position of the closure trigger 512, the advancement of the closure drive system 510 and/or components of the closure mechanism, the thickness of the clamped tissue, the position of the knife bar 1320 and/or other components of the firing drive system 530, the presence of the RF cartridge 1700, the status of the RF cartridge 1700, the closure speed of the end effector 1500, and various other operational statuses of the surgical instrument 2100. These states, parameters, positions, or other information associated with the operation of the surgical instrument 2100 can be tracked by the controller 2102 through feedback signals transmitted from the various sensing assemblies. The controller 2102 can then cause the display 2108 to display one or more of the monitored variables associated with the operation of the surgical instrument 2100 in a graphical format for viewing by the operators of the surgical instrument 2100.

FIGS. 26-39 are displays depicting various statuses, parameters, or other information associated with the operation of the surgical instrument, in accordance with one or more aspects of the present disclosure. In various aspects depicted in FIGS. 26-29, the display 2200 of the surgical instrument can be configured to graphically represent the status of the RF energy being supplied to the tissue engaged by the end effector 1500 (FIG. 1). The status of the supplied RF energy can be represented in the format of a graph 2202, a numerical value 2204, a dial 2206, or a bar graph 2208. The RF energy delivered to the tissue corresponds to the tissue impedance 2210 measured, for example, by a tissue impedance sensor, as described above. Furthermore, the tissue impedance 2210 varies as a function of time 2212 because the properties of the engaged tissue change due to the application of mechanical force from the jaws of the end effector 1500 and RF energy. One such change in the properties of the engaged tissue is the egress of water from the tissue. Another such change in the properties of the engaged tissue is the change in conductance of the tissue fibers as RF energy is applied. Therefore in some aspects, the display 2200 can be configured to depict the change in tissue impedance 2210 over time 2212 as, for example, a curve 2216 in a graph 2202 or a series of bars 2224 indicating measurements of the tissue impedance 2210 at discrete time intervals in a bar graph 2208. The display 2200 can additionally be configured to depict an expected curve 2217 of the impedance 2210 over time 2212 that is calculated by the controller 2102 according to an algorithm executed thereby. In other aspects, the display 2200 can represent the tissue impedance 2210 as a numeral 2218. The numeral 2218 can represent the absolute value of the measured impedance in, for example, ohms. Alternatively, the numeral 2218 can represent the relative value or ratio of the measured impedance between a maximum and minimum impedance value. Furthermore, the size that the numeral 2218 is depicted on the display 2200 can correspond to the relative size of the value. The dial 2206 format of the display 2200 can likewise depict the measured tissue impedance relative to a maximum impedance 2222 and a minimum impedance 2220.

The display 2200 can also be configured to depict one or more alerts 2214 or statuses 2226 according to the operation of the surgical instrument 2100. The alerts 2214 can include warnings that the tissue impedance has exceeded a maximum tissue impedance, that the electrodes have lost energy, that the measured tissue impedance is deviating from an expected tissue impedance as calculated by the controller 2102 or stored on the memory 2110, and that the application time of the RF energy has exceeded a maximum or expected time. The statuses 2226 can include the current or subsequent stage or step of the process of using the surgical instrument 2100.

In addition to displaying the RF energy being supplied to the tissue, the display 2200 can also be configured to depict a variety of other parameters, statuses, or other information as determined by the sensing assemblies in communication with the controller 2102. In one aspect, the display 2200 can be configured to depict a temperature status 2228 of the tissue to which RF energy is being applied. The temperature can be determined by, for example, a temperature sensing circuit, as described above. In various aspects, the temperature status 2228 can be depicted as an absolute value of the measured temperature or a relative value of the measured temperature between a minimum and maximum temperature. In one aspect, the temperature status 2228 can be depicted as a curve 2239 of the absolute or relative temperature 2236 as a function of time 2238. The display 2200 can additionally be configured to depict an expected curve 2240 of the temperature 2236 over time 2238 that is calculated by the controller 2102 according to an algorithm executed thereby.

In another aspect, the display 2200 can be configured to depict the water content status 2230 of the tissue. The water content of the tissue can be determined, for example, as a function of the change in impedance of the tissue during the clamping and RF sealing operations executed by the surgical instrument 2100. As the change in mechanical properties of a particular tissue type over time are experimentally known and the change in tissue impedance as a result of the change in tissue mechanical properties is likewise experimentally known, the controller 2102 can isolate these effects from the measured change in tissue impedance over time, calculate the change in tissue water content, and then cause the display 2200 to depict the calculated water content status 2230. As described above with respect to other tissue or surgical instrument parameters, the display 2200 can depict the tissue water content status 2230 in the format of a graph, a numeral, a dial, or any other such graphical representation. In one aspect, the display 2200 can depict the change in tissue water content 2242 over time 2244 as a curve 2246. The display 2200 can additionally be configured to depict an expected curve 2248 of the water content 2242 over time 2244 that is calculated by the controller 2102 according to an algorithm executed thereby.

In other aspects, the display 2200 can be configured to depict the seal completion status 2232 or completion status 2234 according to the operation of the surgical instrument 2100. The seal completion status 2232 can correspond, for example, to the RF energy status depicted in FIGS. 26-29 and indicate the currently measured delivery of RF energy relative to an expected value. For example, in FIG. 32 the seal completion status 2232 is depicted graphically as a measured curve 2254 of the tissue impedance 2250 over time 2252 as compared to an expected curve 2256 of the tissue impedance 2250 over time 2252. The ratio between the measured curve 2254 and the expected curve 2256 graphically depicts the relative progress of the application of RF energy relative to an expected progress, which can be determined experimentally and stored on the memory 2110 to be accessed by the controller 2102. In one aspect, the completion status 2234 can represent the seal completion status in an alternative graphical format. In another aspect, the completion status 2234 can represent the percentage of number of steps executed or completed by the surgical instrument 2100 or the percentage completion of any individual step, such as the advancement of the closure mechanism or the current longitudinal displacement of the knife bar 1320 (FIG. 4) relative to the total longitudinal displacement thereof in the step of firing the knife bar 1320. The current progress can be tracked by the controller 2102 in combination with the various sensing assemblies of the surgical instrument 2100. The completion status 2234 can be displayed in the format of a dial depicting a percentage 2258 between a minimum percentage 2260 and a maximum percentage 2262.

In various aspects depicted in FIGS. 34-37, the display 2200 can be configured to display the thickness of the tissue engaged by the end effector 1500, the advancement of a displacement member, such as the knife bar 1320, and various statuses associated with the tissue thickness and/or the displacement member. The thickness of the tissue engaged by the end effector 1500 can be detected, e.g., by a tissue thickness sensing assembly 2022 in communication with the controller 2102, as described above. In various aspects, the controller 2102 can cause the display 2200 to depict the tissue thickness according to the feedback signal generated by the tissue thickness sensing assembly 2202 as either an absolute or a relative value in a variety of different graphical formats, such as a series of discrete zones 2264 ranging from thin to thick, as a graph 2266, or as a dial 2268, among others.

Figure 35:
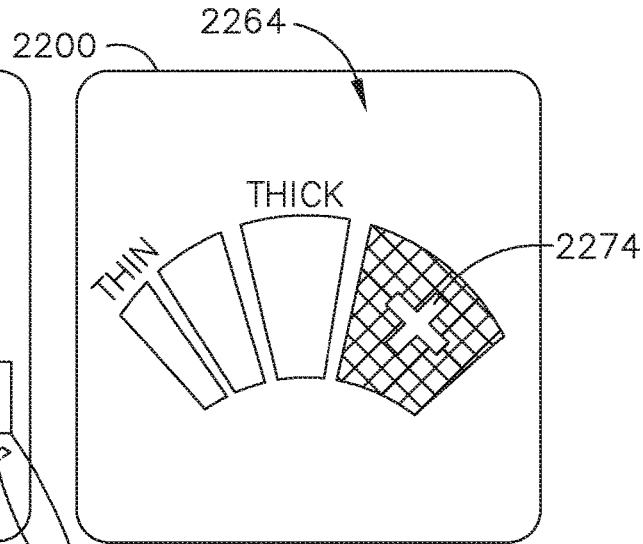
FIG. 35 is a display depicting a warning of the surgical instrument according to one aspect of this disclosure.
Figure 36:
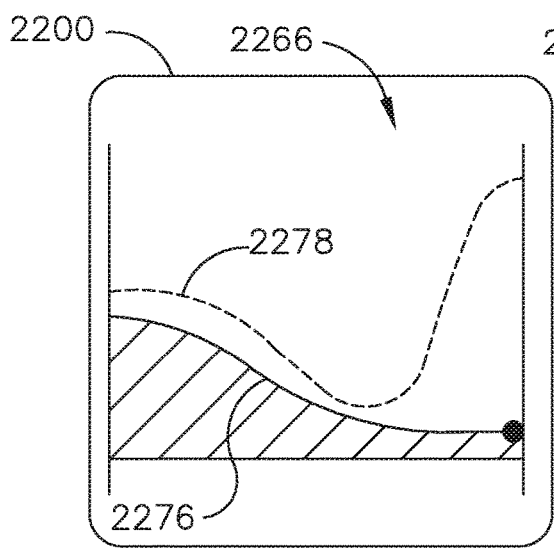
FIG. 36 is a display depicting a warning of the surgical instrument according to one aspect of this disclosure.
Figure 37:
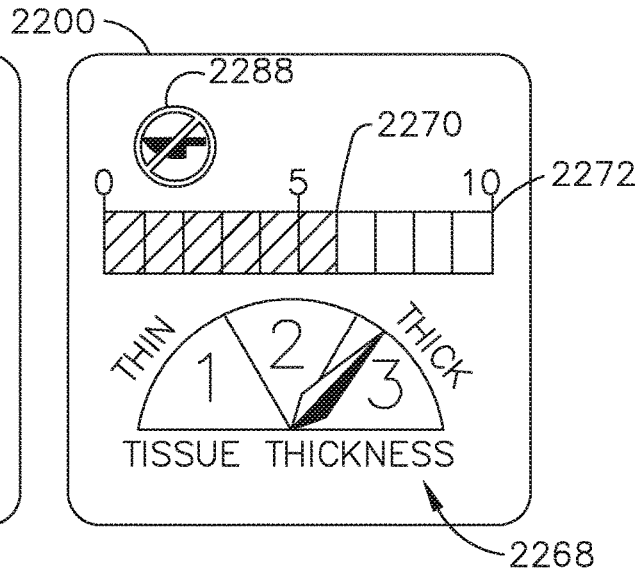
FIG. 37 is a display depicting status, operational progress, and tissue information of the surgical instrument according to one aspect of this disclosure.
Figure 38:
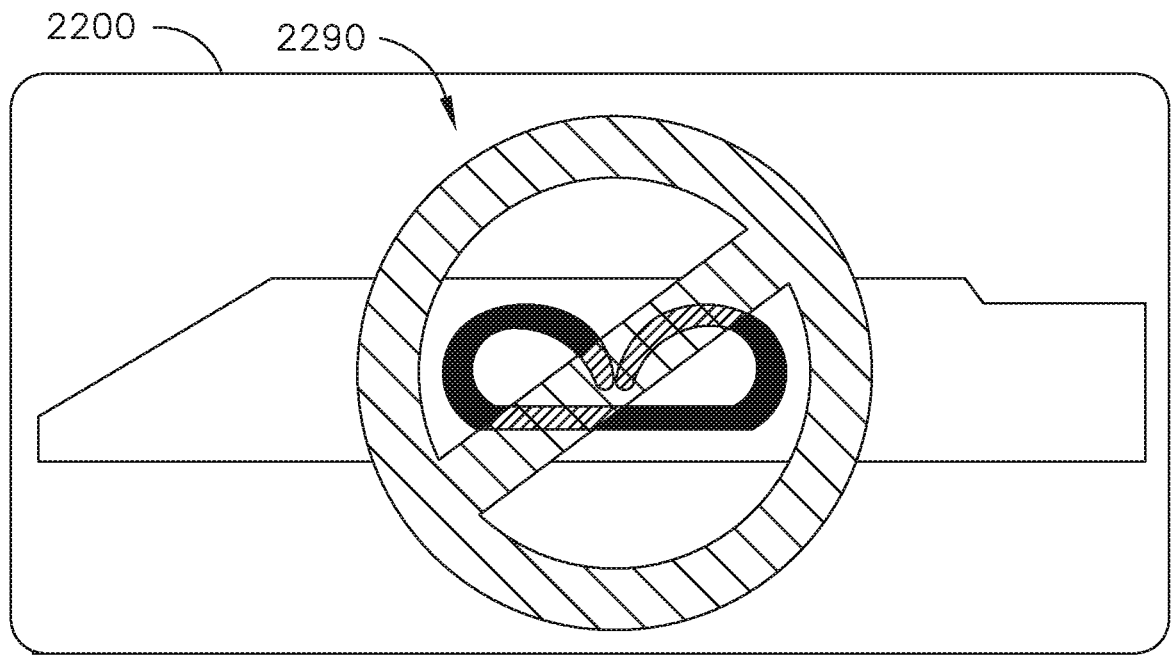
FIG. 38 is a display depicting RF cartridge status information of the surgical instrument according to one aspect of this disclosure.

The display 2200 can additionally comprise alerts to provide graphical warnings to users that the tissue is too thick or too thin for a particular operation. For example, an alert can comprise an icon 2274, such as an "X" as depicted in FIG. 35, that is overlaid on the display 2200 to indicate to the operator that the surgical instrument 2100 is currently or will be operating outside of desired conditions. In other aspects, the icon 2274 may or may not be overlaid on the various graphical formats 2264, 2266, 2268 indicating tissue thickness. Various other graphical warnings can be utilized, including icons of different designs, changes in color, or textual warnings. As another example, an alert can comprise a graphical depiction that a curve 2276 of the tissue thickness, displacement member velocity, or other parameter measured by or calculated from the various sensing assemblies is deviating from an expected curve 2278. In such aspects, various other additional alerts can accompany the depicted alert, such as textual alerts, icons, changes in color, and the like.

In one aspect, the display 2200 can additionally be configured to depict the position of the knife bar 1320. The position of the knife bar 1320 can be detected by, for example, a position sensing assembly 2050 in communication with the controller 2102, as described above. In various aspects, the controller 2102 can cause the display 2200 to depict the knife bar 1320 displacement according to the feedback signal generated by the position sensing assembly 2050 as, for example, a linear measured position 2270 of the knife bar 1320 relative to a maximum position 2272 thereof. The maximum position 2272 can include a maximum incision length desired for a particular surgical operation or an absolute maximum length that the knife bar 1320 can translate.

In another aspect, the display 2200 can additionally be configured to depict the advancement or status of the closure mechanism. The advancement of the closure mechanism can be detected, e.g., by a closure trigger sensing assembly 2005 in communication with the controller 2102, as discussed above, or a position sensing assembly 2050 configured to detect a position of a displacement member 2118 of the closure mechanism, as described above with respect to FIG. 25. In various aspects, the controller 2102 can cause the display 2200 to depict the closure mechanism advancement according to the feedback signal generated by the trigger sensing assembly 2005 or the position sensing assembly 2050 as, for example, a detected position of the closure shuttle 1914 relative to a maximum position thereof.

In some aspects, the controller 2102 can be configured to populate the display 2200 with a variety of icons when certain events or statuses occur. For example, a first icon 2280 can indicate that RF energy is currently or has been successfully applied to the tissue. A second icon 2282 can indicate that the knife bar 1320 is currently or has been successfully fired. A third icon 2284 can indicate that an error has occurred at some point during the operation of the instrument. A fourth icon 2286 can indicate that all of the steps of the operation of the instrument have been successfully completed. A fifth icon 2288 can indicate that an error has occurred with a specific component of the instrument, such as the knife bar 1320. The display 2200 can additionally be configured to display any other such type of icon indicating that a step or process is complete or that an event has occurred, such as an error. The various icons can be configured to illuminate, become visible, or change color when the status is active or the event has occurred.

In some aspects, the display 2200 can be configured to indicate whether a correct or incorrect cartridge type has been loaded into the end effector 1500, i.e., inserted into the elongate channel 1602 (FIG. 10). The channel circuit 1670 can be configured to read or detect the type of cartridge that is received by the end effector 1500 via a sensor or electrical communication between the channel circuit 1670 and the cartridge. In one aspect, the cartridges comprise a memory storing an identifier or value indicative of the cartridge type that is transmitted to the channel circuit 1670 upon the cartridge being inserted into the elongate channel 1602 of the end effector 1500. The channel circuit 1670, which is communicably coupled to the controller 2102, is configured to then transmit the cartridge type identifier or value to the controller 2102. The logic executed by the controller 2102 can then compare the cartridge type to the expected cartridge type. If the cartridge type and the expected cartridge type do not match, then the controller 2102 can cause the display 2200 to depict a first icon 2290. If the cartridge type and the expected cartridge type do match, then the controller 2102 can cause the display 2200 to depict a second icon 2292. In the aspect depicted in FIGS. 38-39, the first icon 2290 corresponds to a staple cartridge being inserted when an RF cartridge is expected and the second icon 2292 corresponds to an RF cartridge being inserted when an RF cartridge is expected.

The various aspects of the display 2200 depicted in FIGS. 26-39 can represent individual representations of a screen displayed to an operator or portions of a screen displayed to an operator. In various aspects, operators can switch between the various screens via user input or the controller 2102 can automatically adjust the display 2200 according to the operation of the surgical instrument 2100. In various aspects, the display 2200 can include a graphical user interface that can be manipulated via, for example, a capacitive touchscreen.

The display 2200 as described herein can include one or more screens disposed on or connected with the surgical instrument for graphically displaying information captured by the various sensing assemblies. In one aspect, the display 2200 comprises a single screen positioned on the exterior casing of the surgical instrument, as depicted in FIG. 1. In aspects utilizing multiple screens, the screens can be positioned adjacently to each other or separately from each other. The display 2200 can be positioned directly on the surgical instrument, can be removably connectable to the surgical instrument such that the display 2200 is brought into signal communication with the controller when connected to the surgical instrument, or can be otherwise associated with the surgical instrument.

The functions or processes of monitoring various statuses of the surgical instrument via various sensing assemblies described herein may be executed by any of the processing circuits, either individually or in combination, described herein, such as the onboard circuit board 1152 described in connection with FIGS. 5 and 15, the channel circuit 1670 described in connection with FIG. 10, the flexible circuit assemblies 1730L, 1730R described in connection with FIGS. 10-13, the controller 2080 described in connection with FIG. 24, and the controller 2102 described in connection with FIG. 25.

Various aspects of the subject matter described herein are set out in the following examples:

EXAMPLE 1

A surgical instrument comprising: a circuit configured to deliver RF energy to a cartridge disposed in an end effector configured to receive the cartridge; a closure mechanism configured to transition the end effector between an open position and a closed position; a display; and a control circuit operably coupled to the display, the control circuit configured to: determine an amount of RF energy delivered to a tissue through the cartridge; display the amount of RF energy on the display; determine a position of the closure mechanism; and display the position of the closure mechanism on the display.

EXAMPLE 2

The surgical instrument of Example 1, wherein the control circuit is configured to receive a signal from an impedance sensor configured to measure an impedance of the tissue disposed between a first electrode and a second electrode, wherein the control circuit is configured to determine the amount of RF energy delivered to the tissue according to the impedance of the tissue.

EXAMPLE 3

The surgical instrument of one or more of Example 1 through Example 2, wherein the control circuit is configured to receive a signal from a position sensor configured to detect a position of a displacement member of the closure mechanism, wherein the control circuit is configured to determine the position of the closure mechanism according to the position of the displacement member.

EXAMPLE 4

The surgical instrument of one or more of Example 1 through Example 3, further comprising: a closure trigger configured to drive the closure mechanism between a first position and a second position; and a closure trigger sensor configured to detect a position of the closure trigger; wherein the control circuit is configured to determine the position of the closure mechanism according to the position of the closure trigger.

EXAMPLE 5

The surgical instrument of one or more of Example 1 through Example 4, wherein the control circuit is configured to receive a signal from a sensor configured to detect a position of the end effector between the open position and the closed position, wherein the control circuit is configured to determine the position of the closure mechanism according to the position of the end effector.

EXAMPLE 6

The surgical instrument of one or more of Example 1 through Example 5, wherein the control circuit is configured to receive a signal from a cartridge sensor configured to detect a cartridge type of the cartridge received by the end effector, wherein the control circuit is configured to display whether the cartridge type matches an expected cartridge type on the display.

EXAMPLE 7

A surgical instrument comprising: a circuit configured to deliver RF energy to a cartridge disposed in an end effector; a closure mechanism configured to transition the end effector between an open position and a closed position; a display; and a processor operably coupled to the display; a memory operably coupled to the processor, the memory storing program instructions that, when executed by the processor, cause the processor to: determine a status of RF energy delivered to a tissue through the cartridge; display the status of RF energy; determine a status of the closure mechanism; and display the status of the closure mechanism.

EXAMPLE 8

The surgical instrument of Example 7, wherein the memory stores program instructions that when executed by the processor, cause the processor to receive a signal from an impedance sensor configured to measure an impedance of the tissue between a first electrode and a second electrode, wherein the processor is configured to determine the status of RF energy applied to the tissue according to the impedance of the tissue.

EXAMPLE 9

The surgical instrument of Example 7, wherein the memory stores program instructions that when executed by the processor, cause the processor to receive a signal from a position sensor configured to detect a position of a displacement member of the closure mechanism, wherein the processor is configured to determine the status of the closure mechanism according to the position of the displacement member.

EXAMPLE 10

The surgical instrument of one or more of Example 7 through Example 9, further comprising: a closure trigger configured to drive the closure mechanism between a first position and a second position; and a closure trigger sensor configured to detect a position of the closure trigger; wherein the surgical instrument determines the status of the closure mechanism according to the position of the closure trigger.

EXAMPLE 11

The surgical instrument of one or more of Example 7 through Example 10, wherein the memory stores program instructions that when executed by the processor, cause the processor to receive a signal from a sensor configured to detect a position of the end effector between the open position and the closed position, wherein the processor is configured to determine the status of the closure mechanism according to the position of the end effector.

EXAMPLE 12

The surgical instrument of one or more of Example 7 through Example 11, wherein the memory further stores program instructions that when executed by the processor, cause the processor to receive a signal from a cartridge sensor configured to detect a cartridge type of the cartridge received by the end effector, wherein the processor is configured to display whether the cartridge type matches an expected cartridge type on the display.

EXAMPLE 13

A method of controlling a display in a surgical instrument, the surgical instrument comprising a circuit configured to deliver RF energy to a cartridge disposed within an end effector configured to receive the cartridge, a closure mechanism configured to transition the end effector between an open position and a closed position, a display, and a control circuit coupled to the display, the method comprising: determining, by the control circuit, an amount of RF energy applied to a tissue through the cartridge; displaying, by the control circuit, the amount of RF energy on the display; determining, by the control circuit, a position of the closure mechanism; and displaying, by the control circuit, the position of the closure mechanism on the display.

EXAMPLE 14

The method of Example 13, further comprising: measuring, by an impedance sensor, an impedance of the tissue between a first electrode and a second electrode: wherein the control circuit determines the amount of RF energy applied to the tissue according to the impedance of the tissue.

EXAMPLE 15

The method of one or more of Example 13 through Example 14, further comprising: detecting, by a position sensor, a position of a displacement member of the closure mechanism; wherein the control circuit determines the position of the closure mechanism according to the position of the displacement member.

EXAMPLE 16

The method of one or more of Example 13 through Example 15, further comprising: detecting, by a closure trigger sensor, a position of a closure trigger configured to drive the closure mechanism between a first position and a second position; wherein the control circuit determines the position of the closure mechanism according to the position of the closure trigger.

EXAMPLE 17

The method of one or more of Example 13 through Example 16, further comprising: detecting, by a sensor, a position of the end effector between the open position and the closed position: wherein the control circuit determines the position of the closure mechanism according to the position of the end effector.

EXAMPLE 18

The method of one or more of Example 13 through Example 17, further comprising: detecting, by a cartridge sensor, a cartridge type of the cartridge received by the end effector; and displaying, by the control circuit, whether the cartridge type matches an expected cartridge type on the display.

Shaft Module Circuitry Arrangements

In a surgical sealing and stapling system, it may be useful to employ a modular design that allows a single handle assembly to attach to multiple nozzle assemblies, and for a nozzle assembly to attach to multiple handle assemblies. Since the nozzle assembly would include the various surgical instruments in the end effector, special circuitry in the nozzle may be required to allow for instrumentation in a handle assembly to control the various functions in the end effector of the modular nozzle assembly. In addition, energy may need to be applied to the end effector that may or may not originate from the handle assembly. For example, the handle assembly may be battery powered to control the functions of the handle assembly, but may not possess power sufficient to control the end effector.

In some aspects, a unique circuitry system is included in the nozzle assembly that allows for a user of the modular surgical instruments described herein to manipulate the end effector directly from the instrumentation contained in the handle assembly. The nozzle assembly may include an onboard circuit board that allows for an electrosurgical generator to attach directly to the nozzle assembly and supply radio frequency (RF) energy to the end effector, while also interfacing with the processor or control circuit of the handle assembly. In some aspects, the unique circuitry of the nozzle assembly also allows for shaft rotation while still supplying proper energy and functionality to the end effector.

In one aspect, connecting the surgical instrument to a generator enables certain shaft functions. For example, attachment of RF leads to the generator allow the surgical instrument onboard circuit board to isolate some of the elongated shaft integral circuit wiring for RF application to an RF cartridge interchangeably usable with stapling cartridges. The onboard circuit board is a segmented circuit configured to isolate the generator inputs (e.g., RF energy, etc.) from the handle electronics where appropriate. A flex circuit contains electrical conductors with different geometries to accommodate RF energy transfer.

Referring to FIG. 40, in some aspects, the nozzle assembly 1240 that constitutes a modular portion of the surgical tool assembly 1000 may include shaft module circuitry uniquely configured to control various functions in the shaft assembly while also communicating with the handle assembly 500 and allowing for the RF generator 400 to be controlled from the powered stapling handle. In FIG. 40, the circuitry of FIG. 15 is shown in the context of an example nozzle assembly 1240. The circuitry according to some aspects of the present disclosures includes the onboard circuit board 1152 with various connectors. Female connectors 410 are electrically coupled to the circuit board 1152, which allows for connection with the male plug assembly 406 that couple to the generator 400, not shown.

In addition, the onboard on/off power switch 420 is electrically coupled to the circuit board 1152 and positioned in such a way so as to be pressed when the nozzle assembly 1240 is attached to the handle assembly 500, according to some aspects. For example, when the nozzle assembly locks into place (see e.g., FIG. 9), the on/off power switch 420 may be positioned to face proximally to the handle assembly and may be pressed as the nozzle assembly slides into the slot of the handle assembly via the closure link 514 (see FIG. 9). In other cases, the on/off power switch 420 is exposed so that it may be manually pressed by an operator of the surgical tool assembly 1000.

The circuit board 1152 includes the onboard connector 1154 configured to interface with the housing connector 562 (see FIG. 9) communicating with the microprocessor 560 contained in the handle assembly 500. In this way, the handle assembly 500 is capable of commanding the circuit board 1152 that controls several functions in the nozzle assembly 1240. The design of the circuitry in the nozzle assembly 1240 allows for an operator to perform a number of functions from the various controls of the handle assembly 500, such as through the various controls and display consoles available in the handle assembly 500.

The circuit board 1152 also includes the proximal connector 1153 that is configured to interface with the slip ring assembly 1150. Power may be supplied to the end effector even while the shaft rotates due to power being supplied throughout the slip ring assembly 1150 and the distal connector 1162 being in constant contact with the slip ring assembly as the flexible shaft circuit strip 1164 rotates within the proximal closure tube 1910. The shaft circuit strip 1164 may include a number of electrical conductors, such as the narrow electrical conductors 1166 for stapling related activities and the wider electrical conductors 1168 for RF purposes (see FIG. 15).

Based on the various components described in the nozzle assembly 1240, the circuitry 1152 may be configured to control the RF generator 400 from the powered handle assembly 500, allowing for communication with the various functions and interfaces of the handle assembly 500, and allowing for operation of the RF and stapling functions of the end effector from the handle assembly 500. Other functions may include controlling a type of algorithm for performing various surgical procedures and energy applications at the end effector, enabling warning functionality viewable at the handle assembly 500 of any part of the nozzle assembly 1240, and varying energy modulation from the RF generator 400. In some aspects, the circuit board 1152 may be programmed to facilitate these functions, while in other cases the onboard connecter 1154 may allow for the handle assembly circuitry to be programmed to facilitate these functions and the circuit board 1152 is configured to command the end effector accordingly.

In some aspects, the onboard circuit includes the segmented RF circuit 1160, which may allow for the RF energy of the generator 400 to be supplied to the flexible shaft circuit strip via the slip ring assembly (see, e.g., FIG. 15). The RF generator may be coupled to the onboard circuit board 1152 via the RF segmented circuit 1160. The on/off power switch 420 may be similarly connected to the segmented RF circuit 1160.

FIG. 41 illustrates a block diagram of a surgical system 3200 programmed to communicate power and control signals with an end effector 3250 according to one aspect of this disclosure. In an example aspect, the surgical system 3200 may include a control circuit 3210 (e.g., microprocessor 560, segmented RF circuit 1160, or distal micro-chip 1740) having an electrosurgical energy control segment (or an RF energy control segment) 3220 and a shaft control segment 3230 (e.g., shaft segment (Segment 5), motor circuit segment (Segment 7), or power segment (Segment 8)). The control circuit 3210 may be programed to provide electrosurgical energy (e.g., RF energy) to electrodes in the end effector 3250 (e.g., end effector 1500). The surgical system 3200 may include one or more electrical conductors 3260 (e.g., electrical conductors 1168) used for providing the electrosurgical energy, from an electrosurgical energy generator 3240 (e.g., RF generator 400), to the end effector 3250. The one or more electrical conductors 3260 may be electrically connected between the end effector 3250 and the control circuit 3210 (e.g., the electrosurgical energy control segment 3220 and the shaft control segment 3230).

The electrosurgical energy control segment 3220 may be programed to provide the electrosurgical energy to the electrodes through the one or more electrical conductors 3260. In an example aspect, the shaft control segment 3230 may be programed to provide and/or receive a control signal to/from the end effector 3250 (and/or the surgical tool assembly 1000, the shaft assembly 704) through the one or more electrical conductors 3260. That is, the one or more electrical conductors 3260 may be used not only for providing the electrosurgical energy to the end effector 3250, but also for communicating control signals with the end effector 3250. In an example aspect, at least some portions of the electrosurgical energy control segment 3220 and the shaft control segment 3230 may be electrically isolated from each other.

In an example aspect, the electrosurgical energy control segment 3220 may electrically isolate the one or more electrical conductors 3260 from the shaft control segment 3230, for example, when providing the electrosurgical energy to the electrodes in the end effector 3250 through the one or more electrical conductors 3260. In an example aspect, the electrosurgical energy control segment 3220 may control a switch 3270 located between the one or more electrical conductors 3260 and the shaft control segment 3230 by providing a signal through a control line 3280 to electrically isolate the one or more electrical conductors 3260 from the shaft control segment 3230. The switch 3270 may be configured to switch between an open state and a closed state. The shaft control segment 3230 and the one or more electrical conductors 3260 may be electrically isolated when the switch 3270 is in the open state, and may be in electrical communication when the switch 3270 is in the closed state. In another example aspect, the electrosurgical energy control segment 3220 may electrically isolate the one or more electrical conductors 3260 from the shaft control segment 3230 in any other suitable manner. Other configurations of the switch 3270 may enable electrical isolation of the one or more electrical conductors 3260 from the shaft control segment 3230 by closing the switch 3270.

In an example aspect, the electrosurgical energy control segment 3220 may electrically isolate the one or more electrical conductors 3260 from the shaft control segment 3230 when the control circuit 3210 detects that the electrosurgical energy generator 3240 is connected to the connector 3265 (e.g., female connectors 410), for example, by continuously checking the connector 3265 or sensing the application of the electrosurgical energy. For example, when the male plug assembly 406 is plugged into the female connectors 410, the electrosurgical energy control segment 3220 may isolate the electrical conductors 3260 from the shaft control segment 3230. In another example aspect, the electrosurgical energy control segment 3220 may electrically isolate the one or more electrical conductors 3260 from the shaft control segment 3230 when the electrosurgical energy is provided to the end effector 3250 or at any other suitable moment.

In an example aspect, the surgical system may include one or more electrical conductors 3290 (e.g., electrical conductors 1166) used for operating the end effector 3250 (and/or the surgical tool assembly 1000, the shaft assembly 704). In an example aspect, the one or more electrical conductors 3290 may not be used to deliver the electrosurgical energy to the end effector 3250. The shaft control segment 3230 may be programed to provide and/or receive a control signal to/from the end effector 3250 through the one or more electrical conductors 3290. In an example aspect, the shaft control segment 3230 may use the one or more electrical conductors 3290 to provide and/or receive the control signal to/from the end effector 3250 while the switch 3270 is in an open state (e.g., while the electrosurgical energy control segment 3220 is providing the electrosurgical energy to the end effector 3250 through the one or more electrical conductors 3260). In an example aspect, the shaft control segment 3230 also may use the one or more electrical conductors 3290 to provide and/or receive the control signal to/from the end effector 3250 while the switch 3270 is in a closed state.

The switch 3270 may be a transistor switch, a mechanical switch, or any other suitable switch. In an example aspect, the control signals communicated between the control circuit 3210 and the end effector 3250 (and/or the surgical tool assembly 1000, the shaft assembly 704) through the electrical conductors 3260, 3290 include, but are not limited to, signals for driving the end effector 3250 (and/or the surgical tool assembly 1000, the shaft assembly 704) in cutting and/or coagulation operating modes, measuring electrical characteristics of the surgical system 3200 and/or the tissue clamped in the end effector 3250, providing feedback to use, communicating sensor signals, and identifying certain characteristics of the end effector 3250 (e.g., used/unused status).

Accordingly, aspects of the present disclosure may advantageously reduce the number of electrical conductors necessary for communicating control signals between the control circuit 3210 and the end effector 3250 (and/or the surgical tool assembly 1000, the shaft assembly 704) by using some of the electrical conductors (e.g., electrical conductors 3260) used for the delivery of the electrosurgical energy to communicate the control signals when those electrical conductors are not used for the electrosurgical energy. Moreover, by isolating those electrical conductors from other circuit segments (e.g., shaft control segment 3230) when providing the electrosurgical energy through those electrical conductors, aspects of the present disclosure may prevent the electrosurgical energy from flowing into the other circuit segments and/or electrical conductors (e.g., electrical conductors 3290) connected to those circuit segments, preventing damages to those circuit segments and/or electrical conductors.

Various aspects of the subject matter described herein are set out in the following examples:

EXAMPLE 1

A control circuit for a surgical instrument, the control circuit comprising: a shaft control segment; an electrosurgical energy control segment; and a connector coupled to the electrosurgical energy control segment configured to couple to an electrosurgical generator; wherein the shaft control segment is configured to: communicate with a handle portion of the surgical instrument; and receive user input controls; wherein the electrosurgical energy control segment is configured to: detect connection of the electrosurgical generator to the connector; communicate with the electrosurgical generator; electrically isolate the handle control segment from the electrosurgical energy control segment when the connection of the electrosurgical generator to the connector is detected; and provide electrosurgical energy from the electrosurgical generator to an end effector portion of the surgical instrument through a first set of electrical conductors.

EXAMPLE 2

The control circuit of Example 1, further comprising a first electrical conductor to electrically connect the control circuit to an end effector; wherein the shaft control segment is configured to provide a control signal for operating the end effector to the end effector through the first electrical conductor; and wherein the electrosurgical energy control segment is configured to provide the electrosurgical energy to the at least one electrode through the first electrical conductor.

EXAMPLE 3

The control circuit of Example 2, wherein the electrosurgical energy control segment is configured to electrically isolate the first electrical conductor from the shaft control segment when providing the electrosurgical energy to at least one electrode located in the end effector.

EXAMPLE 4

The control circuit of Example 3, further comprising a switch electrically coupled between the electrosurgical energy control segment and the shaft control segment, wherein the electrosurgical energy control segment is configured to electrically isolate the first electrical conductor from the shaft control segment by controlling the switch.

EXAMPLE 5

The control circuit of Example 4, wherein the electrosurgical energy control segment is configured to electrically isolate the first electrical conductor from the shaft control segment by opening the switch.

EXAMPLE 6

The control circuit of one or more of Example 2 through Example 5, further comprising a second electrical conductor, wherein the shaft control segment is configured to provide the control signal to the end effector through the second electrical conductor and wherein the shaft control segment is configured to provide the control signal to the end effector through the second electrical conductor when the electrosurgical energy control segment is providing the electrosurgical energy to the electrode through the first electrical conductor.

EXAMPLE 7

The control circuit of one or more of Example 2 through Example 6, wherein the shaft control segment is configured to receive executable instructions to operate the end effector.

EXAMPLE 8

The control circuit of one or more of Example 2 through Example 7, wherein the shaft control segment is configured to coordinate a stapling function and an energy delivery function.

EXAMPLE 9

The control circuit of one or more of Example 1 through Example 8, wherein the shaft control segment is configured to provide a warning signal.

EXAMPLE 10

The control circuit of one or more of Example 1 through Example 9, wherein the shaft control segment is configured to transmit instructions to an end effector.

EXAMPLE 11

The control circuit of one or more of Example 1 through Example 10, further comprising a slip ring assembly coupled to the shaft control segment and the electrosurgical energy control segment.

EXAMPLE 12

A nozzle assembly of a surgical system, the nozzle assembly comprising: an onboard circuit board; an onboard connector coupled to the onboard circuit board and proximally located on the nozzle assembly, the onboard connector configured to interface with a housing connector of a handle assembly when the nozzle assembly is attached to the handle assembly; a shaft attachment lug proximally located on the nozzle assembly and configured to be coupled to an attachment cradle of the handle assembly to attach the nozzle assembly to the handle assembly; and a control circuit comprising: a shaft control segment; an electrosurgical energy control segment; and a connector coupled to the electrosurgical energy control segment configured to couple to an electrosurgical generator; wherein the shaft control segment is configured to: communicate with a handle portion of the surgical instrument; and receive user input controls; wherein the electrosurgical energy control segment is configured to: detect connection of the electrosurgical generator to the connector; communicate with the electrosurgical generator; electrically isolate the handle control segment from the electrosurgical energy control segment when the connection of the electrosurgical generator to the connector is detected; and provide electrosurgical energy from the electrosurgical generator to an end effector portion of the surgical instrument through a first set of electrical conductors; wherein the nozzle assembly is detachable from and attachable to the handle assembly.

EXAMPLE 13

The nozzle assembly of Example 12, further comprising: an electrosurgical generator connector electrically coupled to the onboard circuit board and configured to be coupled to a plug assembly of an electrosurgical generator such that the onboard circuit board receives electrosurgical energy from the electrosurgical generator.

EXAMPLE 14

The nozzle assembly of one or more of Example 12 through Example 13, wherein the onboard circuit board is configured to transmit the electrosurgical energy to the end effector via the one or more electrical conductors.

EXAMPLE 15

The nozzle assembly of one or more Example 12 through Example 14, further configured to receive instructions from a handle assembly to an end effector through an interface between a housing connector of the handle assembly and the onboard connector of the nozzle assembly.

EXAMPLE 16

The nozzle assembly of Example 15, further configured to receive the instructions from a microprocessor of the handle assembly through the interface between the housing connector and the onboard connector.

EXAMPLE 17

The nozzle assembly of one or more of Example 12 through Example 16, wherein the nozzle assembly further comprises a power switch electrically coupled to the onboard circuit board and is configured to activate and deactivate transmission of electrosurgical energy.

EXAMPLE 18

The nozzle assembly of one or more of Example 12 through Example 17, further comprising a slip ring assembly distally located to the onboard circuit board and configured to interface with the onboard circuit board.

EXAMPLE 19

The nozzle assembly of Example 18, further comprising: a proximal connector coupled to a distal end of the onboard circuit board and a proximal end of the slip ring assembly; and a distal connector configured to interface with a distal end of the slip ring assembly and coupled to the one or more electrical conductors.

EXAMPLE 20

The nozzle assembly of one or more of Example 12 through Example 19, further comprising a flexible shaft circuit strip configured to house the one or more electrical conductors.

EXAMPLE 21

The nozzle assembly of one or more of Example 12 through Example 20, wherein the one or more electrical conductors comprises: a first electrical conductor configured to deliver energy to the end effector for stapler functionality; and a second electrical conductor configured to deliver electrosurgical energy to the end effector for electrosurgical functionality.

Systems and Methods for Controlling Control Circuits for Independent Energy Delivery Over Segmented Sections In various open, endoscopic, and/or laparoscopic surgeries, for example, it may be desirable to coagulate, seal, and/or fuse tissue. One method of sealing tissue relies upon the application of energy, such as electrical energy, for example, to tissue captured or clamped within an end-effector or an end-effector assembly of a surgical instrument in order to cause thermal effects within the tissue. Various mono-polar and bi-polar radio frequency (RF) surgical instruments and surgical techniques have been developed for such purposes. In general, the delivery of RF energy to the captured tissue can elevate the temperature of the tissue and, as a result, the energy can at least partially denature proteins within the tissue. Such proteins, such as collagen, for example, can be denatured into a proteinaceous amalgam that intermixes and fuses, or seals, together as the proteins renature. As the treated region heals over time, this biological seal may be reabsorbed by the body's wound healing process.

In certain arrangements of a bi-polar radiofrequency (RF) surgical instrument, the surgical instrument can comprise opposing first and second jaws, wherein each jaw can comprise an electrode. In use, the tissue can be captured between the jaws such that energy can flow between the electrodes in the opposing jaws and through the tissue positioned therebetween. Such instruments may have to seal many types of tissues, such as anatomic structures having walls with irregular or thick fibrous content, bundles of disparate anatomic structures, and/or substantially thick or thin anatomic structures.

Generally, it is difficult to provide electrosurgical energy to low impedance tissue continuously until welding of the tissue is substantially completed. For example, when providing the electrosurgical energy to low impedance tissue, there is a point where the tissue impedance becomes too low, acting like a short circuit so that the tissue merely draws a lot of current while providing no or little electrosurgical energy to the tissue. This can result in several undesirable outcomes including, for example, incomplete tissue welding, excessive heating of the electrodes, a delay of the surgery, clinician inconvenience or frustration, etc.

Aspects of the present disclosure may address the above noted deficiency by controlling control circuits for an independent energy delivery over segmented sections. In an example aspect, a surgical instrument may include an end effector having a first jaw with a distal portion and a proximate portion, a second jaw that is movable relative to the first jaw, a first set of electrodes located in the distal portion of the first jaw, and a second set of electrodes located in the proximate portion of the first jaw. The surgical instrument also may include a control circuit configured to provide electrosurgical energy (e.g., RF energy) to the first set of electrodes and the second set of electrodes. The electrosurgical energy provided to the first set of electrodes and the second set of electrodes may repeatedly alternate between the first set of electrodes and the second set of electrodes at a predetermined time interval. For example, the electrosurgical energy may be provided to the first set of electrodes for a first period of time (e.g., 0.25 seconds), to the second set of electrodes for a second period of time (e.g., 0.25 seconds) after the first period of time and, then, to the first set of electrodes for a third period of time (0.25 seconds), and so on. The alternation of the electrosurgical energy between the first set of electrodes and the second set of electrodes may be repeated, for example, until the welding of the tissue starts to complete or is substantially completed. The alternation of the electrosurgical energy at a very short period of time interval (e.g., 0.25 seconds) between the first set of electrodes and the second set of electrodes may facilitate the complete welding of low impedance tissue without excessive heating of the electrodes or a delay of the surgery. In an example, this alternation of the electrosurgical energy may be carried out by a microchip in the first jaw or a processor in the body of the surgical instrument using the RF energy provided from a conventional RF energy generator.

In this way, aspects of the present disclosure may enable the surgical instrument to provide the electrosurgical energy to the tissue having low impedance until the welding of the low impedance tissue is substantially completed. Moreover, aspects of the present disclosure may advantageously use the microchip in the first jaw or a processor in the body of the surgical instrument to alternate the electrosurgical energy between the two sets of electrodes using the RF energy from a conventional RF energy generator.

FIG. 42 shows a schematic top view of a jaw 3000 in an end effector (e.g., end effector 1500) of a surgical instrument (e.g., surgical system 10 or surgical tool assembly 1000) according to one aspect of this disclosure. The jaw 3000 may include a cartridge 3010, a flex circuit 3020 having flex circuit contacts 3025 (e.g., exposed contacts 1756), and an elongate slot 3030, within which a cutting member (e.g., knife member 1330) is slideably receivable to cut tissue clamped within the end effector along a cutting line 3035. The elongate slot may extend from a proximate end of the jaw 3000. In an example aspect, the flex circuit 3020 also may include a microchip (e.g., distal micro-chip 1740) and, then, the cartridge 3010 may be referred to as a smart cartridge. The jaw 3000 also may include a first set of electrodes 3040L, 3040R in a first zone 3060, and a second set of electrodes 3050L, 3050R in a second zone 3065. In an example aspect, the first zone 3060 may be located in a proximate portion of the jaw 3000 and the second zone 3065 may be located in a distal portion of the jaw 3000. In another example aspect, the first zone 3060 and the second zone 3065 may be located in any other suitable places of the jaw 3000.

The first and second set of electrodes 3040L, 3040R, 3050L, 3050R may be in communication with and/or deposited on the flex circuit 3020. In an example, the elongate slot 3030 may be disposed in the center of the jaw 3000. In another example, the elongate slot 3000 may be disposed in any other suitable places in the jaw 3000. As seen in FIG. 16, the electrodes 3040L and 3050L may be located on the left side of the elongate slot 3030 and the electrodes 3040R and 3050R may be located on the right side of the elongate slot 3030. In an example aspect, a control circuit (e.g., microprocessor 560, segmented RF circuit 1160, or distal microchip 1740) may be configured to provide electrosurgical energy to the first set of electrodes 3040L, 3040R and the second set of electrodes 3050L, 3050R.

The electrosurgical energy may be in the form of radio frequency (RF) energy. RF energy is a form of electrical energy that may be in the frequency range of 200 kilohertz (kHz) to 1 megahertz (MHz). In application, an electrosurgical device can transmit low frequency RF energy through tissue, which causes ionic agitation, or friction, in effect resistive heating, thereby increasing the temperature of the tissue. The low operating temperatures of RF energy is useful for removing, shrinking, or sculpting soft tissue while simultaneously sealing blood vessels. RF energy works particularly well on connective tissue, which is primarily comprised of collagen and shrinks when contacted by heat.

The first set of electrodes 3040L, 3040R and the second set of electrodes 3050L, 3050R may be electronically connected to the control circuit through the flex circuit 3020. The first set of electrodes 3040L, 3040R and the second set of electrodes 3050L, 3050R may be configured to emit RF energy to form a hemostatic (or a coagulation) line on the tissue adjacent the electrodes 3040L, 3040R, 3050L, 3050R along the cutting line 3035.

In an example aspect, the length 3070 of the first set of electrodes 3040L, 3040R may be in the range of about 10 mm to about 100 mm, preferably in the range of about 20 mm to about 50 mm, more preferably in the range of about 25 mm to about 35 mm. Similarly, in an example aspect, the length 3075 of the second set of electrodes 3050L, 3050R may be in the range of about 10 mm to about 100 mm, preferably in the range of about 20 mm to about 50 mm, more preferably in the range of about 25 mm to about 35 mm. In another example aspect, the first set of electrodes 3040L, 3040R and the second set of electrodes 3050L, 3050R may have any other suitable length. In an example aspect, a gap between the first set of electrodes 3040L, 3040R and the second set of electrodes 3050L, 3050R may be very small so that the claimed tissue may be welded from the first zone 3060 to the second zone 3065 continuously with no tissue located between the two zones 3060 and 3065 being unsealed/welded. In an example aspect, the length 3072 of the gap between the first set of electrodes 3040L, 3040R and the second set of electrodes 3050L, 3050R may be in the range of about 0.1 mm to about 20 mm, preferably in the range of about 0.5 mm to about 5 mm, more preferably in the range of about 1 mm to about 3 mm. In another example aspect, the length 3072 of the gap between the first set of electrodes 3040L, 3040R and the second set of electrodes 3050L, 3050R may have any other suitable length. The total length 3080 of the first set of electrodes 3040L, 3040R, the second set of electrodes 3050L, 3050R, and the gap may be in the range of about 20 mm to about 210 mm, preferably in the range of about 60 mm to about 100 mm, more preferably in the range of about 50 mm to about 70 mm.

In an example aspect, the first set of electrodes 3040L, 3040R and the second set of electrodes 3050L, 3050R may be electrically coupled to the wider electrical conductors 1168 from which the first set of electrodes 3040L, 3040R and the second set of electrodes 3050L, 3050R may receive the electrosurgical energy (e.g., RF energy). The first set of electrodes 3040L, 3040R and the second set of electrodes 3050L, 3050R may be electronically coupled to a plurality of electrical conductors (e.g., electrical conductors 1732L and 1732R) on the flex circuit 3020 through which the wider electrical conductors 1168 may provide the RF energy to the electrodes 3040L, 3040R, 3050L, 3050R. In an example aspect, each of the electrodes 3040L, 3040R, 3050L, 3050R may be separately connected to the control circuit (e.g., micro-chip 1740) through a different electrical conductor. For example, a first electrical conductor of the left electrical conductors 1732L may be connected to the electrode 3040L and a second electrical conductor of the left electrical conductors 1732L may be connected to the electrode 3050L. Similarly, a first electrical conductor of the right electrical conductors 1732R may be connected to the electrode 3040R and a second electrical conductor of the right electrical conductors 1732R may be connected to the electrode 3050R.

In an example aspect, the jaw 3000 may include a multiplexer to individually address the electrodes 3040L, 3040R, 3050L, 3050R. The multiplexer may be included in the control circuit (e.g., microprocessor 560, segmented RF circuit 1160, or distal micro-chip 1740) or located between the control circuit and the electrodes 3040L, 3040R, 3050L, 3050R. The multiplexer may distribute the electrosurgical energy to the electrodes 3040L, 3040R, 3050L, 3050R under the control of the control circuit. In an example aspect, the multiplexer may be configured to detect a short of the electrodes 3040L, 3040R, 3050L, 3050R, for example, caused by a metal staple line or other electrically conductive object left in the tissue from a previous instrument firing or surgical procedure, and the electrosurgical energy could be modulated in a manner appropriate for the short circuit. In an example aspect, the electrical conductors 1168, 1732L, 1732R may be insulated to protect components (e.g., a microchip 1740, a spine assembly 1250, laminated plates 1322, a flex circuit 3020) adjacent the electrical conductors 1168, 1732L, 1732R from inadvertent RF energy. In an example aspect, the cartridge 3010 may be interchangeable. When changing the cartridge, the narrow and wider electrical conductors 1166, 1168 in the surgical instrument may be connected to the new electrical conductors and electrodes in the new cartridge.

In an example aspect, the cutting member (e.g., knife member 1330) may be directly or indirectly coupled with a motor (e.g., motor 505). When the control circuit provides voltage to the motor, the cutting member may be advanced to the first zone 3060 or the second zone 3065 to cut the tissue in the first and second zones 3060, 3065.

FIG. 43 shows a graph 3100 depicting voltage applied to electrodes 3040L, 3040R, 3050L, 3050R as a function of time in accordance with a non-limiting aspect. The pulses 3110 may represent the voltage applied to the electrodes 3040L, 3040R in the first zone 3060. The pulses 3120 may represent the voltage applied to the electrodes 3050L, 3050R in the second zone 3065. When the voltage is on for the first zone 3060, electrosurgical energy may be applied to the tissue adjacent to the first set of electrodes 3040L, 3040R to form a coagulation/welding line there. Similarly, when the voltage is on for the second zone 3065, electrosurgical energy may be applied to the tissue adjacent to the second set of electrodes 3050L, 3050R to form a coagulation/welding line there. As shown in FIG. 43, in an example aspect, the control circuit may apply a set voltage alternatively throughout the alternation cycles. Then, the power/energy applied to the tissue may change as the tissue impedance changes. In another example aspect, the control circuit or the generator 400 may change the voltage applied to the electrodes (e.g., 30 volts for the first 5 cycles, 50 volts for the next 5 cycles, 80 volts for the next 5 cycles). In another example aspect, the control circuit or the generator 400 may change the voltage applied to the electrodes to provide a constant power to the tissue. In this case, the voltage may change as the tissue impedance changes.

In an example aspect, the electrosurgical energy may repeatedly alternate between the first set of electrodes 3040L, 3040R and the second set of electrodes 3050L, 3050R at a predetermined time interval. For example, the electrosurgical energy may be provided to the first set of electrodes 3040L, 3040R for a first period of time (e.g., 0.25 seconds) and, then, to the second set of electrodes 3050L, 3050R for a second period of time (e.g., 0.25 seconds). Then, it may be switched back to the first set of electrodes 3040L, 3040R and the alternation of the electrosurgical energy between the first set of electrodes 3040L, 3040R and the second set of electrodes 3050L, 3050R may be repeated, for example, until the impedance of the clamped tissue reaches a predetermined impedance value. In an example aspect, the predetermined time interval may be in the range of from about 0.05 seconds to about 0.5 seconds, preferably in the range of about 0.1 seconds to about 0.4 seconds, more preferably in the range of about 0.2 seconds to about 0.3 seconds. In another example aspect, the predetermined time interval may have any other suitable time period. In an example aspect, the predetermined time interval for the alternation of the electrosurgical energy may be sufficiently fast enough that the providing of the electrosurgical energy to the first set of electrodes 3040L, 3040R and the second set of electrodes 3050L, 3050R may appear to be simultaneous.

In an example aspect, the alternation of the electrosurgical energy may be started once the onboard on/off power switch 420 is turned on and may continue the alternation without an input from a user of the electrosurgical device until the onboard on/off power switch 420 is turned off. The onboard on/off power switch 420 may be automatically turned off when the measured tissue impedance reaches a predetermined impedance value (e.g., an impedance value indicating that the clamped tissue is completely sealed). The number of cycles (e.g., n times) of the alternation of the electrosurgical energy that is necessary for reaching the predetermined impedance value may vary depending on various parameters, including tissue type, tissue thickness, how much moisture is in the tissue, etc.

In an example aspect, as shown in FIG. 43, the time interval for the first set of electrodes 3040L, 3040R may be the same as the time interval for the second set of electrodes 3050L, 3050R. In another example aspect, the time interval for the first set of electrodes 3040L, 3040R may be different from the time interval for the second set of electrodes 3050L, 3050R. For example, the time interval for the first set of electrodes 3040L, 3040R may be 0.3 seconds, while the time interval for the second set of electrodes 3050L, 3050R may be 0.2 seconds. That is, in this case, the electrosurgical energy may be provided to the first set of electrodes 3040L, 3040R for 0.3 seconds, then to the second set of electrodes 3050L, 3050R for 0.2 seconds, then repeat this alternation. In an example aspect, the predetermined time interval may decrease over time. For example, the predetermined time interval may be 0.3 seconds in the beginning (e.g., for a couple of cycles), 0.2 seconds after then (for the next couple of cycles), 0.1 seconds after then (for the next couple of cycles before the tissue starts to complete to weld or is welded). In another example aspect, the predetermined time interval may increase over time.

FIG. 41 illustrates a block diagram of a surgical system 3200 programmed to communicate power and control signals with an end effector 3250 according to one aspect of this disclosure. In an example aspect, the surgical system 3200 may include a control circuit 3210 (e.g., microprocessor 560, segmented RF circuit 1160, or distal micro-chip 1740) having an electrosurgical energy control segment (or an RF energy control segment) 3220 and a shaft control segment 3230 (e.g., shaft segment (Segment 5), motor circuit segment (Segment 7), or power segment (Segment 8)). The control circuit 3210 may be configured to provide electrosurgical energy (e.g., RF energy) to the electrodes (e.g., electrodes 3040L, 3040R, 3050L, 3050R) in the end effector 3250 (e.g., end effector 1500). The surgical system 3200 may include one or more electrical conductors 3260 (e.g., electrical conductors 1168) used for providing the electrosurgical energy, from an electrosurgical energy generator 3240 (e.g., RF generator 400), to the effector 3250. The one or more electrical conductors 3260 may be electrically connected between the end effector 3250 and the control circuit 3210 (e.g., the electrosurgical energy control segment 3220 and the shaft control segment 3230). The shaft control segment 3230 may store shaft control programs in a memory and controls sensors and outputs, for example.

The electrosurgical energy control segment 3220 may be configured to provide the electrosurgical energy to the electrodes through the one or more electrical conductors 3260. In an example aspect, the shaft control segment 3230 may be configured to provide and/or receive a control signal to/from the end effector 3250 (and/or the surgical tool assembly 1000, the shaft assembly 704) through the one or more electrical conductors 3260. That is, the one or more electrical conductors 3260 may be used not only for providing the electrosurgical energy to the end effector 3250, but also for communicating control signals with the end effector 3250. In an example aspect, at least some portions of the electrosurgical energy control segment 3220 and the shaft control segment 3230 may be electrically isolated from each other.

In an example aspect, the electrosurgical energy control segment 3220 may electrically isolate the one or more electrical conductors 3260 from the shaft control segment 3230, for example, when providing the electrosurgical energy to the electrodes in the end effector 3250 through the one or more electrical conductors 3260. In an example aspect, the electrosurgical energy control segment 3220 may control a switch 3270 located between the one or more electrical conductors 3260 and the shaft control segment 3230 by providing a signal through a control line 3280 to electrically isolate the one or more electrical conductors 3260 from the shaft control segment 3230. The switch 3270 may be configured to switch between an open state and a closed state. The shaft control segment 3230 and the one or more electrical conductors 3260 may be electrically isolated when the switch 3270 is in the open state, and may be in electrical communication when the switch 3270 is in the closed state. In another example aspect, the electrosurgical energy control segment 3220 may electrically isolate the one or more electrical conductors 3260 from the shaft control segment 3230 in any other suitable manner. Other configurations of the switch 3270 may enable electrical isolation of the one or more electrical conductors 3260 from the shaft control segment 3230 by closing the switch 3270.

In an example aspect, the electrosurgical energy control segment 3220 may electrically isolate the one or more electrical conductors 3260 from the shaft control segment 3230 when the control circuit 3210 detects that the electrosurgical energy generator 3240 is connected to the connector 3265 (e.g., female connectors 410), for example, by continuously checking the connector 3265 or sensing the application of the electrosurgical energy. For example, when the male plug assembly 406 is plugged into the female connectors 410, the electrosurgical energy control segment 3220 may isolate the electrical conductors 3260 from the shaft control segment 3230. In another example aspect, the electrosurgical energy control segment 3220 may electrically isolate the one or more electrical conductors 3260 from the shaft control segment 3230 when the electrosurgical energy is provided to the end effector 3250 or at any other suitable moment.

In an example aspect, the surgical system may include one or more electrical conductors 3290 (e.g., electrical conductors 1166) used for operating the end effector 3250 (and/or the surgical tool assembly 1000, the shaft assembly 704). In an example aspect, the one or more electrical conductors 3290 may not be used to deliver the electrosurgical energy to the end effector 3250. The shaft control segment 3230 may be programmed to provide and/or receive a control signal to/from the end effector 3250 through the one or more electrical conductors 3290. In an example aspect, the shaft control segment 3230 may use the one or more electrical conductors 3290 to provide and/or receive the control signal to/from the end effector 3250 while the switch 3270 is in an open state (e.g., while the electrosurgical energy control segment 3220 is providing the electrosurgical energy to the end effector 3250 through the one or more electrical conductors 3260). In an example aspect, the shaft control segment 3230 also may use the one or more electrical conductors 3290 to provide and/or receive the control signal to/from the end effector 3250 while the switch 3270 is in a closed state.

The switch 3270 may be a transistor switch, a mechanical switch, electromechanical, relay, or any other suitable switch. In an example aspect, the control signals communicated between the control circuit 3210 and the end effector 3250 (and/or the surgical tool assembly 1000, the shaft assembly 704) through the electrical conductors 3260, 3290 include, but are not limited to, signals for driving the end effector 3250 (and/or the surgical tool assembly 1000, the shaft assembly 704) in cutting and/or coagulation operating modes, measuring electrical characteristics of the surgical system 3200 and/or the tissue clamped in the end effector 3250, providing feedback to use, communicating sensor signals, and identifying certain characteristics of the end effector 3250 (e.g., used/unused status).

Accordingly, aspects of the present disclosure may advantageously reduce the number of electrical conductors necessary for communicating control signals between the control circuit 3210 and the end effector 3250 (and/or the surgical tool assembly 1000, the shaft assembly 704) by using some of the electrical conductors (e.g., electrical conductors 3260) used for the delivery of the electrosurgical energy to communicate the control signals when those electrical conductors are not used for the electrosurgical energy. Moreover, by isolating those electrical conductors from other circuit segments (e.g., shaft control segment 3230) when providing the electrosurgical energy through those electrical conductors, aspects of the present disclosure may prevent the electrosurgical energy from flowing into the other circuit segments and/or electrical conductors (e.g., electrical conductors 3290) connected to those circuit segments, preventing damages to those circuit segments and/ore electrical conductors.

In an example aspect, the control circuit may include two operation modes, Mode I and Mode II. In Mode I, the control circuit may cut the tissue when or after the welding of the tissue is completed. In Mode 2, the control circuit may cut the tissue while the welding of the tissue is in progress. Examples of these modes are described in greater detail below and as shown in FIGS. 44-49.

FIG. 44 is a logic flow diagram depicting a process 4500 of a control program or a logic configuration for operating the surgical instrument in accordance with Mode I. Although the example process 4500 is described with reference to the logic flow diagram illustrated in FIG. 44, it will be appreciated that many other methods of performing the acts associated with the method may be used. For example, the order of some of the blocks may be changed, certain blocks may be combined with other blocks, and some of the blocks described are optional.

In the illustrated example and with reference also to FIG. 18, a control circuit 610 (FIG. 18), may receive 4510 information about impedance of tissue. For example, the control circuit 610 may include an impedance feedback circuit and measure the impedance of the tissue clamped in the end effector 602 (e.g., end effector 1500) such as, for example, the tissue adjacent the first set of electrodes 3040L, 3040R and the second set of electrodes 3050L, 3050R. In an example aspect, the control circuit 610 may measure the tissue impedance periodically (e.g., every 0.1 seconds, every 0.5 seconds, or every second). In another example aspect, the control circuit 610 may measure the tissue impedance randomly or in any other suitable manner. The control circuit 610 may provide 4520 electrosurgical energy to a first set of electrodes and a second set of electrodes, where the providing of the electrosurgical energy repeatedly alternates between the first set of electrodes and the second set of electrodes at a predetermined time interval. For example, the control circuit 610 may provide electrosurgical energy to the first set of electrodes 3040L, 3040R and a second set of electrodes 3050L, 3050R alternatively at a predetermined time interval as described above with regard to FIG. 43.

Then, at some points, the control circuit 610 may determine 4530 that the impedance of the tissue reaches a predetermined impedance value. For example, the predetermined impedance value may be a value indicating that the tissue adjacent the first set of electrodes 3040L, 3040R and the second set of electrodes 3050L, 3050R is substantially or completely welded or coagulated. The control circuit 610 may determine that the welding of the tissue is substantially completed by comparing the measured tissue impedance with the predetermined termination impedance value. Then, the control circuit 610 may stop 4540 the provision of the electrosurgical energy to the first set of electrodes and the second set of electrodes. Then, the control circuit 610 may advance 4550 a cutting member, such as the I-beam 614, to cut the tissue. In an example aspect, the control circuit 610 may advance the cutting member (e.g., I-beam 614) to the first zone 3060 to cut the tissue in the first zone 3060 and, then, to the second zone 3065 to cut the tissue in the second zone 3065. In another example aspect, the control circuit 610 may cut the tissue in the first zone 3060 and the second zone 3065 at the same time.

FIG. 45 shows a graph 4600 of a tissue impedance curve 4605 as a function of time. The tissue impedance curve 4605 may represent a change in the impedance of the tissue claimed in the end effector 1500 when the control circuit 610 (FIG. 18) is operating in Mode I. As shown in FIG. 45, the tissue impedance tends to follow a common "bathtub" pattern, decreasing in the beginning of the energy alternation for a first time period 4625 (e.g., 0.3-1.5 seconds), reaching a minimum impedance value ($Z_M$) at a first time ($t_1$) 4615 and, then, increasing during a second time period 4630 (e.g., 0.3-1.5 seconds) as the clamped tissue is being welded. Then, the tissue impedance may reach a point 4610 at a second time ($t_2$) 4620, where the tissue impedance at the point 4610 is equal to a predetermined termination impedance ($Z_T$).

In the first period of time 4625, the tissue impedance drops from an initial value and decreases, e.g., has a negative slope, until it reaches the minimum impedance value ($Z_M$) because after energy is applied to the tissue for a certain period the moisture content of the tissue evaporates causing the tissue to dry out and causes the tissue impedance to begin rising, e.g., positive slope, after then in the second period of time 4630 until the tissue impedance reaches the predetermined termination impedance $Z_T$, at which point in time the energy to the end effector may be shut off. In an example aspect, the tissue impedance may maintain the minimum impedance $Z_M$ for a certain period of time (e.g., 0.5-5 seconds), where the tissue impedance curve 4605 almost flattens out for that period of time. If the electrosurgical energy (e.g., RF energy) were to be applied continuously instead of being shut off at the termination impedance point 4610, the tissue impedance may increase continuously passing the point 4610.

In an example aspect, the predetermined termination impedance ($Z_T$) may correspond to a point where the tissue adjacent the electrodes 3040L, 3040R, 3050L, 3050R may be substantially or completely welded so as to cut the tissue (e.g., blood vessel) without bleeding. The predetermined termination impedance may be stored in a memory device of the surgical instrument (e.g., surgical system 10 or surgical tool assembly 1000).

When the tissue impedance reaches the predetermined termination impedance, the control circuit may stop providing the electrosurgical energy to the first set of electrodes 3040L, 3040R and the second set of electrodes 3050L, 3050R, resulting in the sudden drop of the tissue impedance at $t_2$ 4620. In an example aspect, this sudden drop of the tissue impedance may occur because the control circuit stops measuring the tissue impedance when the provision of the electrosurgical energy is stopped. As shown in FIG. 46 depicting a graph 4650 of an example motor voltage curve, when or after the provision of the electrosurgical energy is stopped at $t_2$, the control circuit may provide voltage 4660 to the motor (e.g., motor 505) to cut the tissue in the first zone 3060. Then, the control circuit also may provide voltage 4670 to the motor to cut the tissue in the second zone 3065. As shown in FIGS. 45 and 46, in Mode I, the cutting of the clamped tissue may start during a third time period 4635 after the tissue impedance reaches the predetermined termination impedance value (e.g., completion of the tissue welding).

FIG. 47 is a logic flow diagram depicting a process 4700 of a control program or a logic configuration for operating the surgical instrument in accordance with Mode II. Although the example process 4700 is described with reference to the logic flow diagram illustrated in FIG. 47, it will be appreciated that many other methods of performing the acts associated with the method may be used. For example, the order of some of the blocks may be changed, certain blocks may be combined with other blocks, and some of the blocks described are optional.

In the illustrated example and with reference also to FIG. 18, a control circuit 610 may receive 4710 information about impedance of tissue. For example, the control circuit 610 may measure the impedance of the tissue clamped in the end effector 602 (e.g., end effector 1500). In an example aspect, the control circuit 610 may measure the tissue impedance periodically (e.g., every 0.1 seconds, every 0.5 seconds, or every second). In another example aspect, the control circuit 610 may measure the tissue impedance randomly or in any other suitable manner. The control circuit 610 may provide 4720 electrosurgical energy to a first set of electrodes in a proximate portion of a jaw and a second set of electrodes in a distal portion of the jaw, where the providing of the electrosurgical energy repeatedly alternates between the first set of electrodes and the second set of electrodes at a predetermined time interval. For example, the control circuit 610 may provide electrosurgical energy to the first set of electrodes 3040L, 3040R and the second set of electrodes 3050L, 3050R alternatively at a predetermined time interval as described above with regard to FIG. 43.

Then, at some points, the control circuit 610 may determine 4730 that the impedance of the tissue reaches a predetermined impedance value. For example, the predetermined impedance value may be a value indicating that welding of the tissue adjacent the first set of electrodes 3040L, 3040R and the second set of electrodes 3050L, 3050R starts to complete. Then, the control circuit 610 may advance 4740 the cutting member such as the I-beam 614 to cut the tissue in the proximate portion while providing the electrosurgical energy to the first set of electrodes and the second set of electrodes. After cutting the tissue in the proximate portion of the jaw, the control circuit 610 may advance 4740 the cutting member (e.g., I-beam 614) to cut the tissue in the distal portion while providing the electrosurgical energy to the second set of electrodes.

In an example aspect, the control circuit 610 may advance 4750 the cutting member (e.g., I-beam 614) to cut the tissue in the distal portion while providing the electrosurgical energy to both the first set of electrodes 3040L, 3040R and the second set of electrodes 3050L, 3050R. In another example aspect, the control circuit 610 may stop providing the electrosurgical energy to the first set of electrodes after cutting the tissue in the proximate portion, and provide the electrosurgical energy only to the second set of electrodes while cutting the tissue in the distal portion. In this case, the provision of the electrosurgical energy to the second set of electrodes 3050L, 3050R may still be discontinuous. For example, the electrosurgical energy may be provided to the second set of electrodes 3050L, 3050R for a set period of time (e.g., 0.25 seconds) and, then, no electrosurgical energy may be provided to the second set of electrodes 3050L, 3050R for the next set period of time (e.g., 0.25 seconds) and, then the electrosurgical energy may be provided to the second set of electrodes 3050L, 3050R for the next set period of time (e.g., 0.25 seconds). This may be repeated while cutting the tissue in the distal portion of the jaw (e.g., the second zone 3065).

In another example aspect, the control circuit 610 may stop providing the electrosurgical energy to the first set of electrodes 3040L, 3040R and the second set of electrodes 3050L, 3050R after cutting the tissue in the first zone. In this case, no electrosurgical energy may be provided to the tissue while cutting the tissue in the second zone 3065. In an example aspect, the control circuit 610 may stop providing the electrosurgical energy to the first set of electrodes 3040L, 3040R and the second set of electrodes 3050L, 3050R when the tissue impedance reaches a predetermined termination impedance value while cutting the tissue in the first zone 3060 and/or the second zone 3065.

FIG. 48 shows a graph 4800 of a tissue impedance curve 4805 as a function of time. The tissue impedance curve 4805 may represent a change in the impedance of the tissue claimed in the end effector 1500 when the control circuit is operating in Mode II. As seen in FIG. 45, the tissue impedance here also tends to follow a common "bathtub" pattern, decreasing in the beginning of the energy alternation (e.g., between the first set of electrodes 3040L, 3040R and the second set of electrodes 3050L, 3050R) for a first time period 4835 (e.g. 0.3-1.5 seconds), reaching a minimum impedance value ($Z_M$) at a first time ($t_1$) 4820 and, then, increasing during a second time period 4840 (e.g., 0.3-1.5 seconds). As explained above, in the first period of time 4835, the tissue impedance drops from an initial value and decreases, e.g., has a negative slope, until it reaches the minimum impedance value ($Z_M$) because after energy is applied to the tissue for a certain period the moisture content of the tissue evaporates causing the tissue to dry out and causes the tissue impedance to begin rising, e.g., positive slope, after then in the second period of time 4840 until the tissue impedance reaches the termination impedance $Z^{T1}$. In an example aspect, the tissue impedance may maintain the minimum impedance for a period of time (e.g., 0.5-5 seconds), where the tissue impedance curve 4805 almost flattens out for that period of time.

In an example aspect, when the tissue impedance reaches the minimum impedance value ($Z_M$), a rate of impedance change (e.g., decrease) may become approximately zero as shown in FIG. 45. The welding of the clamped tissue may start to complete at this point. In an example aspect, in Mode II, the control circuit may start advancing the cutting member when the tissue impedance reaches the minimum impedance value ($Z_M$). For example, the control circuit may determine that the tissue impedance reaches the minimum impedance value ($Z_M$) when the rate of impedance change (e.g., decrease) becomes approximately zero. In another example aspect, in Mode II, the control circuit may start advancing the cutting member at any other suitable time before the clamped tissue is completely welded. If the tissue impedance maintains the minimum impedance for a period of time (e.g., 0.5-5 seconds), the control circuit may start advancing the cutting member at any suitable moment during that period of time (e.g., in the beginning/middle/end of the flat curve).

As shown in FIG. 49, and with reference also to FIG. 18, the control circuit 610 may provide voltage 4860 to the motor 604 (e.g., motor 505) to cut the tissue in the first zone 3060 when or after the tissue impedance reaches the minimum impedance value ($Z_M$) before the tissue welding is completed. The termination impedance $Z^{T1}$ may represent the tissue impedance at the completion of the cutting at a second time ($t_2$) 4825. Then, the control circuit may provide voltage 4870 to the motor 604 (e.g., motor 505) to cut the tissue in the second zone 3065 after cutting the tissue in the first zone 3060. The termination impedance $Z_{T2}$ may represent the tissue impedance at the completion of the cutting at a third time ($t_3$) 4830. The impedance curve 4805 may drop near at the second time 4825 right after the cutting of the tissue in the first zone 3060 because the clamped tissue may be wet with some fluids (e.g., blood or any other body fluids) that are produced while cutting the tissue in the first zone 3060. Thus, although the measured impedance value 4805 may appear to drop after the cutting of the tissue in the first zone 3060, the actual tissue impedance may not drop, but may be similar to or higher than $Z^{T1}$ throughout the third time period 4845. As the moisture content of the tissue evaporates causing the tissue to dry out because of the electrosurgical energy applied to the clamped tissue during the third time period 4845, the measured impedance value also may increase quickly to reflect the actual tissue impedance.

In an example aspect, the control circuit 610 may consider the amount of time required to cut the clamped tissue in the end effector 602 in determining when to start advancing the cutting member such as the I-beam 614. For example, if it takes 1 second to cut the tissue in the first zone 3060, the control circuit 610 may start advancing the cutting member (e.g. I-beam 614) around 1 second before the tissue impedance reaches a predetermined termination impedance value (where around this time the tissue welding is normally completed) such that the tissue welding is substantially completed by the time the cutting of the tissue in the first zone 3060 is completed. In another example aspect, the cutting speed may be adjusted so that the tissue welding is substantially completed by the end of the cutting. For example, if it takes 0.5 seconds from the moment the tissue impedance reaches the minimum impedance to the moment it reaches the termination impedance (e.g., where the tissue welding is completed), the cutting speed may be adjusted so that it would take 0.5 seconds to cut the tissue in the first or second zones 3060, 3065.

As explained above, in an example aspect, the control circuit 610 may provide the electrosurgical energy to both the first set of electrodes 3040L, 3040R and the second set of electrodes 3050L, 3050R while cutting the tissue in the second zone 3065 during the third time period 4845. In this case, since the clamped tissue received additional electrosurgical energy for the third time period 4845, the termination impedance $Z_{T2}$ at the third time 4830 may be higher than the termination impedance $Z^{T1}$ at the second time 4825 as seen in FIG. 48.

In an example aspect, the control circuit 610 may stop providing the electrosurgical energy to the first set of electrodes after cutting the tissue in the first zone 3060 and provide the electrosurgical energy only to the second set of electrodes while cutting the tissue in the second zone 3065. In this case, the termination impedance of the tissue in the second zone 3065 may be higher than the termination impedance of the tissue in the first zone 3060 since the tissue in the second zone 3065 received more electrosurgical energy for the third time period 4845 than the tissue in the first zone 3060, assuming that the predetermined time intervals for the two sets of electrodes are the same.

The functions or processes 4500, 4700 described herein may be executed by any of the processing circuits described herein, such as the control circuit 700 described in connection with FIGS. 16-17, the control circuit 610 described in connection with FIG. 18.

Various aspects of the subject matter described herein are set out in the following examples:

EXAMPLE 1

A surgical instrument comprising: an end effector comprising: a first jaw comprising a distal portion and a proximate portion; a second jaw that is movable relative to the first jaw; and at least one electrode in the first jaw; a control circuit configured to provide electrosurgical energy to the at least one electrode, wherein the control circuit comprises a shaft control segment and an electrosurgical energy control segment; and a first electrical conductor electrically connected between the end effector and the control circuit; wherein the shaft control segment is configured to provide a control signal for operating the end effector to the end effector through the first electrical conductor; wherein the electrosurgical energy control segment is configured to provide the electrosurgical energy to the at least one electrode through the first electrical conductor.

EXAMPLE 2

The surgical instrument of Example 1, wherein the electrosurgical energy control segment is electrically isolated from the shaft control segment.

EXAMPLE 3

The surgical instrument of one or more of Example 1 through Example 2, wherein the electrosurgical energy control segment is configured to electrically isolate the first electrical conductor from the shaft control segment when providing the electrosurgical energy to the at least one electrode.

EXAMPLE 4

The surgical instrument of Example 3, further comprising a switch electrically coupled between the electrosurgical energy control segment and the shaft control segment, wherein the electrosurgical energy control segment is configured to electrically isolate the first electrical conductor from the shaft control segment by controlling the switch.

EXAMPLE 5

The control circuit of Example 4, wherein the electrosurgical energy control segment is configured to electrically isolate a first electrical conductor from the shaft control segment by opening a switch located between the first electrical conductor and the shaft control segment.

EXAMPLE 6

The surgical instrument of one or more of Example 1 through Example 5, further comprising a second electrical conductor, wherein the shaft control segment is configured to provide the control signal to the end effector through the second electrical conductor and wherein the shaft control segment is configured to provide the control signal to the end effector through the second electrical conductor when the electrosurgical energy control segment is providing the electrosurgical energy to the at least one electrode through the first electrical conductor.

EXAMPLE 7

The surgical instrument of one or more of Example 1 through Example 6, wherein the second jaw comprises an anvil.

EXAMPLE 8

The surgical instrument of one or more of Example 1 through Example 7, wherein the electrosurgical energy comprises radio frequency (RF) energy.

EXAMPLE 9

The surgical instrument of one or more of Example 1 through Example 8, wherein the at least one electrode comprises a first set of electrodes located in the proximate portion of the first jaw and a second set of electrodes located in the distal portion of the first jaw, and wherein electrosurgical energy segment is configured to repeatedly alternate electrosurgical energy between the first set of electrodes and the second set of electrodes at a predetermined time interval.

EXAMPLE 10

The surgical instrument of Example 9, further comprising a cutting member, wherein the first jaw and the second jaw define an elongate slot therebetween extending from the proximate portion of the first jaw and wherein the cutting member is slideably receivable within the elongate slot to cut tissue located between the first jaw and the second jaw.

EXAMPLE 11

The surgical instrument of Example 10, wherein the first set of electrodes comprises a first electrode and a second electrode, wherein the first electrode is located on the left side of the elongate slot and the second electrode is located on the right side of the elongate slot.

EXAMPLE 12

The surgical instrument of one or more of Example 10 through Example 11, wherein the second set of electrodes comprise a third electrode and a fourth electrode, wherein the third electrode is located on the left side of the elongate slot and the fourth electrode is located on the right side of the elongate slot.

EXAMPLE 13

The surgical instrument of one or more of Example 9 through Example 12, wherein the predetermined time interval comprises a first time interval for the first set of electrodes and a second time interval for the second set of electrodes, wherein the first time interval is different from the second time interval.

EXAMPLE 14

The surgical instrument of one or more of Example 9 through Example 12, wherein the predetermined time interval for the alternation is sufficiently fast enough that the providing of the electrosurgical energy to the first set of electrodes and the second set of electrodes appears to be simultaneous.

EXAMPLE 15

The surgical instrument of one or more of Example 9 through Example 14, wherein the predetermined time interval is in the range of from about 0.1 to 0.5 seconds.

EXAMPLE 16

A surgical system comprising: a radio frequency (RF) energy generator; a handle body; an end effector comprising: a first jaw comprising a distal portion and a proximate portion; a second jaw that is movable relative to the first jaw; and at least one electrode in the first jaw; a control circuit configured to provide RF energy, from the RF energy generator, to the at least one electrode, wherein the control circuit comprises a shaft control segment and an RF control segment; and a first electrical conductor electrically connected between the end effector and the control circuit; wherein the shaft control segment is configured to provide a control signal for operating the end effector to the end effector through the first electrical conductor; wherein the RF control segment is configured to provide the RF energy to the at least one electrode through the first electrical conductor.

EXAMPLE 17

The surgical system of Example 16, wherein the RF control segment is electrically isolated from the shaft control segment.

EXAMPLE 18

The surgical system of one or more of Example 16 through Example 17, wherein the RF control segment is configured to electrically isolate the first electrical conductor from the shaft control segment when providing the RF energy to the at least one electrode.

EXAMPLE 19

The surgical system of Example 18, further comprising a switch electrically coupled between the first electrical conductor and the shaft control segment, wherein the RF control segment is configured to electrically isolate the first electrical conductor from the shaft control segment by controlling the switch.

EXAMPLE 20

The control circuit of Example 19, wherein the electrosurgical energy control segment is configured to electrically isolate a first electrical conductor from the shaft control segment by opening a switch located between the first electrical conductor and the shaft control segment.

EXAMPLE 21

The surgical system of one or more of Example 16 through Example 20, further comprising a second electrical conductor, wherein the shaft control segment is configured to provide the control signal to the end effector through the second electrical conductor, and wherein the shaft control segment is configured to provide the control signal to the end effector to the second electrical conductor when the RF control segment is providing the RF energy to the at least one electrode through the first electrical conductor.

EXAMPLE 22

The surgical system of one or more of Example 16 through Example 21, wherein the at least one electrode comprises a first set of electrodes located in the proximate portion of the first jaw and a second set of electrodes located in the distal portion of the first jaw, and wherein electrosurgical energy segment is configured to repeatedly alternate RF energy between the first set of electrodes and the second set of electrodes at a predetermined time interval.

Flexible Circuit Arrangement for Surgical Fastening Instruments

In some aspects, an electrosurgical device may have an articulating shaft to permit a user to adjust an angle of an end effector with respect to a handle assembly in order to access tissues at any orientation with respect to the user. Electrical signals exchanged between the end effector and the handle assembly should be unimpeded regardless of the type or extent of the articulation of the shaft.

Typical electrical wires running between the handle assembly and an end effector may become tangled and potentially severed over time due to repeated bending of the articulating shaft. Therefore, the present disclosure provides a flexible circuit element that may withstand repeated shaft articulation and any other mechanical motions required to operate the end effector of the electrosurgical device.

As depicted in FIG. 14, the flexible shaft circuit strip 1164 may be disposed in part within the proximal closure tube 1910 and extend through the articulation connector 1920 into the surgical end effector 1500. Similarly, the knife bar 1320 may also be disposed in part within the proximal closure tube 1910 and extend through the articulation connector 1920 into the surgical end effector 1500. The flexible shaft circuit strip 1164 may be centrally supported between the laminated plates or bars 1322 that form the knife bar 1320. Such arrangement facilitates sufficient flexing of the knife bar 1320 and flexible shaft circuit strip 1164 during articulation of the end effector 1500 while remaining sufficiently stiff so as to enable the knife member 1330 to be distally advanced through the clamped tissue. Together, the flexible shaft circuit strip 1164 and the laminated plates or bars 1322 that form the knife bar 1320 may comprise a flexible assembly to permit the knife bar 1320 to reciprocate while the articulation connector 1920 is bent.

FIG. 50 depicts in greater detail an aspect of a flexible assembly 3500. In the aspect of the flexible assembly 3500 depicted in FIG. 50, the knife bar 1320 is composed of two pairs of laminated plates 1322, in which one pair of laminated plates 1322 is disposed along a first side of the flexible shaft circuit strip 1164 and a second pair of laminated plates 1322 is disposed along a second side of the flexible shaft circuit strip 1164. Although the knife bar 1320 is disclosed as having two pairs of laminated plates 1322, it may be recognized that the knife bar 1320 may be composed of any even number of laminated plates 1322 in which a first half of the even number of laminated plates 1322 are disposed along a first side of the flexible shaft circuit strip 1164 and a second half of the even number of the laminated plates 1322 are disposed along a second side of the flexible shaft circuit strip 1164.

As depicted in FIG. 10, the flexible shaft circuit strip 1164 includes a distal contact portion 1169 that may be in electrical communication with a proximal contact portion 1672 of a channel circuit 1670 disposed within a wall recess 1625 formed in one of the channel walls 1622 of the elongate channel 1602. Thus, the distal end of the flexible shaft circuit strip 1164 may be in a fixed position relative to the elongate channel 1602 of the surgical end effector 1500. As depicted in FIG. 15, a proximal end of the flexible shaft circuit strip 1164 may be in electrical communication with a distal connector 1162 of a slip ring assembly 1150 disposed in the tool frame assembly 1200. Thus, the proximal end of the flexible shaft circuit strip 1164 may be in a fixed position relative to the tool frame assembly 1200. As depicted in FIG. 14, the flexible shaft circuit strip 1164 may thus traverse the articulation connector 1920 and may therefore bend on articulation of the articulation connector 1920.

The knife bar 1320 may similarly traverse the articulation connector 1920 from a proximal connection to the intermediate firing shaft portion 1310 disposed in the nozzle assembly 1240 to a distal connection at the knife member 1330, as depicted in FIG. 3. The knife bar 1320 may therefore be configured to reciprocate in order to activate the knife member 1330 while being flexible enough to bend when the articulation connector 1920 articulates.

It may be recognized that the reciprocating action of the knife bar 1320 along the sides of the flexible shaft circuit strip 1164 may cause rubbing and/or abrasion of any electrical traces or wires disposed on the flexible shaft circuit strip 1164. The electrical traces or wires may comprise wider wires/conductors for RF purposes and thinner wires for conventional stapling purposes (for example to conduct electrical control or sensing signals). Such wear may result in tears or gaps in the electrical wires that may compromise the ability of the electrical wires to conduct electrical, including RF, signals. Consequently, additional protection of the flexible shaft circuit strip 1164 may be required.

As depicted in FIG. 50, such protection may be provided by one or more leaf springs 3505 disposed on opposing sides of the flexible shaft circuit strip 1164. Each leaf spring 3505 may be disposed between a side of the flexible shaft circuit strip 1164 and an inner side of a laminated plate 1322. The leaf springs 3505 may remain fixed with respect to the flexible shaft circuit strip 1164, and may therefor protect each side of the flexible shaft circuit strip 1164 from wear from the knife bar 1320 during deployment of the knife member 1330. Each leaf spring 3505 may also provide physical support for the flexible shaft circuit strip 1164. Further, each leaf spring 3505 may provide a restoring force to the flexible shaft circuit strip 1164 to return the flexible shaft circuit strip 1164 to an essentially longitudinal (or unbent) geometry once the end effector 1500 is returned to a position co-axial with the shaft of the electrosurgical device. It may be recognized that in some aspect, the flexible assembly 3500 may also include one or more of such leaf springs 3505 in addition to the flexible shaft circuit strip 1164 and the plurality of laminated plates 1322.

FIG. 51A depicts the flexible assembly 3500 disposed within an electrosurgical device, in which the knife member 1330 is disposed at a proximal knife position 3530. FIG. 51B depicts the flexible assembly 3500 disposed within the electrosurgical device, in which the knife member 1330 is disposed at a distal knife position 3531. Although the articulation of the shaft of the electrosurgical device is depicted in a right direction (from the perspective of a use of the device) in FIGS. 51A and 51B, it should be recognized that the articulation of an electrosurgical device shaft may also be in a left direction (from the perspective of a use of the device), with the components of the flexible assembly 3500 suitably bent in the left direction.

FIG. 51A is similar to FIG. 14 and further points out additional details. For example, a proximal end of the flexible assembly 3500 may be stabilized within the spine assembly 1250 disposed within the proximal closure tube (1910, see FIG. 14). The distal end of the flexible assembly 2500 may be stabilized within the proximal end portion 1610 of the elongate channel (1602, see FIG. 4). The distal contact portion 1169 of the flexible shaft circuit strip 1164 may be both electrically and physically coupled to the proximal contact portion 1672 of the channel circuit (1670, see FIG. 10).

As depicted in FIG. 51A, the knife member may be located at a proximal knife position 3530. In one non-limiting aspect, the proximal knife position 3530 of the knife member may have a proximal knife distance (PKD), for example measured from a proximal end of the knife member to a distal end of the distal contact portion 1169 of the flexible shaft circuit strip 1164. FIG. 51B depicts the knife member located at a distal knife position 3531. In one non-limiting aspect, the distal knife position 3531 of the knife member may have a distal knife distance (DKD), for example measured from a proximal end of the knife member to a distal end of the distal contact portion 1169 of the flexible shaft circuit strip 1164. No limitation is implied regarding any explicit measurements of either the proximal knife distance PKD or the distal knife distance DKD. However, for the purpose of this disclosure, it may be accepted that the distal knife distance DKD is larger than the proximal knife distance PKD. It may be recognized during the use of the electrosurgical system that the knife member 1330 may traverse from the proximal knife position 3530 to the distal knife position 3531 or from the distal knife position 3531 to the proximal knife position 3530.

As disclosed above, the distal end of the flexible shaft circuit strip 1164 may be in a fixed position relative to the surgical end effector 1500 and the proximal end of the flexible shaft circuit strip 1164 may be in a fixed position relative to the tool frame assembly 1200. Additionally, the leaf springs 3505 may remain in a fixed position with respect to the flexible shaft circuit strip 1164. In one non-limiting aspect, a first leaf spring 3505 may be disposed proximate to or against a first side of the flexible shaft circuit strip 1164, and a second leaf spring 3505 may be disposed proximate to or against a second or opposing side of the flexible shaft circuit strip 1164. As the knife bar 1320 moves the knife member 1330 to either the distal knife position 3531 or the proximal knife position 3530, the laminated plates 1322 of the knife bar 1320 move in a sliding manner in a longitudinal direction with respect to the fixed position of the flexible shaft circuit strip 1164 and the leaf springs 3505.

While the knife bar 1320 is in a proximal aspect and the knife member 1330 is at the proximal knife position 3530, a portion of the first pair of laminated plates 1322 may be located at a first proximal position 3522*a* along an outer side of a first leaf spring 3505 and a portion of the second pair of laminated plates 1322 may be located at a second proximal position 3522*b* along an outer side of a second leaf spring 3505. In this configuration, at portion of the flexible shaft circuit strip 1164 and a portion of the leaf springs 3505 separate those portions of the laminated plates 1322 located at the first proximal position 3522*a* and the second proximal position 3522*b*. When the knife bar 1320 is moved distally so that the knife member 1330 is at the distal knife position 3531, the portion of the first pair of laminated plates 1322 located at the first proximal position 3522*a* may traverse in the distal direction to a first distal position 3522*c*. Similarly, when the knife bar 1320 is moved distally so that the knife member 1330 is at the distal knife position 3531, the portion of the second pair of laminated plates 1322 located at the second proximal position 3522*b* may traverse in the distal direction to a second distal position 3522*d*. In this manner at least some portion of the laminated plates 1322 move in a sliding manner with respect to the leaf springs 3505.

As a result of the motion of the knife bar 1320 in the distal direction, the portion of the first pair of laminated plates in the first distal position 3522*c* and the portion of the second pair of laminated plates in the second distal position 3522*d* are no longer separated by the flexible shaft circuit strip 1164 and the leaf springs 3505. Thus, an inner surface of the portion of the first pair of laminated plates in the first distal position 3522*c* may contact an inner surface of the portion of the second pair of laminated plates in the second distal position 3522*d* when the knife bar 1320 is moved in the distal direction.

It may similarly be understood that when the knife bar 1320 is moved in a proximal direction, thereby moving the knife member 1330 from the distal knife position 3531 to the proximal knife position 3530, the portion of the first pair of laminated plates 1322 located at the first distal position 3522*c* may traverse in the proximal direction to the first proximal position 3522*a*. Similarly, when the knife bar 1320 is moved in a proximal direction, the portion of the second pair of laminated plates 1322 located at the second distal position 3522*d* may traverse in the proximal direction to the second proximal position 3522*b*. As a result of the motion of the knife bar 1320 in the proximal direction, the portion of the first pair of laminated plates in the first proximal position 3522*a* and the portion of the second pair of laminated plates in the second proximal position 3522*b* may be separated by the leaf springs 3505 and the flexible shaft circuit strip 1164.

FIGS. 52A and 52B depict the flexible assembly 3500 of FIGS. 51A and 51B independent of structures that may house the flexible assembly 3500 in an electrosurgical device. In particular, FIG. 52A depicts an unarticulated flexible assembly 3501 (dotted line) and an articulated flexible assembly 3502 after a right articulation RA. FIG. 52B depicts the effect of a motion of the knife bar 1320 in a distal direction DD, thereby moving the knife member 1330 from the proximal knife position 3530 to the distal knife position 3531. FIG. 52B additionally depicts the effect of a motion of the knife bar 1320 in a proximal direction PD thereby moving the knife member 1330 from the distal knife position 3531 to the proximal knife position 3530.

As disclosed above with respect to FIGS. 51 and 52A, B, a flexible assembly 3500 may include a flexible shaft circuit strip 1164 disposed between a pair of leaf springs 3505, and a knife bar 1320 comprising two pairs of laminated plates 1322, in which a pair of laminated plates 1322 is disposed along an outer surface of each of the leaf springs 3505. Such leaf springs 3505 may provide protection of the surfaces of the flexible shaft circuit strip 1164 against abrasion and wear caused by the reciprocating motion of the laminated plates 1322. In an alternative aspect, the flexible assembly 3500 may lack the pair of leaf springs 3505 and the laminated plates 1322 may be disposed directly against the sides of the flexible shaft circuit strip 1164. The motion of the laminated plates 1322 against the sides of the flexible shaft circuit strip 1164 may include such motions as disclosed above in detail with respect to FIGS. 52A, B. Such an alternative aspect of a flexible assembly 3500 lacking the leaf springs 3505 may find use for a flexible assembly 3500 in which the flexible shaft circuit strip 1164 includes a protective coating on its sides, thereby obviating the need for protective leaf springs 3505.

It may be further recognized that the flexible assembly 3500 disclosed above may find utility in an electrosurgical device that includes an end effector configured to include a surgical staple/fastener cartridge, a radio frequency (RF) cartridge, or to releasably accept either a surgical staple/fastener cartridge or a radio frequency (RF) cartridge.

Disclosed above are aspects of a flexible assembly configured for use within an electrosurgical system comprising an articulating shaft. The flexible assembly may span an articulation connector and include a flexible shaft circuit strip configured to bend in accordance with the bending of the articulation connector. The flexible shaft circuit strip may be configured to permit communication of electrical signals from a handle assembly at a proximal end of the articulating shaft to an end effector at a distal end of the articulating shaft. The flexible assembly may also include one or more components configured to move in a transverse manner along a longitudinal axis of the articulating shaft to control one or more operations of the end effector. The flexible assembly may further include additional components configured to support or protect the flexible shaft circuit strip and/or the components configured to move in a transverse manner along the longitudinal axis of the articulating shaft.

Although a flexible assembly is described with respect to a motor driven surgical system as depicted in FIGS. 1-15 and as disclosed above, it may be recognized that a flexible assembly may not be limited to a surgical system having the specific components or functions of such a motor driven surgical system. Such a flexible assembly may be incorporated into any surgical system comprising at least an articulating shaft having a body or handle assembly at a proximal end of the articulating shaft and an end effector at a distal end of the articulating shaft.

Thus, a flexible shaft circuit strip of a flexible assembly may be configured to conduct any one or more electrical signals including DC electrical signals, AC electrical signals, digital electrical signals, analog electrical signals, RF electrical signals, or any combination or combinations of such electrical signals. The flexible shaft circuit strip may comprise any flexible non-conducting material on which or in which are disposed any number, type, or size of conducting wires or traces. The flexible shaft circuit strip may comprise any number of layers. The flexible shaft circuit strip may further comprise any one or more electronic components such as discrete circuits (for example, resistors, capacitors, and inductors) or integrated circuits. The flexible shaft circuit strip may further include protective layers to cover over the one or more conducting wires or traces, and or electronic components. The flexible assembly may include one or more springs, such as leaf springs, disposed on one or more sides of the flexible shaft circuit strip to provide a restoring force after the surgical system is returned from an articulated position. Alternatively, the flexible shaft circuit strip may incorporate such leaf springs in the body of the flexible shaft circuit strip.

The components configured to move in a transverse manner along the longitudinal axis of the articulating shaft may include any number or type of component or components capable of both a transverse motion and a flexible bending motion. Non-limiting examples of such components may include wires, bands, plates, and flexible shafts. One or more of such components configured to move in a transverse manner may be included in the flexible assembly. Multiple components may move in a concerted manner or may move independently. Multiple components may be disposed along a single side of the flexible shaft circuit strip. Alternatively, some number of the multiple components may be disposed along a first side of the flexible shaft circuit strip while a different number of the multiple components may be disposed along a second side of the flexible shaft circuit strip. The components configured to move in a transverse manner may be operatively coupled to any movable components either in a proximal end or a distal end of the articulating shaft, without limitation regarding the functions of such movable components.

The flexible assembly may also include any number or type of components configured to protect or support the flexible shaft circuit strip and/or the components configured to move in a transverse manner. For example, additional components may include any number or type of component configured to protect one or more surfaces of the flexible shaft circuit strip including, for example, protective sheets or sheaths. The additional components may include a frame to support the flexible shaft circuit strip. The additional components may further include protective enclosures for the components configured to move in a transverse manner such as cannulae.

Various aspects of the subject matter described herein are set out in the following numbered examples:

EXAMPLE 1

A motor driven surgical system comprising: a handle assembly; and an interchangeable surgical tool assembly, operatively coupled to the handle assembly, comprising: a nozzle assembly; a proximal closure tube having a proximal end operatively coupled to a distal end of the nozzle assembly; an articulation connector having a proximal end operatively coupled to a distal end of the proximal closure tube; a surgical end effector comprising a first jaw and a second jaw and having a proximal end operatively coupled to a distal end of the articulation connector; a flexible shaft circuit strip disposed within at least a portion of the proximal closure tube, at least a portion of the articulation connector, and at least a portion of the surgical end effector; a knife member slideably disposed within the surgical end effector; and a knife bar operatively connected to a proximal end of the knife member, wherein the knife bar comprises a first laminated plate disposed on a first side of the flexible shaft circuit strip and a second laminated plate disposed on a second side of the flexible shaft circuit strip, and wherein the knife bar is configured to reciprocate along a longitudinal axis of the proximal closure tube.

EXAMPLE 2

The motor driven surgical system of Example 1, wherein the first laminated plate comprises a first pair of laminated plates and the second laminated plate comprises a second pair of laminated plates.

EXAMPLE 3

The motor driven surgical system of one or more of Example 1 through Example 2, wherein the first laminated plate is configured to reciprocate along the first side of the flexible shaft circuit strip and the second laminated plate is configured to reciprocate along the second side of the flexible shaft circuit strip.

EXAMPLE 4

The motor driven surgical system of one or more of Example 1 through Example 3, further comprising a first leaf spring disposed between the first side of the flexible shaft circuit strip and the first laminated plate, and a second leaf spring disposed between the second side of the flexible shaft circuit strip and the second laminated plate.

EXAMPLE 5

The motor driven surgical system of Example 4, wherein the first laminated plate is configured to reciprocate along a first side of the first leaf spring and the second laminated plate is configured to reciprocate along a first side of the second leaf spring.

EXAMPLE 6

The motor driven surgical system of one or more of Example 4 through Example 5, wherein the first leaf spring and the second leaf spring are disposed within at least a portion of the articulation connector and at least a portion of the surgical end effector.

EXAMPLE 7

The motor driven surgical system of one or more of Example 4 through Example 6, wherein the first leaf spring and the second leaf spring are configured to bend around an articulation axis transverse to a longitudinal axis of the proximal closure tube.

EXAMPLE 8

The motor driven surgical system of one or more of Example 1 through Example 7, further comprising an elongated channel disposed within the first jaw, wherein the elongated channel is configured to releasably receive a surgical fastener cartridge.

EXAMPLE 9

The motor driven surgical system of one or more of Example 1 through Example 8, further comprising an elongated channel disposed within the first jaw, wherein the elongated channel is configured to releasably receive a radiofrequency cartridge.

EXAMPLE 10

The motor driven surgical system of Example 9, further comprising a channel circuit disposed along an inner longitudinal side of the elongated channel, wherein the channel circuit comprises a proximal contract portion configured to electrically couple to a distal contact portion of the flexible shaft circuit strip, and wherein the channel circuit comprises a distal contract portion configured to electrically couple to a flexible cartridge circuit disposed on a surface of the radiofrequency cartridge.

EXAMPLE 11

A flexible assembly for use within an articulated component of a motor driven surgical system, the flexible assembly comprising: a flexible shaft circuit strip; and a knife bar comprising a first laminated plate disposed along a first side of the flexible shaft circuit strip and a second laminated plate disposed along a second side of the flexible shaft circuit strip, wherein the knife bar is configured to reciprocate along a longitudinal axis of the flexible shaft circuit strip.

EXAMPLE 12

The flexible assembly of Example 11, wherein the flexible assembly is configured to bend around an articulation axis transverse to a longitudinal axis of the flexible shaft circuit strip.

EXAMPLE 13

The flexible assembly of one or more of Example 11 through Example 12, wherein the first laminated plate comprises a first pair of laminated plates and the second laminated plate comprises a second pair of laminated plates.

EXAMPLE 14

The flexible assembly of one or more of Example 11 through Example 13, wherein a side of a first portion of the first laminated plate is disposed along the first side of the flexible shaft circuit strip and a side of a first portion of the second laminated plate is disposed along the second side of the flexible shaft circuit strip when the flexible assembly is in a first state, and wherein the side of the first portion of the first laminated plate is disposed along the side of the first portion of the second laminated plate when the flexible assembly is in a second state.

EXAMPLE 15

The flexible assembly of one or more of Example 11 through Example 14, further comprising a first leaf spring disposed between the first side of the flexible shaft circuit strip and the first laminated plate, and a second leaf spring disposed between the second side of the flexible shaft circuit strip and the second laminated plate.

EXAMPLE 16

The flexible assembly of Example 15, wherein the first laminated plate is configured to reciprocate along a first side of the first leaf spring and the second laminated plate is configured to reciprocate along a first side of the second leaf spring.

EXAMPLE 17

The flexible assembly of one or more of Example 15 through Example 16, wherein a side of a first portion of the first laminated plate is disposed along a first side of the first leaf spring and a side of a first portion of the second laminated plate is disposed along a first side of the second leaf spring when the flexible assembly is in a first state, and wherein the side of the first portion of the first laminated plate is disposed along the side of the first portion of the second laminated plate when the flexible assembly is in a second state.

EXAMPLE 18

The flexible assembly of one or more of Example 11 through Example 17, wherein the flexible shaft circuit strip comprises a distal contact portion.

EXAMPLE 19

The flexible assembly of one or more of Example 11 through Example 18, wherein the flexible shaft circuit strip comprises a plurality of narrow wires and a plurality of wider wires.

EXAMPLE 20

The flexible assembly of Example 19, wherein the plurality of wider wires is configured to conduct a radiofrequency signal.

Surgical System Coupleable with Staple Cartridge and Radio Frequency Cartridge, and having a Plurality of Radio-Frequency Energy Return Paths In some aspects, an electrosurgical device may be configured to induce a hemostatic seal in a tissue and/or between tissues. The hemostatic seal may be created by a combination of an applied compressive force to the tissue and an application of electrical energy to the tissue. In some aspects of an electrosurgical device, the compressive force may be supplied by a compression of the tissue between jaw assemblies. Additionally, the electrical energy may be supplied by one or more electrodes disposed within or on some components of the jaw assemblies. The amount of electrical energy sufficient to effect the hemostatic seal may depend, in part, on the thickness, density, and/or quality of tissue to be sealed.

It may be understood that an application of excessive electrical energy to a tissue may result in burning or scaring of the tissue. However, the application of insufficient electrical energy to a tissue may result in an ineffective hemostatic seal. Thus, a user of the electrosurgical device may be required to adjust the amount of electrical energy delivered to the tissue compressed between the jaw assemblies of the device based on the tissue thickness, density, and quality. If a tissue compressed between the jaw assemblies is essentially homogeneous, the user of the electrosurgical device may use simple controls to adjust the amount of electrical energy delivered to the tissue. However, it may be recognized that some tissues for hemostatic sealing are inhomogeneous in any one or more of their thickness, density, and/or quality. As a result, a single control for the amount of electrical energy delivered to the tissue compressed between the jaw assemblies may result in burned portions as well as insufficiently sealed portions of the tissue. It is therefore desirable to have an electrosurgical device that may be configured to deliver a variety of electrical energies to a piece of tissue compressed between the jaw assemblies.

Electrosurgical instruments apply electrosurgical energy to seal tissue. However, at times tissue may be sealed with staples delivered by a staple cartridge and at other times the tissue may be sealed by the application of electrosurgical energy. This requires the user to inventory two separate instruments. Therefore, it would be desirable to provide an elongate shaft for use with a surgical stapler where an interchangeable RF cartridge is used in place of a staple cartridge. In situations where an interchangeable RF cartridge is used in place of a staple cartridge, the present disclosure provides various techniques for covering select surfaces with non-conductive coatings to determine the electrical path of radio frequency (RF) applied energy when the interchangeable RF cartridges is used in place of the staple cartridge.

FIG. 53 is a perspective view of a surgical system 4000. The surgical system 4000 is similar to the motor-driven surgical system 10 in that the surgical system 4000 is configured to be used in connection with the conventional surgical stapler/fastener cartridges 1400 and the radio-frequency cartridges 1700. However, the surgical system 4000 is different from the motor-driven surgical system 10 in that the surgical system 4000 is also configured to be used in connection with radio-frequency cartridges 4002 which are similar to but different from the radio-frequency cartridges 1700 and are described in more detail below. The surgical system 4000 is also different from the motor-driven surgical system 10 in that the surgical system 4000 includes a firing system 4004 (See FIG. 56) which is similar to but different from the firing system 1300 of the motor driven surgical system 10 and is described in more detail below.

As shown in FIG. 53, the surgical system 4000 includes a handle assembly 4006 and an interchangeable tool assembly 4008 coupleable to the handle assembly 4006. The handle assembly 4006 is similar or identical to the handle assembly 500 and the interchangeable tool assembly 4008 is similar or identical to the interchangeable tool assembly 1000. The interchangeable tool assembly 4008 includes an end effector 4010 which includes a first jaw 4012 and a second jaw 4014. The first jaw 4012 includes an elongate channel 4016 which is configured to removably support the radio-frequency cartridge 4002. According to various aspects, the elongate channel 4016 may also be configured to removably support the surgical stapler/fastener cartridge 1400 and the radio frequency cartridge 1700. The second jaw 4014 includes an anvil 4018. The end effector 4010 is similar or identical to the end effector 1500, the first jaw 4012 is similar or identical to the first jaw 1600, the second jaw 4014 is similar or identical to the second jaw 1800, the elongate channel 4016 is similar or identical to the elongate channel 1602 and the anvil 4018 is similar or identical to the anvil 1810.

FIG. 54 is a partial cross-section of the end effector 4010 of the surgical system 4000 according to various aspects, showing the interface between the radio-frequency cartridge 4002 and the anvil 4018 when the end effector 4010 in a fully closed position. For purposes of clarity, the elongate channel 4016 is not shown in FIG. 54. The radio-frequency cartridge 4002 is similar to the radio frequency cartridge 1700 but is different in that the radio-frequency cartridge 4002 includes a cartridge deck surface 4020 which defines at least two protrusions 4022. Although only one of the protrusions 4022 is shown in the cross-section of FIG. 54, it will be appreciated that a first one of the protrusions 4022 is positioned on one side of a centrally disposed elongate slot 4024 of the radio-frequency cartridge 4002 and a second one of the protrusions 4022 is positioned on the opposite side of the centrally disposed elongate slot 4024 of the radio-frequency cartridge 4002 (See, e.g., FIG. 55).

The radio-frequency cartridge 4002 is also different from the radio frequency cartridge 1700 in that the radio-frequency cartridge 4002 includes insulative sheath members 4026 which respectively define protrusions 4028 which are associated with the protrusions 4022. Although only one of the insulative sheath members 4026 and one of the protrusions 4028 are shown in the cross-section of FIG. 54, it will be appreciated that a first one of the insulative sheath members 4026 and a first one of the protrusions 4028 are positioned on one side of the centrally disposed elongate slot 4024 of the radio-frequency cartridge 4002, and a second one of the insulative sheath members 4026 and a second one of the protrusions 4028 are positioned on the opposite side of the centrally disposed elongate slot 4024 of the radio-frequency cartridge 4002 (See, e.g., FIG. 55). The protrusions 4028 are positioned between the protrusions 4022 of the cartridge deck surface 4020 and the anvil 4018 of the interchangeable tool assembly 4008.

The radio-frequency cartridge 4002 is also different from the radio frequency cartridge 1700 in that the radio-frequency cartridge 4002 further includes flexible circuit assemblies 4030 which respectively define protrusions 4032 which are associated with the protrusions 4022 and the protrusions 4028. Although only one of the flexible circuit assemblies 4030 and one of the protrusions 4032 are shown in the cross-section of FIG. 54, it will be appreciated that a first one of the flexible circuit assemblies 4030 and a first one of the protrusions 4032 are positioned on one side of the centrally disposed elongate slot 4024 of the radio-frequency cartridge 4002, and a second one of the flexible circuit assemblies 4030 and a second one of the protrusions 4032 are positioned on the opposite side of the centrally disposed elongate slot 4024 of the radio-frequency cartridge 4002 (See, e.g., FIG. 55). The protrusions 4032 are positioned between the protrusions 4028 and the anvil 4020 of the interchangeable tool assembly 4004. Other than the protrusions 4022, 4028, 4032, the cartridge deck surface 4020 is similar to the cartridge deck surface 1711, the insulative sheath members 4026 are similar to the insulator/sheath members 1734, and the flexible circuit assemblies 4030 are similar to the flexible circuit assemblies 1730.

When tissue T (FIG. 6) is positioned between the radio-frequency cartridge 4002 and the anvil 4018, and the anvil 4018 is moved towards the radio-frequency cartridge 4002 to clamp the tissue positioned between the radio-frequency cartridge 4002 and the anvil 4018, the minimum gap or distance $d_1$ between the anvil 4018 and the radio-frequency staple cartridge 4002 proximate the distal end of the end effector 4010 is realized when the insulation material 1819 positioned on the tissue facing segments 1817 of the fastener forming undersurface 1813 of the anvil 4018 is brought into physical contact with the protrusions 4032. Once this physical contact between the insulation material 1819 and the protrusions 4032 is established, the protrusions 4032 physically prevent (1) the anvil 4018 from being brought closer to the radio-frequency cartridge 4002 and (2) the tissue from being further compressed. The establishment of this minimum gap or distance $d_1$ also operates to help prevent the formation of an electrical short circuit between the radio-frequency cartridge 4002 and the anvil 4018.

An example of an RF cartridge that routes RF energy through tissue from an electrode to an inner surface of a staple pocket is shown in FIGS. 6 and 7. Accordingly, turning briefly to FIGS. 6 and 7, there is shown a partial cross-sectional view of the end effector 1500 depicted in FIGS. 1-5 supporting an RF cartridge 1700 (FIGS. 10-12), 4002 (FIGS. 53 and 55) therein and with tissue T clamped between the cartridge 1400 (FIG. 4) and the anvil 1810 and a partial cross-sectional view of the anvil 1810. In the example illustrated in FIGS. 6 and 7, the anvil 1810 comprises non-conductive masking except in pockets 1814 such that all of the surfaces not for staple formation are masked off and coated with a non-conductive electrically insulative material 1819 creating a varying return path surface containing dimples and extension minimizing the charring and tissue sticking experienced by flat opposed electrodes. As shown in FIG. 6, in at least one form, the anvil 1810 includes an anvil body portion 1812 that is fabricated from an electrically conductive metal material for example and has a staple forming undersurface 1813 that has a series of fastener forming pockets 1814 formed therein on each side of a centrally disposed anvil slot 1815 that is configured to slidably accommodate the knife member 1330 (FIGS. 2-4, 56) therein. The anvil slot 1815 opens into an upper opening 1816 that extends longitudinally through the anvil body to accommodate the anvil engagement features 1336 (FIG. 4) on the knife member 1330 during firing. When a conventional mechanical surgical staple/fastener cartridge 1400 (FIG. 4) is installed in the elongate channel 1602 (FIG. 4), the staples/fasteners are driven into forming contact with the corresponding fastener forming pockets 1814. The anvil body 1812 may have an opening in the upper portion thereof to facilitate ease of installation for example. An anvil cap 1818 may be inserted therein and welded to the anvil body 1812 to enclose the opening and improve the overall stiffness of the anvil body 1812. As shown in FIG. 7, to facilitate use of the end effector 1500 (FIGS. 1 and 2) in connection with RF cartridges 1700, 4002 the tissue facing segments 1817 of the fastener forming undersurface 1813 may have electrically insulative material 1819 thereon. Accordingly, the features described in reference to FIGS. 6 and 7 can be applied to the end effector 4010 (FIGS. 53 and 55) and the RF cartridge 4002 (FIGS. 53-55).

FIG. 55 is a partial perspective view of the radio-frequency cartridge 4002 supported by the elongate channel 4016 according to various aspects. As described above, the radio-frequency cartridge 4002 includes flexible circuit assemblies 4030 and protrusions 4032 on each side of the centrally disposed elongate slot 4024. For purposes of clarity, the insulative sheath members 4026 are not shown in FIG. 55. Additionally, it will be appreciated that the protrusions 4022, 4028 are hidden from view in FIG. 55.

FIG. 56 is an exploded perspective assembly view of portions of the handle assembly 4006 and the interchangeable tool assembly 4008 according to various aspects. The handle assembly 4006 is similar or identical to the handle assembly 500. The interchangeable tool assembly 4008 is similar to the interchangeable tool assembly 1000, but is different in that the portion of the firing system 4004 associated with the interchangeable tool assembly 4008 is different from the portion of the firing system 1300 associated with the interchangeable tool system 1000. The portion of the firing system 4004 associated with the handle assembly 4006 is similar or identical to the portion of the firing system 1300 associated with the handle assembly 500. The portion of the firing system 4004 associated with the handle assembly 4006 includes a firing drive system 4034 which includes a longitudinal drive member 4036. The longitudinal drive member 4036 has a rack of teeth 4038 formed thereon and has an attachment cradle 4040 on its distal end. The firing drive system 4034, the longitudinal drive member 4036, the rack of teeth 4038 and the attachment cradle 4040 are similar or identical to the firing drive system 530, the longitudinal drive member 540, the rack of teeth 542 and the attachment cradle 544 of the firing system 1300.

The portion of the firing system 4004 associated with the interchangeable tool assembly 4008 includes a nozzle assembly 4042, an intermediate firing shaft portion 4044, a firing shaft attachment lug 4046, a knife bar 4048, a firing member/knife member 4050 and a proximal closure tube 4054 which are similar or identical to the nozzle assembly 1240, the intermediate firing shaft portion 1310, the firing shaft attachment lug 1314, the knife bar 1320, the firing member/knife member 1330 and the proximal closure tube 1910. However, the portion of the firing system 4004 associated with the interchangeable tool assembly 4008 is different from the portion of the firing system 1300 associated with the interchangeable tool assembly 1000 in that the portion of the firing system 4004 associated with the interchangeable tool assembly 4008 further includes an electrically insulative material 4056 (an electrically non-conductive material) which operates to prevent radio-frequency energy from inadvertently passing from the portion of the firing system 4004 associated with the interchangeable tool assembly 4008 to the handle assembly 4006. In situations where radio-frequency energy is applied to the surgical instrument 4000, the firing member/knife member 4050 may conduct radio-frequency energy. Without the electrically insulative material 4056, the firing member/knife member 4050 may inadvertently conduct radio-frequency energy through the knife bar 4048, through the intermediate firing shaft portion 4044 and/or through the firing shaft attachment lug 4046 to the portion of the firing system 4004 associated with the handle assembly 4006.

According to various aspects, the electrically insulative material 4056 is a coating which covers the firing shaft attachment lug 4046. When the firing shaft attachment lug 4046 is seated into the attachment cradle 4040 within the handle assembly 4006, electrically insulative material 4056 operates to electrically isolate the longitudinal drive member 4036 of the firing drive system 4034 and the handle assembly 4006 from the interchangeable tool assembly 4008. In other words, the longitudinal drive member 4036 and the handle assembly 4006 are protected from receiving inadvertent radio-frequency energy from the interchangeable tool assembly 4008. According to other aspects, the electrically insulative material 4056 may also cover other portions of the firing system 4004 to electrically isolate the longitudinal drive member 4036 and the handle assembly 4006 from the interchangeable tool assembly 4008. For example, the electrically insulative material 4056 may also cover other portions of a proximal end 4058 of intermediate firing shaft portion 4044. Thus, by selectively covering various portions of the firing system 4004 associated with the interchangeable tool assembly 4008 with the electrically insulative material 4056, the conductive path of radio-frequency energy can be designed to electrically isolate the handle assembly 4006 from the interchangeable tool assembly 4008 for instances where the radio-frequency cartridge 1700 or the radio-frequency cartridge 4002 is being utilized with the surgical system 4000.

Various aspects of the subject matter described herein are set out in the following numbered examples:

EXAMPLE 1

An interchangeable tool assembly, comprising: a first jaw configured to support a staple cartridge during a first time period and a radio-frequency cartridge during a second time period; a second jaw coupled to the first jaw, wherein a surface of the second jaw defines a plurality of staple forming pockets configured to form staples driven from the staple cartridge; and an electrically insulative material covering segments of the surface of the second jaw other than the staple forming pockets, wherein the staple forming pockets define at least one return path for radio-frequency energy delivered by the radio-frequency cartridge.

EXAMPLE 2

The interchangeable tool assembly of Example 1, wherein the interchangeable tool assembly is configured to be releasably coupleable to a handle assembly, and wherein at least one component positioned within the interchangeable tool assembly comprises electrical insulation to electrically insulate the handle assembly from inadvertent radio-frequency energy from the interchangeable tool assembly.

EXAMPLE 3

The interchangeable tool assembly of one or more of Example 1 through Example 2, wherein the interchangeable tool assembly is configured to be releasably coupleable to a handle assembly, and wherein at least one component positioned within the interchangeable tool assembly comprises electrical insulation to electrically insulate the handle assembly from inadvertent radio-frequency energy from the interchangeable tool assembly.

EXAMPLE 4

The interchangeable tool assembly of one or more of Example 1 through Example 3, wherein the plurality of staple forming pockets comprise: a first plurality of staple forming pockets positioned to a first side of a centrally disposed anvil slot; and a second plurality of staple forming pockets positioned to a second side of the centrally disposed anvil slot.

EXAMPLE 5

The interchangeable tool assembly of one or more of Example 1 through Example 4, wherein the plurality of staple forming pockets provide for a plurality of different return paths for radio-frequency energy delivered by the radio-frequency cartridge.

EXAMPLE 6

The interchangeable tool assembly of one or more of Example 1 through Example 5, wherein the segments of the surface of the second jaw face the first jaw.

EXAMPLE 7

The interchangeable tool assembly of one or more of Example 1 through Example 6, further comprising a firing system positioned within the interchangeable tool assembly, wherein the firing system is configured to couple to a handle assembly, wherein the firing system is electrically insulated to electrically insulate the handle assembly from inadvertent radio-frequency energy.

EXAMPLE 8

The interchangeable tool assembly of one or more of Example 1 through Example 7, further comprising a staple cartridge.

EXAMPLE 9

The interchangeable tool assembly of one or more of Example 1 through Example 8, wherein the surgical system further comprises the radio-frequency cartridge.

EXAMPLE 10

The interchangeable tool assembly of Example 9, wherein the radio-frequency cartridge comprises at least two protrusions which collectively provide for a minimum gap distance between the first and second jaws.

EXAMPLE 11

A surgical tool assembly, comprising: an elongate channel configured to support a staple cartridge during a first time period and a radio-frequency cartridge during a second time period; and an anvil coupled to the elongate channel, wherein the anvil comprises: a surface which faces the elongate channel and defines a plurality of staple forming pockets configured to form staples driven from the staple cartridge; and an electrically insulative material which covers segments of the surface of the second jaw, wherein the plurality of staple forming pockets provide for a plurality of different return paths for radio-frequency energy delivered by the radio-frequency cartridge.

EXAMPLE 12

The surgical tool assembly of Example 11, wherein the elongate channel and the anvil collectively form an end effector.

EXAMPLE 13

The surgical tool assembly of one or more of Example 11 through Example 12, wherein the plurality of staple forming pockets comprise: a first plurality of staple forming pockets positioned to a first side of a centrally disposed anvil slot; and a second plurality of staple forming pockets positioned to a second side of the centrally disposed anvil slot.

EXAMPLE 14

The surgical tool assembly of one or more of Example 11 through Example 13, wherein the segments of the surface of the second jaw are other than the staple forming pockets.

EXAMPLE 15

The surgical tool assembly of one or more of Example 11 through Example 14, wherein the surgical tool assembly further comprises the staple cartridge.

EXAMPLE 16

The surgical tool assembly of one or more of Example 11 through Example 15, wherein the surgical tool assembly further comprises the radio-frequency cartridge.

EXAMPLE 17

The surgical tool assembly of Example 16, wherein the radio-frequency cartridge comprises at least two protrusions which collectively provide for a minimum gap distance between the elongate channel and the anvil.

EXAMPLE 18

An interchangeable tool assembly, comprising: an end effector configured to releasably couple to a shaft assembly, wherein the end effector comprises: an elongate channel configured to support a staple cartridge during a first time period and a radio-frequency cartridge during a second time period; and an anvil coupled to the elongate channel, wherein the anvil comprises an electrically insulative material and defines a plurality of different return paths for radio frequency energy delivered by the radio-frequency cartridge.

EXAMPLE 19

The interchangeable tool assembly of Example 18, wherein the electrically insulative material faces the elongate channel.

EXAMPLE 20

The interchangeable tool assembly of one or more of Example 18 through Example 19, further comprising the radio-frequency cartridge.

Systems and Methods for Controlling Control Circuits for an Independent Energy Delivery Over Segmented Sections In various open, endoscopic, and/or laparoscopic surgeries, for example, it may be desirable to coagulate, seal, and/or fuse tissue. One method of sealing tissue relies upon the application of energy, such as electrical energy, for example, to tissue captured or clamped within an end-effector or an end-effector assembly of a surgical instrument in order to cause thermal effects within the tissue. Various mono-polar and bi-polar radio frequency (RF) surgical instruments and surgical techniques have been developed for such purposes. In general, the delivery of RF energy to the captured tissue can elevate the temperature of the tissue and, as a result, the energy can at least partially denature proteins within the tissue. Such proteins, such as collagen, for example, can be denatured into a proteinaceous amalgam that intermixes and fuses, or seals, together as the proteins renature. As the treated region heals over time, this biological seal may be reabsorbed by the body's wound healing process.

In certain arrangements of a bi-polar radio frequency (RF) surgical instrument, the surgical instrument can comprise opposing first and second jaws, wherein each jaw can comprise an electrode. In use, the tissue can be captured between the jaws such that energy can flow between the electrodes in the opposing jaws and through the tissue positioned therebetween. Such instruments may have to seal many types of tissues, such as anatomic structures having walls with irregular or thick fibrous content, bundles of disparate anatomic structures, and/or substantially thick or thin anatomic structures.

Generally, it is difficult to provide electrosurgical energy to low impedance tissue continuously until welding of the tissue is substantially completed. For example, when providing the electrosurgical energy to low impedance tissue, there is a point where the tissue impedance becomes too low, acting like a short circuit so that the tissue merely draws a lot of current while providing no or little electrosurgical energy to the tissue. This can result in several undesirable outcomes including, for example, incomplete tissue welding, excessive heating of the electrodes, a delay of the surgery, clinician inconvenience or frustration, etc.

Aspects of the present disclosure may address the above noted deficiency by controlling control circuits for an independent energy delivery over segmented sections. In an example aspect, a surgical instrument may include an end effector having a first jaw with a distal portion and a proximate portion, a second jaw that is movable relative to the first jaw, a first set of electrodes located in the distal portion of the first jaw, and a second set of electrodes located in the proximate portion of the first jaw. The surgical instrument also may include a control circuit programed to provide electrosurgical energy (e.g., RF energy) to the first set of electrodes and the second set of electrodes. The electrosurgical energy provided to the first set of electrodes and the second set of electrodes may repeatedly alternate between the first set of electrodes and the second set of electrodes at a predetermined time interval. For example, the electrosurgical energy may be provided to the first set of electrodes for a first period of time (e.g., 0.25 seconds), to the second set of electrodes for a second period of time (e.g., 0.25 seconds) after the first period of time and, then, to the first set of electrodes for a third period of time (0.25 seconds), and so on. The alternation of the electrosurgical energy between the first set of electrodes and the second set of electrodes may be repeated, for example, until the welding of the tissue starts to complete or is substantially completed. The alternation of the electrosurgical energy at a very short period of time interval (e.g., 0.25 seconds) between the first set of electrodes and the second set of electrodes may facilitate the complete welding of low impedance tissue without excessive heating of the electrodes or a delay of the surgery. In an example, this alternation of the electrosurgical energy may be carried out by a microchip in the first jaw or a processor in the body of the surgical instrument using the RF energy provided from a conventional RF energy generator.

In this way, aspects of the present disclosure may enable the surgical instrument to provide the electrosurgical energy to the tissue having low impedance until the welding of the low impedance tissue is substantially completed. Moreover, aspects of the present disclosure may advantageously use the microchip in the first jaw or a processor in the body of the surgical instrument to alternate the electrosurgical energy between the two sets of electrodes using the RF energy from a conventional RF energy generator.

FIG. 42 shows a schematic top view of a jaw 3000 in an end effector (e.g., end effector 1500) of a surgical instrument (e.g., surgical system 10 or surgical tool assembly 1000) according to one aspect of this disclosure. The jaw 3000 may include a cartridge 3010, a flex circuit 3020 having flex circuit contacts 3025 (e.g., exposed contacts 1756), and an elongate slot 3030, within which a cutting member (e.g., knife member 1330) is slideably receivable to cut tissue clamped within the end effector along a cutting line 3035. The elongate slot may extend from a proximate end of the jaw 3000. In an example aspect, the flex circuit 3020 also may include a microchip (e.g., distal micro-chip 1740) and, then, the cartridge 3010 may be referred to as a smart cartridge. The jaw 3000 also may include a first set of electrodes 3040L, 3040R in a first zone 3060, and a second set of electrodes 3050L, 3050R in a second zone 3065. In an example aspect, the first zone 3060 may be located in a proximate portion of the jaw 3000 and the second zone 3065 may be located in a distal portion of the jaw 3000. In another example aspect, the first zone 3060 and the second zone 3065 may be located in any other suitable places of the jaw 3000.

The first and second set of electrodes 3040L, 3040R, 3050L, 3050R may be in communication with and/or deposited on the flex circuit 3020. In an example, the elongate slot 3030 may be disposed in the center of the jaw 3000. In another example, the elongate slot 3000 may be disposed in any other suitable places in the jaw 3000. As seen in FIG. 42, the electrodes 3040L and 3050L may be located on the left side of the elongate slot 3030 and the electrodes 3040R and 3050R may be located on the right side of the elongate slot 3030. In an example aspect, a control circuit (e.g., microprocessor 560, segmented RF circuit 1160, or distal micro-chip 1740) may be configured to provide electrosurgical energy to the first set of electrodes 3040L, 3040R and the second set of electrodes 3050L, 3050R.

The electrosurgical energy may be in the form of radio frequency (RF) energy. RF energy is a form of electrical energy that may be in the frequency range of 200 kilohertz (kHz) to 1 megahertz (MHz). In application, an electrosurgical device can transmit low frequency RF energy through tissue, which causes ionic agitation, or friction, in effect resistive heating, thereby increasing the temperature of the tissue. The low operating temperatures of RF energy is useful for removing, shrinking, or sculpting soft tissue while simultaneously sealing blood vessels. RF energy works particularly well on connective tissue, which is primarily comprised of collagen and shrinks when contacted by heat. The first set of electrodes 3040L, 3040R and the second set of electrodes 3050L, 3050R may be electronically connected to the control circuit through the flex circuit 3020. The first set of electrodes 3040L, 3040R and the second set of electrodes 3050L, 3050R may be configured to emit RF energy to form a hemostatic (or a coagulation) line on the tissue adjacent the electrodes 3040L, 3040R, 3050L, 3050R along the cutting line 3035.

In an example aspect, the length 3070 of the first set of electrodes 3040L, 3040R may be in the range of about 10 mm to about 100 mm, preferably in the range of about 20 mm to about 50 mm, more preferably in the range of about 25 mm to about 35 mm. Similarly, in an example aspect, the length 3075 of the second set of electrodes 3050L, 3050R may be in the range of about 10 mm to about 100 mm, preferably in the range of about 20 mm to about 50 mm, more preferably in the range of about 25 mm to about 35 mm. In another example aspect, the first set of electrodes 3040L, 3040R and the second set of electrodes 3050L, 3050R may have any other suitable length. In an example aspect, a gap between the first set of electrodes 3040L, 3040R and the second set of electrodes 3050L, 3050R may be very small so that the claimed tissue may be welded from the first zone 3060 to the second zone 3065 continuously with no tissue located between the two zones 3060 and 3065 being unsealed/welded. In an example aspect, the length 3072 of the gap between the first set of electrodes 3040L, 3040R and the second set of electrodes 3050L, 3050R may be in the range of about 0.1 mm to about 20 mm, preferably in the range of about 0.5 mm to about 5 mm, more preferably in the range of about 1 mm to about 3 mm. In another example aspect, the length 3072 of the gap between the first set of electrodes 3040L, 3040R and the second set of electrodes 3050L, 3050R may have any other suitable length. The total length 3080 of the first set of electrodes 3040L, 3040R, the second set of electrodes 3050L, 3050R, and the gap may be in the range of about 20 mm to about 210 mm, preferably in the range of about 60 mm to about 100 mm, more preferably in the range of about 50 mm to about 70 mm.

In an example aspect, the first set of electrodes 3040L, 3040R and the second set of electrodes 3050L, 3050R may be electrically coupled to the wider wires 1168 from which the first set of electrodes 3040L, 3040R and the second set of electrodes 3050L, 3050R may receive the electrosurgical energy (e.g., RF energy). The first set of electrodes 3040L, 3040R and the second set of electrodes 3050L, 3050R may be electronically coupled to a plurality of wires (e.g., wires 1732L and 1732R) on the flex circuit 3020 through which the wider wires 1168 may provide the RF energy to the electrodes 3040L, 3040R, 3050L, 3050R. In an example aspect, the wires 1168, 1732L, 1732R may be insulated to protect components (e.g., a microchip 1740, a spine assembly 1250, laminated plates 1322, a flex circuit 3020) adjacent the wires 1168, 1732L, 1732R from inadvertent RF energy. In an example aspect, the cartridge 3010 may be interchangeable. When changing the cartridge, the narrow and wider wires 1166, 1168 in the surgical instrument may be connected to the new wires and electrodes in the new cartridge.

In an example aspect, the cutting member (e.g., knife member 1330) may be directly or indirectly coupled with a motor (e.g., motor 505). When the control circuit provides voltage to the motor, the cutting member may be advanced to the first zone 3060 or the second zone 3065 to cut the tissue in the first and second zones 3060, 3065.

FIG. 43 shows a graph 3100 depicting voltage applied to electrodes 3040L, 3040R, 3050L, 3050R as a function of time in accordance with a non-limiting aspect. The pulses 3110 may represent the voltage applied to the electrodes 3040L, 3040R in the first zone 3060. The pulses 3120 may represent the voltage applied to the electrodes 3050L, 3050R in the second zone 3065. When the voltage is on for the first zone 3060, electrosurgical energy may be applied to the tissue adjacent to the first set of electrodes 3040L, 3040R to form a coagulation/welding line there. Similarly, when the voltage is on for the second zone 3065, electrosurgical energy may be applied to the tissue adjacent to the second set of electrodes 3050L, 3050R to form a coagulation/welding line there. As shown in FIG. 43, in an example aspect, the control circuit may apply a set voltage alternatively throughout the alternation cycles. Then, the power/energy applied to the tissue may change as the tissue impedance changes. In another example aspect, the control circuit or the generator 400 may change the voltage applied to the electrodes (e.g., 30 volts for the first 5 cycles, 50 volts for the next 5 cycles, 80 volts for the next 5 cycles). In another example aspect, the control circuit or the generator 400 may change the voltage applied to the electrodes to provide a constant power to the tissue. In this case, the voltage may change as the tissue impedance changes.

In an example aspect, the electrosurgical energy may repeatedly alternate between the first set of electrodes 3040L, 3040R and the second set of electrodes 3050L, 3050R at a predetermined time interval. For example, the electrosurgical energy may be provided to the first set of electrodes 3040L, 3040R for a first period of time (e.g., 0.25 seconds) and, then, to the second set of electrodes 3050L, 3050R for a second period of time (e.g., 0.25 seconds). Then, it may be switched back to the first set of electrodes 3040L, 3040R and the alternation of the electrosurgical energy between the first set of electrodes 3040L, 3040R and the second set of electrodes 3050L, 3050R may be repeated, for example, until the impedance of the clamped tissue reaches a predetermined impedance value. In an example aspect, the predetermined time interval may be in the range of from about 0.05 seconds to about 0.5 seconds, preferably in the range of about 0.1 seconds to about 0.4 seconds, more preferably in the range of about 0.2 seconds to about 0.3 seconds. In another example aspect, the predetermined time interval may have any other suitable time period. In an example aspect, the predetermined time interval for the alternation of the electrosurgical energy may be sufficiently fast enough that the providing of the electrosurgical energy to the first set of electrodes 3040L, 3040R and the second set of electrodes 3050L, 3050R may appear to be simultaneous.

In an example aspect, the alternation of the electrosurgical energy may be started once the onboard on/off power switch 420 is turned on and may continue the alternation without an input from a user of the electrosurgical device until the onboard on/off power switch 420 is turned off. The onboard on/off power switch 420 may be automatically turned off when the measured tissue impedance reaches a predetermined impedance value (e.g., an impedance value indicating that the clamped tissue is completely sealed). The number of cycles (e.g., n times) of the alternation of the electrosurgical energy that is necessary for reaching the predetermined impedance value may vary depending on various parameters, including tissue type, tissue thickness, how much moisture is in the tissue, etc.

In an example aspect, as shown in FIG. 43, the time interval for the first set of electrodes 3040L, 3040R may be the same as the time interval for the second set of electrodes 3050L, 3050R. In another example aspect, the time interval for the first set of electrodes 3040L, 3040R may be different from the time interval for the second set of electrodes 3050L, 3050R. For example, the time interval for the first set of electrodes 3040L, 3040R may be 0.3 seconds, while the time interval for the second set of electrodes 3050L, 3050R may be 0.2 seconds. That is, in this case, the electrosurgical energy may be provided to the first set of electrodes 3040L, 3040R for 0.3 seconds, then to the second set of electrodes 3050L, 3050R for 0.2 seconds, then repeat this alternation. In an example aspect, the predetermined time interval may decrease over time. For example, the predetermined time interval may be 0.3 seconds in the beginning (e.g., for a couple of cycles), 0.2 seconds after then (for the next couple of cycles), 0.1 seconds after then (for the next couple of cycles before the tissue starts to complete to weld or is welded). In another example aspect, the predetermined time interval may increase over time.

In an example aspect, the control circuit may include two operation modes, Mode I and Mode II. In Mode I, the control circuit may cut the tissue when or after the welding of the tissue is completed. In Mode 2, the control circuit may cut the tissue while the welding of the tissue is in progress. Examples of these modes are described in greater detail below and as shown in FIGS. 44-49.

FIG. 41 illustrates a block diagram of a surgical system 3200 programmed to communicate power and control signals with an end effector 3250 according to one aspect of this disclosure. In an example aspect, the surgical system 3200 may include a control circuit 3210 (e.g., microprocessor 560, segmented RF circuit 1160, or distal micro-chip 1740) having an electrosurgical energy control segment (or an RF energy control segment) 3220 and a shaft control segment 3230 (e.g., shaft segment (Segment 5), motor circuit segment (Segment 7), or power segment (Segment 8)). The control circuit 3210 may be programed to provide electrosurgical energy (e.g., RF energy) to electrodes in the end effector 3250 (e.g., end effector 1500). The surgical system 3200 may include one or more electrical conductors 3260 (e.g., electrical conductors 1168) used for providing the electrosurgical energy, from an electrosurgical energy generator 3240 (e.g., RF generator 400), to the end effector 3250. The one or more electrical conductors 3260 may be electrically connected between the end effector 3250 and the control circuit 3210 (e.g., the electrosurgical energy control segment 3220 and the shaft control segment 3230).

The electrosurgical energy control segment 3220 may be programed to provide the electrosurgical energy to the electrodes through the one or more electrical conductors 3260. In an example aspect, the shaft control segment 3230 may be programed to provide and/or receive a control signal to/from the end effector 3250 (and/or the surgical tool assembly 1000, the shaft assembly 704) through the one or more electrical conductors 3260. That is, the one or more electrical conductors 3260 may be used not only for providing the electrosurgical energy to the end effector 3250, but also for communicating control signals with the end effector 3250. In an example aspect, at least some portions of the electrosurgical energy control segment 3220 and the shaft control segment 3230 may be electrically isolated from each other.

In an example aspect, the electrosurgical energy control segment 3220 may electrically isolate the one or more electrical conductors 3260 from the shaft control segment 3230, for example, when providing the electrosurgical energy to the electrodes in the end effector 3250 through the one or more electrical conductors 3260. In an example aspect, the electrosurgical energy control segment 3220 may control a switch 3270 located between the one or more electrical conductors 3260 and the shaft control segment 3230 by providing a signal through a control line 3280 to electrically isolate the one or more electrical conductors 3260 from the shaft control segment 3230. The switch 3270 may be configured to switch between an open state and a closed state. The shaft control segment 3230 and the one or more electrical conductors 3260 may be electrically isolated when the switch 3270 is in the open state, and may be in electrical communication when the switch 3270 is in the closed state. In another example aspect, the electrosurgical energy control segment 3220 may electrically isolate the one or more electrical conductors 3260 from the shaft control segment 3230 in any other suitable manner. Other configurations of the switch 3270 may enable electrical isolation of the one or more electrical conductors 3260 from the shaft control segment 3230 by closing the switch 3270.

In an example aspect, the electrosurgical energy control segment 3220 may electrically isolate the one or more electrical conductors 3260 from the shaft control segment 3230 when the control circuit 3210 detects that the electrosurgical energy generator 3240 is connected to the connector 3265 (e.g., female connectors 410), for example, by continuously checking the connector 3265 or sensing the application of the electrosurgical energy. For example, when the male plug assembly 406 is plugged into the female connectors 410, the electrosurgical energy control segment 3220 may isolate the electrical conductors 3260 from the shaft control segment 3230. In another example aspect, the electrosurgical energy control segment 3220 may electrically isolate the one or more electrical conductors 3260 from the shaft control segment 3230 when the electrosurgical energy is provided to the end effector 3250 or at any other suitable moment.

In an example aspect, the surgical system may include one or more electrical conductors 3290 (e.g., electrical conductors 1166) used for operating the end effector 3250 (and/or the surgical tool assembly 1000, the shaft assembly 704). In an example aspect, the one or more electrical conductors 3290 may not be used to deliver the electrosurgical energy to the end effector 3250. The shaft control segment 3230 may be programed to provide and/or receive a control signal to/from the end effector 3250 through the one or more electrical conductors 3290. In an example aspect, the shaft control segment 3230 may use the one or more electrical conductors 3290 to provide and/or receive the control signal to/from the end effector 3250 while the switch 3270 is in an open state (e.g., while the electrosurgical energy control segment 3220 is providing the electrosurgical energy to the end effector 3250 through the one or more electrical conductors 3260). In an example aspect, the shaft control segment 3230 also may use the one or more electrical conductors 3290 to provide and/or receive the control signal to/from the end effector 3250 while the switch 3270 is in a closed state.

The switch 3270 may be a transistor switch, a mechanical switch, or any other suitable switch. In an example aspect, the control signals communicated between the control circuit 3210 and the end effector 3250 (and/or the surgical tool assembly 1000, the shaft assembly 704) through the electrical conductors 3260, 3290 include, but are not limited to, signals for driving the end effector 3250 (and/or the surgical tool assembly 1000, the shaft assembly 704) in cutting and/or coagulation operating modes, measuring electrical characteristics of the surgical system 3200 and/or the tissue clamped in the end effector 3250, providing feedback to use, communicating sensor signals, and identifying certain characteristics of the end effector 3250 (e.g., used/unused status).

Accordingly, aspects of the present disclosure may advantageously reduce the number of electrical conductors necessary for communicating control signals between the control circuit 3210 and the end effector 3250 (and/or the surgical tool assembly 1000, the shaft assembly 704) by using some of the electrical conductors (e.g., electrical conductors 3260) used for the delivery of the electrosurgical energy to communicate the control signals when those electrical conductors are not used for the electrosurgical energy. Moreover, by isolating those electrical conductors from other circuit segments (e.g., shaft control segment 3230) when providing the electrosurgical energy through those electrical conductors, aspects of the present disclosure may prevent the electrosurgical energy from flowing into the other circuit segments and/or electrical conductors (e.g., electrical conductors 3290) connected to those circuit segments, preventing damages to those circuit segments and/ore electrical conductors.

FIG. 44 is a logic flow diagram depicting a process 4500 of a control program or a logic configuration for operating the surgical instrument in accordance with Mode I. Although the example process 4500 is described with reference to the logic flow diagram illustrated in FIG. 44, it will be appreciated that many other methods of performing the acts associated with the method may be used. For example, the order of some of the blocks may be changed, certain blocks may be combined with other blocks, and some of the blocks described are optional.

In the illustrated example and with reference also to FIG. 18, a control circuit 610 (FIG. 18), may receive 4510 information about impedance of tissue. For example, the control circuit 610 may include an impedance feedback circuit and measure the impedance of the tissue clamped in the end effector 602 (e.g., end effector 1500) such as, for example, the tissue adjacent the first set of electrodes 3040L, 3040R and the second set of electrodes 3050L, 3050R. In an example aspect, the control circuit 610 may measure the tissue impedance periodically (e.g., every 0.1 seconds, every 0.5 seconds, or every second). In another example aspect, the control circuit 610 may measure the tissue impedance randomly or in any other suitable manner. The control circuit 610 may provide 4520 electrosurgical energy to a first set of electrodes and a second set of electrodes, where the providing of the electrosurgical energy repeatedly alternates between the first set of electrodes and the second set of electrodes at a predetermined time interval. For example, the control circuit 610 may provide electrosurgical energy to the first set of electrodes 3040L, 3040R and a second set of electrodes 3050L, 3050R alternatively at a predetermined time interval as described above with regard to FIG. 43.

Then, at some points, the control circuit 610 may determine 4530 that the impedance of the tissue reaches a predetermined impedance value. For example, the predetermined impedance value may be a value indicating that the tissue adjacent the first set of electrodes 3040L, 3040R and the second set of electrodes 3050L, 3050R is substantially or completely welded or coagulated. The control circuit 610 may determine that the welding of the tissue is substantially completed by comparing the measured tissue impedance with the predetermined termination impedance value. Then, the control circuit 610 may stop 4540 the provision of the electrosurgical energy to the first set of electrodes and the second set of electrodes. Then, the control circuit 610 may advance 4550 a cutting member, such as the I-beam 614, to cut the tissue. In an example aspect, the control circuit 610 may advance the cutting member (e.g., I-beam 614) to the first zone 3060 to cut the tissue in the first zone 3060 and, then, to the second zone 3065 to cut the tissue in the second zone 3065. In another example aspect, the control circuit 610 may cut the tissue in the first zone 3060 and the second zone 3065 at the same time.

FIG. 45 shows a graph 4600 of a tissue impedance curve 4605 as a function of time. The tissue impedance curve 4605 may represent a change in the impedance of the tissue claimed in the end effector 1500 when the control circuit 610 (FIG. 18) is operating in Mode I. As shown in FIG. 45, the tissue impedance tends to follow a common "bathtub" pattern, decreasing in the beginning of the energy alternation for a first time period 4625 (e.g., 0.3-1.5 seconds), reaching a minimum impedance value ($Z_M$) at a first time ($t_1$) 4615 and, then, increasing during a second time period 4630 (e.g., 0.3-1.5 seconds) as the clamped tissue is being welded. Then, the tissue impedance may reach a point 4610 at a second time ($t_2$) 4620, where the tissue impedance at the point 4610 is equal to a predetermined termination impedance ($Z_T$).

In the first period of time 4625, the tissue impedance drops from an initial value and decreases, e.g., has a negative slope, until it reaches the minimum impedance value ($Z_M$) because after energy is applied to the tissue for a certain period the moisture content of the tissue evaporates causing the tissue to dry out and causes the tissue impedance to begin rising, e.g., positive slope, after then in the second period of time 4630 until the tissue impedance reaches the predetermined termination impedance $Z_T$, at which point in time the energy to the end effector may be shut off. In an example aspect, the tissue impedance may maintain the minimum impedance $Z_M$ for a certain period of time (e.g., 0.5-5 seconds), where the tissue impedance curve 4605 almost flattens out for that period of time. If the electrosurgical energy (e.g., RF energy) were to be applied continuously instead of being shut off at the termination impedance point 4610, the tissue impedance may increase continuously passing the point 4610.

In an example aspect, the predetermined termination impedance ($Z_T$) may correspond to a point where the tissue adjacent the electrodes 3040L, 3040R, 3050L, 3050R may be substantially or completely welded so as to cut the tissue (e.g., blood vessel) without bleeding. The predetermined termination impedance may be stored in a memory device of the surgical instrument (e.g., surgical system 10 or surgical tool assembly 1000).

When the tissue impedance reaches the predetermined termination impedance, the control circuit may stop providing the electrosurgical energy to the first set of electrodes 3040L, 3040R and the second set of electrodes 3050L, 3050R, resulting in the sudden drop of the tissue impedance at $t_2$ 4620. In an example aspect, this sudden drop of the tissue impedance may occur because the control circuit stops measuring the tissue impedance when the provision of the electrosurgical energy is stopped. As shown in FIG. 46 depicting a graph 4650 of an example motor voltage curve, when or after the provision of the electrosurgical energy is stopped at $t_2$, the control circuit may provide voltage 4660 to the motor (e.g., motor 505) to cut the tissue in the first zone 3060. Then, the control circuit also may provide voltage 4670 to the motor to cut the tissue in the second zone 3065. As shown in FIGS. 45 and 46, in Mode I, the cutting of the clamped tissue may start during a third time period 4635 after the tissue impedance reaches the predetermined termination impedance value (e.g., completion of the tissue welding).

FIG. 47 is a logic flow diagram depicting a process 4700 of a control program or a logic configuration for operating the surgical instrument in accordance with Mode II. Although the example process 4700 is described with reference to the logic flow diagram illustrated in FIG. 47, it will be appreciated that many other methods of performing the acts associated with the method may be used. For example, the order of some of the blocks may be changed, certain blocks may be combined with other blocks, and some of the blocks described are optional.

In the illustrated example and with reference also to FIG. 18, a control circuit 610 may receive 4710 information about impedance of tissue. For example, the control circuit 610 may measure the impedance of the tissue clamped in the end effector 602 (e.g., end effector 1500). In an example aspect, the control circuit 610 may measure the tissue impedance periodically (e.g., every 0.1 seconds, every 0.5 seconds, or every second). In another example aspect, the control circuit 610 may measure the tissue impedance randomly or in any other suitable manner. The control circuit 610 may provide 4720 electrosurgical energy to a first set of electrodes in a proximate portion of a jaw and a second set of electrodes in a distal portion of the jaw, where the providing of the electrosurgical energy repeatedly alternates between the first set of electrodes and the second set of electrodes at a predetermined time interval. For example, the control circuit 610 may provide electrosurgical energy to the first set of electrodes 3040L, 3040R and the second set of electrodes 3050L, 3050R alternatively at a predetermined time interval as described above with regard to FIG. 43.

Then, at some points, the control circuit 610 may determine 4730 that the impedance of the tissue reaches a predetermined impedance value. For example, the predetermined impedance value may be a value indicating that welding of the tissue adjacent the first set of electrodes 3040L, 3040R and the second set of electrodes 3050L, 3050R starts to complete. Then, the control circuit 610 may advance 4740 the cutting member such as the I-beam 614 to cut the tissue in the proximate portion while providing the electrosurgical energy to the first set of electrodes and the second set of electrodes. After cutting the tissue in the proximate portion of the jaw, the control circuit 610 may advance 4740 the cutting member (e.g., I-beam 614) to cut the tissue in the distal portion while providing the electrosurgical energy to the second set of electrodes.

In an example aspect, the control circuit 610 may advance 4750 the cutting member (e.g., I-beam 614) to cut the tissue in the distal portion while providing the electrosurgical energy to both the first set of electrodes 3040L, 3040R and the second set of electrodes 3050L, 3050R. In another example aspect, the control circuit 610 may stop providing the electrosurgical energy to the first set of electrodes after cutting the tissue in the proximate portion, and provide the electrosurgical energy only to the second set of electrodes while cutting the tissue in the distal portion. In this case, the provision of the electrosurgical energy to the second set of electrodes 3050L, 3050R may still be discontinuous. For example, the electrosurgical energy may be provided to the second set of electrodes 3050L, 3050R for a set period of time (e.g., 0.25 seconds) and, then, no electrosurgical energy may be provided to the second set of electrodes 3050L, 3050R for the next set period of time (e.g., 0.25 seconds) and, then the electrosurgical energy may be provided to the second set of electrodes 3050L, 3050R for the next set period of time (e.g., 0.25 seconds). This may be repeated while cutting the tissue in the distal portion of the jaw (e.g., the second zone 3065).

In another example aspect, the control circuit 610 may stop providing the electrosurgical energy to the first set of electrodes 3040L, 3040R and the second set of electrodes 3050L, 3050R after cutting the tissue in the first zone. In this case, no electrosurgical energy may be provided to the tissue while cutting the tissue in the second zone 3065. In an example aspect, the control circuit 610 may stop providing the electrosurgical energy to the first set of electrodes 3040L, 3040R and the second set of electrodes 3050L, 3050R when the tissue impedance reaches a predetermined termination impedance value while cutting the tissue in the first zone 3060 and/or the second zone 3065.

FIG. 48 shows a graph 4800 of a tissue impedance curve 4805 as a function of time. The tissue impedance curve 4805 may represent a change in the impedance of the tissue claimed in the end effector 1500 when the control circuit is operating in Mode II. As seen in FIG. 48, the tissue impedance here also tends to follow a common "bathtub" pattern, decreasing in the beginning of the energy alternation (e.g., between the first set of electrodes 3040L, 3040R and the second set of electrodes 3050L, 3050R) for a first time period 4835 (e.g. 0.3-1.5 seconds), reaching a minimum impedance value $(Z_M)$ at a first time $(t_1)$ 4820 and, then, increasing during a second time period 4840 (e.g., 0.3-1.5 seconds). As explained above, in the first period of time 4835, the tissue impedance drops from an initial value and decreases, e.g., has a negative slope, until it reaches the minimum impedance value $(Z_M)$ because after energy is applied to the tissue for a certain period the moisture content of the tissue evaporates causing the tissue to dry out and causes the tissue impedance to begin rising, e.g., positive slope, after then in the second period of time 4840 until the tissue impedance reaches the termination impedance $Z^{T1}$. In an example aspect, the tissue impedance may maintain the minimum impedance for a period of time (e.g., 0.5-5 seconds), where the tissue impedance curve 4805 almost flattens out for that period of time.

In an example aspect, when the tissue impedance reaches the minimum impedance value $(Z_M)$, a rate of impedance change (e.g., decrease) may become approximately zero as shown in FIG. 48. The welding of the clamped tissue may start to complete at this point. In an example aspect, in Mode II, the control circuit may start advancing the cutting member when the tissue impedance reaches the minimum impedance value $(Z_M)$. For example, the control circuit may determine that the tissue impedance reaches the minimum impedance value $(Z_M)$ when the rate of impedance change (e.g., decrease) becomes approximately zero. In another example aspect, in Mode II, the control circuit may start advancing the cutting member at any other suitable time before the clamped tissue is completely welded. If the tissue impedance maintains the minimum impedance for a period of time (e.g., 0.5-5 seconds), the control circuit may start advancing the cutting member at any suitable moment during that period of time (e.g., in the beginning/middle/end of the flat curve).

As shown in FIG. 49, and with reference also to FIG. 18, the control circuit 610 may provide voltage 4860 to the motor 604 (e.g., motor 505) to cut the tissue in the first zone 3060 when or after the tissue impedance reaches the minimum impedance value $(Z_M)$ before the tissue welding is completed. The termination impedance $Z^{T1}$ may represent the tissue impedance at the completion of the cutting at a second time $(t_2)$ 4825. Then, the control circuit may provide voltage 4870 to the motor 604 (e.g., motor 505) to cut the tissue in the second zone 3065 after cutting the tissue in the first zone 3060. The termination impedance $Z_{T2}$ may represent the tissue impedance at the completion of the cutting at a third time $(t_3)$ 4830. The impedance curve 4805 may drop near at the second time 4825 right after the cutting of the tissue in the first zone 3060 because the clamped tissue may be wet with some fluids (e.g., blood or any other body fluids) that are produced while cutting the tissue in the first zone 3060. Thus, although the measured impedance value 4805 may appear to drop after the cutting of the tissue in the first zone 3060, the actual tissue impedance may not drop, but may be similar to or higher than $Z^{T1}$ throughout the third time period 4845. As the moisture content of the tissue evaporates causing the tissue to dry out because of the electrosurgical energy applied to the clamped tissue during the third time period 4845, the measured impedance value also may increase quickly to reflect the actual tissue impedance.

In an example aspect, the control circuit 610 may consider the amount of time required to cut the clamped tissue in the end effector 602 in determining when to start advancing the cutting member such as the I-beam 614. For example, if it takes 1 second to cut the tissue in the first zone 3060, the control circuit 610 may start advancing the cutting member (e.g. I-beam 614) around 1 second before the tissue impedance reaches a predetermined termination impedance value (where around this time the tissue welding is normally completed) such that the tissue welding is substantially completed by the time the cutting of the tissue in the first zone 3060 is completed. In another example aspect, the cutting speed may be adjusted so that the tissue welding is substantially completed by the end of the cutting. For example, if it takes 0.5 seconds from the moment the tissue impedance reaches the minimum impedance to the moment it reaches the termination impedance (e.g., where the tissue welding is completed), the cutting speed may be adjusted so that it would take 0.5 seconds to cut the tissue in the first or second zones 3060, 3065.

As explained above, in an example aspect, the control circuit 610 may provide the electrosurgical energy to both the first set of electrodes 3040L, 3040R and the second set of electrodes 3050L, 3050R while cutting the tissue in the second zone 3065 during the third time period 4845. In this case, since the clamped tissue received additional electrosurgical energy for the third time period 4845, the termination impedance $Z_{T2}$ at the third time 4830 may be higher than the termination impedance $Z^{T1}$ at the second time 4825 as seen in FIG. 48.

In an example aspect, the control circuit 610 may stop providing the electrosurgical energy to the first set of electrodes after cutting the tissue in the first zone 3060 and provide the electrosurgical energy only to the second set of electrodes while cutting the tissue in the second zone 3065. In this case, the termination impedance of the tissue in the second zone 3065 may be higher than the termination impedance of the tissue in the first zone 3060 since the tissue in the second zone 3065 received more electrosurgical energy for the third time period 4845 than the tissue in the first zone 3060, assuming that the predetermined time intervals for the two sets of electrodes are the same.

The functions or processes 4500, 4700 described herein may be executed by any of the processing circuits described herein, such as the control circuit 700 described in connection with FIGS. 16-17, the control circuit 610 described in connection with FIG. 18.

Various aspects of the subject matter described herein are set out in the following numbered examples:

EXAMPLE 1

A surgical instrument comprising: an end effector comprising: a first jaw and a second jaw, wherein the first jaw includes a proximate portion and a distal portion and the second jaw is movable relative to the first jaw; a first set of electrodes and a second set of electrodes, wherein the first set of electrodes are located in a proximate portion of the first jaw and the second set of electrodes are located in a distal portion of the first jaw; and a slot defined between the first set of electrodes and the second set of electrodes; a cutting member configured to reciprocate within the slot; and a control circuit configured to: receive information about impedance of tissue located between the first jaw and the second jaw of the end effector; provide electrosurgical energy to the first set of electrodes and the second set of electrodes and repeatedly alternate the electrosurgical energy between the first set of electrodes and the second set of electrodes at a predetermined time interval; and advance the cutting member.

EXAMPLE 2

The surgical instrument of Example 1, wherein the control circuit is configured to advance the cutting member to the proximate portion to cut the tissue in the proximate portion after or when welding of the tissue is substantially completed.

EXAMPLE 3

The surgical instrument of Example 2, wherein the control circuit is configured to stop providing the electrosurgical energy to the first set of electrodes and the second set of electrodes before advancing the cutting member to the proximate portion.

EXAMPLE 4

The surgical instrument of one or more of Example 2 through Example 3, wherein the control circuit is configured to advance the cutting member to the distal portion to cut the tissue in the distal portion after cutting the tissue in the proximate portion.

EXAMPLE 5

The surgical instrument of one or more of Example 2 through Example 4, wherein the control circuit is configured to determine that the welding of the tissue is substantially completed by comparing the information about the impedance of the tissue with a predetermined termination impedance value.

EXAMPLE 6

The surgical instrument of one or more of Example 1 through Example 5, wherein the control circuit is configured to advance the cutting member to the proximate portion to cut the tissue in the proximate portion before welding of the tissue in the proximate portion is completed while providing the electrosurgical energy to the first set of electrodes and the second set of electrodes.

EXAMPLE 7

The surgical instrument of Example 6, wherein the control circuit is configured to advance the cutting member to the proximate portion to cut the tissue in the proximate portion when the welding of the tissue starts to complete.

EXAMPLE 8

The surgical instrument of Example 7, wherein the control circuit is configured to determine that the welding of the tissue starts to complete when a rate of impedance decrease becomes approximately zero.

EXAMPLE 9

The surgical instrument of one or more of Example 6 through Example 8, wherein the control circuit is configured to advance the cutting member to the distal portion to cut the tissue in the distal portion after cutting the tissue in the proximate portion while providing the electrosurgical energy to the second set of electrodes.

EXAMPLE 10

The surgical instrument of one or more of Example 1 through Example 9, wherein the predetermined time interval is in the range of from about 0.1 to 0.5 seconds.

EXAMPLE 11

The surgical instrument of one or more of Example 1 through Example 10, wherein the electrosurgical energy comprises radio frequency energy.

EXAMPLE 12

A surgical instrument comprising: an end effector comprising: a first jaw comprising a proximate portion and a distal portion; a second jaw that is movable relative to the first jaw; a first set of electrodes located in the proximate portion of the first jaw; and a second set of electrodes located in the distal portion of the first jaw; a cutting member, wherein the first jaw and the second jaw define an elongate slot therebetween extending from a proximate end of the first jaw and wherein the cutting member is slideably receivable within the elongate slot to cut tissue located between the first jaw and the second jaw; a control circuit configured to provide electrosurgical energy to the first set of electrodes and the second set of electrodes, wherein the providing of the electrosurgical energy repeatedly alternates between the first set of electrodes and the second set of electrodes at a predetermined time interval, wherein the control circuit is configured to receive information about impedance of the tissue located between the first jaw and the second jaw.

EXAMPLE 13

The surgical instrument of Example 12, wherein the control circuit is configured to advance the cutting member to the proximate portion to cut the tissue in the proximate portion after or when welding of the tissue is substantially completed.

EXAMPLE 14

The surgical instrument of Example 13, wherein the control circuit is configured to stop providing the electrosurgical energy to the first set of electrodes and the second set of electrodes and thereafter advance the cutting member to the proximate portion.

EXAMPLE 15

The surgical instrument of one or more of Example 13 through Example 14, wherein the control circuit is configured to advance the cutting member to the distal portion to cut the tissue in the distal portion and after cutting the tissue in the proximate portion.

EXAMPLE 16

The surgical instrument of one or more of Example 13 through Example 15, wherein the control circuit is configured to determine that the welding of the tissue is substantially completed and to compare the information about the impedance of the tissue with a predetermined termination impedance value.

EXAMPLE 17

The surgical instrument of one or more of Example 12 through Example 16, wherein the control circuit is configured to advance the cutting member to the proximate portion to cut the tissue in the proximate portion before welding of the tissue in the proximate portion is completed and provide the electrosurgical energy to the first set of electrodes and the second set of electrodes.

EXAMPLE 18

The surgical instrument of Example 17, wherein the control circuit is configured to advance the cutting member to the proximate portion to cut the tissue in the proximate portion when the welding of the tissue starts to complete.

EXAMPLE 19

The surgical instrument of Example 18, wherein the control circuit is configured to determine that the welding of the tissue starts to complete when a rate of impedance decrease becomes approximately zero.

EXAMPLE 20

The surgical instrument of one or more of Example 17 through Example 19, wherein the control circuit is configured to advance the cutting member to the distal portion to cut the tissue in the distal portion after cutting the tissue in the proximate portion and simultaneously provide the electrosurgical energy to the second set of electrodes.

Surgical End Effector for Applying Electrosurgical Energy to Different Electrodes on Different Time Periods In some aspects, an electrosurgical device may be configured to induce a hemostatic seal in a tissue and/or between tissues. The hemostatic seal may be created by a combination of an applied compressive force to the tissue and an application of electrical energy to the tissue. In some aspects of an electrosurgical device, the compressive force may be supplied by a compression of the tissue between jaw assemblies. Additionally, the electrical energy may be supplied by one or more electrodes disposed within or on some components of the jaw assemblies. The amount of electrical energy sufficient to effect the hemostatic seal may depend, in part, on the thickness, density, and/or quality of tissue to be sealed.

It may be understood that an application of excessive electrical energy to a tissue may result in burning or scaring of the tissue. However, the application of insufficient electrical energy to a tissue may result in an ineffective hemostatic seal. Thus, a user of the electrosurgical device may be required to adjust the amount of electrical energy delivered to the tissue compressed between the jaw assemblies of the device based on the tissue thickness, density, and quality. If a tissue compressed between the jaw assemblies is essentially homogeneous, the user of the electrosurgical device may use simple controls to adjust the amount of electrical energy delivered to the tissue. However, it may be recognized that some tissues for hemostatic sealing are inhomogeneous in any one or more of their thickness, density, and/or quality. As a result, a single control for the amount of electrical energy delivered to the tissue compressed between the jaw assemblies may result in burned portions as well as insufficiently sealed portions of the tissue. It is therefore desirable to have an electrosurgical device that may be configured to deliver a variety of electrical energies to a piece of tissue compressed between the jaw assemblies.

Electrosurgical instruments apply electrosurgical energy to seal tissue. However, the application of electrosurgical energy is not optimized for all tissue types. Some types of tissue require the application of electrosurgical energy in one form and other types of tissue require the application of electrosurgical energy in another form. Therefore, it would be desirable, to treat different tissue types by applying electrosurgical energy in one form during a clamping procedure to cut and spread apart the tissue and after the clamping process, applying electrosurgical energy in another form to seal the tissue before advancing a knife to sever the tissue. Therefore, the present disclosure provides an electrosurgical cartridge that is configured to energize different electrode configurations over different time periods to combine or coordinate each of the different functions of the jaws of the end effector such as closing the jaws on tissue, applying electrosurgical energy to seal the tissue, and firing the cutting element to cut the tissue.

FIG. 57 is a cross-sectional view of a jaw member 5000 comprising an electrosurgical cartridge such as, for example, a radio frequency (RF) cartridge 5002 supported by an elongated channel 5004, according to some aspects of the present disclosure. The RF cartridge 5002 may comprise an elongated slot 5014 extending through the RF cartridge 5002. The RF cartridge 5002 may comprise a first electrode 5006, 5008 and a second electrode 5010, 5012. The first electrode may comprise a first electrode segment 5006 and a second electrode segment 5008 separated by the elongated slot 5014. The second electrode may comprise a third electrode segment 5010 and a fourth electrode segment 5012 separated by the elongated slot 5014. The first and second electrode segments 5006, 5008 may be closer to the lateral edges 5016, 5018 of the RF cartridge, and the third and fourth electrode segments 5010, 5012 may be closer to the elongated slot 5014. The first and second electrodes may be arranged such that when the jaw member 5000 is in a closed position with another jaw member, a distance between the first electrode 5006, 5008 and the other jaw member is larger than a distance between the second electrode 5010, 5012 and the other jaw member. Further, central edges 5020, 5022 of the first and second electrode segments 5006, 5008 may be closer to the other jaw member than lateral edges 5024, 5026 of the first and second electrode segments 5006, 5008. For example, the first and second electrode segments 5006, 5008 may be at an angle α with the third and fourth electrode segments 5010, 5012. A width W1 of the first and second electrode segments 5006, 5008 may be larger than a width W2 of the third and fourth electrode segments 5010, 5012. As an example, the width W1 of the first and second electrode segments 5006, 5008 may be 0.060 inch, and the width W2 of the third and fourth electrode segments 5006, 5008 may be 0.020 inch.

FIG. 58 is a diagram 5100 illustrating an operation of the first electrode, according to some aspects of the present disclosure. The horizontal axis represents time t, and the vertical axis represents a force to close ("FTC"). An end effector comprising two jaws, one of which being the jaw member 5000 for example, may be inserted into an organ, for example liver, with the jaws open. Then the end effector begins clamping. For example, the jaw member 5000 shown in FIG. 57 approaches another jaw member and applies a force on a tissue therebetween. During the clamping, RF energy is supplied to the first electrode 5006, 5008, as indicated by the shaded region 5104. The RF energy supplied to the first electrode 5006, 5008, for example, cut and spread apart parenchyma. As shown in FIG. 58, FTC 5102 increases in the beginning, and then decreases gradually. The RF energy supplied to the first electrode 5006, 5008 may be stopped at a first time point t1, which may be determined as the time when the FTC 5102 falls below a threshold. The first time point t1 may also be determined as a time point when a proper tissue gap, for example 0.0005 inch to 0.1 inch, is formed.

FIG. 59 is a diagram 5200 illustrating an operation of the second electrode, according to some aspects of the present disclosure. The horizontal axis represents time t, and the vertical axis represents a force to fire ("FTF"). As shown in FIG. 59, RF energy is switched to the second electrode 5010, 5012 after the first time t1, as indicated by the shaded area 5204. Although the two shaded areas 5104 and 5204 are shown as having the same height, the RF energy supplied to the first electrode 5006, 5008 may be different from the RF energy supplied to the second electrode 5010, 5012. RF energy supplied to the second electrode 5010, 5012, for example, seals one or more vessels. At a second time point t2 after the first time point t1, a cutting member, for example a knife, may begin to advance or fire, as indicated by a FTF curve 5202. At a third time point t3 after the second time point t2. RF energy supplied to the second electrode 5010, 5012, for example, may be stopped. In some aspects of the present disclosure, the beginning of RF energy supplied to the second electrode 5010, 5012 may not immediately follow the end of RF energy supplied to the first electrode 5006, 5008.

FIG. 60 is a logic flow diagram of a process 5300 depicting a control program or a logic configuration for applying therapeutic electrosurgical energy according to one aspect of this disclosure. In one aspect, the electrosurgical energy is RF energy, for example. The therapeutic electrosurgical energy may be applied to prepare for cutting and coagulating a surgical site such as, a liver, for example. The electrosurgical energy may be applied by lateral segmented electrodes for use in tissue welding during closing or clamping (including display feedback of the tissue welding progress). A secondary energy switch may be employed to allow automated application of the electrosurgical energy concurrent with closure or clamping. A secondary set of electrodes with a thinner gap for vessel welding after parenchyma tissue welding also may be provided.

The process 5300 may be implemented with the surgical instrument 600 shown in FIG. 18 and controlled by the control circuit 610. Accordingly, the control circuit 610 is configured to supply 5302 electrosurgical energy through the RF energy source 400 to the RF cartridge 609 of the end effector 602 in a first period of time as measured by the timer/counter circuit 631. In one aspect, the RF cartridge 609 is removably coupleable to an elongated channel of a first jaw of the end effector 602 of the surgical instrument 600. The anvil 616 is then closed on the RF cartridge 609 apply 5304 a force to tissue located between the anvil 616 and the RF cartridge 609 during at least a part of the first time period as determined b the timer/counter circuit 631. The control circuit 610 then supplies 5306 electrosurgical energy to a second electrode of the RF cartridge 609 of the end effector 602 in a second period of time as determined by the timer/counter circuit 631 after the end of the first period of time. The control circuit 610 is configured to operate the motor 608 to advance a knife such as the I-beam 614 through the tissue during at least a part of the second time period.

Various aspects of the subject matter described herein are set out in the following numbered examples:

EXAMPLE 1

An end effector for a surgical instrument, comprising: a first jaw; and a second jaw, wherein at least one of the first and second jaws is configured to move from a first position spaced apart from the other one of the first and second jaws to a second position in which the space between the first and second jaws is less than that of the first position, wherein the second jaw comprises: an elongated channel, and a cartridge removably coupled to the elongated channel, comprising a first electrode configured to apply electrosurgical energy to a tissue and a second electrode configured to apply electrosurgical energy to the tissue, wherein in the second position a distance between the first electrode and the first jaw is greater than a distance between the second electrode and the first jaw.

EXAMPLE 2

The end effector of Example 1, wherein the cartridge further comprises a centrally located elongated slot; the first electrode comprises a first electrode segment and a second electrode segment separated by the elongated slot; and the second electrode comprises a third electrode segment and a fourth electrode segment separated by the elongated slot.

EXAMPLE 3

The end effector of Example 2, wherein a width of the first and second electrode segments is greater than a width of the third and fourth electrode segments.

EXAMPLE 4

The end effector of one or more of Example 2 through Example 3, wherein the third and fourth electrode segments are located between the first electrode segment and the second electrode segment.

EXAMPLE 5

The end effector of one or more of Example 2 through Example 4, wherein in the second position a distance between an central edge of the first electrode segment and the first jaw is smaller than a distance between an lateral edge of the first electrode segment and the first jaw; and a distance between an central edge of the second electrode segment and the first jaw is smaller than a distance between an lateral edge of the second electrode segment and the first jaw.

EXAMPLE 6

The end effector of one or more of Example 1 through Example 5, wherein the first electrode is configured to apply electrosurgical energy to the tissue in a first time period; and the second electrode is configured to apply electrosurgical energy to the tissue in a second time period after the first time period.

EXAMPLE 7

The end effector of Example 6, wherein the first and second jaws are configured to apply a force to the tissue during at least a part of the first time period; and the end effector further comprises a knife configured to advance to the tissue during at least a part of the second time period.

EXAMPLE 8

The end effector of Example 7, wherein the knife is configured to begin advancing after the start of the second time period.

EXAMPLE 9

The end effector of one or more of Example 1 through Example 8, wherein the electrosurgical energy radio frequency (RF) energy.

EXAMPLE 10

A cartridge for use in an end effector for a surgical instrument, the surgical instrument comprising a first jaw and a second jaw, wherein at least one of the first and second jaws is configured to move from a first position spaced apart from the other one of the first and second jaws to a second position in which the space between the first and second jaws is less than that of the first position, wherein the cartridge is configured to be removably coupled to an elongated channel of the second jaw, the cartridge comprising: a first electrode configured to apply electrosurgical energy to a tissue; and a second electrode configured to apply electrosurgical energy to the tissue, wherein in the second position a distance between the first electrode and the first jaw is greater than a distance between the second electrode and the first jaw.

EXAMPLE 11

The cartridge of Example 10, further comprising a centrally located elongated slot, wherein the first electrode comprises a first electrode segment and a second electrode segment separated by the elongated slot; and the second electrode comprises a third electrode segment and a fourth electrode segment separated by the elongated slot.

EXAMPLE 12

The cartridge of Example 11, wherein a width of the first and second electrode segments is greater than a second width of the third and fourth electrode segments.

EXAMPLE 13

The cartridge of one or more of Example 11 through Example 12, wherein the third and fourth electrode segments are located between the first electrode segment and the second electrode segment.

EXAMPLE 14

The cartridge of one or more of Example 11 through Example 13, wherein in the second position a distance between an central edge of the first electrode segment and the first jaw is smaller than a distance between an lateral edge of the first electrode segment and the first jaw; and a distance between an central edge of the second electrode segment and the first jaw is smaller than a distance between an lateral edge of the second electrode segment and the first jaw.

EXAMPLE 15

The cartridge of one or more of Example 10 through Example 14, wherein the first electrode is configured to apply electrosurgical energy to the tissue in a first time period; and the second electrode is configured to apply electrosurgical energy to the tissue in a second time period after the first time period.

EXAMPLE 16

The cartridge of one or more of Example 10 through Example 15, wherein the electrosurgical energy radio frequency (RF) energy.

EXAMPLE 17

A method, comprising: supplying electrosurgical energy to a first electrode of a cartridge in a first period of time, wherein the cartridge is removably coupleable to an elongated channel of a first jaw of an end effector of a surgical instrument; and supplying electrosurgical energy to a second electrode of the cartridge in a second period of time after the first period of time.

EXAMPLE 18

The method of Example 17, further comprising: applying a force to a tissue with the first jaw during at least a part of the first time period; and advancing a knife to the tissue during at least a part of the second time period.

EXAMPLE 19

The method of Example 18, wherein advancing the knife begins after the start of the second time period.

EXAMPLE 20

The method of one or more of Example 17 through Example 19, wherein the end effector further comprises a second jaw, the method further comprising moving at least one of the first and second jaws from a first position spaced apart from the other one of the first and second jaws to a second position in which the space between the first and second jaws is less than that of the first position and in the second position a distance between the first electrode and the second jaw is greater than a distance between the second electrode and the second jaw.

EXAMPLE 21

The method of one or more of Example 17 through Example 20, wherein supplying electrosurgical energy comprises supplying radio frequency (RF) energy.

Electrosurgical Cartridge for Use in Thin Profile Surgical Cutting and Stapling Instrument In various open, endoscopic, and/or laparoscopic surgeries, for example, it may be desirable to coagulate, seal, and/or fuse tissue. One method of sealing tissue relies upon the application of energy, such as electrical energy, for example, to tissue captured or clamped within an end-effector or an end-effector assembly of a surgical instrument in order to cause thermal effects within the tissue. Various mono-polar and bi-polar radio frequency (RF) surgical instruments and surgical techniques have been developed for such purposes. In general, the delivery of RF energy to the captured tissue can elevate the temperature of the tissue and, as a result, the energy can at least partially denature proteins within the tissue. Such proteins, such as collagen, for example, can be denatured into a proteinaceous amalgam that intermixes and fuses, or seals, together as the proteins renature. As the treated region heals over time, this biological seal may be reabsorbed by the body's wound-healing process.

In certain arrangements of a bi-polar RF surgical instrument, the surgical instrument can comprise opposing first and second jaws, wherein each jaw can comprise an electrode. In use, the tissue can be captured between the jaws such that energy can flow between the electrodes in the opposing jaws and through the tissue positioned therebetween. Such instruments may have to seal many types of tissues, such as anatomic structures having walls with irregular or thick fibrous content, bundles of disparate anatomic structures, and/or substantially thick or thin anatomic structures.

Generally, when electrosurgical energy is applied, through electrodes, to a target tissue clamped in an electrosurgical end effector of a surgical device, heat provided to the target tissue in the target zone (e.g., near the electrodes) may be transferred laterally, damaging the tissue outside of the target zone and increasing the zone of coagulated tissue laterally from the target zone. Excessive lateral spread of the coagulation zone may be harmful to patients undergoing surgical procedures because more tissue is damaged and this may require more recovery time. Moreover, the electrodes used to transmit the electrosurgical energy may be typically placed on an electrically and thermally insulating material, and this may lead to overheating of tissue, which may cause more lateral thermal spread to the tissue outside of the target zone and collateral tissue damage.

Aspects of the present disclosure may address the above noted problems. In an example aspect, an end effector may include a first jaw (e.g., a cartridge and a channel) and a second jaw (e.g., anvil), a hot zone in a center portion of the end effector, and cool zones in the side portions of the end effector. The first jaw and the second jaw may define an elongate slot therebetween, and a cutting member is slideably receivable within the elongate slot to cut tissue located between the first jaw and the second jaw. The first jaw may include electrically and thermally nonconductive insulative layers on each side of the centrally disposed elongate slot, and electrode layers configured to transmit electrosurgical energy may be placed on the insulative layers in the hot zone. The first jaw also may include electrically insulating, thermally conductive heat sink layers in the side portions of the first jaw in the cool zones. The heat sink layers may include tissue contacting surfaces that may be in direct contact with the tissue when the tissue is clamped in the end effector. The heat sink layers may be configured to cool the tissue in the cool zones by transferring the heat in the tissue in the cool zones to the outside area to minimize the damage from the transfer of heat from the target tissue in the hot zone to the tissue just outside of the hot zone.

In an example aspect, the first jaw may include raised pads on each side of the elongate slot under the electrode layers. The raised pads may allow the electrode layers to be raised compared with the tissue contacting surfaces of the heat sink layers so that more pressure, and ultimately more heat, can be applied only to the target tissue more precisely while reducing the thermal spread to the lateral tissue. The raised pads, in combination with the heat sink layers cooling the tissue just outside of the target zone (e.g., hot zone) may lower the temperature of the tissue just outside of the target zone significantly and, thus, enable a physician to perform more precise sealing of tissue without excessive lateral thermal spread.

In an example aspect, the insulative layers may include an edge defined by a first surface facing the electrode layers and a second surface facing the elongate slot, and this edge may be chamfered to allow steam to escape through the elongate slot to prevent burning or overheating of tissue, preventing lateral thermal spread that may be caused by the excessive heat from the overheating.

FIG. 61 shows a schematic cross-sectional view of an end effector 5500 according to one aspect of this disclosure. The end effector 5500 may include a first jaw 5505 and a second jaw 5610. In an example aspect, the first jaw 5505 may include an elongate channel 5530 (e.g., elongate channel 1602) that is configured to operably support a cartridge (e.g., a cartridge 5700) therein. In an example aspect, the first jaw 5505 and the second jaw 5610 may define a slot therebetween. A cutting member (e.g., a blade or a knife member 1330) may be slideably receivable within the slot to cut tissue clamped within the end effector 5500. The slot in the first jaw 5505 is an elongate slot 5560 (e.g., elongate slot 1712). The elongate slot 5560 may extend from a proximate end of the first jaw 5505. The slot in the second jaw 5610 is an anvil slot 5630 (e.g., anvil slot 1815). In an example, the slots 5560, 5630 may be disposed in the center of the first and second jaws 5505, 5610. In another example, the slots 5560, 5630 may be disposed in any other suitable places in the first and second jaws 5505, 5610.

In an example aspect, the first jaw 5505 may include a first insulative layer 5510L and a second insulative layer 5510R. The first insulative layer 5510L may be on the left side of the elongate slot 5560 and the second insulative layer 5510R may be on the right side of the elongate slot 5560. In the illustrated example, the first insulative layer 5510L, the second insulative layer, and the elongate slot 5560 are disposed in a center portion of the first jaw 5505. In an example aspect, the center portion of the jaws 5505, 5610 may cover around ⅓-½ of the entire portions of the jaws 5505, 5610 and be located in the center thereof. In an example aspect, the first insulative layer 5510L and the second insulative layer 5510R may comprise a thermally and electrically non-conductive material such as a molded plastic.

In an example aspect, the first jaw 5505 also may include a first electrode layer 5540L on the first insulative layer 5510L and a second electrode layer 5540R on the second insulative layer 5510R. The first electrode layer 5540L and the second electrode layer 5540R may be configured for direct application of electrosurgical energy (e.g., RF energy) to the tissue (T) to form a hemostatic (coagulation or cauterization) line on the tissue adjacent the electrode layers 5540L, 5540R along the elongate slot 5560. The first electrode layer 5540L and the second electrode layer 5540R may be located in the center portion of the first jaw 5505. In an example aspect, the first electrode layer 5540L and the second electrode layer 5540R may include a direct contact metal electrode. In an example aspect, each of the first electrode layer 5540L and the second electrode layer 5540R may further include a flex circuit. In this case, the direct contact metal electrode may be deposited on the flex circuit. In an example aspect, the first electrode layer 5540L and the second electrode layer 5540R may define a hot zone 5650 near the first and second electrode layers 5540L, 5540R. As illustrated in FIG. 61, the hot zone 5650 may be in the center portion of the end effector 5500 (and the first and second jaws 5505, 5610).

In an example aspect, the first jaw 5505 may include a first heat sink layer 5520L in a left side portion of the first jaw 5505 and a second heat sink layer 5520R in a right side portion of the first jaw 5505. The first heat sink layer 5520L may include a first tissue contacting surface 5525L, and the second heat sink layer 5520R may include a second tissue contacting surface 5525R. The tissue contacting surfaces 5525L, 5525R may be in direct contact with the tissue (T) when the tissue (T) is clamped in the end effector 5500. In an example aspect, the first heat sink layer 5520L may define a first cool zone 5660 in the left side portion of the end effector 5500 (or the first jaw 5505) and the second heat sink layer 5520R may define a second cool zone 5670 in the right side portion of the end effector 5500 (or the first jaw 5505). The first heat sink layer 5520L and the second heat sink layer 5520R may be configured to cool the tissue (T) in the first and second cool zones 5560, 5570 to minimize the transfer of heat from the tissue in the hot zone 5650 to the tissue outside of the hot zone 5560, preventing damages to the tissue just outside of the hot zone 5560 (and ultimately just outside of the end effector 5500). In an example aspect, the first and second heat sink layers 5520L, 5520R may be made of an electrically insulating, thermally conductive material, such as a ceramic material (e.g., aluminum nitride) to dissipate heat from the tissue adjacent the heat sink layers 5520L, 5520R.

In an example aspect, the first and second insulative layers 5510L, 5510R may be around 0.01-0.10 inches away from a center line C of the end effector 5500. In an example aspect, the horizontal distance 5555 between the electrode layer 5540L/5540R and the center line C may be in the range of about 0.01 inches to 0.10 inches. In an example aspect, the first and second heat sink layers 5520L, 5520R may be around 0.03-0.20 inches away from the center line C.

In an example aspect, the first electrode layers 5540L and the first heat sink layers 5520L may define a first horizontal distance 5545L between the first electrode layers 5540L and the first heat sink layers 5520L. Similarly, the second electrode layers 5540R and the second heat sink layers 5520R may define a second horizontal distance 5545R between the second electrode layers 5540R and the second heat sink layers 5520R. The first and second horizontal distances 5545L, 5545R may be very small to provide a precise tissue sealing for a thin profile end effector with no or little lateral thermal spread. In an example aspect, the first and second horizontal distances 5545L, 5545R may be in the range of 0.00 to about 0.50 inches, preferably in the range of about 0.00 to 0.10 inches, more preferably in the range of 0.00 to about 0.03 inches. In an example aspect, the first and second horizontal distances 5545L, 5545R may be less than half of the width of the electrode layers 5540L, 5540R. In another example aspect, the first and second horizontal distances 5545L, 5545R may have any other suitable length.

In an example aspect, the first jaw 5505 may include a feature that is configured to apply a pressure to the tissue by the first electrode layer 5540L and the second electrode layer 5540R in the hot zone 5650 that is greater than a pressure applied to the tissue (T) by the tissue contacting surfaces 5525L, 5525R of the first and second heat sink layers 5520L, 5520R. In an example aspect, this feature may comprise a first raised pad 5550L and a second raised pad 5550R. The first raised pad 5550L and the second raised pad 5550R may allow the first electrode layer 5540L and the second electrode layer 5540R to be raised compared with the tissue contacting surfaces 5525L, 5525R so that more pressure, and ultimately more heat, can be applied only to a target tissue (e.g., tissue in the hot zone 5650 adjacent the electrode layers 5540L, 5540R) more precisely with less lateral thermal spread.

Generally, the thickness of typical electrodes itself may be too thin to provide a meaningful pressure to compress the target tissue so that the energy and heat can be centered in the target tissue with less lateral thermal spread. In an example aspect, the raised pads 5550L, 5550R may not include the electrode layers 5540L, 5540R. The raised pads 5550L, 5550R may comprise the insulative layers 5510L, 5510R, or a combination of the insulative layers 5510L, 5510R and the heat sink layers 5520L, 5520R. In another example aspect, the raised pads 5550L, 5550R also may include the electrode layers 5540L, 5540R in addition to the insulative layers 5510L, 5510R and/or the heat sink layers 5520L, 5520R. In an example aspect, the thickness of the raised pads 5550L, 5550R (e.g., the vertical distance between the electrode layers 5540L, 5540R and the tissue contacting surfaces 5525L, 5525R) may be at least three to five times of the thickness of the electrode layers 5540L, 5540R. In an example aspect, the thickness of the raised pads 5550L, 5550R may be in the range of about 0.05.inches to 0.10 inches. In another example aspect, the raised pads 5550L, 5550R may have any suitable thickness that is sufficient to reduce the lateral thermal spread.

In an example aspect, the first insulative layer 5510L may include a first surface 5512L facing the first electrode layer 5540L and a second surface 5514L facing the elongate slot 5560. The first surface 5512L and the second surface 5514L of the first insulative layer 5510L may define a first edge 5570L. Similarly, the second insulative layer 5510R may include a first surface 5512R facing the first electrode layer 5540R and a second surface 5514R facing the elongate slot 5560. The first surface 5512R and the second surface 5514R of the second insulative layer 5510R may define a second edge 5570R. In an example aspect, the first and second edges 55740L, 5570R may be chamfered to allow steam to escape through the elongate slot 5560 to prevent burning or overheating of tissue that can lead to collateral tissue damage.

The elongate channel 5530 may be formed under the insulative layers 5510L, 551OR and heat sink layers 5520L, 5520R. In an example aspect, the elongate channel 5530 may comprise a thermally conductive metallic material and in direct contact with the first and second heat sink layers 5520L, 5520R to facilitate the cooling of the tissue in the first and second cool zones 5660, 5670. For example, the heat in the heat sink layers 5520L, 5520R transferred from the tissue may be further transferred to the metallic channel 5530 and this may help reduce the tissue temperature in the cool zones 5660, 5670 more quickly.

In an example aspect, during coagulating or cutting, the average temperature of tissue in the cool zones 5660, 5670 may be much lower than the average temperature of tissue in the hot zone 5650. After the coagulating or cutting, the temperature of tissue in the cool zones 5660, 5670 may decrease more quickly than the temperature of tissue in the hot zone 5650.

In an example aspect, the second jaw 5610 may comprise an anvil that is pivotally supported relative to the elongate channel 5530. The second jaw 5610 may be selectively moved toward and away from a surgical cartridge supported in the elongate channel 5630 between open and closed positions by actuating a closure drive system (e.g., closure drive system 510). In FIG. 61, the end effector 5500 is in a closed position with tissue (T) clamped between the first jaw 5505 and the second jaw 5610. The anvil slot 5630 may open into an upper opening 5640 that is wider than the anvil slot 5630 as shown in FIG. 61. The upper opening may extend longitudinally through the second jaw 5610, for example, to accommodate the anvil engagement features (e.g., anvil engagement feature 1336) on the cutting member (e.g., knife member 1330) during firing. The second jaw 5610 also may include fastener forming pockets 5620 (e.g., fastener forming pockets 1814) formed therein on each side of the anvil slot 5630.

FIG. 62 shows a perspective view of the end effector 5500 according to one aspect of this disclosure. In FIG. 62, the end effector 5500 is in an open position. The second jaw 5610 may be moveable relative to the first jaw 5505. The first jaw 5505 may include a cartridge 5700 that is sized and shaped to be removably received and supported in the elongate channel 5530. In an example aspect, the cartridge 5700 may include the insulative layers 5510L, 5510R, the heat sink layers 5520L, 5520R, and the electrode layers 5540L, 5540R. In an example aspect, a distal end of the first electrode layer 5540L may be connected to a distal end of the second electrode layer 5540R as shown in FIG. 62, and the elongate slot 5560 may extend through the center of the electrodes 5540L, 5540R. In another example aspect, the first electrode layer 5540L may be separate from the second electrode layer 5540R. The first tissue contacting surface 5525L of the first heat sink layer 5520L may be disposed on the left side of the first electrode layer 5540L, and the second tissue contacting surface 5525R of the second heat sink layer 5520R may be disposed on the right side of the second electrode layer 5540R.

The first jaw 5505 may include a microchip 5710 in the distal portion of the first jaw 5505. The microchip 5710 may be configured to control the electrode layers 5540L, 5540R (e.g., providing electrosurgical energy). The microchip 5710 may be connected to a flexible cartridge circuit 5720 (e.g., flexible cartridge circuit 1750), which may in turn connected to a channel circuit (e.g., channel circuit 1670). The first jaw 5505 also may include a dissector electrode 5730 at a distal end 5740. The dissector electrode 5730 may be connected to a source of electrical energy (e.g., RF generator 400) and configured to transmit electrosurgical energy (RF energy) to the tissue for dissecting the tissue and/or coagulating blood. The dissector electrode 5730 may be isolated from and operated separately from the electrode layers 5540L, 5540R.

Various aspects of the subject matter described herein are set out in the following numbered examples:

EXAMPLE 1

An surgical instrument comprising: an end effector comprising: a first jaw; a second jaw that is movable relative to the first jaw; a hot zone in a center portion of the end effector; a first cool zone in a left side portion of the end effector; and a second cool zone in a right side portion of the end effector; and an elongate slot defined between the first jaw and the second jaw, the elongate slot configured to slideably receive a cutting member within the elongate slot to cut tissue located between the first jaw and the second jaw, wherein the elongate slot is located in the center portion of the end effector; wherein the first jaw comprises: a first insulative layer in the hot zone, wherein the first insulative layer is on the left side of the elongate slot; a second insulative layer in the hot zone, wherein the second insulative layer is on the right side of the elongate slot; a first electrode layer on the first insulative layer; a second electrode layer on the second insulative layer, wherein the first electrode layer and the second electrode layer are configured for direct application of electrosurgical energy to the tissue in the hot zone; a first heat sink layer in the first cool zone; and a second heat sink layer in the second cool zone, wherein the first heat sink layer and the second heat sink layer are configured to cool the tissue in the first and second cool zones to minimize lateral thermal spread.

EXAMPLE 2

The surgical instrument of Example 1, wherein each of the first and second heat sink layers comprises a thermally conductive ceramic material.

EXAMPLE 3

The surgical instrument of one or more Example 1 through Example 2, wherein each of the first electrode layer and the second electrode layer comprises a direct contact metal electrode.

EXAMPLE 4

The surgical instrument of Example 3, wherein each of the first electrode layer and the second electrode layer further comprises a flex circuit wherein the direct contact metal electrode is deposited on the flex circuit.

EXAMPLE 5

The surgical instrument of one or more Example 1 through Example 4, wherein each of the first heat sink layer and the second heat sink layer comprises a tissue contacting surface.

EXAMPLE 6

The surgical instrument of Example 5, wherein each of the first electrode layer and the second electrode layer are raised compared with the tissue contacting surfaces of the first heat sink layer and the second heat sink layer, which allows the end effector to apply a pressure to the tissue by the first electrode layer and the second electrode layer in the hot zone that is greater than a pressure applied to the tissue by the tissue contacting surfaces of the first heat sink layer and the second heat sink layer.

EXAMPLE 7

The surgical instrument of one or more Example 1 through Example 6, wherein the first insulative layer and the second insulative layer comprise a thermally and electrically non-conductive material.

EXAMPLE 8

The surgical instrument of one or more Example 1 through Example 7, wherein the first insulative layer comprises a first surface facing the first electrode layer and a second surface facing the elongate slot, wherein the first surface and the second surface define a first edge, wherein the first edge is chamfered to allow steam to escape.

EXAMPLE 9

The surgical instrument of Example 8, wherein the second insulative layer comprises a third surface facing the second electrode layer and a fourth surface facing the elongate slot, wherein the third surface and the fourth surface define a second edge, wherein the second edge is chamfered to allow the steam to escape.

EXAMPLE 10

The surgical instrument of one or more Example 1 through Example 9, wherein the first jaw further comprises a channel under the first and second heat sink layers.

EXAMPLE 11

The surgical instrument of Example 10, wherein the channel comprises a thermally conductive metallic material, and the channel is in direct contact with the first and second heat sink layers to facilitate the cooling of the tissue in the first and second cool zones.

EXAMPLE 12

An surgical instrument comprising: an end effector comprising: a first jaw; a second jaw that is movable relative to the first jaw; a hot zone in a center portion of the end effector; a first cool zone in a left side portion of the end effector; a second cool zone in a right side portion of the end effector; and a dissector tip at a distal end of the end effector; and an elongate slot defined between the first jaw and the second jaw, the elongate slot configured to slideably receive a blade within the elongate slot to cut tissue located between the first jaw and the second jaw, wherein the elongate slot is located in the center portion of the end effector; wherein the first jaw comprises: a first insulative layer in the hot zone, wherein the first insulative layer is on the left side of the elongate slot; a second insulative layer in the hot zone, wherein the second insulative layer is on the right side of the elongate slot; a first electrode layer on the first insulative layer; a second electrode layer on the second insulative layer, wherein the first electrode layer and the second electrode layer are configured for direct application of electrosurgical energy to the tissue in the hot zone, wherein each of the first electrode layer and the second electrode layer comprises a direct contact metal electrode; a first heat sink layer in the first cool zone; and a second heat sink layer in the second cool zone, wherein the first heat sink layer and the second heat sink layer are configured to cool the tissue in the first and second cool zones to minimize lateral thermal spread.

EXAMPLE 13

The surgical instrument of Example 12, wherein each of the first and second heat sink layers comprises a thermally conductive ceramic material.

EXAMPLE 14

The surgical instrument of one or more Example 12 through Example 12, wherein each of the first electrode layer and the second electrode layer further comprises a flex circuit wherein the direct contact metal electrode is deposited on the flex circuit.

EXAMPLE 15

The surgical instrument of one or more Example 12 through Example 14, wherein each of the first heat sink layer and the second heat sink layer comprises a tissue contacting surface.

EXAMPLE 16

The surgical instrument of Example 15, wherein each of the first electrode layer and the second electrode layer are raised compared with the tissue contacting surfaces of the first heat sink layer and the second heat sink layer, which allows the end effector to apply a pressure to the tissue by the first electrode layer and the second electrode layer in the hot zone that is greater than a pressure applied to the tissue by the tissue contacting surfaces of the first heat sink layer and the second heat sink layer.

EXAMPLE 17

The surgical instrument of one or more Example 12 through Example 16, wherein the first insulative layer and the second insulative layer comprise a thermally and electrically non-conductive material.

EXAMPLE 18

The surgical instrument of one or more Example 12 through Example 17, wherein the first insulative layer comprises a first surface facing the first electrode layer and a second surface facing the elongate slot, wherein the first surface and the second surface define a first edge, wherein the first edge is chamfered to allow steam to escape.

EXAMPLE 19

The surgical instrument of one or more Example 12 through Example 18, wherein the first jaw further comprises a channel under the first and second heat sink layers.

EXAMPLE 20

The surgical instrument of Example 19, wherein the channel comprises a thermally conductive metallic material, and the channel is in direct contact with the first and second heat sink layers to facilitate the cooling of the tissue in the first and second cool zones.

Surgical End Effector to Adjust Jaw Compression

In an electrosurgical instrument the density of tissue located between the jaws of an end effector varies along the length of the end effector. High density tissue may be located in a proximal portion of the end effector, medium density tissue may be located at a mid portion of the end effector and the low density tissue may be located at a distal portion of the end effector. A compliant jaw may be employed to apply variable compression on the variable density tissue. A constant energy density may not be effective to seal the variable density tissue along the length of a compliant jaw for applying variable compression. Therefore, the present disclosure provides an electrosurgical cartridge that is configured to deliver variable energy density along the length of the compliant jaw for variable compression to provide a suitable seal of the variable density tissue.

As disclosed above, with respect to FIGS. 10-12, an electrosurgical device may include an end effector 1500 that includes a removable electrosurgical cartridge, such as, for example, a radio frequency (RF) surgical cartridge 1700 disposed within an elongate channel 1602 of a first jaw assembly 1600. In some aspects, the electrosurgical device may be electrically connected to an RF generator designed to supply RF energy to the RF surgical cartridge and to its components. FIG. 10 particularly depicts an aspect of the RF surgical cartridge 1700 having a cartridge body 1712 formed with a centrally disposed raised electrode pad 1720. As can be most particularly seen in FIG. 6, the elongate slot 1712 extends through the center of the electrode pad 1720 and serves to divide the pad 1720 into a left pad segment 1720L and a right pad segment 1720R. Returning to FIG. 10, a right flexible circuit assembly 1730R is attached to the right pad segment 1720R and a left flexible circuit assembly 1730L is attached to the left pad segment 1720L. In addition, the right flexible circuit assembly 1730R includes a "phase one", proximal right electrode 1736R and a "phase two" distal right electrode 1738R. Further, the left flexible circuit assembly 1730L includes a "phase one", proximal left electrode 1736L and a "phase two" distal left electrode 1738L.

FIGS. 63A and 63B depict an alternative aspect of an end effector 1500 having a replaceable electrosurgical cartridge, such as, for example, an RF surgical cartridge 1700. FIG. 63A depicts the end effector 1500 in an open configuration and FIG. 63B depicts the end effector 1500 in a closed configuration. In the closed configuration, a first jaw assembly 1600 and a second jaw assembly 1800 of the end effector 1500 may be spaced proximate to each other at a distance that may result in a piece of tissue 6070 placed therebetween being subjected to a clamping pressure. In the open configuration, the first jaw assembly 1600 and the second jaw assembly may be spaced at a greater distance. The open or closed configuration of the end effector 1500 may be determined by the position and operative action of a proximal closure tube 1910.

As depicted in FIG. 63A, the end effector 1500 includes a first jaw assembly 1600 that may include an elongate channel to receive the replaceable RF surgical cartridge 1700. The RF surgical cartridge 1700 includes a cartridge body 1710 on which one or more electrodes may be disposed. In the aspect depicted in FIG. 63A, the RF surgical cartridge 1700 may include two types of electrodes, including one or more shear electrodes 6038 and a dissector electrode 6238. The one or more shear electrodes 6038 may generally have an elongated aspect that may extend along a longitudinal axis of the RF surgical cartridge 1700. In some non-limiting aspects, one of a pair of shear electrodes 6038 may be disposed on either side of the elongate slot. The dissector electrode 6238 may be disposed at a distal end of the cartridge body 1710. Further features of the RF surgical cartridge 1700 may include a jaw spacer 6060 at the distal end of the cartridge body 1710. The jaw spacer may act to prevent an inner surface of the anvil 1810 from contacting any one or more of the shear electrodes 6038 and the dissector electrode 6238, as depicted in FIG. 63B.

The one or more shear electrodes 6038 in addition to the dissector electrode 6238 may be disposed on the flexible circuit assembly that may be part of a flexible cartridge circuit 1750. The one or more shear electrodes 6038 may operate to deliver any amount of RF energy to a tissue 6070 disposed proximate to the one or more shear electrodes 6038. FIG. 63B, for example, depicts a piece of tissue 6070 clamped between the first jaw assembly 1600 and the second jaw assembly 1800 according to clamping motion CM. In some aspects, a combination of RF energy delivered to the tissue 6070 proximate to the shear electrodes 6038 and the compressive force generated by the first jaw assembly 1600 and the second jaw assembly 1800 due to the clamping motion CM, may result in the generation of a hemostatic seal in the tissue. The dissector electrode 6238 may be used to specifically spot treat tissue by the application of RF energy. Each of the one or more shear electrodes 6038 and the dissector electrode 6238 may be electrically coupled to the RF energy generator.

Each of the one or more shear electrodes 6038 may further include one or more electrode portions. For example, as depicted in FIG. 10, each of the right and left shear electrodes may include a separate proximal electrode and a distal electrode (1736R, 1738R, and 1736L, 1738L, respectively). For each of the right and left shear electrodes, each of the proximal electrodes and distal electrodes may be disposed along or parallel to a longitudinal axis of the RF cartridge. The proximal electrodes (1736R,L) may be separately activated during a "phase one" procedure and the distal electrodes (1738R,L) may be separately activated during a "phase two" procedure. In the aspect depicted in FIG. 63A, each of the shear electrodes 6038 may be functionally separated into multiple functional electrode portions, 6138a-c. Similar to the aspect depicted in FIG. 10, the electrode portions 6138a-c may be disposed along or parallel to a longitudinal axis of the RF cartridge. Each electrode portion 6138a-c may deliver an amount of RF energy to a tissue proximate thereto, but an amount of RF energy delivered by any one electrode portion may differ from an amount of RF energy delivered by a different electrode portion. In one non-limiting example, an amount of RF energy delivered to a tissue proximate to a low-energy electrode portion 6138a may be less than an amount of RF energy delivered to a tissue proximate to a mid-energy electrode portion 6138b. Similarly, an amount of RF energy delivered to a tissue proximate to the mid-energy electrode portion 6138b may be less than an amount of RF energy delivered to a tissue proximate to the high-energy electrode portion 6138c. In some aspects, each of the electrode portions 6138a-c may be separately actuatable by means of any appropriate RF electrical switching component. In some alternative aspects, all or some number of the electrode portions 6138a-c may be actuated together.

As noted above, the effectiveness of a hemostatic seal of a tissue may be dependent on both a compressive pressure applied to the tissue as well as an amount of RF energy delivered to the compressed tissue. The amount of RF energy delivered to the tissue should be sufficient to form an effective hemostatic seal. If too little RF energy is delivered to the tissue, the hemostatic seal may not properly form. Alternatively, if too much RF energy is delivered to the tissue, the tissue may be charred or damaged and be unable to form the hemostatic seal. The amount of RF energy necessary to form the effective hemostatic seal may depend on characteristics of the tissue including, without limitation, a tissue thickness, a tissue density, and a tissue composition. In some examples, a piece of tissue to receive a hemostatic seal may be effectively homogeneous with respect to the tissue thickness, the tissue density, and/or the tissue composition. Alternatively, a piece of tissue to receive a hemostatic seal may be heterogeneous with respect to the tissue thickness, the tissue density, and/or the tissue composition.

An electrosurgical device having shear electrodes composed of a variety of electrode portions may be used to form an effective hemostatic seal across such a heterogeneous tissue. In the aspect of the end effector 1500 depicted in FIG. 63B, the tissue 6070 may be heterogeneous and have tissue sections that may differ in any one or more of the tissue thickness, the tissue density, and/or the tissue composition. In a non-limiting example, the tissue 6070 may have a high-density composition 6170a, a mid-density composition 6170b, and a low-density composition 6170c. A comparison of FIG. 63A with FIG. 63B illustrates that an effective hemostatic seal of a tissue having a high-density composition 6170a may be made using a low energy electrode portion 6138a. Similarly, an effective hemostatic seal of a tissue having a mid-density composition 6170b may be made using a mid-energy electrode portion 6138b and an effective hemostatic seal of a tissue having a low-density composition 6170c may be made using a high-energy electrode portion 6138c.

The amount of RF energy delivered by an electrode may depend, at least in part, on the RF energy density at the electrode surface. Thus, a variation in one or more of the electrode surface properties may be used to adjust the RF energy delivered by the electrode at that portion of the surface. In one aspect, the resistivity of the electrode surface material may be adjusted to control the RF energy delivered at that electrode surface. In another aspect, the dimensions of the electrode surface (for example, electrode width) may be adjusted to control the RF energy delivered at that electrode surface. In another aspect, the electrode surface may incorporate physical features that may permit control of the RF energy delivered at that electrode surface. Examples of such features may include the inclusion of resistive or electrically insulative components on or within the electrode surface.

FIG. 64 depicts some example shear electrodes 6038a-d that may incorporate any number or type of features 6139a-d. Each of the shear electrodes 6038a-d may comprise a shear electrode surface 6039a-d which may be composed of an electrically conductive material, especially one designed to conduct RF energy. The disposition of the features 6139a-d on the shear electrode surface may encompass one or more patterned energy delivery surfaces. Thus, one aspect of a shear electrode 6038a may have a shear electrode surface 6039a having a patterned energy delivery surface incorporating a set of transverse rectilinear features 6139a. Another aspect of a shear electrode 6038b may have a shear electrode surface 6039b having a patterned energy delivery surface incorporating a set of circular features 6139b. Yet another aspect of a shear electrode 6038c may have a shear electrode surface 6039c having a patterned energy delivery surface incorporating a set of concave quadrilateral ("chevron-shaped") features 6139c. While the features, such as 6139a-c may be formed from discrete geometrical shapes, the features may also comprise complex components resulting in a graduated feature 6139d which may continuously or almost-continuously span a portion or portions of the surface of the shear electrode surface 6039d.

It may be recognized that an amount of RF energy that may be delivered by a portion of a shear electrode 6038 to a tissue may be controlled by a number, type, size, and/or area density of the features 6139a-d forming a particular aspect of a patterned energy delivery surface. FIG. 64, for example, depicts that a low-energy portion 6138a of a shear electrode may have a patterned energy delivery surface incorporating a larger number of features (for example 6139a-d) than a mid-energy portion 6138b of a shear electrode. Similarly, a mid-energy portion 6138b of a shear electrode may have a patterned energy delivery surface incorporating a larger number of features (for example 6139a-d) than a high-energy portion 6138c of a shear electrode.

Although three energy portions 6138a-c are depicted in FIGS. 63A and 64, it may be recognized that a shear electrode 6038 may have any number of discrete energy portions. Each of the discrete energy portion may be composed of a patterned energy delivery surface. Non-limiting examples of the number of energy portions incorporated into a shear electrode 6038 may include two energy portions, three energy portions, four energy portions, five energy portions, or any finite number of energy portions. Further, as disclosed above with respect to example shear electrode 6038d, the surface of the shear electrode 6038d may have a patterned energy delivery surface incorporating a graduated feature 6039d configured to supply a continuum of RF energies across the surface of the shear electrode 6038d. The continuum of RF energies supplied by the graduated feature 6039d may include, without limitation, a linear continuum of RF energies across the surface of the shear electrode 6038d, a quadratic continuum of RF energies, a logarithmic continuum of RF energies across the surface of the shear electrode 6038*d*, or an exponential continuum of RF energies across the surface of the shear electrode 6038*d*.

It should be recognized that the individual features 6139*a-d* as depicted in FIG. 64 are non-limiting examples of features 6139*a-d* that may be incorporated on a shear electrode surface 6039*a-d*. Other non-limiting example of such features may include features that are linear, circular, elliptical, oval, rectangular, square, rounded rectangular, or have a geometry defined by any closed two-dimensional shape. For any aspect of a shear electrode 6038, all of the features may have the same shape or may have differing shapes. For any aspect of a shear electrode 6038, all of the features may have the same size or may have differing sizes. For any aspect of a shear electrode 6038, all of the features may be physically isolated from each other, may be contiguous to each other, or may be a combination of physically isolated and continuous with respect to each other.

As further disclosed above, each of the energy portions may include a patterned energy delivery surface. Each patterned energy delivery surface may incorporate any number, size, shape, or area density of features. Each patterned energy delivery surface of a particular aspect of a shear electrode may have features having identical shapes although the features may differ in number, size, and/or area density between any two patterned energy delivery surfaces of the electrode. Each patterned energy delivery surface of a particular aspect of a shear electrode may have an identical number of features although the features may differ in shape, size, and/or area density between any two patterned energy delivery surfaces of the electrode. Each patterned energy delivery surface of a particular aspect of a shear electrode may have features having identical sizes although the features may differ in number, shape, and/or area density between any two patterned energy delivery surfaces of the electrode. Each patterned energy delivery surface of a particular aspect of a shear electrode may have features having identical feature area density on the shear electrode surface although the features may differ in number, size, and/or shape between any two patterned energy delivery surfaces of the electrode.

As disclosed above, the features 6139*a-d* may be formed from an electrically insulative material deposited on or in a shear electrode 6038. In one non-limiting aspect, the features 6139*a-d* depicted in FIG. 64 may be fabricated by removing portions from the shear electrode surface 6039*a-d* to form recessed features, for example by the use of an end-mill, and then using a fabrication method to deposit the electrically insulative material in the recessed features to form the features. Alternative methods of fabricating the features 6139*a-d* may include, for example, molding the electrode to include the recessed features before depositing the electrically insulative material therewithin. The one or more recessed features may extend partially through a thickness of the shear electrode 6038*a-d*.

Alternatively, the one or more recessed features may extend completely through the thickness of the shear electrode 6038*a-d*, thereby allowing the recessed feature to receive the electrically insulative material either from a top side or a bottom side of the electrode. The electrically insulative material may completely fill the recessed features, thereby forming a surface co-planar with the shear electrode surface 6039*a-d*. In an alternative aspect, the electrically insulative material may incompletely fill the recessed features, thereby forming a surface recessed from the shear electrode surface 6039*a-d*. In yet an additional aspect, the electrically insulative material may overfill the recessed features, thereby forming a surface protruding above the shear electrode surface 6039*a-d*.

In anther non-limiting aspect, the features 6139*a-d* depicted in FIG. 64 may be fabricated by a deposition method. In one non-limiting example, the shear electrode surface 6039*a-d* may be coated with an electrically insulative material from which portions have been removed, thereby uncovering the electrode surface therebelow. The features 6139*a-d* may be fabricated by removing portions of the deposited electrically insulative material, for example by first contacting the electrically insulative material with the shear electrode surface 6039*a-d* and then using a fabrication method to remove the portions of the material to form the features 6139*a-d*. Alternative deposition methods of fabricating the features 6139*a-d* may include, for example, printing the features 6139*a-d* directly on the shear electrode surface 6039*a-d*. Additional alternative methods for producing the features 6139*a-d* on the shear electrode surface 6039*a-d* may also be employed.

Disclosed above are aspects of an RF electrode that may be a component of a removable RF cartridge for use with an electrosurgical system. Such an RF electrode may incorporate one or more features incorporated into one or more patterned energy delivery surfaces designed to modify an amount of RF energy that may be sourced by a surface or one or more surface portions of the electrode to a tissue placed proximate thereto. Although a plurality of aspects of such features and/or patterned energy delivery surfaces has been disclosed herein, such aspects are not to be construed as limiting. Thus, the patterned energy delivery surfaces may include any appropriate features that may be configured on a surface of one or more jaw assemblies or electrodes of an electrosurgical system. The patterned energy delivery surfaces may generally include features applied to a planar surface of an electrode, to one or more raised or elevated features that extend vertically above a surface of an electrode, or to one or more depressed features that extend vertically below a surface of an electrode. It may be understood that the term "electrically insulative material disposed on an electrode" encompasses the application of the material on a planar surface of an electrode, to one or more raised or elevated features that extend vertically above a surface of an electrode, or to one or more depressed features that extend vertically below a surface of an electrode. No limitations, expressed or implied, are herein imposed on methods of fabricating the features.

The patterned energy delivery surfaces may encompass a single feature or multiple features. The single feature or multiple features may have a limited extent, such as a small circular portion of the electrically insulative material disposed on an electrode. The single feature or multiple features may have a more extended extent such as an elongated portion of the electrically insulative material disposed on an electrode. The single feature or multiple features—either of limited extent or of extended extent—are not limited in their respective shapes, sizes, or dimensions on an electrode surface. The single feature or multiple features—either of limited extent or of extended extent—are not limited in their respective dispositions about the surface of the electrode. Thus, as an example, an elongated portion of the electrically insulative material may extend along an axis essentially parallel to a longitudinal axis of the electrode. Alternatively, an elongated portion of the electrically insulative material may extend along an axis essentially perpendicular to a longitudinal axis of the electrode. In yet another alternative example, an elongated portion of the electrically insulative material may extend along an axis neither essentially parallel to nor essentially perpendicular to a longitudinal axis of the first electrode.

The patterned energy delivery surfaces may incorporate multiple features that may include any combination or combinations of portions of the electrically insulative material disposed on an electrode surface or portions removed from a coating of an electrically insulative material disposed on the electrode surface. Multiple features may be combined. Further, multiple features may be symmetrically disposed about the surface of the electrode or they may be asymmetrically disposed about the surface of the electrode. Multiple features—either of limited extent or of extended extent—are not limited in their dispositions about the surface of the electrode with respect to each other. contemplated. It is intended that the claims submitted herewith define the overall scope.

Various aspects of the subject matter described herein are set out in the following numbered examples:

EXAMPLE 1

An electrosurgical device, comprising: a cartridge configured to be disposed within an elongate channel of an end effector, wherein the cartridge comprises an electrode having a plurality of electrode portions disposed along a longitudinal axis of the cartridge, wherein the electrode is configured to electrically couple to a generator; wherein each electrode portion of the plurality of electrode portions is configured to deliver an amount of energy to a tissue placed proximate thereto; and wherein an amount of energy delivered by a first electrode portion of the plurality of electrode portions differs from an amount of energy delivered by a second electrode portion of the plurality of electrode portions.

EXAMPLE 2

The electrosurgical device of Example 1, wherein the cartridge is configured to be releasably disposed within the elongate channel.

EXAMPLE 3

The electrosurgical device of one or more of Example 1 through Example 2, wherein the plurality of electrode portions comprise a proximal right electrode, a distal right electrode, a proximal left electrode, and a distal left electrode.

EXAMPLE 4

The electrosurgical device of Example 3, further comprising a right flexible circuit and a left flexible circuit, wherein the proximal right electrode and the distal right electrode are electrically coupled to the right flexible circuit, and wherein the proximal left electrode and the distal left electrode are electrically coupled to the left flexible circuit.

EXAMPLE 5

The electrosurgical device of Example 4, wherein the right flexible circuit and the left flexible circuit each has an overall width of 0.025 inches, and wherein the proximal right electrode, the distal right electrode, the proximal left electrode and the distal left electrode each has a width of 0.010 inches.

EXAMPLE 6

An electrosurgical device, comprising: a cartridge configured to be disposed within an elongate channel of an end effector, wherein the cartridge comprises an electrode having a plurality of electrode portions disposed along a longitudinal axis of the cartridge, wherein the electrode is configured to electrically couple to a generator; a flexible cartridge circuit electrically coupled to the electrode, wherein the flexible cartridge circuit is configured to electrically couple to a plurality of exposed contacts on a distal end of a channel circuit disposed within the elongate channel; wherein each electrode portion of the plurality of electrode portions is configured to deliver an amount of energy to a tissue placed proximate thereto; and wherein an amount of energy delivered by a first electrode portion of the plurality of electrode portions differs from an amount of energy delivered by a second electrode portion of the plurality of electrode portions.

EXAMPLE 7

The electrosurgical device of Example 6, wherein the channel circuit further comprises a proximal contact portion electrically coupled to a distal contact portion of a flexible shaft circuit strip.

EXAMPLE 8

The electrosurgical device of Example 7, wherein a proximal contact portion of the flexible shaft circuit strip is configured to electrically couple to the generator.

EXAMPLE 9

An end effector, comprising: a first jaw assembly comprising: an elongate channel; and an electrosurgical cartridge disposed within the elongate channel, wherein the electrosurgical cartridge further comprises: a shear electrode having a plurality of shear electrode portions disposed along a longitudinal axis of the electrosurgical cartridge; and a dissector electrode disposed at a distal end of the electrosurgical cartridge; and a second jaw assembly comprising an anvil configured to move proximate to a surface of the electrosurgical cartridge, wherein the shear electrode and the dissector electrode are each configured to receive electrosurgical energy from an electrosurgical generator, wherein each shear electrode portion of the plurality of shear electrode portions is configured to deliver an amount of electrosurgical energy to a tissue placed proximate thereto, and wherein an amount of electrosurgical energy delivered by a first shear electrode portion of the plurality of shear electrode portions differs from an amount of electrosurgical energy delivered by a second shear electrode portion of the plurality of shear electrode portions.

EXAMPLE 10

The end effector of Example 9, wherein the electrosurgical cartridge is releasably disposed within the elongate channel.

EXAMPLE 11

The end effector of one or more of Example 9 through Example 10, wherein the first shear electrode portion is proximal to the second shear electrode portion.

EXAMPLE 12

The end effector of Example 11, wherein the amount of electrosurgical energy delivered by the first shear electrode portion is less than the amount of electrosurgical energy delivered by the second shear electrode portion.

EXAMPLE 13

The end effector of one or more of Example 11 through Example 12, wherein the first shear electrode portion has a first patterned energy delivery surface, and the second shear electrode portion has a second patterned energy delivery surface.

EXAMPLE 14

The end effector of Example 13, wherein the first patterned energy delivery surface differs from the second patterned energy delivery surface.

EXAMPLE 15

The end effector of one or more of Example 13 through Example 14, wherein the first patterned energy delivery surface and the second patterned energy delivery surface each comprise a plurality of surface features.

EXAMPLE 16

The end effector of Example 15, wherein the plurality of surface features comprises an electrically insulative material.

EXAMPLE 17

The end effector of one or more of Example 15 through Example 16, wherein the first patterned energy delivery surface has a first area density of a plurality of surface features, the second patterned energy delivery surface has a second area density of a plurality of surface features, and the first area density of a plurality of surface features is greater than the second area density of a plurality of surface features.

EXAMPLE 18

The end effector of one or more of Example 15 through Example 17, wherein the plurality of surface features comprises a plurality of transverse rectilinear features.

EXAMPLE 19

The end effector of one or more of Example 15 through Example 18, wherein the plurality of surface features comprises a plurality of circular features.

EXAMPLE 20

The end effector of one or more of Example 15 through Example 19, wherein the plurality of surface features comprises a plurality of concave quadrilateral features.

EXAMPLE 21

The end effector of one or more of Example 15 through Example 20, wherein the first patterned energy delivery surface comprises a first plurality of surface features disposed directly on a surface of the first shear electrode portion, and the second patterned energy delivery surface comprises a second plurality of surface features disposed directly on a surface of the second shear electrode portion.

EXAMPLE 22

The end effector of one or more of Example 15 through Example 21, wherein first patterned energy delivery surface comprises a first plurality of recessed surface features disposed in a surface of the first shear electrode portion, and the second patterned energy delivery surface comprises a second plurality of recessed surface features disposed in a surface of the second shear electrode portion.

EXAMPLE 23

The end effector of one or more of Example 9 through Example 22, wherein the shear electrode comprises a left shear electrode and a right shear electrode.

EXAMPLE 24

The end effector of Example 23, wherein the left shear electrode comprises a plurality of left shear electrode portions disposed along a longitudinal axis of the electrosurgical cartridge, and the right shear electrode comprises a plurality of right shear electrode portions disposed along a longitudinal axis of the electrosurgical cartridge.

EXAMPLE 25

The end effector of Example 24, wherein the left shear electrode comprises three left shear electrode portions disposed along a longitudinal axis of the electrosurgical cartridge, and the right shear electrode comprises three right shear electrode portions disposed along a longitudinal axis of the electrosurgical cartridge.

Cartridge Arrangements for Surgical Cutting and Fastening Instruments with Lockout Disablement Features In a surgical instrument it may be useful to control when the cutting member can be advanced through an end effector. In order to control when the cutting member may be advanced, the surgical instrument may provide a type of lockout mechanism to prevent advancement of the cutting member in a staple/fastener cartridge in various circumstances. Lockout mechanisms for staple/fastener cartridge mechanically prevent the cutting member from being advanced by engaging part of the cutting member to prohibit distal movement. Preventing advancement of the cutting member may be useful when a surgical cartridge has not been inserted into the end effector, is improperly inserted into the end effector, or when the staple/fastener cartridge is spent.

During use of a surgical instrument it is possible that a mechanical stapling surgical cartridge may be inserted improperly, not inserted at all, or may be spent. Therefore, it may be desirable to provide a lockout mechanism that mechanically prevents advancement of a cutting member through an end effector when a staple/fastener cartridge is absent, improperly placed in the end effector, or is spent. Such lockout mechanisms, however, interfere with the operation of a radio frequency (RF) cartridge configured to be used in an end effector configured to receive mechanical staple/fastener cartridges and/or radio frequency cartridges. Thus, the present disclosure provides a lockout disablement mechanism to accommodate an RF cartridge in an end effector configured to receive mechanical staple/fastener cartridges or radio frequency cartridges and includes a lockout mechanism suitable to lockout a mechanical staple/fastener cartridge.

As shown in FIGS. 10-12, in at least one arrangement, the RF surgical cartridge 1700 includes a cartridge body 1710 that is sized and shaped to be removably received and supported in the elongate channel 1602. For example, the cartridge body 1710 may be configured to be removably retained in snap engagement with the elongate channel 1602. In various arrangements, the cartridge body 1710 may be fabricated from a polymer material, such as, for example, an engineering thermoplastic such as the liquid crystal polymer (LCP) VECTRA™ and the elongate channel 1602 may be fabricated from metal. In at least one aspect, the cartridge body 1710 includes a centrally disposed elongate slot 1712 that extends longitudinally through the cartridge body to accommodate longitudinal travel of the knife 1330 therethrough. As shown in FIGS. 10 and 11, a pair of lockout engagement tails 1714 extends proximally from the cartridge body 1710 to disable the lockout mechanism intended to lockout the staple/fastener cartridge 1400. Each lockout engagement tail 1714 has a lockout pad 1716 formed on the underside thereof that are sized to be received within a corresponding proximal opening portion 1642 in the channel bottom 1620. Thus, when the cartridge 1700 is properly installed in the elongate channel 1602, the lockout engagement tails 1714 cover the openings 1642 and ledges 1654 to retain the knife 1330 in an unlocked position ready for firing.

Turning now to FIG. 65, with reference still to FIGS. 10-12, in at least one arrangement, the surgical staple cartridge 1900 includes a cartridge body 1918 that is sized and shaped to be removably received and supported in the elongate channel 1602. For example, the cartridge body 1918 may be configured to be removably retained in snap engagement with the elongate channel 1602. In various arrangements, the cartridge body 1918 may be fabricated from a polymer material, such as, for example, an engineering thermoplastic such as the liquid crystal polymer (LCP) VECTRA™ and the elongate channel 1602 may be fabricated from metal. In at least one aspect, the cartridge body 1918 includes a centrally disposed elongate slot 1912 that extends longitudinally through the cartridge body to accommodate longitudinal travel of the knife 1330 therethrough. As shown in FIG. 65, a pair of lockout engagement tails 1914 extends proximally from the cartridge body 1918. Each lockout engagement tail 1914 has a lockout pad 1916 formed on the underside thereof that are sized to be received within a corresponding proximal opening portion 1642 in the channel bottom 1620. Thus, when the cartridge 1900 is properly installed in the elongate channel 1602, the lockout engagement tails 1914 cover the openings 1642 and ledges 1654 to retain the knife 1330 in an unlocked position ready for firing.

Various aspects of the subject matter described herein are set out in the following numbered examples:

EXAMPLE 1

A surgical cartridge assembly, comprising: a proximal end; a distal end; an elongate channel, comprising: a base; and at least one opening within the base; a cartridge body configured to be removably received within the elongate channel; a slot configured to receive a cutting member; at least one lockout tab extending from the proximal end of the cartridge body, wherein the at least one lockout tab is configured to cover the at least one opening when the cartridge body is received within the elongate channel, and wherein the at least one lockout tab disables a lockout mechanism to allow the cutting member to advance distally through the slot.

EXAMPLE 2

The surgical cartridge assembly of Example 1, wherein the elongate channel further comprises at least one ledge on the base positioned distal to the at least one opening.

EXAMPLE 3

The surgical cartridge assembly of Example 2, wherein the at least one lockout tab is configured to cover the at least one ledge when the cartridge body is received within the elongate channel.

EXAMPLE 4

The surgical cartridge assembly of one or more of Example 1 through Example 3, wherein the at least one lockout tab comprises at least one lockout pad configured to be received within the at least one opening when the cartridge body is received within the elongate channel.

EXAMPLE 5

The surgical cartridge assembly of one or more of Example 1 through Example 4, wherein a portion of the cutting member is configured to be received within the at least one opening of the elongate channel in the absence of a cartridge body.

EXAMPLE 6

The surgical cartridge assembly of one or more of Example 1 through Example 5, wherein the surgical cartridge assembly comprises a staple cartridge.

EXAMPLE 7

The surgical cartridge assembly of one or more of Example 1 through Example 6, wherein the surgical cartridge assembly comprises a RF cartridge.

EXAMPLE 8

An end effector for a surgical instrument, the end effector comprising: a proximal end; a distal end; a first jaw; a second jaw comprising an elongate channel including a base, wherein the base of the elongate channel comprises: a first opening; and a second opening; and a surgical cartridge configured to be removably received within the elongate channel, the surgical cartridge comprising: a cartridge body; a slot configured to receive a cutting member; a first tab extending from the proximal end of the cartridge body on a first side of the slot, wherein the first tab is configured to cover the first opening and the first ledge when the surgical cartridge is received within the elongate channel; and a second tab extending from the proximal end of the cartridge body on a second side of the slot, wherein the second tab is configured to cover the second opening and the second ledge when the surgical cartridge is received within the elongate channel, and wherein the first tab and the second tab disable a lockout mechanism to allow a cutting member to advance distally through the slot.

EXAMPLE 9

The end effector of Example 8, wherein the elongate channel further comprises a first ledge and a second ledge, wherein the first ledge is positioned on the base distal to the first opening, and wherein the second ledge is positioned on the base distal to the second opening.

EXAMPLE 10

The end effector of Example 9, wherein the first tab is configured to cover the first ledge when the surgical cartridge is received within the elongate channel, and the second tab is configured to cover the second ledge when the surgical cartridge is received within the elongate channel.

EXAMPLE 11

The end effector of one or more of Example 8 through Example 10, wherein the first tab comprises a first pad configured to be received within the first opening when the surgical cartridge is received within the elongate channel.

EXAMPLE 12

The end effector of one or more of Example 8 through Example 11, wherein a first portion of the cutting member is configured to be received within the first opening of the elongate channel in the absence of a surgical cartridge, and wherein a second portion of the cutting member is configured to be received within the second opening of the elongate channel in the absence of a surgical cartridge.

EXAMPLE 13

The end effector of one or more of Example 8 through Example 12, wherein the surgical cartridge comprises a staple cartridge.

EXAMPLE 14

The end effector of one or more of Example 8 through Example 13, wherein the surgical cartridge comprises a RF cartridge.

EXAMPLE 15

A surgical cartridge assembly, comprising: a proximal end; a distal end; an elongate channel, comprising: a base; a first opening; and a second opening; a surgical cartridge configured to be removably received within the elongate channel, the surgical cartridge comprising: a cartridge body; a longitudinal slot configured to receive a cutting member; a first lockout projection extending proximally from the proximal end of the cartridge body on a first side of the slot, wherein the first lockout projection is configured to cover the first opening when the surgical cartridge is received within the elongate channel; and a second lockout projection extending proximally from the proximal end of the cartridge body on a second side of the slot, wherein the second lockout projection is configured to cover the second opening when the surgical cartridge is received within the elongate channel, and wherein the first lockout projection and the second lockout projection disable a lockout mechanism to allow a cutting member to advance distally through the slot.

EXAMPLE 16

The surgical cartridge assembly of Example 15, wherein the elongate channel further comprises a first ledge on the base positioned distal to the first opening and a second ledge on the base positioned distal to the second opening.

EXAMPLE 17

The surgical cartridge assembly of Example 16, wherein the first lockout projection is configured to cover the first ledge when the surgical cartridge is received within the elongate channel, and the second lockout projection is configured to cover the second ledge when the surgical cartridge is received within the elongate channel.

EXAMPLE 18

The surgical cartridge assembly of one or more of Example 15 through Example 17, wherein the first lockout projection comprises a first lockout pad configured to be received within the first opening when the surgical cartridge is received within the elongate channel.

EXAMPLE 19

The surgical cartridge assembly of one or more of Example 15 through Example 18, wherein the surgical cartridge comprises a staple cartridge.

EXAMPLE 20

The surgical cartridge assembly of one or more of Example 15 through Example 19, wherein the surgical cartridge comprises a RF cartridge.

Surgical Cutting and Fastening Instruments with Dual Power Sources

In a surgical sealing and stapling system, it may be useful to employ a modular design that allows a single handle assembly to attach to multiple nozzle assemblies, and for a nozzle assembly to attach to multiple handle assemblies. Since the nozzle assembly would include the various surgical instruments in the end effector, special circuitry in the nozzle may be required to allow for instrumentation in a handle assembly to control the various functions in the end effector of the modular nozzle assembly. In some examples, each of the various surgical instruments may be designed to effect a specific surgical function, for example one or more types of tissue sealing functions. In addition, it may be necessary to apply energy to the end effector, which may or may not originate from the handle assembly. For example, the handle assembly may be battery powered to control the functions of the handle assembly, but may not possess power sufficient to control the end effector. Additionally, a system including a surgical sealing function may have specific power requirements, for example a requirement for sourcing RF energy for applying a hemostatic seal to a tissue, which is not otherwise associated with a handle assembly.

A modular design of a surgical system having multiple nozzle assemblies may include various surgical instruments, each configured for a different surgical function. In one example, a nozzle assembly may include an end effector further modularized to accept releasable end effector cartridges, in which the surgical function is determined by the end effector cartridge. In such an example, circuitry within the nozzle assembly should be capable of conducting electrical signals to the end effector cartridge as necessary to permit the end effector cartridge to operate properly. For some surgical procedures, a hemostatic seal may be induced in the target tissue. Such a hemostatic seal may require the application of RF energy to the tissue. Thus, the circuitry may be designed to have some electrical conductors configured to deliver the RF energy to the end effector cartridge. However, the circuitry may have only a limited number of electrical conductors. It is therefore desirable for the circuitry to supply RF energy to the end effector when needed through dedicated RF electrical conductors, but to reconfigure the RF electrical conductors and/or other components of the circuitry for conducting non-RF energy when RF energy is not required.

In some aspects, a circuitry system is included in the nozzle assembly that allows for a user of the modular surgical instruments described herein to manipulate the end effector directly from the instrumentation contained in the handle assembly. In some examples, the nozzle assembly may be configured to impart a hemostatic seal to tissue through the application of both a clamping force and the application of RF energy to the tissue. The nozzle assembly may include an onboard circuit board that allows for an electrosurgical generator to attach directly to the nozzle assembly and supply radio frequency (RF) energy to the end effector for such a surgical function. In some aspects, the circuitry of the nozzle assembly also allows for shaft rotation while still supplying proper energy and functionality to the end effector.

It may be recognized that care should be taken to assure that RF energy conducted by some electrical conductors of the onboard circuit board is properly isolated from any of the other components of the onboard circuit board. Failure to provide such isolation may result in RF energy or noise being introduced into the other electronic components (such as digital electronics) or signal conductors of the onboard circuit board. In some aspects, RF energy isolation may be accomplished by isolating conductors of RF energy to a segmented circuit component of the onboard circuit board. The segmented circuit component may be configured to incorporate proper electrical conductor geometry, and appropriate localization of ground planes around the RF conductors thereby isolating the RF energy from the other components of the onboard circuit board. Such a segmented circuit component may be located on a portion of the onboard circuit board physically separated from the other electrical components. In one aspect, connecting the surgical instrument to an RF generator enables certain shaft functions. For example, attachment of RF leads to the RF generator allow the surgical instrument onboard circuit board to isolate some of the elongated shaft integral circuit wiring for RF application to an RF cartridge interchangeably usable with stapling cartridges.

Referring to FIG. 40, in some aspects, the nozzle assembly 1240 that constitutes a modular portion of the surgical tool assembly 1000 may include shaft module circuitry configured to control various functions in the shaft assembly while also communicating with the handle assembly 500 and allowing for the RF generator 400 to be controlled from the powered stapling handle. In FIG. 40, the circuitry of FIG. 15 is shown in the context of an example nozzle assembly 1240. The circuitry according to some aspects of the present disclosures includes the onboard circuit board 1152 with various connectors. Female connectors 410 are electrically coupled to the circuit board 1152, which allows for connection with the male plug assembly 406 that couple to the generator 400, not shown.

In addition, the onboard on/off power switch 420 is electrically coupled to the circuit board 1152 and positioned in such a way so as to be pressed when the nozzle assembly 1240 is attached to the handle assembly 500, according to some aspects. For example, when the nozzle assembly locks into place (see e.g., FIG. 9), the on/off power switch 420 may be positioned to face proximally to the handle assembly and may be pressed as the nozzle assembly slides into the slot of the handle assembly via the closure link 514 (see FIG. 9). In other cases, the on/off power switch 420 is exposed so that it may be manually pressed by an operator of the surgical tool assembly 1000.

The circuit board 1152 includes the onboard connector 1154 configured to interface with the housing connector 562 (see FIG. 9) communicating with the microprocessor 560 contained in the handle assembly 500. In this way, the handle assembly 500 is capable of communicating with the circuit board 1152 that controls several functions in the nozzle assembly 1240. Electrical power, for example from the power assembly 706, may also be conducted through the onboard connector 1154 to the onboard circuit board 1152. The design of the circuitry in the nozzle assembly 1240 allows for an operator to perform a number of functions from the various controls of the handle assembly 500, such as through the various controls and display consoles available in the handle assembly 500.

The circuit board 1152 also includes the proximal connector 1153 that is configured to interface with the slip ring assembly 1150. Power may be supplied to the end effector even while the shaft rotates due to power being supplied throughout the slip ring assembly 1150 and the distal connector 1162 being in constant contact with the slip ring assembly as the flexible shaft circuit strip 1164 rotates within the proximal closure tube 1910. The shaft circuit strip 1164 may include a number of electrical conductors, such as the narrow electrical conductors 1166 for stapling related activities and the wider electrical conductors 1168 for RF purposes (see FIG. 15).

Based on the various components described in the nozzle assembly 1240, the circuitry 1152 may be configured to control the RF generator 400 from the powered handle assembly 500, allowing for communication with the various functions and interfaces of the handle assembly 500, and allowing for operation of the RF and stapling functions of the end effector from the handle assembly 500. Other functions may include controlling a type of algorithm for performing various surgical procedures and energy applications at the end effector, enabling warning functionality viewable at the handle assembly 500 of any part of the nozzle assembly 1240, and varying energy modulation from the RF generator 400. In some aspects, the circuit board 1152 may be programmed to facilitate these functions, while in other cases the onboard connecter 1154 may allow for the handle assembly circuitry to be programmed to facilitate these functions and the circuit board 1152 is configured to communicate with the end effector accordingly.

In some aspects, the onboard circuit 1152 includes the segmented RF circuit 1160, which may allow for the RF energy of the generator 400 to be supplied to the flexible shaft circuit strip via the slip ring assembly (see, e.g., FIG. 15). The segmented RF circuit 1160 may incorporate electrical conductors for supplying the RF energy and provide electrical isolation of the other components of the onboard circuit board 1152 from RF energy and/or noise. The RF generator may be coupled to the onboard circuit board 1152 via the RF segmented circuit 1160. The on/off power switch 420 may be similarly connected to the segmented RF circuit 1160.

FIG. 41 illustrates a block diagram of a surgical system 3200 programmed to conduct power and control signals to or from an end effector 3250 according to one aspect of this disclosure. In an example aspect, the surgical system 3200 may include a control circuit 3210 (e.g., microprocessor 560, segmented RF circuit 1160, or distal micro-chip 1740) having an electrosurgical energy control segment (or an RF energy control segment) 3220 and a shaft control segment 3230 (e.g., shaft segment (Segment 5), motor circuit segment (Segment 7), or power segment (Segment 8)). In some aspects, the electrosurgical energy control segment 3220 may be localized on, in, or proximate to the segmented RF circuit 1160 of the onboard circuit board 1152. The control circuit 3210 may be programed to provide electrosurgical energy (e.g., RF energy) to the electrodes (e.g., electrodes 3040L, 3040R, 3050L, 3050R) in the end effector 3250 (e.g., end effector 1500). The surgical system 3200 may include one or more electrical conductors 3260 (e.g., electrical conductors 1168) used for providing the electrosurgical energy, from an electrosurgical energy generator 3240 (e.g., RF generator 400), to the end effector 3250. The one or more electrical conductors 3260 may also be electrically connected between the end effector 3250 and the control circuit 3210 (e.g., the electrosurgical energy control segment 3220 and the shaft control segment 3230). The electrical conductors 3260 may provide additional control signals to the end effector 3250 from the shaft control segment 3230 or provide additional sensor signals from the end effector 3250 to the shaft control segment 3230, especially for surgical systems having an end effector not requiring RF energy for its function.

The electrosurgical energy control segment 3220 may be programed to provide the electrosurgical energy to the electrodes through the one or more electrical conductors 3260. In an example aspect, the shaft control segment 3230 may be programed to provide and/or receive a control signal to/from the end effector 3250 (and/or the surgical tool assembly 1000, the shaft assembly 704) through the one or more electrical conductors 3260. That is, the one or more electrical conductors 3260 may be used not only for providing the electrosurgical energy to the end effector 3250, but also for communicating control signals with the end effector 3250. In an example aspect, at least some portions of the electrosurgical energy control segment 3220 and the shaft control segment 3230 may be electrically isolated from each other.

In an example aspect, the electrosurgical energy control segment 3220 may electrically isolate the one or more electrical conductors 3260 from the shaft control segment 3230, for example, when providing the electrosurgical energy to the electrodes in the end effector 3250 through the one or more electrical conductors 3260. In an example aspect, the electrosurgical energy control segment 3220 may control a switch 3270 located between the one or more electrical conductors 3260 and the shaft control segment 3230 by providing a signal through a control line 3280 to electrically isolate the one or more electrical conductors 3260 from the shaft control segment 3230. The switch 3270 may be configured to switch between an open state and a closed state. The shaft control segment 3230 and the one or more electrical conductors 3260 may be electrically isolated when the switch 3270 is in the open state, and may be in electrical communication when the switch 3270 is in the closed state. In another example aspect, the electrosurgical energy control segment 3220 may electrically isolate the one or more electrical conductors 3260 from the shaft control segment 3230 in any other suitable manner. Other configurations of the switch 3270 may enable electrical isolation of the one or more electrical conductors 3260 from the shaft control segment 3230 by closing the switch 3270.

In an example aspect, the electrosurgical energy control segment 3220 may electrically isolate the one or more electrical conductors 3260 from the shaft control segment 3230 when the control circuit 3210 detects that the electrosurgical energy generator 3240 is connected to the connector 3265 (e.g., female connectors 410), for example, by continuously checking the connector 3265 or sensing the application of the electrosurgical energy. For example, when the male plug assembly 406 is plugged into the female connectors 410, the electrosurgical energy control segment 3220 may isolate the electrical conductors 3260 from the shaft control segment 3230. In another example aspect, the electrosurgical energy control segment 3220 may electrically isolate the one or more electrical conductors 3260 from the shaft control segment 3230 when the electrosurgical energy is provided to the end effector 3250 or under any other suitable condition.

In an example aspect, the surgical system may include one or more electrical conductors 3290 (e.g., electrical conductors 1166) used for operating the end effector 3250 (and/or the surgical tool assembly 1000, the shaft assembly 704). In an example aspect, the one or more electrical conductors 3290 may not be used to deliver the electrosurgical energy to the end effector 3250. The shaft control segment 3230 may be programed to provide and/or receive a control signal and/or a sensor signal to/from the end effector 3250 through the one or more electrical conductors 3290. In an example aspect, the shaft control segment 3230 may use the one or more electrical conductors 3290 to provide and/or receive the control signal to/from the end effector 3250 while the switch 3270 is in an open state (e.g., while the electrosurgical energy control segment 3220 is providing the electrosurgical energy to the end effector 3250 through the one or more electrical conductors 3260). In an example aspect, the shaft control segment 3230 also may use the one or more electrical conductors 3290 to provide and/or receive the control signal to/from the end effector 3250 while the switch 3270 is in a closed state. In some aspects, the one or more electrical conductors 3290 may be dedicated signal conductors (for either control signals or sensor signals or both control signals and sensor signals) between the end effector 3250 and the shaft control segment 3230 regardless of the state of switch 3270.

The switch 3270 may be a transistor switch, a mechanical switch, or any other suitable switch. In an example aspect, the control signals communicated between the control circuit 3210 and the end effector 3250 (and/or the surgical tool assembly 1000, the shaft assembly 704) through the electrical conductors 3260, 3290 include, but are not limited to, signals for driving the end effector 3250 (and/or the surgical tool assembly 1000, the shaft assembly 704) in cutting and/or coagulation operating modes, measuring electrical characteristics of the surgical system 3200 and/or the tissue clamped in the end effector 3250, providing feedback to a user of the surgical system, communicating sensor signals, and identifying certain characteristics of the end effector 3250 (e.g., used/unused status).

Accordingly, aspects of the present disclosure may advantageously reduce the number of electrical conductors necessary for communicating control signals between the control circuit 3210 and the end effector 3250 (and/or the surgical tool assembly 1000, the shaft assembly 704) by using some of the electrical conductors (e.g., electrical conductors 3260) used for the delivery of the electrosurgical energy to communicate the control signals when those electrical conductors are not used for the electrosurgical energy. Moreover, by isolating those electrical conductors from other circuit segments (e.g., shaft control segment 3230) when providing the electrosurgical energy through those electrical conductors, aspects of the present disclosure may prevent the electrosurgical energy or electrosurgical energy noise from flowing into the other circuit segments and/or electrical conductors (e.g., electrical conductors 3290) connected to those circuit segments, preventing damages to those circuit segments and/ore electrical conductors.

As depicted in, for example in FIGS. 40 and 41 and as disclosed above, a modular nozzle assembly may include an onboard circuit board configured to permit a user to communicate with and control an end effector of a surgical system. The control of and/or communication with the end effector may include control and/or communication with the end effector as a whole or with any one or more components of the end effector. For example, the end effector may be configured to releasably incorporate one or more modules and/or cartridges as disclosed above, each of which may be designed for a specific surgical function. In one example, the end effector may incorporate a releasable stapling cartridge. In another example, the end effector may incorporate a releasable RF cartridge. Each of the releasable cartridges may have any number or type of electrical conductors configured to electrically couple with the one or more electrical conductors of the onboard circuit board. The electrical conductors of each releasable cartridge may be configured to conduct any type of electrical signal, including, without limitation, an analog signal, a digital signal, a DC signal, an AC signal, and an electrical power signal. Such electrical signals may originate from the onboard circuit board or from electrical components of a releasable cartridge.

Although the electrical circuitry as disclosed above is referred to as an onboard "circuit board," the circuitry itself may be fabricated according to any appropriate means using any appropriate material. Thus, for example, the circuit board may be a single layer board, a multi-layer board, a flex circuit, or any other appropriate device on which electrical components may be suitably mounted. Similarly, electrical conductors may include, without limitation, wires and circuit board traces.

Various aspects of the subject matter described herein are set out in the following numbered examples:

EXAMPLE 1

A control circuit for a surgical instrument, the control circuit comprising: a shaft control segment; a first electrical conductor configured to conduct a first electrical signal between the shaft control segment and a releasable surgical instrument cartridge; an electrosurgical energy control segment; a second electrical conductor configured to conduct a second electrical signal between the electrosurgical energy control segment and the releasable surgical instrument cartridge; and a connector electrically coupled to the electrosurgical energy control segment and configured to receive electrosurgical generator energy from an electrosurgical generator, wherein the electrosurgical energy control segment is configured to: detect a connection of the electrosurgical generator to the connector; and electrically isolate the shaft control segment from the electrosurgical generator energy when the electrosurgical energy control segment detects the connection of the electrosurgical generator to the connector.

EXAMPLE 2

The control circuit of Example 1, wherein the first electrical signal comprises a control signal transmitted to the releasable surgical instrument cartridge.

EXAMPLE 3

The control circuit of any one or more of Example 1 through Example 2, wherein the first electrical signal comprises a sensor signal received from the releasable surgical instrument cartridge.

EXAMPLE 4

The control circuit of any one or more of Example 1 through Example 3, wherein the second electrical signal comprises the electrosurgical generator energy when the electrosurgical energy control segment detects the connection of the electrosurgical generator to the connector.

EXAMPLE 5

The control circuit of any one or more of Example 1 through Example 4, wherein the second electrical conductor is configured to conduct a third electrical signal between the shaft control segment and the releasable surgical instrument cartridge when the electrosurgical energy control segment detects no connection of the electrosurgical generator to the connector.

EXAMPLE 6

The control circuit of Example 5, wherein the third electrical signal comprises a second control signal transmitted to the releasable surgical instrument cartridge.

EXAMPLE 7

The control circuit of Example 5, wherein the third electrical signal comprises a second sensor signal received from the releasable surgical instrument cartridge

EXAMPLE 8

The control circuit of any one or more of Example 1 through Example 7, further comprising a switch electrically coupled between the electrosurgical energy control segment and the shaft control segment, wherein the electrosurgical energy control segment is configured to electrically isolate the shaft control segment by controlling the switch.

EXAMPLE 9

The control circuit of Example 8, wherein the electrosurgical energy control segment is configured to electrically isolate the shaft control segment by opening the switch.

EXAMPLE 10

The control circuit of any one or more of Example 1 through Example 9, wherein the electrosurgical generator comprises an RF generator and the electrosurgical generator energy comprises RF energy.

EXAMPLE 11

The control circuit of any one or more of Example 1 through Example 10, further comprising a slip ring assembly electrically coupled to the shaft control segment and electrically coupled to the electrosurgical energy control segment.

EXAMPLE 12

A nozzle assembly of a surgical system comprising: an onboard circuit board comprising a shaft control segment and an electrosurgical energy control segment; a first electrical conductor configured to conduct a first electrical signal between the shaft control segment and a releasable surgical instrument cartridge in an end effector; a second electrical conductor configured to conduct a second electrical signal between the electrosurgical energy control segment and the releasable surgical instrument cartridge in the end effector; an onboard connector coupled to the onboard circuit board and proximally located on the nozzle assembly, the onboard connector configured to interface with a housing connector of a handle assembly when the nozzle assembly is attached to the handle assembly; a connector electrically coupled to the electrosurgical energy control segment and configured to receive electrosurgical generator energy from an electrosurgical generator; and a shaft attachment lug proximally located on the nozzle assembly and configured to be coupled to an attachment cradle of the handle assembly to attach the nozzle assembly to the handle assembly, wherein the electrosurgical energy control segment is configured to: detect a connection of the electrosurgical generator to the connector; and electrically isolate the shaft control segment from the electrosurgical generator energy when the electrosurgical energy control segment detects the connection of the electrosurgical generator to the connector.

EXAMPLE 13

The nozzle assembly of Example 12, wherein the onboard circuit board comprises a segmented RF circuit on the onboard circuit board and the segmented RF circuit comprises the electrosurgical energy control segment.

EXAMPLE 14

The nozzle assembly of any one or more of Example 12 through Example 13, wherein the onboard circuit board is configured to receive electrical power from a power assembly releasably mounted to the handle assembly.

EXAMPLE 15

The nozzle assembly of Example 14, wherein the onboard circuit board is configured to receive electrical power through the onboard connector.

EXAMPLE 16

The nozzle assembly of any one or more of Example 12 through Example 15, wherein the nozzle assembly further comprises a power switch electrically coupled to the onboard circuit board and is configured to activate and deactivate transmission of electrosurgical energy.

EXAMPLE 17

The nozzle assembly of any one or more of Example 12 through Example 16, further comprising a slip ring assembly distally located to the onboard circuit board and configured to interface with the onboard circuit board.

EXAMPLE 18

The nozzle assembly of Example 17, further comprising: a proximal connector coupled to a distal end of the onboard circuit board and a proximal end of the slip ring assembly; and a distal connector configured to interface with a distal end of the slip ring assembly and electrically coupled to the first electrical conductor and the second electrical conductor.

EXAMPLE 19

The nozzle assembly any one or more of Example 12 through Example 19, further comprising a flexible shaft circuit strip electrically coupled to the first electrical conductor and the second electrical conductor.

Surgical System Couplable with Staple Cartridge and Radio Frequency Cartridge, and Method of Using Same FIG. 66 illustrates a method 1950 of utilizing the interchangeable tool assembly 1000 according to various aspects. For a first procedure, the surgical staple/fastener cartridge 1400 may be inserted 1952 into and retained within the elongate channel 1602 of the first jaw 1600 of the end effector 1500 of the interchangeable surgical tool assembly 1000, thereby coupling the surgical staple/fastener cartridge 1400 to the interchangeable surgical tool assembly 1000. The surgical staple/fastener cartridge 1400 may then be utilized to deliver 1954 staples from the surgical staple/fastener cartridge 1400 to a tissue in a patient.

After at least some of the staples are delivered to the tissue in the patient, the surgical staple/fastener cartridge 1400 may be removed 1956 from the end effector 1500 of the interchangeable surgical tool assembly 1000, effectively uncoupling the surgical staple/fastener cartridge 1400 from the interchangeable surgical tool assembly 1000. For instances where at least a portion of the interchangeable surgical tool assembly 1000 is positioned within the patient's body, the end effector 1500 is removed from the patient's body prior to the removal of the surgical staple/fastener cartridge 1400 from the end effector 1500. The interchangeable tool assembly 1000, or portions thereof, may then be cleaned and sterilized to properly prepare the interchangeable tool assembly 1000 for subsequent use.

After the surgical staple/fastener cartridge 1400 has been removed from the end effector 1500 of the interchangeable surgical tool assembly 1000, for a second procedure, the radio-frequency cartridge 1700 may be inserted 1958 into and retained within the elongate channel 1602 of the first jaw 1600 of the end effector 1500 of the interchangeable surgical tool assembly 1000, thereby coupling the radio-frequency cartridge 1700 to the interchangeable surgical tool assembly 1000 and effectively replacing the surgical staple/fastener cartridge 1400. Once the radio-frequency cartridge 1700 is in place and the radio-frequency generator 400 is coupled to the segmented radio-frequency circuit 1160 of the interchangeable surgical tool assembly 1000, the radio-frequency cartridge 1700 may then be utilized to deliver 1960 radiofrequency energy (e.g., coagulating electrical current) to a tissue in a patient. The first procedure occurs during a first time period and the second procedure occurs during a second time period. The second procedure may be a continuation of, or different from the first procedure. Therefore, the tissue receiving the radio-frequency energy may be the same general tissue which previously received the staples, or may be a different tissue from the tissue which previously received the staples. Similarly, the patient associated with the first procedure may be the same as, or different from, the patient associated with the second procedure.

After at least some of the radio-frequency energy is delivered to the tissue in the patient, the radio-frequency cartridge 1700 may be removed 1962 from the end effector 1500 of the interchangeable surgical tool assembly 1000, effectively uncoupling the radio-frequency cartridge 1700 from the interchangeable surgical tool assembly 1000. Once the radio-frequency cartridge is removed from the interchangeable tool assembly 1000, the segmented radio-frequency circuit 1160 of the interchangeable surgical tool assembly 1000 may also be uncoupled from the radio-frequency generator 400. For instances where at least a portion of the interchangeable surgical tool assembly 1000 is positioned within the patient's body, the end effector 1500 is removed from the patient's body prior to the removal of the radio-frequency cartridge 1700 from the end effector 1500. The interchangeable tool assembly 1000, or portions thereof, may then be cleaned and sterilized to properly prepare the interchangeable tool assembly 1000 for subsequent use. Each instance of such subsequent use can involve either the surgical staple/fastener cartridge 1400 (effectively replacing the radio-frequency cartridge 1700) or the radio-frequency cartridge 1700.

Although the above description of the method 1950 describes the surgical staple/fastener cartridge 1400 being utilized with the interchangeable surgical tool assembly 1000 for a first procedure and the radio-frequency cartridge 1700 being utilized with the interchangeable surgical tool assembly 1000 for a second procedure, the above-described method 1950 is not strictly limited to the described order of the uses or to strictly alternating uses of the surgical staple/fastener cartridge 1400 and the radio-frequency cartridge 1700. For example, as shown in FIG. 66, the radio-frequency cartridge 1700 may be utilized by the interchangeable surgical tool assembly 1000 for an initial procedure and the surgical staple/fastener cartridge 1400 may be utilized for a subsequent procedure. Also, the interchangeable surgical tool assembly 1000 may utilize respective surgical staple/fastener cartridges 1400 for any number of sequential procedures before utilizing the radio-frequency cartridge 1700 for a subsequent procedure (or respective radio-frequency cartridges 1700 1400 for any number of subsequent procedures). When respective surgical staple/fastener cartridges 1400 are used sequentially, the respective surgical staple/fastener cartridges 1400 may be the same or different. For example, one of the respective surgical staple/fastener cartridges 1400 may have an effective longitudinal stapling length which is different from an effective longitudinal stapling length of a different one of the respective surgical staple/fastener cartridges 1400. Similarly, the interchangeable surgical tool assembly 1000 may utilize respective radio-frequency cartridges 1700 for any number of sequential procedures prior to utilizing the surgical staple/fastener cartridge 1400 for a subsequent procedure (or respective surgical staple/fastener cartridges 1400 for any number of subsequent procedures). When respective radio-frequency cartridges 1700 are used sequentially, the respective radio-frequency cartridges 1700 may be the same or different.

Various aspects of the subject matter described herein are set out in the following numbered examples:

EXAMPLE 1

A method is provided. The method comprises delivering staples from a surgical staple cartridge of a surgical instrument to a first tissue during a first procedure, removing the surgical staple cartridge from the surgical instrument, and delivering radio-frequency energy from a radio-frequency cartridge of the surgical instrument to a second tissue during a second procedure.

EXAMPLE 2

The method of Example 1, wherein the delivering of the radio-frequency energy from the radio-frequency cartridge occurs before the delivering of the staples from the surgical staple cartridge.

EXAMPLE 3

The method of one or more of Example 1 through Example 2, wherein the second procedure is different from the first procedure.

EXAMPLE 4

The method of one or more of Example 1 through Example 3, further comprising inserting the surgical staple cartridge into the surgical instrument prior to the delivering of the staples.

EXAMPLE 5

The method of Example 4, wherein inserting the surgical staple cartridge into the surgical instrument comprises inserting the surgical staple cartridge into an interchangeable tool assembly.

EXAMPLE 6

The method of one or more of Example 1 through Example 5, further comprising, prior to the delivering of the radio-frequency energy, inserting a second surgical staple cartridge into the surgical instrument.

EXAMPLE 7

The method of one or more of Example 1 through Example 6, further comprising, prior to the delivering of the radio-frequency energy, (1) inserting the radio-frequency cartridge into the surgical instrument and (2) coupling the radio-frequency cartridge to a radio-frequency generator.

EXAMPLE 8

The method of Example 7, wherein inserting the radio-frequency cartridge into the surgical instrument comprises inserting the radio-frequency cartridge into an interchangeable tool assembly.

EXAMPLE 9

The method of one or more of Example 1 through Example 8, further comprising removing the radio-frequency cartridge from the surgical instrument.

EXAMPLE 10

The method of Example 9, further comprising inserting a second radio-frequency cartridge into the surgical instrument.

EXAMPLE 11

The method of Example 9, further comprising inserting a second surgical staple cartridge into the surgical instrument.

EXAMPLE 12

A method of utilizing an interchangeable tool assembly is provided. The method comprises utilizing a staple cartridge coupled to the interchangeable tool assembly to deliver staples to seal a first tissue during the first period of time, replacing the staple cartridge, and utilizing a radio-frequency cartridge coupled to the interchangeable tool assembly to deliver radio-frequency energy to seal a second tissue during the second period of time.

EXAMPLE 13

The method of Example 12, wherein replacing the staple cartridge comprises (1) uncoupling the staple cartridge from the interchangeable tool assembly and (2) coupling the radio-frequency cartridge to the interchangeable tool assembly.

EXAMPLE 14

The method of one or more of Example 12 through Example 13, wherein coupling the radio-frequency cartridge to the interchangeable tool assembly comprises coupling the radio-frequency cartridge to an end effector of the interchangeable tool assembly.

EXAMPLE 15

The method of one or more of Example 12 through Example 14, further comprising, prior to the utilizing of the staple cartridge, coupling the staple cartridge to an end effector of the interchangeable tool assembly.

EXAMPLE 16

The method of one or more of Example 12 through Example 15, further comprising, prior to utilizing the radio-frequency cartridge, (1) coupling the radio-frequency cartridge to the interchangeable tool assembly and (2) coupling the interchangeable tool assembly to a radio-frequency generator.

EXAMPLE 17

The method of one or more of Example 12 through Example 16, further comprising coupling a second staple cartridge to the interchangeable tool assembly.

EXAMPLE 18

The method of one or more of Example 12 through Example 17, further comprising coupling a second radio-frequency cartridge to the interchangeable tool assembly.

EXAMPLE 19

A method is provided. The method comprises sealing a first tissue with staples from a removable staple cartridge of a surgical instrument, sterilizing the surgical instrument, and sealing a second tissue with radio-frequency energy delivered by a removable radio-frequency cartridge of the surgical instrument.

Aspects of the surgical instrument may be practiced without the specific details disclosed herein. Some aspects have been shown as block diagrams rather than detail. Parts of this disclosure may be presented in terms of instructions that operate on data stored in a computer memory. Generally, aspects described herein which can be implemented, individually and/or collectively, by a wide range of hardware, software, firmware, or any combination thereof can be viewed as being composed of various types of "electrical circuitry." Consequently, "electrical circuitry" includes electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer or processor configured by a computer program, which at least partially carries out processes and/or devices described herein), electrical circuitry forming a memory device (e.g., forms of random access memory), and/or electrical circuitry forming a communications device (e.g., a modem, communications switch, or optical-electrical equipment). These aspects may be implemented in analog or digital form, or combinations thereof.

The foregoing description has set forth aspects of devices and/or processes via the use of block diagrams, flowcharts, and/or examples, which may contain one or more functions and/or operation. Each function and/or operation within such block diagrams, flowcharts, or examples can be implemented, individually and/or collectively, by a wide range of hardware, software, firmware, or virtually any combination thereof. In one aspect, several portions of the subject matter described herein may be implemented via Application Specific Integrated Circuits (ASICs), Field Programmable Gate Arrays (FPGAs), digital signal processors (DSPs), Programmable Logic Devices (PLDs), circuits, registers and/or software components, e.g., programs, subroutines, logic and/or combinations of hardware and software components, logic gates, or other integrated formats. Some aspects disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

The mechanisms of the disclosed subject matter are capable of being distributed as a program product in a variety of forms, and that an illustrative aspect of the subject matter described herein applies regardless of the particular type of signal bearing medium used to actually carry out the distribution. Examples of a signal bearing medium include the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a electrical conductor communications link, a electrical conductorless communication link (e.g., transmitter, receiver, transmission logic, reception logic, etc.).

The foregoing description of these aspects has been presented for purposes of illustration and description. It is not intended to be exhaustive or limiting to the precise form disclosed. Modifications or variations are possible in light of the above teachings. These aspects were chosen and described in order to illustrate principles and practical application to thereby enable one of ordinary skill in the art to utilize the aspects and with modifications as are suited to the particular use contemplated. It is intended that the claims submitted herewith define the overall scope.

The invention claimed is:

1. A method of using a surgical instrument comprising an end effector configured to receive multiple cartridges, the method comprising:
   delivering staples from a surgical staple cartridge inserted into the end effector of the surgical instrument to a first tissue during a first procedure;
   removing the surgical staple cartridge from the surgical instrument end effector;
   opening a switch dispositioned between a first circuit segment and a second circuit segment to electrically isolate the first circuit segment from the second circuit segment without removing the end effector from the surgical instrument, wherein the first circuit segment is configured to deliver radio-frequency energy to a radio-frequency cartridge; and
   delivering radio-frequency energy from the radio-frequency cartridge of the surgical instrument to a second tissue during a second procedure.

2. The method of claim 1, wherein the delivering of the radio-frequency energy from the radio-frequency cartridge occurs before the delivering of the staples from the surgical staple cartridge.

3. The method of claim 1, wherein the second procedure is different from the first procedure.

4. The method of claim 1, further comprising inserting the surgical staple cartridge into the surgical instrument prior to the delivering of the staples.

5. The method of claim 4, wherein inserting the surgical staple cartridge into the surgical instrument comprises inserting the surgical staple cartridge into an interchangeable tool assembly.

6. The method of claim 1, further comprising, prior to the delivering of the radio-frequency energy, inserting a second surgical staple cartridge into the surgical instrument.

7. The method of claim 1, further comprising, prior to the delivering of the radio-frequency energy:
   inserting the radio-frequency cartridge into the surgical instrument; and
   coupling the radio-frequency cartridge to a radio-frequency generator.

8. The method of claim 7, wherein inserting the radio-frequency cartridge into the surgical instrument comprises inserting the radio-frequency cartridge into an interchangeable tool assembly.

9. The method of claim 1, further comprising removing the radio-frequency cartridge from the surgical instrument.

10. The method of claim 9, further comprising inserting a second radio-frequency cartridge into the surgical instrument.

11. The method of claim 9, further comprising inserting a second surgical staple cartridge into the surgical instrument.

12. The method of claim 1, further comprising:
    detecting a connection of the surgical instrument to a radio-frequency energy generator; and
    wherein opening the switch to electrically isolate the first circuit segment from the second circuit segment occurs automatically in response to the surgical instrument being connected to the radio-frequency energy generator in response to the detection of the connection of the surgical instrument to the radio-frequency energy generator.

13. The method of claim 1, wherein the second circuit segment is a shaft control segment configured to transmit control signals to and from the end effector, and wherein opening the switch prohibits the shaft control segment from transmitting control signals to and from the end effector.

14. A method of utilizing an interchangeable tool assembly, the method comprising:
    utilizing a staple cartridge coupled to the interchangeable tool assembly to deliver staples to seal a first tissue during a first period of time;
    replacing the staple cartridge;
    electrically isolating a first circuit segment configured to deliver radio-frequency energy from a second circuit segment by opening a switch dispositioned between the first circuit segment and the second circuit segment, without decoupling a structural component from the interchangeable tool assembly, wherein the second circuit segment is a shaft control segment configured to transmit control signals to and from an end effector, and wherein opening the switch prohibits the shaft control segment from transmitting control signals to and from the end effector; and
    utilizing a radio-frequency cartridge coupled to the interchangeable tool assembly to deliver radio-frequency energy to seal a second tissue during a second period of time.

15. The method of claim 14, wherein replacing the staple cartridge comprises:
    uncoupling the staple cartridge from the interchangeable tool assembly; and
    coupling the radio-frequency cartridge to the interchangeable tool assembly.

16. The method of claim 15, wherein coupling the radio-frequency cartridge to the interchangeable tool assembly comprises coupling the radio-frequency cartridge to the end effector of the interchangeable tool assembly.

17. The method of claim 14, further comprising, prior to the utilizing of the staple cartridge, coupling the staple cartridge to the end effector of the interchangeable tool assembly.

18. The method of claim 14, further comprising, prior to utilizing the radio-frequency cartridge:
    coupling the radio-frequency cartridge to the interchangeable tool assembly; and
    coupling the interchangeable tool assembly to a radio-frequency generator.

19. The method of claim 14, further comprising coupling a second staple cartridge to the interchangeable tool assembly.

20. The method of claim 14, further comprising coupling a second radio-frequency cartridge to the interchangeable tool assembly.

21. A method of using a surgical instrument comprising an end effector configured to receive multiple cartridges, the method comprising:
- sealing a first tissue with staples from a removable staple cartridge of the surgical instrument;
- sterilizing the surgical instrument;
- electrically isolating a first circuit segment configured to deliver radio-frequency energy from a second circuit segment by opening a switch dispositioned between the first circuit segment and the second circuit segment, without removing the end effector from the surgical instrument; and
- sealing a second tissue with radio-frequency energy delivered by a removable radio-frequency cartridge of the surgical instrument.

* * * * *